(12) United States Patent
Lorenz et al.

(10) Patent No.: US 9,540,391 B2
(45) Date of Patent: Jan. 10, 2017

(54) ISOMANNIDE DERIVATIVES AS INHIBITORS OF SOLUBLE EPOXIDE HYDROLASE

(71) Applicant: SANOFI, Paris (FR)

(72) Inventors: Katrin Lorenz, Frankfurt am Main (DE); Kristin Breitschopf, Frankfurt am Main (DE); Hartmut Strobel, Frankfurt am Main (DE); Maria Mendez-Perez, Frankfurt am Main (DE); Li-hsing Wang, Frankfurt am Main (DE); Alexander Schiffer, Frankfurt am Main (DE); Joseph T. Kim, Bridgewater, NJ (US); Hans-Peter Nestler, Bridgewater, NJ (US); Mark Drew, Bridgewater, NJ (US)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/761,270

(22) PCT Filed: Jan. 16, 2014

(86) PCT No.: PCT/EP2014/050796
§ 371 (c)(1),
(2) Date: Jul. 15, 2015

(87) PCT Pub. No.: WO2014/111465
PCT Pub. Date: Jul. 24, 2014

(65) Prior Publication Data
US 2015/0336979 A1 Nov. 26, 2015

(30) Foreign Application Priority Data

Jan. 17, 2013 (EP) .................................. 13305051

(51) Int. Cl.
*C07D 493/04* (2006.01)
*C07D 519/00* (2006.01)

(52) U.S. Cl.
CPC ........... *C07D 493/04* (2013.01); *C07D 519/00* (2013.01)

(58) Field of Classification Search
CPC .............................. C07D 493/04; C07D 519/00
See application file for complete search history.

(56) References Cited

U.S. PATENT DOCUMENTS 5,591,758 A 1/1997 Nallet et al.

FOREIGN PATENT DOCUMENTS

| BR | 2009/02520 A2 | 4/2011 |
| BR | 2010/00099 A2 | 9/2011 |
| EP | 0 449 932 A1 | 10/1991 |
| WO | WO-93/03037 A1 | 2/1993 |
| WO | WO-2004/089296 A2 | 10/2004 |
| WO | WO-2004/089296 A3 | 10/2004 |
| WO | WO-2006/045119 A2 | 4/2006 |
| WO | WO-2006/045119 A3 | 4/2006 |
| WO | WO-2006/121719 A2 | 11/2006 |
| WO | WO-2006/121719 A3 | 11/2006 |
| WO | WO-2007/043652 A1 | 4/2007 |
| WO | WO-2007/043653 A1 | 4/2007 |
| WO | WO-2007/067836 A2 | 6/2007 |
| WO | WO-2007/067836 A3 | 6/2007 |
| WO | WO-2007/106525 A1 | 9/2007 |
| WO | WO-2007/106706 A1 | 9/2007 |
| WO | WO-2007/121883 A2 | 11/2007 |
| WO | WO-2007/121883 A3 | 11/2007 |
| WO | WO-2008/016884 A2 | 2/2008 |
| WO | WO-2008/016884 A3 | 2/2008 |
| WO | WO-2008/105968 A1 | 9/2008 |
| WO | WO-2009/011872 A1 | 1/2009 |
| WO | WO-2009/087379 A2 | 7/2009 |
| WO | WO-2009/087379 A3 | 7/2009 |
| WO | WO-2009/111207 A1 | 9/2009 |
| WO | WO-2009/111447 A2 | 9/2009 |

(Continued)

OTHER PUBLICATIONS

ZINC Database—For Sale Feb. 21, 2008.*
CAS Registry compounds: Shoichet Laboratory ZINC Databse, Ambinter and Aurora Fine Chemicals—Mar. 2008, Mar. 2010 and Apr. 2010.*
De Taeye, B.M. et al. (Mar. 2010). "Expression and Regulation of Soluble Epoxide Hydrolase in Adipose Tissue," *Obesity* (*Silver Spring*) 18(3):489-498.
Imig, J.D. et al. (Oct. 2009). "Soluble Epoxide Hydrolase as a Therapeutic Target for Cardiovascular Diseases," *Nat. Rev. Drug Discov.* 8(10):794-805.

(Continued)

*Primary Examiner* — Valerie Rodriguez-Garcia
(74) *Attorney, Agent, or Firm* — Morrison & Foerster LLP

(57) ABSTRACT

The present invention relates to compounds of the formula (I), wherein R1, R11, R12 and X have the meanings indicated in the claims. The compounds of formula I are valuable pharmacologically active compounds. They are highly potent and selective soluble epoxide hydrolase inhibitors and are suitable, for example, for the therapy and prophylaxis of renal failure, diabetic nephropathy, type 2 diabetes mellitus, inflammation or could show beneficial effects in pain, dyslipidemia and atherosclerosis. The invention furthermore relates to processes for the preparation of compounds of the formula (I), their use, in particular as active ingredients in pharmaceuticals, and pharmaceutical preparations comprising them.

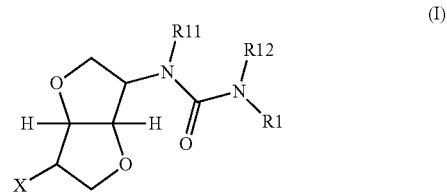

8 Claims, No Drawings

(56) References Cited

FOREIGN PATENT DOCUMENTS

| WO | WO-2009/111447 A3 | 9/2009 |
|---|---|---|
| WO | WO-2011/002871 A2 | 1/2011 |
| WO | WO-2011/002871 A3 | 1/2011 |

OTHER PUBLICATIONS

International Search Report mailed on Mar. 25, 2014, for PCT Patent Application No. PCT/EP2014/050796, filed on Jan. 16, 2014, three pages.

Jones, P.D. et al. (Aug. 1, 2005). "Fluorescent Substrates for Soluble Epoxide Hydrolase and Application to Inhibition Studies," *Anal. Biochem.* 343(1):66-75.

Kaspera, R. et al. (Jul. 2009). "Epoxyeicosatrienoic Acids: Formation, Metabolism and Potential Role in Tissue Physiology and Pathophysiology," *Expert Opin. Drug Metab. Toxicol.* 5(7):757-771.

Kumar, V. et al. (Sep. 27, 2007). "Synthesis and Applications of Novel bis(Ammonium) Chiral Ionic Liquids Derived from Isomannide," *Org. Lett.* 9(20):3905-3908.

Larock, R.C. (1999). *Comprehensive Organic Transformations, A Guide to Functional Group Preparations*, "Ethers," and "Alcohols and Phenols," $2^{nd}$ Edition, Wiley-VCH, pp. 881-974.

Larock, R.C. (1999). *Comprehensive Organic Transformations, A Guide to Functional Group Preparations*, "Oxidation, Substitution and Addition," $2^{nd}$ Edition, Wiley-VCH, pp. 1625-1675.

Larock, R.C. (1999). *Comprehensive Organic Transformations, A Guide to Functional Group Preparations*, "Coupling Reactions," $2^{nd}$ Edition, Wiley-VCH, pp. 77-127.

Larock, R.C. (1999). *Comprehensive Organic Transformations, A Guide to Functional Group Preparations*, "Sulfur, Selenium and Tellurium Reagents," $2^{nd}$ Edition, Wiley-VCH, pp. 1451-1460.

Luo, P. et al. (Aug. 2010). "Inhibition or Deletion of Soluble Epoxide Hydrolase Prevents Hyperglycemia, Promotes Insulin Secretion, and Reduces Islet Apoptosis," *J. Pharmacol. Exp. Ther.* 334(2):430-438.

Monti, J. et al. (May 2008). "Soluble Epoxide Hydrolase is a Susceptibility Factor for Heart Failure in a Rat Model of Human Disease," *Nat. Genet.* 40(5):529-537.

Mustafa, S. et al. (2009). "Insulin Resistance and Endothelial Dysfunction: Are Epoxyeicosatrienoic Acids the Link?" *Exp. Clin. Cardiol.* 14(2):e41-e50.

Olearczyk, J.J. et al. (Jan. 2009). "Administration of a Substituted Adamantyl Urea Inhibitor of Soluble Epoxide Hydrolase Protects the Kidney from Damage in Hypertensive Goto-Kakizaki Rats," *Clin. Sci. (Lond).* 116(1):61-70.

Shen, H.C. (Jul. 2010). "Soluble Epoxide Hydrolase Inhibitors: A Patent Review," *Expert Opin. Ther. Pat.* 20(7):941-956.

Shen, H.C. et al. (Mar. 8, 2012). "Discovery of Inhibitors of Soluble Epoxide Hydrolase: A Target with Multiple Potential Therapeutic Indications," *J. Med. Chem.* 55(5):1789-1808.

Smith, M.B. et al. (2007). *March's Advanced Organic Chemistry: Reactions, Mechanisms, and Structure*, $6^{th}$ Edition, Wiley-Interscience, pp. 425-656.

Smith, M.B. et al. (2007). *March's Advanced Organic Chemistry: Reactions, Mechanisms, and Structure*, $6^{th}$ Edition, Wiley-Interscience, pp. 850-853.

Vogler, M. et al. (2004). "Dianhydrohexitole-Based Benzamidines: An Efficient Synthesis of New Factor Xa Inhibitors," *Synthesis* 8:1211-1228.

Wuts, P.G.M. et al. (1999). Greene's Protective Groups in Organic Synthesis, 3rd Edition, John Wiley and Sons, pp. 17-248.

Wuts, P.G.M. et al. (1999). Greene's Protective Groups in Organic Synthesis, 3rd Edition, John Wiley and Sons, pp. 369-453.

Wuts, P.G.M. et al. (1999). Greene's Protective Groups in Organic Synthesis, 3rd Edition, John Wiley and Sons, pp. 494-653.

\* cited by examiner

ISOMANNIDE DERIVATIVES AS INHIBITORS OF SOLUBLE EPOXIDE HYDROLASE

CROSS-REFERENCE TO RELATED APPLICATIONS

This application is a National Phase application under 35 U.S.C. §371 of International Application No. PCT/EP2014/050796 filed Jan. 16, 2014, which claims priority to European Application No. 13305051.8 filed Jan. 17, 2013, the disclosures of each of which are incorporated herein by reference in their entirety.

The present invention relates to compounds of the formula I,

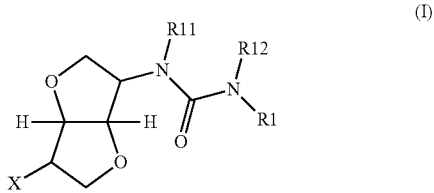

(I)

wherein R1 and X have the meanings indicated below. The compounds of formula I are valuable pharmacologically active compounds. They are highly potent and selective soluble epoxide hydrolase inhibitors and are suitable, for example, for the therapy and prophylaxis of renal failure, diabetic nephropathy, type 2 diabetes mellitus, cardiovascular diseases, inflammatory diseases or could show beneficial effects in pain, dyslipidemia, atherosclerosis, wound healing and stroke. The invention furthermore relates to processes for the preparation of compounds of the formula I, their use, in particular as active ingredients in pharmaceuticals, and pharmaceutical preparations comprising them.

The soluble epoxide hydrolase, in the following sEH, is operating within the arachidonic and the linoleic acid pathway of human metabolism and plays an important role in the metabolism of these physiologically important signalling molecules. sEH hydrolyzes the CYP-P450 derived epoxymetabolites of the n-6 polyunsaturated fatty acids (epoxyeicosatrienoic acids, EETs; epoxy-octadecenoic acids, EpOMEs) into the corresponding vicinal diols (dihydroxyeicosatrienoic acids, DHETs; and dihydroxyoctadecenoic acids, DiHOMEs, respectively).

Whereas the biological function of EpOMES remains largely unknown, EETs biological function has been intensively studied over the last years. EET formation and action is deeply integrated into various physiological processes and exerts numerous, beneficial biological functions. EETs play a critical role in the regulation of vascular, renal and cardiovascular function (R. Kaspera et al., *Expert Opin. Drug. Metab. Toxicol.* 2009, 5, 757-771). Important new fields emerging may include a role of CYP-derived epoxyeicosanoids in insulin secretion, in the mediation of inflammatory or anti-inflammatory processes and in pain (S. Mustafa et al., *Exp. Clin. Cardiol.* 2009, 14, e41-50).

Numerous data from the literature support the beneficial effect of sEH inhibition (J. D. Imig and B. D. Hammock, *Nat. Rev. Drug Discov.* 2009, 8, 794-805). Inhibition of the sEH by specific inhibitors in various animal models of hypertension (SHR rats, AngII-induced hypertension, salt-sensitive hypertension) reduces blood pressure, provides renal protection and decreases plasma levels of pro-inflammatory cytokines. For instance, sEH inhibitors attenuate AngII- and transverse aortic constriction (TAC)-induced hypertrophy, cardiac fibrosis and cardiac NF-κB activation in mice. In addition, sEH inhibitors ameliorate AngII-induced atherosclerosis in ApoE KO mice. In a rat model of human disease, sEH has been shown to be a susceptibility factor for heart failure (J. Monti et al., *Nat. Genet.* 2008, 40, 529-537).

Furthermore, protection from kidney damage is observed in a hypertensive, diabetic Goto-Kakizaki rat model independent of blood pressure lowering (J. J. Olearczyk et al., *Clinical Science* 2009, 116, 61-70). Further on, it was shown that total adipose sEH activity is higher in obese vs. lean mice and is supposed to influence lipid metabolism, adipogenesis or local inflammation (B. M. De Taeye et al., *Obesity* 2010, 18, 489-498). Moreover, EETs might be involved in mediating stimulus-induced secretion of insulin from pancreatic islets. In diabetic mice, glucose tolerance is improved by sEH inhibition (P. Luo et al., *J. Pharm. Exp. Ther.* 2010, 334, 430-438). It can therefore be concluded, that inhibition of sEH by a specific small molecule inhibitor will stabilize CYP-P450 produced epoxides of polyunsaturated fatty acids resulting in protective effects in diabetes and diabetes-associated co-morbidities including inflammation, renal and cardiac function, and pain.

1,4:3,6-Dianhydromannitol-derivatives and their use as inhibitors of protein-tyrosin-phosphatases are disclosed in WO2007/121883. Isosorbide derivatives and their use as flavor modifiers, tastants and taste enhancers are disclosed in WO2009/111447 and WO2011/002871. Peptide mimetic compounds derived from isomannides as potential inhibitors of NS3 serine protease of hepatitis C virus are described in BR2009/002520 and BR2010/000099. Organic nitrates with an isomannide scaffold and their use for treating cardiovascular diseases are disclosed in WO1993/03037. N-substituted aminodeoxy-1,4;3,6-dianhydrohexitol derivatives and their application are described in EP44932.

sEH inhibitors and their potential therapeutic use are described in H. Shen et al, *J. Med. Chem.* 2012, 55, 1789-1808. The state-of-the-art for sEH inhibitors is reviewed in H. Shen, *Expert Opin. Ther. Patents* 2010, 20(7), 941-956.

A number of sEH inhibitors from other chemical classes have been identified: small molecule inhibitors are described exemplary in WO2007/043652 and WO2007/043653 (Taisho), WO2008/105968 (GSK), WO2009/011872 and WO2009/111207 (Merck), WO2007/067836, WO2007/106706, and WO2006/121719 (Boehringer), WO2007/106525, WO2008/016884, WO2004/089296, and WO2006/045119 (Arete).

Until now, no small molecule inhibitors of human sEH have reached market. Preclinical animal models have suggested that inhibiting sEH by a specific small molecule inhibitor will stabilize CYP-derived epoxyeicosanotrienoic acids resulting in protective effects in diabetes and diabetes-associated co-morbidities including inflammation, renal and cardiac function and pain.

The prior art describes potent in vitro inhibitors, but also highlights the difficulty in developing an sEH inhibitor as a human therapeutic. Many of the compounds described in the aforementioned disclosures lack selectivity, have low exposure in human plasma or are not metabolically stable and, therefore, do not reach sufficient levels over a satisfactory time period for a use as a drug. Also the physical properties of the described compounds are often not satisfactory, for example concerning solubility or chemical stability.

The present invention satisfies the above needs by providing compounds of formula I, which exhibit a highly potent and selective sEH inhibitory activity with good physical properties and a suitable pharmacokinetic profile.

Thus, the present invention relates to compounds of the formula I,

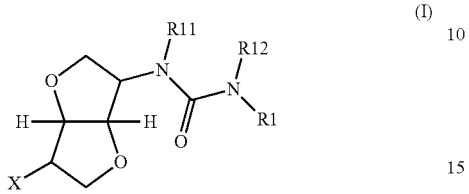

wherein
R1 is —($C_1$-$C_4$)-alkylene-($C_3$-$C_{12}$)-cycloalkyl, wherein cycloalkyl is a ring system containing 3 to 12 carbon atoms in mono-, bi- or tricycles or bridged rings, wherein cycloalkyl is mono-, di-, tri- or tetrasubstituted independently of one another by R2,
—($C_1$-$C_4$)-alkylene-aryl, wherein aryl is an aromatic hydrocarbon radical containing from 6 to 14 carbon atoms depending on the number of carbon atoms in one, two or three rings, and wherein said alkylene or aryl is independently from each other mono-, di- or trisubstituted independently of one another by R3,
—($C_1$-$C_4$)-alkylene-heterocyclyl, wherein heterocyclyl is a ring system containing 4 to 15 ring carbon atoms, wherein depending on the ring size one, two, three or four of the 4 to 15 ring carbon atoms are independently replaced by nitrogen, oxygen or sulfur atoms, and wherein said alkylene or heterocyclyl is independently from each other unsubstituted or mono-, di- or trisubstituted independently of one another by R4,
cyclopropyl-heterocyclyl, wherein heterocyclyl is defined above for heterocyclyl, and wherein said heterocyclyl is unsubstituted or mono-, di- or trisubstituted independently of one another by R4,
heterocyclyl, wherein heterocyclyl is defined above for heterocyclyl, and wherein said heterocyclyl is unsubstituted or mono-, di- or trisubstituted independently of one another by R4,
aryl, wherein aryl is defined above for aryl, and wherein aryl is mono-, di- or trisubstituted independently of one another by R3,
—($C_3$-$C_{12}$)-cycloalkyl, wherein cycloalkyl is defined above and is mono-, di-, tri- or tetrasubstituted independently of one another by R2, or
($C_1$-$C_4$)-alkyl, wherein alkyl is mono-, di- or trisubstituted independently of one another by R14,
X is —O-aryl, wherein aryl is an aromatic hydrocarbon radical containing from 6 to 14 carbon atoms depending on the number of carbon atoms in one, two or three rings, and wherein aryl is mono-, di- or trisubstituted independently of one another by R6,
—O-heterocyclyl, wherein heterocyclyl is a ring system containing 4 to 15 ring carbon atoms, wherein depending on the ring size one, two, three or four of the 4 to 15 ring carbon atoms are independently replaced by nitrogen, oxygen or sulfur atoms, and wherein said heterocyclyl is unsubstituted or mono-, di- or trisubstituted independently of one another by R7,
—($C_1$-$C_4$)-alkyl-R17, wherein said alkyl is unsubstituted or mono-, di- or trisubstituted independently of one another by R17,
—($C_1$-$C_4$)-alkyl-aryl, wherein aryl is defined above and wherein aryl is mono-, di- or trisubstituted independently of one another by R8,
—($C_1$-$C_4$)-alkyl-heterocyclyl, wherein heterocyclyl is defined above for —O-heterocyclyl, and wherein said heterocyclyl is unsubstituted or mono-, di- or trisubstituted independently of one another by R7,
—(CH=CH)-aryl, wherein aryl is defined above and wherein aryl is mono-, di- or trisubstituted independently of one another by R8,
—(CH=CH)-heterocyclyl, wherein heterocyclyl is defined above for —O-heterocyclyl, and wherein said heterocyclyl is unsubstituted or mono-, di- or trisubstituted independently of one another by R7,
—(C≡C)-aryl, wherein aryl is defined above and wherein aryl is mono-, di- or trisubstituted independently of one another by R8,
—(C≡C)-heterocyclyl, wherein heterocyclyl is defined above for —O-heterocyclyl, and wherein said heterocyclyl is unsubstituted or mono-, di- or trisubstituted independently of one another by R7,
—CN,
—OH,
—O—($C_1$-$C_3$)-fluoroalkyl,
—O—C(O)-heteroaryl, wherein heteroaryl is selected out of the group imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, wherein heteroaryl is mono-, di- or trisubstituted independently of one another by R7,
—N(R10)-heteroaryl, wherein heteroaryl is defined above, and wherein said heteroaryl is unsubstituted or mono-, di- or trisubstituted independently of one another by R7,
—S—($C_1$-$C_4$)-alkyl-R17, wherein said alkyl is unsubstituted or mono-, di- or trisubstituted independently of one another by R17,
—S—($C_3$-$C_8$)-cycloalkyl, wherein said cycloalkyl is unsubstituted or mono-, di- or trisubstituted independently of one another by R17,
—$SO_2$—($C_3$-$C_8$)-cycloalkyl, wherein said cycloalkyl is unsubstituted or mono-, di- or trisubstituted independently of one another by R17,
—O—$SO_2$-aryl, wherein aryl is defined above, and wherein aryl is mono-, di- or trisubstituted independently of one another by R8,
—S-aryl, wherein aryl is defined above, and wherein aryl is mono-, di- or trisubstituted independently of one another by R8,
—S-heterocyclyl, wherein heterocyclyl is defined above, and wherein said heterocyclyl is unsubstituted or mono-, di- or trisubstituted independently of one another by R7, or
—S—($C_1$-$C_4$)-alkyl, wherein said alkyl is unsubstituted or mono-, di- or trisubstituted independently of one another by R18,
R2, R3, R14, R17 and R18 are independent of one another are identical or different and are a hydrogen atom, —($C_1$-$C_4$)-alkyl, —OH, —($C_1$-$C_4$)-alkyl-OH, halogen, —($C_1$-$C_3$)-fluoroalkyl, —C(O)—OH, —C(O)—O—($C_1$-$C_4$)-alkyl, —O—($C_1$-$C_4$)-alkyl, —CN, —O—($C_1$-$C_3$)-fluoroalkyl, —N(R10)-R21, —NH—C(O)—($C_1$-$C_4$)-alkyl, —S—($C_1$-$C_4$)-alkyl, —S(O)$_2$—(C$_1$-C$_3$)-alkyl, —(C$_1$-C$_3$)-alkyl-O—(C$_1$-C$_3$)-alkyl, phenyl, or —O—(C$_1$-C$_4$)-alkyl-phenyl, R6 is aryl, wherein aryl is defined above, and wherein aryl is mono-, di- or trisubstituted independently of one another by R10,
- —O-aryl, wherein aryl is defined above, and wherein aryl is mono-, di- or trisubstituted independently of one another by R10,
- —(C$_1$-C$_4$)-alkylene-aryl, wherein aryl is defined above, and wherein aryl is mono-, di- or trisubstituted independently of one another by R10,
- heteroaryl, wherein heteroaryl is defined above, and wherein said heteroaryl is unsubstituted or mono-, di- or trisubstituted independently of one another by R10,
- —O-heteroaryl, wherein heteroaryl is defined above, and wherein said heteroaryl is unsubstituted or mono-, di- or trisubstituted independently of one another by R10,
- —C(O)-heteroaryl, wherein heteroaryl is defined above, and wherein said heteroaryl is unsubstituted or mono-, di- or trisubstituted independently of one another by R10,
- —(C$_1$-C$_4$)-alkylene-heteroaryl, wherein heteroaryl is defined above, and wherein said heteroaryl is unsubstituted or mono-, di- or trisubstituted independently of one another by R10,
- —O—(C$_1$-C$_4$)-alkylene-heteroaryl, wherein heteroaryl is defined above, and wherein said heteroaryl is unsubstituted or mono-, di- or trisubstituted independently of one another by R10,
- —(C$_3$-C$_8$)-cycloalkyl, wherein cycloalkyl is unsubstituted or mono-, di- or trisubstituted independently of one another by R10,
- hydrogen atom, —(C$_1$-C$_4$)-alkylene-N(R10)-R21, —C(O)—N(R10)-R20, —N(R10)-R21, —(C$_1$-C$_4$)-alkyl, —(C$_1$-C$_4$)-alkyl-CN, —(C$_1$-C$_3$)-fluoroalkyl, —O—(C$_1$-C$_4$)-alkyl, halogen, —C(O)—O—R10, —(C$_1$-C$_3$)-alkylene-C(O)—O—R10, —NH—C(O)—(C$_1$-C$_4$)-alkyl, —C(O)—(C$_1$-C$_4$)-alkyl, or —NO$_2$, R4 and R7 are independent of one another are identical or different and are a hydrogen atom, —(C$_1$-C$_4$)-alkyl, —O—(C$_1$-C$_4$)-alkyl, —(C$_1$-C$_5$)-alkyl-OH, halogen, —C(O)—O—R10, =O, phenyl, —(C$_1$-C$_3$)-alkylene-C(O)—O—R10, —C(O)—N(R10)-R20, —N(R10)-R21, —CN, —(C$_1$-C$_3$)-fluoroalkyl, —(C$_1$-C$_3$)-alkyl-O—(C$_1$-C$_3$)-alkyl, —C(O)—(C$_1$-C$_4$)-alkyl, —C(O)—(C$_1$-C$_3$)-fluoroalkyl, —C(O)—(C$_3$-C$_8$)-cycloalkyl, —C(O)-aryl, wherein aryl is defined above, and wherein aryl is mono-, di- or trisubstituted independently of one another by R6, aryl, wherein aryl is defined above, and wherein aryl is mono-, di- or trisubstituted independently of one another by R6,
methanesulfonyl, or heteroaryl, wherein heteroaryl is defined above, R8 and R9 are independent of one another are identical or different and are a hydrogen atom, halogen, —OH, —N(R10)-C(O)—R20, or —(C$_1$-C$_4$)-alkyl, R10 is hydrogen atom, —(C$_1$-C$_4$)-alkyl or —O—(C$_1$-C$_4$)-alkyl, R11 is hydrogen atom, —(C$_1$-C$_4$)-alkyl or benzyl, R12 is hydrogen atom or R1 and R12 together with the nitrogen atom to which they are bonded form a four- to eight-membered monocyclic heterocyclic ring which, as well as the nitrogen atom, may additionally, according to the ring size, also contain one or two identical or different heteroatoms from the group of oxygen, nitrogen and sulfur wherein four- to eight-membered monocyclic heterocyclic ring is mono-, di- or trisubstituted independently of one another by —(C$_1$-C$_4$)-alkyl or halogen, R20 is hydrogen atom, or —(C$_1$-C$_4$)-alkyl, R21 is hydrogen atom, —(C$_1$-C$_4$)-alkyl, —C(O)—R20, —(C$_1$-C$_4$)-alkyl-heteroaryl, wherein heteroaryl is defined above, heteroaryl, wherein heteroaryl is defined above, or —(C$_3$-C$_8$)-cycloalkyl, wherein cycloalkyl is unsubstituted or mono-, di- or trisubstituted independently of one another by R10, in all its stereoisomeric forms and mixtures thereof in any ratio, and its physiologically tolerable salts.

2) Thus, the present invention also relates to compounds of the formula I, wherein R1 is —(C$_1$-C$_4$)-alkylene-(C$_3$-C$_{12}$)-cycloalkyl, wherein cycloalkyl is mono-, di- or trisubstituted independently of one another by R2,
- —(C$_1$-C$_4$)-alkylene-aryl, wherein aryl is selected out of the group phenyl, tetrahydronaphthalenyl, naphthyl, biphenylyl, anthryl, indanyl, and fluorenyl, wherein said alkylene or aryl is independently from each other mono-, di- or trisubstituted independently of one another by R3,
- —(C$_1$-C$_4$)-alkylene-heterocyclyl, wherein heterocyclyl is selected out of the group acridinyl, azaindole (1H-pyrrolopyridinyl), azabenzimidazolyl, azaspirodecanyl, azepinyl, azetidinyl, benzimidazolyl, 2,3-dihydrobenzofuranyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydro-benzo[1,4]-dioxinyl, 4,5-dihydrooxazolinyl, dioxazolyl, dioxazinyl, 1,3-dioxanyl, 1,4-dioxanyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydro-furanyl, furanyl, furazanyl, imidazolidinyl, imidazolinyl, imidazolyl, imidazo[1,2a]pyridyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 7-oxa-bicyclo[2.2.1]heptanelyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2']bi-pyridinyl, tetrahydro-isoquinolinyl, tetrahydroquinolinyl, tetrahydrofuranyl, tetrahydropyranyl, tetrahydropyridinyl, tetrahydrothiophenyl, tetrahydrothiophenyl-1,1-dioxide, tetrahydrothiopyranyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein said alkylene or heterocyclyl is independently from each other unsubstituted or mono-, di- or trisubstituted independently of one another by R4, cyclopropyl-heterocyclyl, wherein heterocyclyl is defined above for heterocyclyl, and wherein said heterocyclyl is unsubstituted or mono-, di- or trisubstituted independently of one another by R4, heterocyclyl, wherein heterocyclyl is defined above for heterocyclyl, and wherein said heterocyclyl is unsubstituted or mono-, di- or trisubstituted independently of one another by R4, aryl, wherein aryl is selected out of the group phenyl, naphthyl, biphenylyl, tetrahydronaphthalenyl, anthryl, indanyl, and fluorenyl, wherein aryl is mono-, di- or trisubstituted independently of one another by R3, —$(C_3-C_{12})$-cycloalkyl, wherein cycloalkyl is mono-, di-, tri- or tetrasubstituted independently of one another by R2, or —$(C_1-C_4)$-alkyl, wherein alkyl is mono-, di- or trisubstituted independently of one another by R14, X is —O-aryl, wherein aryl is selected out of the group phenyl, naphthyl, indanyl, indanyl-1-one, biphenylyl, anthryl and fluorenyl, wherein aryl is mono-, di- or trisubstituted independently of one another by R6, —O-heterocyclyl, wherein heterocyclyl is selected out of the group acridinyl, azaindole (1H-pyrrolopyridinyl), azabenzimidazolyl, azaspirodecanyl, azepinyl, azetidinyl, benzimidazolyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydro-benzofuranyl, 2,3-dihydrobenzo[1,4]-dioxinyl, 4,5-dihydrooxazolinyl, dioxazolyl, dioxazinyl, 1,3-dioxanyl, 1,4-dioxanyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, imidazo[1,2a]pyridyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 7-oxa-bicyclo[2.2.1]heptanelyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2']bi-pyridinyl, tetra-hydrofuranyl, tetrahydro-isoquinolinyl, tetrahydro-quinolinyl, tetrahydropyranyl, tetrahydropyridinyl, tetrahydrothiophenyl, tetrahydrothiophenyl-1,1-dioxide, tetrahydrothiopyranyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R7, —$(C_1-C_4)$-alkyl-R17, wherein said alkyl is unsubstituted or mono-, di- or trisubstituted independently of one another by R17, —$(C_1-C_4)$-alkyl-aryl, wherein aryl is selected out of the group phenyl, naphthyl, indanyl, indanyl-1-one, biphenylyl, anthryl and fluorenyl, wherein aryl is mono-, di- or trisubstituted independently of one another by R8, —$(C_1-C_4)$-alkyl-heterocyclyl, wherein heterocyclyl is defined above for —O-heterocyclyl, and wherein said heterocyclyl is unsubstituted or mono-, di- or trisubstituted independently of one another by R7, —(CH=CH)-aryl, wherein aryl is selected out of the group phenyl, naphthyl, indanyl, indanyl-1-one, biphenylyl, anthryl and fluorenyl, wherein aryl is mono-, di- or trisubstituted independently of one another by R8, —(CH=CH)-heterocyclyl, wherein heterocyclyl is defined above for —O-heterocyclyl, and wherein said heterocyclyl is unsubstituted or mono-, di- or trisubstituted independently of one another by R7, —(C≡C)-aryl, wherein aryl is selected out of the group phenyl, naphthyl, indanyl, indanyl-1-one, biphenylyl, anthryl and fluorenyl, wherein aryl is mono-, di- or trisubstituted independently of one another by R8, —(C≡C)-heterocyclyl, wherein heterocyclyl is defined above for —O-heterocyclyl, and wherein said heterocyclyl is unsubstituted or mono-, di- or trisubstituted independently of one another by R7, —CN, —OH, —O—$(C_1-C_3)$-fluoroalkyl, —O—C(O)-heteroaryl, wherein heteroaryl is selected out of the group imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, wherein heteroaryl is mono-, di- or trisubstituted independently of one another by R7, —N(R10)-heteroaryl, wherein heteroaryl is defined above for heteroaryl, and wherein said heteroaryl is unsubstituted or mono-, di- or trisubstituted independently of one another by R7, —S—$(C_1-C_4)$-alkyl-R17, wherein said alkyl is unsubstituted or mono-, di- or trisubstituted independently of one another by R17, —S—$(C_3-C_8)$-cycloalkyl, wherein said cycloalkyl is unsubstituted or mono-, di- or trisubstituted independently of one another by R17, —$SO_2$—$(C_3-C_8)$-cycloalkyl, wherein said cycloalkyl is unsubstituted or mono-, di- or trisubstituted independently of one another by R17, —O—$SO_2$-aryl, wherein aryl is selected out of the group phenyl, naphthyl, indanyl, indanyl-1-one, biphenylyl, anthryl and fluorenyl, wherein aryl is mono-, di- or trisubstituted independently of one another by R8, —S-aryl, wherein aryl is selected out of the group phenyl, naphthyl, indanyl, indanyl-1-one, biphenylyl, anthryl and fluorenyl, wherein aryl is mono-, di- or trisubstituted independently of one another by R8,
—S-heterocyclyl, wherein heterocyclyl is defined above for —O-heterocyclyl, and wherein said heterocyclyl is unsubstituted or mono-, di- or trisubstituted independently of one another by R7, or
—S—$(C_1-C_4)$-alkyl, wherein said alkyl is unsubstituted or mono-, di- or trisubstituted independently of one another by R18, R2, R3, R14, R17 and R18 are independent of one another are identical or different and are a hydrogen atom, —$(C_1-C_4)$-alkyl, —OH, —$(C_1-C_4)$-alkyl-OH, halogen, —$(C_1-C_3)$-fluoroalkyl, —C(O)—OH, —C(O)—O—$(C_1-C_4)$-alkyl, —O—$(C_1-C_4)$-alkyl, —CN, —O—$(C_1-C_3)$-fluoroalkyl, —N(R10)-R21, —NH—C(O)—$(C_1-C_4)$-alkyl, —S—$(C_1-C_4)$-alkyl, —S(O)$_2$—$(C_1-C_3)$-alkyl, —$(C_1-C_3)$-alkyl-O—$(C_1-C_3)$-alkyl, phenyl, or —O—$(C_1-C_4)$-alkyl-phenyl, R6 is aryl, wherein aryl is selected out of the group phenyl, naphthyl, indanyl, indanyl-1-one, biphenylyl, anthryl and fluorenyl, wherein aryl is mono-, di- or trisubstituted independently of one another by R10,
—O-aryl, wherein aryl is selected out of the group phenyl, naphthyl, indanyl, indanyl-1-one, biphenylyl, anthryl and fluorenyl, wherein aryl is mono-, di- or trisubstituted independently of one another by R10,
—$(C_1-C_4)$-alkylene-aryl, wherein aryl is selected out of the group phenyl, naphthyl, indanyl, indanyl-1-one, biphenylyl, anthryl and fluorenyl, wherein aryl is mono-, di- or trisubstituted independently of one another by R10,
heteroaryl, wherein heteroaryl is defined above for heteroaryl, and wherein said heteroaryl is unsubstituted or mono-, di- or trisubstituted independently of one another by R10,
—O-heteroaryl, wherein heteroaryl is defined above for heteroaryl, and wherein said heteroaryl is unsubstituted or mono-, di- or trisubstituted independently of one another by R10,
—C(O)-heteroaryl, wherein heteroaryl is defined above for heteroaryl, and wherein said heteroaryl is unsubstituted or mono-, di- or trisubstituted independently of one another by R10,
—$(C_1-C_4)$-alkylene-heteroaryl, wherein heteroaryl is defined above for heteroaryl, and wherein said heteroaryl is unsubstituted or mono-, di- or trisubstituted independently of one another by R10,
—O—$(C_1-C_4)$-alkylene-heteroaryl, wherein heteroaryl is defined above for heteroaryl, and wherein said heteroaryl is unsubstituted or mono-, di- or trisubstituted independently of one another by R10,
—$(C_3-C_8)$-cycloalkyl, wherein cycloalkyl is unsubstituted or mono-, di- or trisubstituted independently of one another by R10,
hydrogen atom, —$(C_1-C_4)$-alkylene-N(R10)-R21, —C(O)—N(R10)-R20, —N(R10)-R21, —$(C_1-C_4)$-alkyl, —$(C_1-C_4)$-alkyl-CN, —$(C_1-C_3)$-fluoroalkyl, —O—$(C_1-C_4)$-alkyl, halogen, —C(O)—O—R10, —$(C_1-C_3)$-alkylene-C(O)—O—R10, —NH—C(O)—$(C_1-C_4)$-alkyl, —C(O)—$(C_1-C_4)$-alkyl, or —NO$_2$, R4 and R7 are independent of one another are identical or different and are a hydrogen atom, —$(C_1-C_4)$-alkyl, —O—$(C_1-C_4)$-alkyl, —$(C_1-C_5)$-alkyl-OH, halogen, —C(O)—O—R10, =O, phenyl, —$(C_1-C_3)$-alkylene-C(O)—O—R10, —C(O)—N(R10)-R20, —N(R10)-R21, —CN, —$(C_1-C_3)$-fluoroalkyl, —$(C_1-C_3)$-alkyl-O—$(C_1-C_3)$-alkyl, —C(O)—$(C_1-C_4)$-alkyl, —C(O)—$(C_1-C_3)$-fluoroalkyl, —C(O)—$(C_3-C_8)$-cycloalkyl, —C(O)-aryl, wherein aryl is selected out of the group phenyl, naphthyl, indanyl, indanyl-1-one, biphenylyl, anthryl and fluorenyl, wherein aryl is mono-, di- or trisubstituted independently of one another by R6,
aryl, wherein aryl is selected out of the group phenyl, naphthyl, indanyl, indanyl-1-one, biphenylyl, anthryl and fluorenyl, wherein aryl is mono-, di- or trisubstituted independently of one another by R6,
methanesulfonyl, or heteroaryl, wherein heteroaryl is defined above, R8 and R9 are independent of one another are identical or different and are a hydrogen atom, halogen, —OH, —N(R10)-C(O)—R20, or —$(C_1-C_4)$-alkyl, R10 is hydrogen atom, —$(C_1-C_4)$-alkyl or —O—$(C_1-C_4)$-alkyl, R11 is hydrogen atom, —$(C_1-C_4)$-alkyl or benzyl, R12 is hydrogen atom or R1 and R12 together with the nitrogen atom to which they are bonded form a four- to eight-membered monocyclic heterocyclic ring which, as well as the nitrogen atom, may additionally, according to the ring size, also contain one or two identical or different heteroatoms from the group of oxygen, nitrogen and sulfur wherein four- to eight-membered monocyclic heterocyclic ring is mono-, di- or trisubstituted independently of one another by —$(C_1-C_4)$-alkyl or halogen, R20 is hydrogen atom, or —$(C_1-C_4)$-alkyl, R21 is hydrogen atom, —$(C_1-C_4)$-alkyl, —C(O)—R20, —$(C_1-C_4)$-alkyl-heteroaryl, wherein heteroaryl is defined above, heteroaryl, wherein heteroaryl is defined above, or —$(C_3-C_8)$-cycloalkyl, wherein cycloalkyl is unsubstituted or mono-, di- or trisubstituted independently of one another by R10, in all its stereoisomeric forms and mixtures thereof in any ratio, and its physiologically tolerable salts.

3) Thus, the present invention also relates to compounds of the formula I, wherein R1 is —$(C_1-C_4)$-alkylene-$(C_3-C_{12})$-cycloalkyl, wherein cycloalkyl is mono-, di- or trisubstituted independently of one another by R2,
—$(C_1-C_4)$-alkylene-aryl, wherein aryl is selected out of the group phenyl, tetrahydronaphthalenyl, naphthyl, biphenylyl, anthryl, indanyl, and fluorenyl, wherein said alkylene or aryl is independently from each other mono-, di- or trisubstituted independently of one another by R3,
—$(C_1-C_4)$-alkylene-heterocyclyl, wherein heterocyclyl is selected out of the group acridinyl, azaindole (1H-pyrrolopyridinyl), azabenzimidazolyl, azaspirodecanyl, azepinyl, azetidinyl, benzimidazolyl, 2,3-dihydrobenzofuranyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydro-benzo[1,4]-dioxinyl, 4,5-dihydrooxazolinyl, dioxazolyl, dioxazinyl, 1,3-dioxanyl, 1,4-dioxanyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydro-furanyl, furanyl, furazanyl, imidazolidinyl, imidazolinyl, imidazolyl, imidazo[1,2a]-pyridyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 7-oxa-bicyclo[2.2.1]heptanelyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2']bi-pyridinyl, tetrahydro-isoquinolinyl, tetrahydroquinolinyl, tetrahydrofuranyl, tetrahydropyranyl, tetrahydropyridinyl, tetrahydrothiophenyl, tetrahydrothiophenyl-1,1-dioxide, tetrahydrothiopyranyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein said alkylene or heterocyclyl is independently from each other unsubstituted or mono-, di- or trisubstituted independently of one another by R4, cyclopropyl-heterocyclyl, wherein heterocyclyl is defined above for heterocyclyl, and wherein said heterocyclyl is unsubstituted or mono-, di- or trisubstituted independently of one another by R4, heterocyclyl, wherein heterocyclyl is defined above for heterocyclyl, and wherein said heterocyclyl is unsubstituted or mono-, di- or trisubstituted independently of one another by R4, aryl, wherein aryl is selected out of the group phenyl, naphthyl, biphenylyl, tetrahydronaphthalenyl, anthryl, indanyl, and fluorenyl, wherein aryl is mono-, di- or trisubstituted independently of one another by R3, —(C$_3$-C$_{12}$)-cycloalkyl, wherein cycloalkyl is mono-, di-, tri- or tetrasubstituted independently of one another by R2, or —(C$_1$-C$_4$)-alkyl, wherein alkyl is mono-, di- or trisubstituted independently of one another by R14, X is —O-aryl, wherein aryl is selected out of the group phenyl, naphthyl, indanyl, indanyl-1-one, biphenylyl, anthryl and fluorenyl, wherein aryl is mono-, di- or trisubstituted independently of one another by R6, —O-heterocyclyl, wherein heterocyclyl is selected out of the group acridinyl, azaindole (1H-pyrrolopyridinyl), azabenzimidazolyl, azaspirodecanyl, azepinyl, azetidinyl, benzimidazolyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydro-benzofuranyl, 2,3-dihydrobenzo[1,4]-dioxinyl, 4,5-dihydrooxazolinyl, dioxazolyl, dioxazinyl, 1,3-dioxanyl, 1,4-dioxanyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, imidazo[1,2a]pyridyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 7-oxa-bicyclo[2.2.1]heptanelyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2']bi-pyridinyl, tetra-hydrofuranyl, tetrahydro-isoquinolinyl, tetrahydro-quinolinyl, tetrahydropyranyl, tetrahydropyridinyl, tetrahydrothiophenyl, tetrahydrothiophenyl-1,1-dioxide, tetrahydrothiopyranyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R7,

—OH,

—O—(C$_1$-C$_3$)-fluoroalkyl,

—O—C(O)-heteroaryl, wherein heteroaryl is selected out of the group imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, wherein heteroaryl is mono-, di- or trisubstituted independently of one another by R7, or —O—SO$_2$-aryl, wherein aryl is selected out of the group phenyl, naphthyl, indanyl, indanyl-1-one, biphenylyl, anthryl and fluorenyl, wherein aryl is mono-, di- or trisubstituted independently of one another by R8, R2, R3, R14, R17 and R18 are independent of one another are identical or different and are a hydrogen atom, —(C$_1$-C$_4$)-alkyl, —OH, —(C$_1$-C$_4$)-alkyl-OH, halogen, —(C$_1$-C$_3$)-fluoroalkyl, —C(O)—OH, —C(O)—O—(C$_1$-C$_4$)-alkyl, —O—(C$_1$-C$_4$)-alkyl, —CN, —O—(C$_1$-C$_3$)-fluoroalkyl, —N(R10)-R21, —NH—C(O)—(C$_1$-C$_4$)-alkyl, —S—(C$_1$-C$_4$)-alkyl, —S(O)$_2$—(C$_1$-C$_3$)-alkyl, —(C$_1$-C$_3$)-alkyl-O—(C$_1$-C$_3$)-alkyl, phenyl, or —O—(C$_1$-C$_4$)-alkyl-phenyl, R6 is aryl, wherein aryl is selected out of the group phenyl, naphthyl, indanyl, indanyl-1-one, biphenylyl, anthryl and fluorenyl, wherein aryl is mono-, di- or trisubstituted independently of one another by R10, —O-aryl, wherein aryl is selected out of the group phenyl, naphthyl, indanyl, indanyl-1-one, biphenylyl, anthryl and fluorenyl, wherein aryl is mono-, di- or trisubstituted independently of one another by R10, —($C_1$-$C_4$)-alkylene-aryl, wherein aryl is selected out of the group phenyl, naphthyl, indanyl, indanyl-1-one, biphenylyl, anthryl and fluorenyl, wherein aryl is mono-, di- or trisubstituted independently of one another by R10, heteroaryl, wherein heteroaryl is defined above for heteroaryl, and wherein said heteroaryl is unsubstituted or mono-, di- or trisubstituted independently of one another by R10, —O-heteroaryl, wherein heteroaryl is defined above for heteroaryl, and wherein said heteroaryl is unsubstituted or mono-, di- or trisubstituted independently of one another by R10, —C(O)-heteroaryl, wherein heteroaryl is defined above for heteroaryl, and wherein said heteroaryl is unsubstituted or mono-, di- or trisubstituted independently of one another by R10, —($C_1$-$C_4$)-alkylene-heteroaryl, wherein heteroaryl is defined above for heteroaryl, and wherein said heteroaryl is unsubstituted or mono-, di- or trisubstituted independently of one another by R10, —O—($C_1$-$C_4$)-alkylene-heteroaryl, wherein heteroaryl is defined above for heteroaryl, and wherein said heteroaryl is unsubstituted or mono-, di- or trisubstituted independently of one another by R10, —($C_3$-$C_8$)-cycloalkyl, wherein cycloalkyl is unsubstituted or mono-, di- or trisubstituted independently of one another by R10, hydrogen atom, —($C_1$-$C_4$)-alkylene-N(R10)-R21, —C(O)—N(R10)-R20, —N(R10)-R21, —($C_1$-$C_4$)-alkyl, —($C_1$-$C_4$)-alkyl-CN, —($C_1$-$C_3$)-fluoroalkyl, —O—($C_1$-$C_4$)-alkyl, halogen, —C(O)—O—R10, —($C_1$-$C_3$)-alkylene-C(O)—O—R10, —NH—C(O)—($C_1$-$C_4$)-alkyl, —C(O)—($C_1$-$C_4$)-alkyl, or —NO$_2$, R4 and R7 are independent of one another are identical or different and are a hydrogen atom, —($C_1$-$C_4$)-alkyl, —O—($C_1$-$C_4$)-alkyl, —($C_1$-$C_5$)-alkyl-OH, halogen, —C(O)—O—R10, =O, phenyl, —($C_1$-$C_3$)-alkylene-C(O)—O—R10, —C(O)—N(R10)-R20, —N(R10)-R21, —CN, —($C_1$-$C_3$)-fluoroalkyl, —($C_1$-$C_3$)-alkyl-O—($C_1$-$C_3$)-alkyl, —C(O)—($C_1$-$C_4$)-alkyl, —C(O)—($C_1$-$C_3$)-fluoroalkyl, —C(O)—($C_3$-$C_8$)-cycloalkyl, —C(O)-aryl, wherein aryl is selected out of the group phenyl, naphthyl, indanyl, indanyl-1-one, biphenylyl, anthryl and fluorenyl, wherein aryl is mono-, di- or trisubstituted independently of one another by R6, aryl, wherein aryl is selected out of the group phenyl, naphthyl, indanyl, indanyl-1-one, biphenylyl, anthryl and fluorenyl, wherein aryl is mono-, di- or trisubstituted independently of one another by R6, methanesulfonyl, or heteroaryl, wherein heteroaryl is defined above, R8 and R9 are independent of one another are identical or different and are a hydrogen atom, halogen, —OH, —N(R10)-C(O)—R20, or —($C_1$-$C_4$)-alkyl, R10 is hydrogen atom, —($C_1$-$C_4$)-alkyl or —O—($C_1$-$C_4$)-alkyl, R11 is hydrogen atom, —($C_1$-$C_4$)-alkyl or benzyl, R12 is hydrogen atom or R1 and R12 together with the nitrogen atom to which they are bonded form a four- to eight-membered monocyclic heterocyclic ring which, as well as the nitrogen atom, may additionally, according to the ring size, also contain one or two identical or different heteroatoms from the group of oxygen, nitrogen and sulfur wherein four- to eight-membered monocyclic heterocyclic ring is mono-, di- or trisubstituted independently of one another by —($C_1$-$C_4$)-alkyl or halogen, R20 is hydrogen atom, or —($C_1$-$C_4$)-alkyl, R21 is hydrogen atom, —($C_1$-$C_4$)-alkyl, —C(O)—R20, —($C_1$-$C_4$)-alkyl-heteroaryl, wherein heteroaryl is defined above, heteroaryl, wherein heteroaryl is defined above, or —($C_3$-$C_8$)-cycloalkyl, wherein cycloalkyl is unsubstituted or mono-, di- or trisubstituted independently of one another by R10, in all its stereoisomeric forms and mixtures thereof in any ratio, and its physiologically tolerable salts.

4) Thus, the present invention also relates to compounds of the formula I, wherein R1 is —($C_1$-$C_4$)-alkylene-($C_3$-$C_{12}$)-cycloalkyl, wherein cycloalkyl is mono-, di- or trisubstituted independently of one another by R2, —($C_1$-$C_4$)-alkylene-aryl, wherein aryl is selected out of the group phenyl, tetrahydronaphthalenyl, naphthyl, biphenylyl, anthryl, indanyl, and fluorenyl, wherein said alkylene or aryl is independently from each other mono-, di- or trisubstituted independently of one another by R3, —($C_1$-$C_4$)-alkylene-heterocyclyl, wherein heterocyclyl is selected out of the group acridinyl, azaindole (1H-pyrrolopyridinyl), azabenzimidazolyl, azaspirodecanyl, azepinyl, azetidinyl, benzimidazolyl, 2,3-dihydro-benzofuranyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydro-benzo[1,4]-dioxinyl, 4,5-dihydrooxazolinyl, dioxazolyl, dioxazinyl, 1,3-dioxanyl, 1,4-dioxanyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydro-furanyl, furanyl, furazanyl, imidazolidinyl, imidazolinyl, imidazolyl, imidazo[1,2a]pyridyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 7-oxa-bicyclo[2.2.1]heptanelyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2']bi-pyridinyl, tetrahydro-isoquinolinyl, tetrahydroquinolinyl, tetrahydrofuranyl, tetrahydropyranyl, tetrahydropyridinyl, tetrahydrothiophenyl, tetrahydrothiophenyl-1,1-dioxide, tetrahydrothiopyranyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein said alkylene or heterocyclyl is independently from each other unsubstituted or mono-, di- or trisubstituted independently of one another by R4, cyclopropyl-heterocyclyl, wherein heterocyclyl is defined above for heterocyclyl, and wherein said heterocyclyl is unsubstituted or mono-, di- or trisubstituted independently of one another by R4, heterocyclyl, wherein heterocyclyl is defined above for heterocyclyl, and wherein said heterocyclyl is unsubstituted or mono-, di- or trisubstituted independently of one another by R4, aryl, wherein aryl is selected out of the group phenyl, naphthyl, biphenylyl, tetrahydronaphthalenyl, anthryl, indanyl, and fluorenyl, wherein aryl is mono-, di- or trisubstituted independently of one another by R3, —($C_3$-$C_{12}$)-cycloalkyl, wherein cycloalkyl is mono-, di-, tri- or tetrasubstituted independently of one another by R2, or —($C_1$-$C_4$)-alkyl, wherein alkyl is mono-, di- or trisubstituted independently of one another by R14, X is —($C_1$-$C_4$)-alkyl-R17, wherein said alkyl is unsubstituted or mono-, di- or trisubstituted independently of one another by R17, —($C_1$-$C_4$)-alkyl-aryl, wherein aryl is selected out of the group phenyl, naphthyl, indanyl, indanyl-1-one, biphenylyl, anthryl and fluorenyl, wherein aryl is mono-, di- or trisubstituted independently of one another by R8, —($C_1$-$C_4$)-alkyl-heterocyclyl, wherein heterocyclyl is defined above for —O-heterocyclyl, and wherein said heterocyclyl is unsubstituted or mono-, di- or trisubstituted independently of one another by R7, —(CH=CH)-aryl, wherein aryl is selected out of the group phenyl, naphthyl, indanyl, indanyl-1-one, biphenylyl, anthryl and fluorenyl, wherein aryl is mono-, di- or trisubstituted independently of one another by R8, —(CH=CH)-heterocyclyl, wherein heterocyclyl is defined above for —O-heterocyclyl, and wherein said heterocyclyl is unsubstituted or mono-, di- or trisubstituted independently of one another by R7, —(C≡C)-aryl, wherein aryl is selected out of the group phenyl, naphthyl, indanyl, indanyl-1-one, biphenylyl, anthryl and fluorenyl, wherein aryl is mono-, di- or trisubstituted independently of one another by R8, —(C≡C)-heterocyclyl, wherein heterocyclyl is defined above for —O-heterocyclyl, and wherein said heterocyclyl is unsubstituted or mono-, di- or trisubstituted independently of one another by R7, or

—CN,

R2, R3, R14, R17 and R18 are independent of one another are identical or different and are a hydrogen atom, —($C_1$-$C_4$)-alkyl, —OH, —($C_1$-$C_4$)-alkyl-OH, halogen, —($C_1$-$C_3$)-fluoroalkyl, —C(O)—OH, —C(O)—O—($C_1$-$C_4$)-alkyl, —O—($C_1$-$C_4$)-alkyl, —CN, —O—($C_1$-$C_3$)-fluoroalkyl, —N(R10)-R21, —NH—C(O)—($C_1$-$C_4$)-alkyl, —S—($C_1$-$C_4$)-alkyl, —S(O)$_2$—($C_1$-$C_3$)-alkyl, —($C_1$-$C_3$)-alkyl-O—($C_1$-$C_3$)-alkyl, phenyl, or —O—($C_1$-$C_4$)-alkyl-phenyl, R6 is aryl, wherein aryl is selected out of the group phenyl, naphthyl, indanyl, indanyl-1-one, biphenylyl, anthryl and fluorenyl, wherein aryl is mono-, di- or trisubstituted independently of one another by R10, —O-aryl, wherein aryl is selected out of the group phenyl, naphthyl, indanyl, indanyl-1-one, biphenylyl, anthryl and fluorenyl, wherein aryl is mono-, di- or trisubstituted independently of one another by R10, —($C_1$-$C_4$)-alkylene-aryl, wherein aryl is selected out of the group phenyl, naphthyl, indanyl, indanyl-1-one, biphenylyl, anthryl and fluorenyl, wherein aryl is mono-, di- or trisubstituted independently of one another by R10, heteroaryl, wherein heteroaryl is defined above for heteroaryl, and wherein said heteroaryl is unsubstituted or mono-, di- or trisubstituted independently of one another by R10, —O-heteroaryl, wherein heteroaryl is defined above for heteroaryl, and wherein said heteroaryl is unsubstituted or mono-, di- or trisubstituted independently of one another by R10, —C(O)-heteroaryl, wherein heteroaryl is defined above for heteroaryl, and wherein said heteroaryl is unsubstituted or mono-, di- or trisubstituted independently of one another by R10, —($C_1$-$C_4$)-alkylene-heteroaryl, wherein heteroaryl is defined above for heteroaryl, and wherein said heteroaryl is unsubstituted or mono-, di- or trisubstituted independently of one another by R10, —O—($C_1$-$C_4$)-alkylene-heteroaryl, wherein heteroaryl is defined above for heteroaryl, and wherein said heteroaryl is unsubstituted or mono-, di- or trisubstituted independently of one another by R10, —($C_3$-$C_8$)-cycloalkyl, wherein cycloalkyl is unsubstituted or mono-, di- or trisubstituted independently of one another by R10, hydrogen atom, —($C_1$-$C_4$)-alkylene-N(R10)-R21, —C(O)—N(R10)-R20, —N(R10)-R21, —($C_1$-$C_4$)-alkyl, —($C_1$-$C_4$)-alkyl-CN, —($C_1$-$C_3$)-fluoroalkyl, —O—($C_1$-$C_4$)-alkyl, halogen, —C(O)—O—R10, —($C_1$-$C_3$)-alkylene-C(O)—O—R10, —NH—C(O)—($C_1$-$C_4$)-alkyl, —C(O)—($C_1$-$C_4$)-alkyl, or —NO$_2$, R4 and R7 are independent of one another are identical or different and are a hydrogen atom, —($C_1$-$C_4$)-alkyl, —O—($C_1$-$C_4$)-alkyl, —($C_1$-$C_5$)-alkyl-OH, halogen, —C(O)—O—R10, =O, phenyl, —($C_1$-$C_3$)-alkylene-C(O)—O—R10, —C(O)—N(R10)-R20, —N(R10)-R21, —CN, —($C_1$-$C_3$)-fluoroalkyl, —($C_1$-$C_3$)-alkyl-O—($C_1$-$C_3$)-alkyl, —C(O)—($C_1$-$C_4$)-alkyl, —C(O)—($C_1$-$C_3$)-fluoroalkyl, —C(O)—($C_3$-$C_8$)-cycloalkyl, —C(O)-aryl, wherein aryl is selected out of the group phenyl, naphthyl, indanyl, indanyl-1-one, biphenylyl, anthryl and fluorenyl, wherein aryl is mono-, di- or trisubstituted independently of one another by R6, aryl, wherein aryl is selected out of the group phenyl, naphthyl, indanyl, indanyl-1-one, biphenylyl, anthryl and fluorenyl, wherein aryl is mono-, di- or trisubstituted independently of one another by R6, methanesulfonyl, or heteroaryl, wherein heteroaryl is defined above, R8 and R9 are independent of one another are identical or different and are a hydrogen atom, halogen, —OH, —N(R10)-C(O)—R20, or —($C_1$-$C_4$)-alkyl, R10 is hydrogen atom, —($C_1$-$C_4$)-alkyl or —O—($C_1$-$C_4$)-alkyl, R11 is hydrogen atom, —($C_1$-$C_4$)-alkyl or benzyl, R12 is hydrogen atom or R1 and R12 together with the nitrogen atom to which they are bonded form a four- to eight-membered monocyclic heterocyclic ring which, as well as the nitrogen atom, may additionally, according to the ring size, also contain one or two identical or different heteroatoms from the group of oxygen, nitrogen and sulfur wherein four- to eight-membered monocyclic heterocyclic ring is mono-, di- or trisubstituted independently of one another by —($C_1$-$C_4$)-alkyl or halogen, R20 is hydrogen atom, or —($C_1$-$C_4$)-alkyl, R21 is hydrogen atom, —($C_1$-$C_4$)-alkyl, —C(O)—R20, —($C_1$-$C_4$)-alkyl-heteroaryl, wherein heteroaryl is defined above, heteroaryl, wherein heteroaryl is defined above, or —($C_3$-$C_8$)-cycloalkyl, wherein cycloalkyl is unsubstituted or mono-, di- or trisubstituted independently of one another by R10, in all its stereoisomeric forms and mixtures thereof in any ratio, and its physiologically tolerable salts.

5) Thus, the present invention also relates to compounds of the formula I, wherein R1 is —($C_1$-$C_4$)-alkylene-($C_3$-$C_{12}$)-cycloalkyl, wherein cycloalkyl is mono-, di- or trisubstituted independently of one another by R2, —($C_1$-$C_4$)-alkylene-aryl, wherein aryl is selected out of the group phenyl, tetrahydronaphthalenyl, naphthyl, biphenylyl, anthryl, indanyl, and fluorenyl, wherein said alkylene or aryl is independently from each other mono-, di- or trisubstituted independently of one another by R3, —($C_1$-$C_4$)-alkylene-heterocyclyl, wherein heterocyclyl is selected out of the group acridinyl, azaindole (1H-pyrrolopyridinyl), azabenzimidazolyl, azaspirodecanyl, azepinyl, azetidinyl, benzimidazolyl, 2,3-dihydrobenzofuranyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydro-benzo[1,4]-dioxinyl, 4,5-dihydrooxazolinyl, dioxazolyl, dioxazinyl, 1,3-dioxanyl, 1,4-dioxanyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydro-furanyl, furanyl, furazanyl, imidazolidinyl, imidazolinyl, imidazolyl, imidazo[1,2a]-pyridyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolidinyl, isoxazolinyl, 2-isoxazolinyl, ketopiperazinyl, morpholinyl, naphthyridinyl, octahydroisoquinolinyl, 7-oxa-bicyclo[2.2.1]heptanelyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2']bi-pyridinyl, tetrahydro-isoquinolinyl, tetrahydroquinolinyl, tetrahydrofuranyl, tetrahydropyranyl, tetrahydropyridinyl, tetrahydrothiophenyl, tetrahydrothiophenyl-1,1-dioxide, tetrahydrothiopyranyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein said alkylene or heterocyclyl is independently from each other unsubstituted or mono-, di- or trisubstituted independently of one another by R4, cyclopropyl-heterocyclyl, wherein heterocyclyl is defined above for heterocyclyl, and wherein said heterocyclyl is unsubstituted or mono-, di- or trisubstituted independently of one another by R4, heterocyclyl, wherein heterocyclyl is defined above for heterocyclyl, and wherein said heterocyclyl is unsubstituted or mono-, di- or trisubstituted independently of one another by R4, aryl, wherein aryl is selected out of the group phenyl, naphthyl, biphenylyl, tetrahydronaphthalenyl, anthryl, indanyl, and fluorenyl, wherein aryl is mono-, di- or trisubstituted independently of one another by R3, —($C_3$-$C_{12}$)-cycloalkyl, wherein cycloalkyl is mono-, di-, tri- or tetrasubstituted independently of one another by R2, or —($C_1$-$C_4$)-alkyl, wherein alkyl is mono-, di- or trisubstituted independently of one another by R14, X is —S—($C_1$-$C_4$)-alkyl-R17, wherein said alkyl is unsubstituted or mono-, di- or trisubstituted independently of one another by R17, —S—($C_3$-$C_8$)-cycloalkyl, wherein said cycloalkyl is unsubstituted or mono-, di- or trisubstituted independently of one another by R17, —$SO_2$—($C_3$-$C_8$)-cycloalkyl, wherein said cycloalkyl is unsubstituted or mono-, di- or trisubstituted independently of one another by R17, —S-aryl, wherein aryl is selected out of the group phenyl, naphthyl, indanyl, indanyl-1-one, biphenylyl, anthryl and fluorenyl, wherein aryl is mono-, di- or trisubstituted independently of one another by R8, —S-heterocyclyl, wherein heterocyclyl is defined above for —O-heterocyclyl, and wherein said heterocyclyl is unsubstituted or mono-, di- or trisubstituted independently of one another by R7, or —S—($C_1$-$C_4$)-alkyl, wherein said alkyl is unsubstituted or mono-, di- or trisubstituted independently of one another by R18, R2, R3, R14, R17 and R18 are independent of one another are identical or different and are a hydrogen atom, —($C_1$-$C_4$)-alkyl, —OH, —($C_1$-$C_4$)-alkyl-OH, halogen, —($C_1$-$C_3$)-fluoroalkyl, —C(O)—OH, —C(O)—O—($C_1$-$C_4$)-alkyl, —O—($C_1$-$C_4$)-alkyl, —CN, —O—($C_1$-$C_3$)-fluoroalkyl, —N(R10)-R21, —NH—C(O)—($C_1$-$C_4$)-alkyl, —S—($C_1$-$C_4$)-alkyl, —S(O)$_2$—($C_1$-$C_3$)-alkyl, —($C_1$-$C_3$)-alkyl-O—($C_1$-$C_3$)-alkyl, phenyl, or —O—($C_1$-$C_4$)-alkyl-phenyl, R6 is aryl, wherein aryl is selected out of the group phenyl, naphthyl, indanyl, indanyl-1-one, biphenylyl, anthryl and fluorenyl, wherein aryl is mono-, di- or trisubstituted independently of one another by R10, —O-aryl, wherein aryl is selected out of the group phenyl, naphthyl, indanyl, indanyl-1-one, biphenylyl, anthryl and fluorenyl, wherein aryl is mono-, di- or trisubstituted independently of one another by R10, —($C_1$-$C_4$)-alkylene-aryl, wherein aryl is selected out of the group phenyl, naphthyl, indanyl, indanyl-1-one, biphenylyl, anthryl and fluorenyl, wherein aryl is mono-, di- or trisubstituted independently of one another by R10, heteroaryl, wherein heteroaryl is defined above for heteroaryl, and wherein said heteroaryl is unsubstituted or mono-, di- or trisubstituted independently of one another by R10, —O-heteroaryl, wherein heteroaryl is defined above for heteroaryl, and wherein said heteroaryl is unsubstituted or mono-, di- or trisubstituted independently of one another by R10, —C(O)-heteroaryl, wherein heteroaryl is defined above for heteroaryl, and wherein said heteroaryl is unsubstituted or mono-, di- or trisubstituted independently of one another by R10, —($C_1$-$C_4$)-alkylene-heteroaryl, wherein heteroaryl is defined above for heteroaryl, and wherein said heteroaryl is unsubstituted or mono-, di- or trisubstituted independently of one another by R10, —O—($C_1$-$C_4$)-alkylene-heteroaryl, wherein heteroaryl is defined above for heteroaryl, and wherein said heteroaryl is unsubstituted or mono-, di- or trisubstituted independently of one another by R10, —($C_3$-$C_8$)-cycloalkyl, wherein cycloalkyl is unsubstituted or mono-, di- or trisubstituted independently of one another by R10, hydrogen atom, —($C_1$-$C_4$)-alkylene-N(R10)-R21, —C(O)—N(R10)-R20, —N(R10)-R21, —($C_1$-$C_4$)-alkyl, —($C_1$-$C_4$)-alkyl-CN, —($C_1$-$C_3$)-fluoroalkyl, —O—($C_1$-$C_4$)-alkyl, halogen, —C(O)—O—R10, —($C_1$-$C_3$)-alkylene-C(O)—O—R10, —NH—C(O)—($C_1$-$C_4$)-alkyl, —C(O)—($C_1$-$C_4$)-alkyl, or —$NO_2$, R4 and R7 are independent of one another are identical or different and are a hydrogen atom, —($C_1$-$C_4$)-alkyl, —O—($C_1$-$C_4$)-alkyl, —($C_1$-$C_5$)-alkyl-OH, halogen, —C(O)—O—R10, =O, phenyl, —($C_1$-$C_3$)-alkylene-C(O)—O—R10, —C(O)—N(R10)-R20, —N(R10)-R21, —CN, —($C_1$-$C_3$)-fluoroalkyl, —($C_1$-$C_3$)-alkyl-O—($C_1$-$C_3$)-alkyl, —C(O)—($C_1$-$C_4$)-alkyl, —C(O)—($C_1$-$C_3$)-fluoroalkyl, —C(O)—($C_3$-$C_8$)-cycloalkyl, —C(O)-aryl, wherein aryl is selected out of the group phenyl, naphthyl, indanyl, indanyl-1-one, biphenylyl, anthryl and fluorenyl, wherein aryl is mono-, di- or trisubstituted independently of one another by R6, aryl, wherein aryl is selected out of the group phenyl, naphthyl, indanyl, indanyl-1-one, biphenylyl, anthryl and fluorenyl, wherein aryl is mono-, di- or trisubstituted independently of one another by R6, methanesulfonyl, or heteroaryl, wherein heteroaryl is defined above, R8 and R9 are independent of one another are identical or different and are a hydrogen atom, halogen, —OH, —N(R10)-C(O)—R20, or —($C_1$-$C_4$)-alkyl, R10 is hydrogen atom, —($C_1$-$C_4$)-alkyl or —O—($C_1$-$C_4$)-alkyl, R11 is hydrogen atom, —($C_1$-$C_4$)-alkyl or benzyl, R12 is hydrogen atom or R1 and R12 together with the nitrogen atom to which they are bonded form a four- to eight-membered monocyclic heterocyclic ring which, as well as the nitrogen atom, may additionally, according to the ring size, also contain one or two identical or different heteroatoms from the group of oxygen, nitrogen and sulfur wherein four- to eight-membered monocyclic heterocyclic ring is mono-, di- or trisubstituted independently of one another by —($C_1$-$C_4$)-alkyl or halogen, R20 is hydrogen atom, or —($C_1$-$C_4$)-alkyl, R21 is hydrogen atom, —($C_1$-$C_4$)-alkyl, —C(O)—R20, —($C_1$-$C_4$)-alkyl-heteroaryl, wherein heteroaryl is defined above, heteroaryl, wherein heteroaryl is defined above, or —($C_3$-$C_8$)-cycloalkyl, wherein cycloalkyl is unsubstituted or mono-, di- or trisubstituted independently of one another by R10, in all its stereoisomeric forms and mixtures thereof in any ratio, and its physiologically tolerable salts.

6) Thus, the present invention also relates to compounds of the formula Ia,

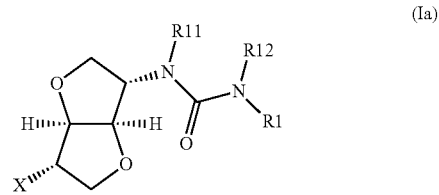

(Ia)

wherein

R1 is —($C_1$-$C_4$)-alkylene-($C_3$-$C_{12}$)-cycloalkyl, wherein cycloalkyl is a ring system containing 3 to 12 carbon atoms in mono-, bi- or tricycles or bridged rings, wherein cycloalkyl is mono-, di-, tri- or tetrasubstituted independently of one another by R2, —($C_1$-$C_4$)-alkylene-aryl, wherein aryl is an aromatic hydrocarbon radical containing from 6 to 14 carbon atoms depending on the number of carbon atoms in one, two or three rings, and wherein said alkylene or aryl is independently from each other mono-, di- or trisubstituted independently of one another by R3, —($C_1$-$C_4$)-alkylene-heterocyclyl, wherein heterocyclyl is a ring system containing 4 to 15 ring carbon atoms, wherein depending on the ring size one, two, three or four of the 4 to 15 ring carbon atoms are independently replaced by nitrogen, oxygen or sulfur atoms, and wherein said alkylene or heterocyclyl is independently from each other unsubstituted or mono-, di- or trisubstituted independently of one another by R4, cyclopropyl-heterocyclyl, wherein heterocyclyl is defined above for heterocyclyl, and wherein said heterocyclyl is unsubstituted or mono-, di- or trisubstituted independently of one another by R4, heterocyclyl, wherein heterocyclyl is defined above for heterocyclyl, and wherein said heterocyclyl is unsubstituted or mono-, di- or trisubstituted independently of one another by R4, aryl, wherein aryl is defined above for aryl, and wherein aryl is mono-, di- or trisubstituted independently of one another by R3, —($C_3$-$C_{12}$)-cycloalkyl, wherein cycloalkyl is defined above and is mono-, di-, tri- or tetrasubstituted independently of one another by R2, or —($C_1$-$C_4$)-alkyl, wherein alkyl is mono-, di- or trisubstituted independently of one another by R14, X is —O-aryl, wherein aryl is an aromatic hydrocarbon radical containing from 6 to 14 carbon atoms depending on the number of carbon atoms in one, two or three rings, and wherein aryl is mono-, di- or trisubstituted independently of one another by R6, —O-heterocyclyl, wherein heterocyclyl is a ring system containing 4 to 15 ring carbon atoms, wherein depending on the ring size one, two, three or four of the 4 to 15 ring carbon atoms are independently replaced by nitrogen, oxygen or sulfur atoms, and wherein said heterocyclyl is unsubstituted or mono-, di- or trisubstituted independently of one another by R7,
—($C_1$-$C_4$)-alkyl-R17, wherein said alkyl is unsubstituted or mono-, di- or trisubstituted independently of one another by R17,
—($C_1$-$C_4$)-alkyl-aryl, wherein aryl is defined above and wherein aryl is mono-, di- or trisubstituted independently of one another by R8,
—($C_1$-$C_4$)-alkyl-heterocyclyl, wherein heterocyclyl is defined above for —O-heterocyclyl, and wherein said heterocyclyl is unsubstituted or mono-, di- or trisubstituted independently of one another by R7,
—(CH=CH)-aryl, wherein aryl is defined above and wherein aryl is mono-, di- or trisubstituted independently of one another by R8,
—(CH=CH)-heterocyclyl, wherein heterocyclyl is defined above for —O-heterocyclyl, and wherein said heterocyclyl is unsubstituted or mono-, di- or trisubstituted independently of one another by R7,
—(C≡C)-aryl, wherein aryl is defined above and wherein aryl is mono-, di- or trisubstituted independently of one another by R8,
—(C≡C)-heterocyclyl, wherein heterocyclyl is defined above for —O-heterocyclyl, and wherein said heterocyclyl is unsubstituted or mono-, di- or trisubstituted independently of one another by R7,
—CN,
—O—($C_1$-$C_3$)-fluoroalkyl,
—O—C(O)-heteroaryl, wherein heteroaryl is selected out of the group imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, wherein heteroaryl is mono-, di- or trisubstituted independently of one another by R7,
—N(R10)-heteroaryl, wherein heteroaryl is defined above, and wherein said heteroaryl is unsubstituted or mono-, di- or trisubstituted independently of one another by R7,
—S—($C_1$-$C_4$)-alkyl-R17, wherein said alkyl is unsubstituted or mono-, di- or trisubstituted independently of one another by R17,
—S—($C_3$-$C_8$)-cycloalkyl, wherein said cycloalkyl is unsubstituted or mono-, di- or trisubstituted independently of one another by R17,
—$SO_2$—($C_3$-$C_8$)-cycloalkyl, wherein said cycloalkyl is unsubstituted or mono-, di- or trisubstituted independently of one another by R17,
—O—$SO_2$-aryl, wherein aryl is defined above, and wherein aryl is mono-, di- or trisubstituted independently of one another by R8,
—S-aryl, wherein aryl is defined above, and wherein aryl is mono-, di- or trisubstituted independently of one another by R8,
—S-heterocyclyl, wherein heterocyclyl is defined above, and wherein said heterocyclyl is unsubstituted or mono-, di- or trisubstituted independently of one another by R7, or
—S—($C_1$-$C_4$)-alkyl, wherein said alkyl is unsubstituted or mono-, di- or trisubstituted independently of one another by R18, R2, R3, R14, R17 and R18 are independent of one another are identical or different and are a hydrogen atom, —($C_1$-$C_4$)-alkyl, —OH, —($C_1$-$C_4$)-alkyl-OH, halogen, —($C_1$-$C_3$)-fluoroalkyl, —C(O)—OH, —C(O)—O—($C_1$-$C_4$)-alkyl, —O—($C_1$-$C_4$)-alkyl, —CN, —O—($C_1$-$C_3$)-fluoroalkyl, —N(R10)-R21, —NH—C(O)—($C_1$-$C_4$)-alkyl, —S—($C_1$-$C_4$)-alkyl,
—$S(O)_2$—($C_1$-$C_3$)-alkyl, —($C_1$-$C_3$)-alkyl-O—($C_1$-$C_3$)-alkyl, phenyl, or —O—($C_1$-$C_4$)-alkyl-phenyl, R6 is aryl, wherein aryl is defined above, and wherein aryl is mono-, di- or trisubstituted independently of one another by R10,
—O-aryl, wherein aryl is defined above, and wherein aryl is mono-, di- or trisubstituted independently of one another by R10,
—($C_1$-$C_4$)-alkylene-aryl, wherein aryl is defined above, and wherein aryl is mono-, di- or trisubstituted independently of one another by R10,
heteroaryl, wherein heteroaryl is defined above, and wherein said heteroaryl is unsubstituted or mono-, di- or trisubstituted independently of one another by R10,
—O-heteroaryl, wherein heteroaryl is defined above, and wherein said heteroaryl is unsubstituted or mono-, di- or trisubstituted independently of one another by R10,
—C(O)-heteroaryl, wherein heteroaryl is defined above, and wherein said heteroaryl is unsubstituted or mono-, di- or trisubstituted independently of one another by R10,
—($C_1$-$C_4$)-alkylene-heteroaryl, wherein heteroaryl is defined above, and wherein said heteroaryl is unsubstituted or mono-, di- or trisubstituted independently of one another by R10,
—O—($C_1$-$C_4$)-alkylene-heteroaryl, wherein heteroaryl is defined above, and wherein said heteroaryl is unsubstituted or mono-, di- or trisubstituted independently of one another by R10,
—($C_3$-$C_8$)-cycloalkyl, wherein cycloalkyl is unsubstituted or mono-, di- or trisubstituted independently of one another by R10,
hydrogen atom, —($C_1$-$C_4$)-alkylene-N(R10)-R21, —C(O)—N(R10)-R20, —N(R10)-R21, —($C_1$-$C_4$)-alkyl, —($C_1$-$C_4$)-alkyl-CN, —($C_1$-$C_3$)-fluoroalkyl, —O—($C_1$-$C_4$)-alkyl, halogen, —C(O)—O—R10, —($C_1$-$C_3$)-alkylene-C(O)—O—R10, —NH—C(O)—($C_1$-$C_4$)-alkyl, —C(O)—($C_1$-$C_4$)-alkyl, or —$NO_2$, R4 and R7 are independent of one another are identical or different and are a hydrogen atom, —($C_1$-$C_4$)-alkyl, —O—($C_1$-$C_4$)-alkyl, —($C_1$-$C_5$)-alkyl-OH, halogen, —C(O)—O—R10, =O, phenyl, —($C_1$-$C_3$)-alkylene-C(O)—O—R10, —C(O)—N(R10)-R20, —N(R10)-R21, —CN, —($C_1$-$C_3$)-fluoroalkyl, —($C_1$-$C_3$)-alkyl-O—($C_1$-$C_3$)-alkyl, —C(O)—($C_1$-$C_4$)-alkyl, —C(O)—($C_1$-$C_3$)-fluoroalkyl, —C(O)—($C_3$-$C_8$)-cycloalkyl, —C(O)-aryl, wherein aryl is defined above, and wherein aryl is mono-, di- or trisubstituted independently of one another by R6, aryl, wherein aryl is defined above, and wherein aryl is mono-, di- or trisubstituted independently of one another by R6, methanesulfonyl, or heteroaryl, wherein heteroaryl is defined above, R8 and R9 are independent of one another are identical or different and are a hydrogen atom, halogen, —OH, —N(R10)-C(O)—R20, or —($C_1$-$C_4$)-alkyl,
R10 is hydrogen atom, —($C_1$-$C_4$)-alkyl or —O—($C_1$-$C_4$)-alkyl,
R11 is hydrogen atom, —($C_1$-$C_4$)-alkyl or benzyl,
R12 is hydrogen atom or
R1 and R12 together with the nitrogen atom to which they are bonded form a four- to eight-membered monocyclic heterocyclic ring which, as well as the nitrogen atom, may additionally, according to the ring size, also contain one or two identical or different heteroatoms from the group of oxygen, nitrogen and sulfur wherein four- to eight-membered monocyclic heterocyclic ring is mono-, di- or trisubstituted independently of one another by —($C_1$-$C_4$)-alkyl or halogen, R20 is hydrogen atom, or —($C_1$-$C_4$)-alkyl, R21 is hydrogen atom, —($C_1$-$C_4$)-alkyl, —C(O)—R20, —($C_1$-$C_4$)-alkyl-heteroaryl, wherein heteroaryl is defined above, heteroaryl, wherein heteroaryl is defined above, or —($C_3$-$C_8$)-cycloalkyl, wherein cycloalkyl is unsubstituted or mono-, di- or trisubstituted independently of one another by R10, in all its stereoisomeric forms and mixtures thereof in any ratio, and its physiologically tolerable salts.

7) Thus, the present invention also relates to compounds of the formula Ia, wherein R1 is —($C_1$-$C_4$)-alkylene-($C_3$-$C_{12}$)-cycloalkyl, wherein cycloalkyl is a ring system containing 3 to 12 carbon atoms in mono-, bi- or tricycles or bridged rings, wherein cycloalkyl is mono-, di-, tri- or tetrasubstituted independently of one another by R2,
—($C_1$-$C_4$)-alkylene-aryl, wherein aryl is an aromatic hydrocarbon radical containing from 6 to 14 carbon atoms depending on the number of carbon atoms in one, two or three rings, and wherein said alkylene or aryl is independently from each other mono-, di- or trisubstituted independently of one another by R3,
—($C_1$-$C_4$)-alkylene-heterocyclyl, wherein heterocyclyl is a ring system containing 4 to 15 ring carbon atoms, wherein depending on the ring size one, two, three or four of the 4 to 15 ring carbon atoms are independently replaced by nitrogen, oxygen or sulfur atoms, and wherein said alkylene or heterocyclyl is independently from each other unsubstituted or mono-, di- or trisubstituted independently of one another by R4,
cyclopropyl-heterocyclyl, wherein heterocyclyl is defined above for heterocyclyl, and wherein said heterocyclyl is unsubstituted or mono-, di- or trisubstituted independently of one another by R4,
heterocyclyl, wherein heterocyclyl is defined above for heterocyclyl, and wherein said heterocyclyl is unsubstituted or mono-, di- or trisubstituted independently of one another by R4,
aryl, wherein aryl is defined above for aryl, and wherein aryl is mono-, di- or trisubstituted independently of one another by R3,
—($C_3$-$C_{12}$)-cycloalkyl, wherein cycloalkyl is defined above and is mono-, di-, tri- or tetrasubstituted independently of one another by R2, or
—($C_1$-$C_4$)-alkyl, wherein alkyl is mono-, di- or trisubstituted independently of one another by R14, X is —O-aryl, wherein aryl is an aromatic hydrocarbon radical containing from 6 to 14 carbon atoms depending on the number of carbon atoms in one, two or three rings, and wherein aryl is mono-, di- or trisubstituted independently of one another by R6,
—O-heterocyclyl, wherein heterocyclyl is a ring system containing 4 to 15 ring carbon atoms, wherein depending on the ring size one, two, three or four of the 4 to 15 ring carbon atoms are independently replaced by nitrogen, oxygen or sulfur atoms, and wherein said heterocyclyl is unsubstituted or mono-, di- or trisubstituted independently of one another by R7,
—O—($C_1$-$C_3$)-fluoroalkyl,
—O—C(O)-heteroaryl, wherein heteroaryl is selected out of the group imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, wherein heteroaryl is mono-, di- or trisubstituted independently of one another by R7, or
—O—$SO_2$-aryl, wherein aryl is defined above, and wherein aryl is mono-, di- or trisubstituted independently of one another by R8, R2, R3, R14, R17 and R18 are independent of one another are identical or different and are a hydrogen atom, —($C_1$-$C_4$)-alkyl, —OH, —($C_1$-$C_4$)-alkyl-OH, halogen, —($C_1$-$C_3$)-fluoroalkyl, —C(O)—OH, —C(O)—O—($C_1$-$C_4$)-alkyl, —O—($C_1$-$C_4$)-alkyl, —CN, —O—($C_1$-$C_3$)-fluoroalkyl, —N(R10)-R21, —NH—C(O)—($C_1$-$C_4$)-alkyl, —S—($C_1$-$C_4$)-alkyl,
—S(O)$_2$—($C_1$-$C_3$)-alkyl, —($C_1$-$C_3$)-alkyl-O—($C_1$-$C_3$)-alkyl, phenyl, or —O—($C_1$-$C_4$)-alkyl-phenyl, R6 is aryl, wherein aryl is defined above, and wherein aryl is mono-, di- or trisubstituted independently of one another by R10,
—O-aryl, wherein aryl is defined above, and wherein aryl is mono-, di- or trisubstituted independently of one another by R10,
—($C_1$-$C_4$)-alkylene-aryl, wherein aryl is defined above, and wherein aryl is mono-, di- or trisubstituted independently of one another by R10,
heteroaryl, wherein heteroaryl is defined above, and wherein said heteroaryl is unsubstituted or mono-, di- or trisubstituted independently of one another by R10,
—O-heteroaryl, wherein heteroaryl is defined above, and wherein said heteroaryl is unsubstituted or mono-, di- or trisubstituted independently of one another by R10,
—C(O)-heteroaryl, wherein heteroaryl is defined above, and wherein said heteroaryl is unsubstituted or mono-, di- or trisubstituted independently of one another by R10,
—($C_1$-$C_4$)-alkylene-heteroaryl, wherein heteroaryl is defined above, and wherein said heteroaryl is unsubstituted or mono-, di- or trisubstituted independently of one another by R10,
—O—($C_1$-$C_4$)-alkylene-heteroaryl, wherein heteroaryl is defined above, and wherein said heteroaryl is unsubstituted or mono-, di- or trisubstituted independently of one another by R10,
—($C_3$-$C_8$)-cycloalkyl, wherein cycloalkyl is unsubstituted or mono-, di- or trisubstituted independently of one another by R10,
hydrogen atom, —($C_1$-$C_4$)-alkylene-N(R10)-R21, —C(O)—N(R10)-R20, —N(R10)-R21, —($C_1$-$C_4$)-alkyl, —($C_1$-$C_4$)-alkyl-CN, —($C_1$-$C_3$)-fluoroalkyl, —O—($C_1$-$C_4$)-alkyl, halogen, —C(O)—O—R10, —($C_1$-$C_3$)-alkylene-C(O)—O—R10, —NH—C(O)—($C_1$-$C_4$)-alkyl, —C(O)—($C_1$-$C_4$)-alkyl, or —$NO_2$, R4 and R7 are independent of one another are identical or different and are a hydrogen atom, —($C_1$-$C_4$)-alkyl, —O—($C_1$-$C_4$)-alkyl, —($C_1$-$C_5$)-alkyl-OH, halogen, —C(O)—O—R10, =O, phenyl, —($C_1$-$C_3$)-alkylene-C(O)—O—R10, —C(O)—N(R10)-R20, —N(R10)-R21, —CN, —($C_1$-$C_3$)-fluoroalkyl, —($C_1$-$C_3$)-alkyl-O—($C_1$-$C_3$)-alkyl, —C(O)—($C_1$-$C_4$)-alkyl, —C(O)—($C_1$-$C_3$)-fluoroalkyl, —C(O)—($C_3$-$C_8$)-cycloalkyl, —C(O)-aryl, wherein aryl is defined above, and wherein aryl is mono-, di- or trisubstituted independently of one another by R6,
aryl, wherein aryl is defined above, and wherein aryl is mono-, di- or trisubstituted independently of one another by R6,
methanesulfonyl, or heteroaryl, wherein heteroaryl is defined above, R8 and R9 are independent of one another are identical or different and are a hydrogen atom, halogen, —OH, —N(R10)-C(O)—R20, or —($C_1$-$C_4$)-alkyl, R10 is hydrogen atom, —($C_1$-$C_4$)-alkyl or —O—($C_1$-$C_4$)-alkyl, R11 is hydrogen atom, —($C_1$-$C_4$)-alkyl or benzyl, R12 is hydrogen atom or R1 and R12 together with the nitrogen atom to which they are bonded form a four- to eight-membered monocyclic heterocyclic ring which, as well as the nitrogen atom, may additionally, according to the ring size, also contain one or two identical or different heteroatoms from the group of oxygen, nitrogen and sulfur wherein four- to eight-membered monocyclic heterocyclic ring is mono-, di- or trisubstituted independently of one another by —($C_1$-$C_4$)-alkyl or halogen, R20 is hydrogen atom, or —($C_1$-$C_4$)-alkyl, R21 is hydrogen atom, —($C_1$-$C_4$)-alkyl, —C(O)—R20, —($C_1$-$C_4$)-alkyl-heteroaryl, wherein heteroaryl is defined above, heteroaryl, wherein heteroaryl is defined above, or —($C_3$-$C_8$)-cycloalkyl, wherein cycloalkyl is unsubstituted or mono-, di- or trisubstituted independently of one another by R10, in all its stereoisomeric forms and mixtures thereof in any ratio, and its physiologically tolerable salts.

8) Thus, the present invention also relates to compounds of the formula Ia, wherein R1 is —($C_1$-$C_4$)-alkylene-($C_3$-$C_{12}$)-cycloalkyl, wherein cycloalkyl is a ring system containing 3 to 12 carbon atoms in mono-, bi- or tricycles or bridged rings, wherein cycloalkyl is mono-, di-, tri- or tetrasubstituted independently of one another by R2, —($C_1$-$C_4$)-alkylene-aryl, wherein aryl is an aromatic hydrocarbon radical containing from 6 to 14 carbon atoms depending on the number of carbon atoms in one, two or three rings, and wherein said alkylene or aryl is independently from each other mono-, di- or trisubstituted independently of one another by R3, —($C_1$-$C_4$)-alkylene-heterocyclyl, wherein heterocyclyl is a ring system containing 4 to 15 ring carbon atoms, wherein depending on the ring size one, two, three or four of the 4 to 15 ring carbon atoms are independently replaced by nitrogen, oxygen or sulfur atoms, and wherein said alkylene or heterocyclyl is independently from each other unsubstituted or mono-, di- or trisubstituted independently of one another by R4, cyclopropyl-heterocyclyl, wherein heterocyclyl is defined above for heterocyclyl, and wherein said heterocyclyl is unsubstituted or mono-, di- or trisubstituted independently of one another by R4, heterocyclyl, wherein heterocyclyl is defined above for heterocyclyl, and wherein said heterocyclyl is unsubstituted or mono-, di- or trisubstituted independently of one another by R4, aryl, wherein aryl is defined above for aryl, and wherein aryl is mono-, di- or trisubstituted independently of one another by R3, —($C_3$-$C_{12}$)-cycloalkyl, wherein cycloalkyl is defined above and is mono-, di-, tri- or tetrasubstituted independently of one another by R2, or —($C_1$-$C_4$)-alkyl, wherein alkyl is mono-, di- or trisubstituted independently of one another by R14, X is —($C_1$-$C_4$)-alkyl-R17, wherein said alkyl is unsubstituted or mono-, di- or trisubstituted independently of one another by R17, —($C_1$-$C_4$)-alkyl-aryl, wherein aryl is defined above and wherein aryl is mono-, di- or trisubstituted independently of one another by R8, —($C_1$-$C_4$)-alkyl-heterocyclyl, wherein heterocyclyl is defined above for —O-heterocyclyl, and wherein said heterocyclyl is unsubstituted or mono-, di- or trisubstituted independently of one another by R7, —(CH=CH)-aryl, wherein aryl is defined above and wherein aryl is mono-, di- or trisubstituted independently of one another by R8, —(CH=CH)-heterocyclyl, wherein heterocyclyl is defined above for —O-heterocyclyl, and wherein said heterocyclyl is unsubstituted or mono-, di- or trisubstituted independently of one another by R7, —(C≡C)-aryl, wherein aryl is defined above and wherein aryl is mono-, di- or trisubstituted independently of one another by R8, —(C≡C)-heterocyclyl, wherein heterocyclyl is defined above for —O-heterocyclyl, and wherein said heterocyclyl is unsubstituted or mono-, di- or trisubstituted independently of one another by R7, or

—CN,

R2, R3, R14, R17 and R18 are independent of one another are identical or different and are a hydrogen atom, —($C_1$-$C_4$)-alkyl, —OH, —($C_1$-$C_4$)-alkyl-OH, halogen, —($C_1$-$C_3$)-fluoroalkyl, —C(O)—OH, —C(O)—O—($C_1$-$C_4$)-alkyl, —O—($C_1$-$C_4$)-alkyl, —CN, —O—($C_1$-$C_3$)-fluoroalkyl, —N(R10)-R21, —NH—C(O)—($C_1$-$C_4$)-alkyl, —S—($C_1$-$C_4$)-alkyl, —S(O)$_2$—($C_1$-$C_3$)-alkyl, —($C_1$-$C_3$)-alkyl-O—($C_1$-$C_3$)-alkyl, phenyl, or —O—($C_1$-$C_4$)-alkyl-phenyl, R6 is aryl, wherein aryl is defined above, and wherein aryl is mono-, di- or trisubstituted independently of one another by R10, —O-aryl, wherein aryl is defined above, and wherein aryl is mono-, di- or trisubstituted independently of one another by R10, —($C_1$-$C_4$)-alkylene-aryl, wherein aryl is defined above, and wherein aryl is mono-, di- or trisubstituted independently of one another by R10, heteroaryl, wherein heteroaryl is defined above, and wherein said heteroaryl is unsubstituted or mono-, di- or trisubstituted independently of one another by R10, —O-heteroaryl, wherein heteroaryl is defined above, and wherein said heteroaryl is unsubstituted or mono-, di- or trisubstituted independently of one another by R10, —C(O)-heteroaryl, wherein heteroaryl is defined above, and wherein said heteroaryl is unsubstituted or mono-, di- or trisubstituted independently of one another by R10, —($C_1$-$C_4$)-alkylene-heteroaryl, wherein heteroaryl is defined above, and wherein said heteroaryl is unsubstituted or mono-, di- or trisubstituted independently of one another by R10, —O—($C_1$-$C_4$)-alkylene-heteroaryl, wherein heteroaryl is defined above, and wherein said heteroaryl is unsubstituted or mono-, di- or trisubstituted independently of one another by R10, —($C_3$-$C_8$)-cycloalkyl, wherein cycloalkyl is unsubstituted or mono-, di- or trisubstituted independently of one another by R10, hydrogen atom, —($C_1$-$C_4$)-alkylene-N(R10)-R21, —C(O)—N(R10)-R20, —N(R10)-R21, —($C_1$-$C_4$)-alkyl, —($C_1$-$C_4$)-alkyl-CN, —($C_1$-$C_3$)-fluoroalkyl, —O—($C_1$-$C_4$)-alkyl, halogen, —C(O)—O—R10, —($C_1$-$C_3$)-alkylene-C(O)—O—R10, —NH—C(O)—($C_1$-$C_4$)-alkyl, —C(O)—($C_1$-$C_4$)-alkyl, or —NO$_2$, R4 and R7 are independent of one another are identical or different and are a hydrogen atom, —($C_1$-$C_4$)-alkyl, —O—($C_1$-$C_4$)-alkyl, —($C_1$-$C_5$)-alkyl-OH, halogen, —C(O)—O—R10, =O, phenyl, —($C_1$-$C_3$)-alkylene-C(O)—O—R10, —C(O)—N(R10)-R20, —N(R10)-R21, —CN, —($C_1$-$C_3$)-fluoroalkyl, —($C_1$-$C_3$)-alkyl-O—($C_1$-$C_3$)-alkyl, —C(O)—($C_1$-$C_4$)-alkyl, —C(O)—($C_1$-$C_3$)-fluoroalkyl, —C(O)—($C_3$-$C_8$)-cycloalkyl, —C(O)-aryl, wherein aryl is defined above, and wherein aryl is mono-, di- or trisubstituted independently of one another by R6,
aryl, wherein aryl is defined above, and wherein aryl is mono-, di- or trisubstituted independently of one another by R6,
methanesulfonyl, or heteroaryl, wherein heteroaryl is defined above, R8 and R9 are independent of one another are identical or different and are a hydrogen atom, halogen, —OH, —N(R10)-C(O)—R20, or —($C_1$-$C_4$)-alkyl, R10 is hydrogen atom, —($C_1$-$C_4$)-alkyl or —O—($C_1$-$C_4$)-alkyl, R11 is hydrogen atom, —($C_1$-$C_4$)-alkyl or benzyl, R12 is hydrogen atom or R1 and R12 together with the nitrogen atom to which they are bonded form a four- to eight-membered monocyclic heterocyclic ring which, as well as the nitrogen atom, may additionally, according to the ring size, also contain one or two identical or different heteroatoms from the group of oxygen, nitrogen and sulfur wherein four- to eight-membered monocyclic heterocyclic ring is mono-, di- or trisubstituted independently of one another by —($C_1$-$C_4$)-alkyl or halogen, R20 is hydrogen atom, or —($C_1$-$C_4$)-alkyl, R21 is hydrogen atom, —($C_1$-$C_4$)-alkyl, —C(O)—R20, —($C_1$-$C_4$)-alkyl-heteroaryl, wherein heteroaryl is defined above, heteroaryl, wherein heteroaryl is defined above, or —($C_3$-$C_8$)-cycloalkyl, wherein cycloalkyl is unsubstituted or mono-, di- or trisubstituted independently of one another by R10, in all its stereoisomeric forms and mixtures thereof in any ratio, and its physiologically tolerable salts.

9) Thus, the present invention also relates to compounds of the formula Ia, wherein R1 is —($C_1$-$C_4$)-alkylene-($C_3$-$C_{12}$)-cycloalkyl, wherein cycloalkyl is a ring system containing 3 to 12 carbon atoms in mono-, bi- or tricycles or bridged rings, wherein cycloalkyl is mono-, di-, tri- or tetrasubstituted independently of one another by R2,
—($C_1$-$C_4$)-alkylene-aryl, wherein aryl is an aromatic hydrocarbon radical containing from 6 to 14 carbon atoms depending on the number of carbon atoms in one, two or three rings, and wherein said alkylene or aryl is independently from each other mono-, di- or trisubstituted independently of one another by R3,
—($C_1$-$C_4$)-alkylene-heterocyclyl, wherein heterocyclyl is a ring system containing 4 to 15 ring carbon atoms, wherein depending on the ring size one, two, three or four of the 4 to 15 ring carbon atoms are independently replaced by nitrogen, oxygen or sulfur atoms, and wherein said alkylene or heterocyclyl is independently from each other unsubstituted or mono-, di- or trisubstituted independently of one another by R4,
cyclopropyl-heterocyclyl, wherein heterocyclyl is defined above for heterocyclyl, and wherein said heterocyclyl is unsubstituted or mono-, di- or trisubstituted independently of one another by R4,
heterocyclyl, wherein heterocyclyl is defined above for heterocyclyl, and wherein said heterocyclyl is unsubstituted or mono-, di- or trisubstituted independently of one another by R4,
aryl, wherein aryl is defined above for aryl, and wherein aryl is mono-, di- or trisubstituted independently of one another by R3,
—($C_3$-$C_{12}$)-cycloalkyl, wherein cycloalkyl is defined above and is mono-, di-, tri- or tetrasubstituted independently of one another by R2, or
—($C_1$-$C_4$)-alkyl, wherein alkyl is mono-, di- or trisubstituted independently of one another by R14, X is —S—($C_1$-$C_4$)-alkyl-R17, wherein said alkyl is unsubstituted or mono-, di- or trisubstituted independently of one another by R17,
—S—($C_3$-$C_8$)-cycloalkyl, wherein said cycloalkyl is unsubstituted or mono-, di- or trisubstituted independently of one another by R17,
—$SO_2$—($C_3$-$C_8$)-cycloalkyl, wherein said cycloalkyl is unsubstituted or mono-, di- or trisubstituted independently of one another by R17,
—S-aryl, wherein aryl is defined above, and wherein aryl is mono-, di- or trisubstituted independently of one another by R8,
—S-heterocyclyl, wherein heterocyclyl is defined above, and wherein said heterocyclyl is unsubstituted or mono-, di- or trisubstituted independently of one another by R7, or
—S—($C_1$-$C_4$)-alkyl, wherein said alkyl is unsubstituted or mono-, di- or trisubstituted independently of one another by R18, R2, R3, R14, R17 and R18 are independent of one another are identical or different and are a hydrogen atom, —($C_1$-$C_4$)-alkyl, —OH, —($C_1$-$C_4$)-alkyl-OH, halogen, —($C_1$-$C_3$)-fluoroalkyl, —C(O)—OH, —C(O)—O—($C_1$-$C_4$)-alkyl, —O—($C_1$-$C_4$)-alkyl, —CN, —O—($C_1$-$C_3$)-fluoroalkyl, —N(R10)-R21, —NH—C(O)—($C_1$-$C_4$)-alkyl, —S—($C_1$-$C_4$)-alkyl,
—S(O)$_2$—($C_1$-$C_3$)-alkyl, —($C_1$-$C_3$)-alkyl-O—($C_1$-$C_3$)-alkyl, phenyl, or —O—($C_1$-$C_4$)-alkyl-phenyl, R6 is aryl, wherein aryl is defined above, and wherein aryl is mono-, di- or trisubstituted independently of one another by R10,
—O-aryl, wherein aryl is defined above, and wherein aryl is mono-, di- or trisubstituted independently of one another by R10,
—($C_1$-$C_4$)-alkylene-aryl, wherein aryl is defined above, and wherein aryl is mono-, di- or trisubstituted independently of one another by R10,
heteroaryl, wherein heteroaryl is defined above, and wherein said heteroaryl is unsubstituted or mono-, di- or trisubstituted independently of one another by R10,
—O-heteroaryl, wherein heteroaryl is defined above, and wherein said heteroaryl is unsubstituted or mono-, di- or trisubstituted independently of one another by R10,
—C(O)-heteroaryl, wherein heteroaryl is defined above, and wherein said heteroaryl is unsubstituted or mono-, di- or trisubstituted independently of one another by R10,
—($C_1$-$C_4$)-alkylene-heteroaryl, wherein heteroaryl is defined above, and wherein said heteroaryl is unsubstituted or mono-, di- or trisubstituted independently of one another by R10,
—O—($C_1$-$C_4$)-alkylene-heteroaryl, wherein heteroaryl is defined above, and wherein said heteroaryl is unsubstituted or mono-, di- or trisubstituted independently of one another by R10, —($C_3$-$C_8$)-cycloalkyl, wherein cycloalkyl is unsubstituted or mono-, di- or trisubstituted independently of one another by R10,
hydrogen atom, —($C_1$-$C_4$)-alkylene-N(R10)-R21, —C(O)—N(R10)-R20, —N(R10)-R21, —($C_1$-$C_4$)-alkyl, —($C_1$-$C_4$)-alkyl-CN, —($C_1$-$C_3$)-fluoroalkyl, —O—($C_1$-$C_4$)-alkyl, halogen, —C(O)—O—R10, —($C_1$-$C_3$)-alkylene-C(O)—O—R10, —NH—C(O)—($C_1$-$C_4$)-alkyl, —C(O)—($C_1$-$C_4$)-alkyl, or —$NO_2$, R4 and R7 are independent of one another are identical or different and are a hydrogen atom, —($C_1$-$C_4$)-alkyl, —O—($C_1$-$C_4$)-alkyl, —($C_1$-$C_5$)-alkyl-OH, halogen, —C(O)—O—R10, =O, phenyl, —($C_1$-$C_3$)-alkylene-C(O)—O—R10, —C(O)—N(R10)-R20, —N(R10)-R21, —CN, —($C_1$-$C_3$)-fluoroalkyl, —($C_1$-$C_3$)-alkyl-O—($C_1$-$C_3$)-alkyl, —C(O)—($C_1$-$C_4$)-alkyl, —C(O)—($C_1$-$C_3$)-fluoroalkyl, —C(O)—($C_3$-$C_8$)-cycloalkyl, —C(O)-aryl, wherein aryl is defined above, and wherein aryl is mono-, di- or trisubstituted independently of one another by R6,
aryl, wherein aryl is defined above, and wherein aryl is mono-, di- or trisubstituted independently of one another by R6,
methanesulfonyl, or heteroaryl, wherein heteroaryl is defined above, R8 and R9 are independent of one another are identical or different and are a hydrogen atom, halogen, —OH, —N(R10)-C(O)—R20, or —($C_1$-$C_4$)-alkyl, R10 is hydrogen atom, —($C_1$-$C_4$)-alkyl or —O—($C_1$-$C_4$)-alkyl, R11 is hydrogen atom, —($C_1$-$C_4$)-alkyl or benzyl, R12 is hydrogen atom or R1 and R12 together with the nitrogen atom to which they are bonded form a four- to eight-membered monocyclic heterocyclic ring which, as well as the nitrogen atom, may additionally, according to the ring size, also contain one or two identical or different heteroatoms from the group of oxygen, nitrogen and sulfur wherein four- to eight-membered monocyclic heterocyclic ring is mono-, di- or trisubstituted independently of one another by —($C_1$-$C_4$)-alkyl or halogen, R20 is hydrogen atom, or —($C_1$-$C_4$)-alkyl, R21 is hydrogen atom, —($C_1$-$C_4$)-alkyl, —C(O)—R20, —($C_1$-$C_4$)-alkyl-heteroaryl, wherein heteroaryl is defined above, heteroaryl, wherein heteroaryl is defined above, or —($C_3$-$C_8$)-cycloalkyl, wherein cycloalkyl is unsubstituted or mono-, di- or trisubstituted independently of one another by R10, in all its stereoisomeric forms and mixtures thereof in any ratio, and its physiologically tolerable salts.

10) The present invention also relates to compounds of the formula Ia, wherein

R1 is —($C_1$-$C_3$)-alkylene-($C_3$-$C_8$)-cycloalkyl, wherein cycloalkyl is monosubstituted by R2,
—($C_1$-$C_4$)-alkylene-aryl, wherein aryl is selected out of the group phenyl, tetrahydronaphthalenyl, naphthyl, biphenylyl, and indanyl, and wherein said alkylene or aryl is independently from each other mono- or disubstituted independently of one another by R3,
—($C_1$-$C_4$)-alkylene-heterocyclyl, wherein heterocyclyl is selected out of the group 2,3-dihydro-benzofuranyl, benzofuranyl, benzo[1,3]dioxolyl, chromanyl, 2,3-dihydro-benzo[1,4]-dioxinyl, 1,3-dioxanyl, 1,4-dioxanyl, 1,3-dioxolanyl, imidazolyl, imidazo[1,2a]-pyridyl, isoxazolyl, morpholinyl, oxetanyl, piperidinyl, pyrazolyl, pyridyl, pyrimidinyl, pyrrolidinyl, tetrahydro-2H[1,2']bi-pyridinyl, tetrahydrofuranyl, tetrahydropyranyl, tetrahydrothiopyranyl, thiazolyl, thienothiophenyl, and thienyl, and wherein said alkylene or heterocyclyl is independently from each other unsubstituted or mono-, di- or trisubstituted independently of one another by R4,
cyclopropyl-heterocyclyl, wherein heterocyclyl is defined above, and wherein said heterocyclyl is unsubstituted or mono-, di- or trisubstituted independently of one another by R4,
heterocyclyl, wherein heterocyclyl is defined above, and wherein said heterocyclyl is unsubstituted or mono-, di- or trisubstituted independently of one another by R4,
aryl, wherein aryl is as defined above, and wherein aryl is mono- or disubstituted independently of one another by R3,
—($C_3$-$C_8$)-cycloalkyl, wherein cycloalkyl is mono- di-, tri- or tetrasubstituted independently of one another by R2, or
—($C_1$-$C_4$)-alkyl, wherein alkyl is mono-, di- or trisubstituted independently of one another by R14, X is —O-aryl, wherein aryl is selected out of the group phenyl, indanyl, indanyl-1-one, and biphenylyl, wherein aryl is mono- or disubstituted independently of one another by R6,
—O-heterocyclyl, wherein heterocyclyl is selected out of the group benzo[1,3]dioxolyl, chromanyl, chromenyl, cinnolinyl, decahydrochinolinyl, 2,3-dihydro-benzofuranyl, 2,3-dihydro-benzo[1,4]-dioxinyl, 1,4-dioxanyl, imidazolyl, imidazo[1,2a]pyridyl, indolyl, 1,3,4-oxadiazolyl, piperidinyl, pyrazolyl, pyridazinyl, pyridinyl, pyridyl, pyrimidinyl, pyrrolidinyl, quinolinyl, tetrahydro-2H[1,2']bi-pyridinyl, tetrahydrofuranyl, tetrahydropyranyl, tetrahydrothiophenyl, tetrahydrothiophenyl-1,1-dioxide, tetrazolyl, thiazolyl, thienothiophenyl, thienyl, and 1,2,4-triazolyl, and wherein said heterocyclyl is unsubstituted or mono-, di- or trisubstituted independently of one another by R7,
—($C_1$-$C_3$)-alkyl-R17, wherein said alkyl is unsubstituted or mono-, di- or trisubstituted independently of one another by R17,
—($C_1$-$C_4$)-alkyl-aryl, wherein aryl is as defined above, and wherein aryl is mono- or disubstituted independently of one another by R8,
—($C_1$-$C_3$)-alkyl-heterocyclyl, wherein heterocyclyl is defined above, and wherein said heterocyclyl is unsubstituted or mono-, di- or trisubstituted independently of one another by R7,
—(CH=CH)-aryl, wherein aryl is as defined above, and wherein aryl is mono- or disubstituted independently of one another by R8,
—(CH=CH)-heterocyclyl, wherein heterocyclyl is defined above, and wherein said heterocyclyl is unsubstituted or mono-, di- or trisubstituted independently of one another by R7,
—(C≡C)-aryl, wherein aryl is as defined above, and wherein aryl is mono- or disubstituted independently of one another by R8,
—(C≡C)-heterocyclyl, wherein heterocyclyl is defined above, and wherein said heterocyclyl is unsubstituted or mono-, di- or trisubstituted independently of one another by R7,
—CN, —O—($C_1$-$C_3$)-fluoroalkyl,
—O—C(O)-heteroaryl, wherein heteroaryl is selected out of the group imidazolyl, morpholinyl, oxadiazolyl, piperazinyl, piperidinyl, pyridyl, pyrrolidinyl, tetrahydrofuranyl, tetrazolyl, thiazolyl, thiophenyl, and triazolyl, wherein heteroaryl is mono- or disubstituted independently of one another by R7, —N(R10)-heteroaryl, wherein heteroaryl is defined above for heteroaryl, and wherein said heteroaryl is mono- or disubstituted independently of one another by R7, —S—$(C_1\text{-}C_4)$-alkyl-R17, wherein said alkyl is unsubstituted or mono- or disubstituted independently of one another by R17, —S—$(C_3\text{-}C_8)$-cycloalkyl, wherein said cycloalkyl is unsubstituted or mono- or ditrisubstituted independently of one another by R17, —$SO_2$—$(C_3\text{-}C_8)$-cycloalkyl, wherein said cycloalkyl is unsubstituted or mono-, di- or trisubstituted independently of one another by R17, —O—$SO_2$-phenyl, wherein phenyl is mono- or disubstituted independently of one another by R8, —S-phenyl, wherein phenyl is mono- or disubstituted independently of one another by R8, —S-heterocyclyl, wherein heterocyclyl is defined above for —O-heterocyclyl, and wherein said heterocyclyl is unsubstituted or is mono- or disubstituted independently of one another by R7, or —S—$(C_1\text{-}C_4)$-alkyl, wherein said alkyl is unsubstituted or is mono- or disubstituted independently of one another by R18, R2, R3, R14, R17 and R18 are independent of one another are identical or different and are a hydrogen atom, —$(C_1\text{-}C_4)$-alkyl, —OH, —$(C_1\text{-}C_4)$-alkyl-OH, halogen, —$(C_1\text{-}C_3)$-fluoroalkyl, —C(O)—OH, —C(O)—O—$(C_1\text{-}C_4)$-alkyl, —O—$(C_1\text{-}C_4)$-alkyl, —CN, —O—$(C_1\text{-}C_3)$-fluoroalkyl, —N(R10)-R21, —NH—C(O)—$(C_1\text{-}C_4)$-alkyl, —S—$(C_1\text{-}C_4)$-alkyl, —$S(O)_2$—$(C_1\text{-}C_3)$-alkyl, —$(C_1\text{-}C_3)$-alkyl-O—$(C_1\text{-}C_3)$-alkyl, phenyl, or —O—$(C_1\text{-}C_4)$-alkyl-phenyl, R6 is phenyl, wherein phenyl is mono- or disubstituted independently of one another by R10, —O-phenyl, wherein phenyl is mono- or disubstituted independently of one another by R10, —$(C_1\text{-}C_4)$-alkylene-phenyl, wherein phenyl is mono- or disubstituted independently of one another by R10, heteroaryl, wherein heteroaryl is defined above, and wherein said heteroaryl is unsubstituted or mono- or disubstituted independently of one another by R10, —O-heteroaryl, wherein heteroaryl is defined above, and wherein said heteroaryl is unsubstituted or mono- or disubstituted independently of one another by R10, —C(O)-heteroaryl, wherein heteroaryl is defined above for heteroaryl, and wherein said heteroaryl is unsubstituted or mono- or disubstituted independently of one another by R10, —$(C_1\text{-}C_4)$-alkylene-heteroaryl, wherein heteroaryl is defined above, and wherein said heteroaryl is unsubstituted or mono- or disubstituted independently of one another by R10, —O—$(C_1\text{-}C_4)$-alkylene-heteroaryl, wherein heteroaryl is defined above, and wherein said heteroaryl is unsubstituted or mono- or disubstituted independently of one another by R10, —$(C_3\text{-}C_6)$-cycloalkyl, wherein cycloalkyl is unsubstituted or mono- or disubstituted independently of one another by R10, hydrogen atom, —$(C_1\text{-}C_4)$-alkylene-N(R10)-R21, —C(O)—N(R10)-R20, —N(R10)-R21, —$(C_1\text{-}C_4)$-alkyl, —$(C_1\text{-}C_4)$-alkyl-CN, —$(C_1\text{-}C_3)$-fluoroalkyl, —O—$(C_1\text{-}C_4)$-alkyl, halogen, —C(O)—O—R10, —$(C_1\text{-}C_3)$-alkylene-C(O)—O—R10, —NH—C(O)—$(C_1\text{-}C_4)$-alkyl, —C(O)—$(C_1\text{-}C_4)$-alkyl, or —$NO_2$, R4 and R7 are independent of one another are identical or different and are a hydrogen atom, —$(C_1\text{-}C_4)$-alkyl, —O—$(C_1\text{-}C_4)$-alkyl, —$(C_1\text{-}C_6)$-alkyl-OH, halogen, —C(O)—O—R10, =O, phenyl, —$(C_1\text{-}C_3)$-alkylene-C(O)—O—R10, —C(O)—N(R10)-R20, —N(R10)-R21, —CN, —$(C_1\text{-}C_3)$-fluoroalkyl, —$(C_1\text{-}C_3)$-alkyl-O—$(C_1\text{-}C_3)$-alkyl, —C(O)—$(C_1\text{-}C_4)$-alkyl, —C(O)—$(C_1\text{-}C_3)$-fluoroalkyl, —C(O)—$(C_3\text{-}C_8)$-cycloalkyl, —C(O)-phenyl, wherein phenyl is mono- or disubstituted independently of one another by R6, phenyl, wherein phenyl is mono- or disubstituted independently of one another by R6, methanesulfonyl, or heteroaryl, wherein heteroaryl is defined above, R8 and R9 are independent of one another are identical or different and are a hydrogen atom, halogen, —OH, —N(R10)-C(O)—R20, or —$(C_1\text{-}C_4)$-alkyl, R10 is hydrogen atom, —$(C_1\text{-}C_4)$-alkyl or —O—$(C_1\text{-}C_4)$-alkyl, R11 is hydrogen atom, —$(C_1\text{-}C_4)$-alkyl or benzyl, R12 is hydrogen atom or R1 and R12 together with the nitrogen atom to which they are bonded form a piperidine ring and wherein said piperidine ring is mono- or disubstituted independently of one another by —$(C_1\text{-}C_4)$-alkyl or halogen, R20 is hydrogen atom, or —$(C_1\text{-}C_4)$-alkyl, R21 is hydrogen atom, —$(C_1\text{-}C_4)$-alkyl, —C(O)—R20, —$(C_1\text{-}C_4)$-alkyl-heteroaryl, wherein heteroaryl is defined above, heteroaryl, wherein heteroaryl is defined above, or —$(C_3\text{-}C_8)$-cycloalkyl, wherein cycloalkyl is unsubstituted or mono-, di- or trisubstituted independently of one another by R10, in all its stereoisomeric forms and mixtures thereof in any ratio, and its physiologically tolerable salts.

11) The present invention also relates to compounds of the formula Ia, wherein

R1 is —$(C_1\text{-}C_4)$-alkylene-$(C_3\text{-}C_{12})$-cycloalkyl, wherein cycloalkyl is mono-, di- or trisubstituted independently of one another by R2, —$(C_1\text{-}C_4)$-alkylene-aryl, wherein aryl is selected out of the group phenyl, tetrahydronaphthalenyl, naphthyl, biphenylyl, anthryl, indanyl, and fluorenyl, wherein said alkylene or aryl is independently from each other mono-, di- or trisubstituted independently of one another by R3, —$(C_1\text{-}C_4)$-alkylene-heterocyclyl, wherein heterocyclyl is selected out of the group acridinyl, azaindole (1H-pyrrolopyridinyl), azabenzimidazolyl, azaspirodecanyl, azepinyl, azetidinyl, benzimidazolyl, 2,3-dihydro-benzofuranyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydro-benzo[1,4]-dioxinyl, 4,5-dihydrooxazolinyl, dioxazolyl, dioxazinyl, 1,3-dioxanyl, 1,4-dioxanyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydro-furanyl, furanyl, furazanyl, imidazolidinyl, imidazolinyl, imidazolyl, imidazo[1,2a]-pyridyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 7-oxa-bicyclo[2.2.1]heptanelyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2- oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2']bi-pyridinyl, tetrahydro-isoquinolinyl, tetrahydroquinolinyl, tetrahydrofuranyl, tetrahydropyranyl, tetrahydropyridinyl, tetrahydrothiophenyl, tetrahydrothiophenyl-1,1-dioxide, tetrahydrothiopyranyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein said alkylene or heterocyclyl is independently from each other unsubstituted or mono-, di- or trisubstituted independently of one another by R4, cyclopropyl-heterocyclyl, wherein heterocyclyl is defined above for heterocyclyl, and wherein said heterocyclyl is unsubstituted or mono-, di- or trisubstituted independently of one another by R4, heterocyclyl, wherein heterocyclyl is defined above for heterocyclyl, and wherein said heterocyclyl is unsubstituted or mono-, di- or trisubstituted independently of one another by R4, aryl, wherein aryl is selected out of the group phenyl, naphthyl, biphenylyl, tetrahydronaphthalenyl, anthryl, indanyl, and fluorenyl, wherein aryl is mono-, di- or trisubstituted independently of one another by R3, —($C_3$-$C_{12}$)-cycloalkyl, wherein cycloalkyl is mono-, di-, tri- or tetrasubstituted independently of one another by R2, or —($C_1$-$C_4$)-alkyl, wherein alkyl is mono-, di- or trisubstituted independently of one another by R14, X is —O-aryl, wherein aryl is selected out of the group phenyl, naphthyl, indanyl, indanyl-1-one, biphenylyl, anthryl and fluorenyl, wherein aryl is mono-, di- or trisubstituted independently of one another by R6, —O-heterocyclyl, wherein heterocyclyl is selected out of the group acridinyl, azaindole (1H-pyrrolopyridinyl), azabenzimidazolyl, azaspirodecanyl, azepinyl, azetidinyl, benzimidazolyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydro-benzofuranyl, 2,3-dihydro-benzo[1,4]-dioxinyl, 4,5-dihydrooxazolinyl, dioxazolyl, dioxazinyl, 1,3-dioxanyl, 1,4-dioxanyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, imidazo[1,2a]pyridyl, indanyl, 1H-indazolyl, indolinyl, indolizinyl, indolyl, 3H-indolyl, isobenzofuranyl, isochromanyl, isoindazolyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 7-oxa-bicyclo[2.2.1]heptanelyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2']bi-pyridinyl, tetra-hydrofuranyl, tetrahydro-isoquinolinyl, tetrahydro-quinolinyl, tetrahydropyranyl, tetrahydropyridinyl, tetrahydrothiophenyl, tetrahydrothiophenyl-1,1-dioxide, tetrahydrothiopyranyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R7, —($C_1$-$C_4$)-alkyl-R17, wherein said alkyl is unsubstituted or mono-, di- or trisubstituted independently of one another by R17, —($C_1$-$C_4$)-alkyl-aryl, wherein aryl is selected out of the group phenyl, naphthyl, indanyl, indanyl-1-one, biphenylyl, anthryl and fluorenyl, wherein aryl is mono-, di- or trisubstituted independently of one another by R8, —($C_1$-$C_4$)-alkyl-heterocyclyl, wherein heterocyclyl is defined above for —O-heterocyclyl, and wherein said heterocyclyl is unsubstituted or mono-, di- or trisubstituted independently of one another by R7, —(CH=CH)-aryl, wherein aryl is selected out of the group phenyl, naphthyl, indanyl, indanyl-1-one, biphenylyl, anthryl and fluorenyl, wherein aryl is mono-, di- or trisubstituted independently of one another by R8, —(CH=CH)-heterocyclyl, wherein heterocyclyl is defined above for —O-heterocyclyl, and wherein said heterocyclyl is unsubstituted or mono-, di- or trisubstituted independently of one another by R7, —(C≡C)-aryl, wherein aryl is selected out of the group phenyl, naphthyl, indanyl, indanyl-1-one, biphenylyl, anthryl and fluorenyl, wherein aryl is mono-, di- or trisubstituted independently of one another by R8, —(C≡C)-heterocyclyl, wherein heterocyclyl is defined above for —O-heterocyclyl, and wherein said heterocyclyl is unsubstituted or mono-, di- or trisubstituted independently of one another by R7, —CN, —O—($C_1$-$C_3$)-fluoroalkyl, —O—C(O)-heteroaryl, wherein heteroaryl is selected out of the group imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, wherein heteroaryl is mono-, di- or trisubstituted independently of one another by R7, —N(R10)-heteroaryl, wherein heteroaryl is defined above for heteroaryl, and wherein said heteroaryl is unsubstituted or mono-, di- or trisubstituted independently of one another by R7, —S—$(C_1$-$C_4)$-alkyl-R17, wherein said alkyl is unsubstituted or mono-, di- or trisubstituted independently of one another by R17, —S—$(C_3$-$C_8)$-cycloalkyl, wherein said cycloalkyl is unsubstituted or mono-, di- or trisubstituted independently of one another by R17, —$SO_2$—$(C_3$-$C_8)$-cycloalkyl, wherein said cycloalkyl is unsubstituted or mono-, di- or trisubstituted independently of one another by R17, —O—$SO_2$-aryl, wherein aryl is selected out of the group phenyl, naphthyl, indanyl, indanyl-1-one, biphenylyl, anthryl and fluorenyl, wherein aryl is mono-, di- or trisubstituted independently of one another by R8, —S-aryl, wherein aryl is selected out of the group phenyl, naphthyl, indanyl, indanyl-1-one, biphenylyl, anthryl and fluorenyl, wherein aryl is mono-, di- or trisubstituted independently of one another by R8, —S-heterocyclyl, wherein heterocyclyl is defined above for —O-heterocyclyl, and wherein said heterocyclyl is unsubstituted or mono-, di- or trisubstituted independently of one another by R7, or —S—$(C_1$-$C_4)$-alkyl, wherein said alkyl is unsubstituted or mono-, di- or trisubstituted independently of one another by R18, R2, R3, R14, R17 and R18 are independent of one another are identical or different and are a hydrogen atom, —$(C_1$-$C_4)$-alkyl, —OH, —$(C_1$-$C_4)$-alkyl-OH, halogen, —$(C_1$-$C_3)$-fluoroalkyl, —C(O)—OH, —C(O)—O—$(C_1$-$C_4)$-alkyl, —O—$(C_1$-$C_4)$-alkyl, —CN, —O—$(C_1$-$C_3)$-fluoroalkyl, —N(R10)-R21, —NH—C(O)—$(C_1$-$C_4)$-alkyl, —S—$(C_1$-$C_4)$-alkyl, —$S(O)_2$—$(C_1$-$C_3)$-alkyl, —$(C_1$-$C_3)$-alkyl-O—$(C_1$-$C_3)$-alkyl, phenyl, or —O—$(C_1$-$C_4)$-alkyl-phenyl, R6 is aryl, wherein aryl is selected out of the group phenyl, naphthyl, indanyl, indanyl-1-one, biphenylyl, anthryl and fluorenyl, wherein aryl is mono-, di- or trisubstituted independently of one another by R10, —O-aryl, wherein aryl is selected out of the group phenyl, naphthyl, indanyl, indanyl-1-one, biphenylyl, anthryl and fluorenyl, wherein aryl is mono-, di- or trisubstituted independently of one another by R10, —$(C_1$-$C_4)$-alkylene-aryl, wherein aryl is selected out of the group phenyl, naphthyl, indanyl, indanyl-1-one, biphenylyl, anthryl and fluorenyl, wherein aryl is mono-, di- or trisubstituted independently of one another by R10, heteroaryl, wherein heteroaryl is defined above for heteroaryl, and wherein said heteroaryl is unsubstituted or mono-, di- or trisubstituted independently of one another by R10, —O-heteroaryl, wherein heteroaryl is defined above for heteroaryl, and wherein said heteroaryl is unsubstituted or mono-, di- or trisubstituted independently of one another by R10, —C(O)-heteroaryl, wherein heteroaryl is defined above for heteroaryl, and wherein said heteroaryl is unsubstituted or mono-, di- or trisubstituted independently of one another by R10, —$(C_1$-$C_4)$-alkylene-heteroaryl, wherein heteroaryl is defined above for heteroaryl, and wherein said heteroaryl is unsubstituted or mono-, di- or trisubstituted independently of one another by R10, —O—$(C_1$-$C_4)$-alkylene-heteroaryl, wherein heteroaryl is defined above for heteroaryl, and wherein said heteroaryl is unsubstituted or mono-, di- or trisubstituted independently of one another by R10, —$(C_3$-$C_8)$-cycloalkyl, wherein cycloalkyl is unsubstituted or mono-, di- or trisubstituted independently of one another by R10, hydrogen atom, —$(C_1$-$C_4)$-alkylene-N(R10)-R21, —C(O)—N(R10)-R20, —N(R10)-R21, —$(C_1$-$C_4)$-alkyl, —$(C_1$-$C_4)$-alkyl-CN, —$(C_1$-$C_3)$-fluoroalkyl, —O—$(C_1$-$C_4)$-alkyl, halogen, —C(O)—O—R10, —$(C_1$-$C_3)$-alkylene-C(O)—O—R10, —NH—C(O)—$(C_1$-$C_4)$-alkyl, —C(O)—$(C_1$-$C_4)$-alkyl, or —$NO_2$, R4 and R7 are independent of one another are identical or different and are a hydrogen atom, —$(C_1$-$C_4)$-alkyl, —O—$(C_1$-$C_4)$-alkyl, —$(C_1$-$C_5)$-alkyl-OH, halogen, —C(O)—O—R10, =O, —$(C_1$-$C_3)$-alkylene-C(O)—O—R10, —C(O)—N(R10)-R20, —N(R10)-R21, —CN, —$(C_1$-$C_3)$-fluoroalkyl, —$(C_1$-$C_3)$-alkyl-O—$(C_1$-$C_3)$-alkyl, —C(O)—$(C_1$-$C_4)$-alkyl, —C(O)—$(C_1$-$C_3)$-fluoroalkyl, —C(O)—$(C_3$-$C_8)$-cycloalkyl, —C(O)-aryl, wherein aryl is selected out of the group phenyl, naphthyl, indanyl, indanyl-1-one, biphenylyl, anthryl and fluorenyl, wherein aryl is mono-, di- or trisubstituted independently of one another by R6, aryl, wherein aryl is selected out of the group phenyl, naphthyl, indanyl, indanyl-1-one, biphenylyl, anthryl and fluorenyl, wherein aryl is mono-, di- or trisubstituted independently of one another by R6, methanesulfonyl, or heteroaryl, wherein heteroaryl is defined above, R8 and R9 are independent of one another are identical or different and are a hydrogen atom, halogen, —OH, —N(R10)-C(O)—R20, or —$(C_1$-$C_4)$-alkyl, R10 is hydrogen atom, —$(C_1$-$C_4)$-alkyl or —O—$(C_1$-$C_4)$-alkyl, R11 is hydrogen atom, —$(C_1$-$C_4)$-alkyl or benzyl, R12 is hydrogen atom or R1 and R12 together with the nitrogen atom to which they are bonded form a four- to eight-membered monocyclic heterocyclic ring which, as well as the nitrogen atom, may additionally, according to the ring size, also contain one or two identical or different heteroatoms from the group of oxygen, nitrogen and sulfur wherein four- to eight-membered monocyclic heterocyclic ring is mono-, di- or trisubstituted independently of one another by —$(C_1$-$C_4)$-alkyl or halogen, R20 is hydrogen atom, or —$(C_1$-$C_4)$-alkyl, R21 is hydrogen atom, —$(C_1$-$C_4)$-alkyl, —C(O)—R20, —$(C_1$-$C_4)$-alkyl-heteroaryl, wherein heteroaryl is defined above, heteroaryl, wherein heteroaryl is defined above, or —$(C_3$-$C_8)$-cycloalkyl, wherein cycloalkyl is unsubstituted or mono-, di- or trisubstituted independently of one another by R10, in all its stereoisomeric forms and mixtures thereof in any ratio, and its physiologically tolerable salts.

12) The present invention also relates to compounds of the formula Ia, wherein

R1 is —$(C_1$-$C_4)$-alkylene-aryl, wherein aryl is selected out of the group phenyl, tetrahydronaphthalenyl, naphthyl, biphenylyl, anthryl, indanyl, and fluorenyl, wherein said alkylene or aryl is independently from each other mono-, or disubstituted independently of one another by R3, heterocyclyl, wherein heterocyclyl is selected out of the group chromanyl, piperidinyl, pyridyl, pyrimidinyl, pyrrolidinyl, tetrahydropyranyl, tetrahydrothiopyranyl, thienothiophenyl, thiophenyl and thiopyranyl, and wherein said heterocyclyl is unsubstituted or mono-substituted by R4, or
—($C_3$-$C_{12}$)-cycloalkyl, wherein cycloalkyl is mono- or-, disubstituted independently of one another by R2, X is —O-aryl, wherein aryl is selected out of the group phenyl, naphthyl, indanyl, indanyl-1-one, biphenylyl, anthryl and fluorenyl, wherein aryl is mono-, di- or trisubstituted independently of one another by R6,
—O-heterocyclyl, wherein heterocyclyl is selected out of the group chromanyl, piperidinyl, pyridyl, pyrimidinyl, pyrrolidinyl, tetrahydropyranyl, tetrahydrothiopyranyl, thienothiophenyl, thiophenyl and thiopyranyl, and wherein said heterocyclyl is unsubstituted or mono-, di- or trisubstituted independently of one another by R7,
—O—($C_1$-$C_3$)-fluoroalkyl,
—S—($C_1$-$C_4$)-alkyl-R17, wherein said alkyl is unsubstituted or mono-, di- or trisubstituted independently of one another by R17, or
—S-heterocyclyl, wherein heterocyclyl is defined above for —O-heterocyclyl, and wherein said heterocyclyl is unsubstituted or mono-, di- or trisubstituted independently of one another by R7, R2, R3 and R17 are independent of one another are identical or different and are a hydrogen atom, —($C_1$-$C_4$)-alkyl, —($C_1$-$C_4$)-alkyl-OH, halogen, —($C_1$-$C_3$)-fluoroalkyl, —O—($C_1$-$C_3$)-fluoroalkyl or —O—($C_1$-$C_4$)-alkyl-phenyl,
R6 is hydrogen atom, —($C_1$-$C_4$)-alkylene-N(R10)-R21, —C(O)—N(R10)-R20 or halogen,
R4 and R7 are independent of one another are identical or different and are a hydrogen atom, —($C_1$-$C_4$)-alkyl, —($C_1$-$C_5$)-alkyl-OH, halogen, —CN, —($C_1$-$C_3$)-fluoroalkyl, or —C(O)—($C_1$-$C_3$)-fluoroalkyl,
R10, R11, R12 and R20 are each a hydrogen atom,
R21 is hydrogen atom or —($C_3$-$C_8$)-cycloalkyl,
in all its stereoisomeric forms and mixtures thereof in any ratio, and its physiologically tolerable salts.

13) The present invention also relates to compounds of the formula Ia, wherein
R1 is —($C_1$-$C_4$)-alkylene-phenyl, wherein said alkylene or phenyl is independently from each other mono-, or disubstituted by R3,
heterocyclyl, wherein heterocyclyl is selected out of the group chromanyl, piperidinyl, tetrahydropyranyl, tetrahydrothiopyranyl, and thiopyranyl, and wherein said heterocyclyl is unsubstituted or mono-substituted by R4, or
—($C_3$-$C_{12}$)-cycloalkyl, wherein cycloalkyl is cyclopentanyl, cyclohexyl or bicyclo[2.2.1]heptanyl wherein said cycloalkyl is mono- or-, disubstituted independently of one another by R2, X is —O-phenyl, wherein phenyl is mono- or di-substituted independently of one another by R6,
—O-heterocyclyl, wherein heterocyclyl is selected out of the group chromanyl, pyridyl, pyrimidinyl and thienothiophenyl, and wherein said heterocyclyl is unsubstituted or mono-, di- or trisubstituted independently of one another by R7,
—O—($C_1$-$C_3$)-fluoroalkyl,
—S—($C_1$-$C_4$)-alkyl-R17, wherein said alkyl is unsubstituted or mono-, di- or trisubstituted independently of one another by R17, or
—S-pyrimidinyl or S-pyrazinyl, wherein pyrimidinyl or pyrazinyl is each unsubstituted or mono-, di- or trisubstituted independently of one another by R7, R2, R3 and R17 are independent of one another are identical or different and are a hydrogen atom, —($C_1$-$C_4$)-alkyl, —($C_1$-$C_4$)-alkyl-OH, halogen, —($C_1$-$C_3$)-fluoroalkyl, —O—($C_1$-$C_3$)-fluoroalkyl or —O—($C_1$-$C_4$)-alkyl-phenyl,
R6 is hydrogen atom, —($C_1$-$C_4$)-alkylene-N(R10)-R21, —C(O)—N(R10)-R20 or halogen,
R4 and R7 are independent of one another are identical or different and are a hydrogen atom, —($C_1$-$C_4$)-alkyl, —($C_1$-$C_5$)-alkyl-OH, halogen, —CN, —($C_1$-$C_3$)-fluoroalkyl, or —C(O)—($C_1$-$C_3$)-fluoroalkyl,
R10, R11, R12 and R20 are each a hydrogen atom,
R21 is hydrogen atom or —($C_3$-$C_8$)-cycloalkyl,
in all its stereoisomeric forms and mixtures thereof in any ratio, and its physiologically tolerable salts.

14) The present invention also relates to compounds of the formula I or Ia and/or in all its stereoisomeric forms and mixtures thereof in any ratio, and/or a physiologically acceptable salt of the compound of the formula I or Ia, where the compound of the formula I or Ia is selected from the group consisting of 1-Cyclohexyl-3-[(3S,3aR,6S,6aS)-6-(4-fluoro-phenoxy)-hexahydro-furo[3,2-b]furan-3-yl]-urea, 1-Cyclohexyl-3-[(3S,3aR,6S,6aS)-6-(6-methyl-pyridin-3-yloxy)-hexahydro-furo[3,2-b]furan-3-yl]-urea, 1-Cyclohexyl-3-[(3S,3aR,6S,6aS)-6-(2-methyl-pyrimidin-5-yloxy)-hexahydro-furo[3,2-b]furan-3-yl]-urea, 1-[(3S,3aR,6S,6aS)-6-(2-Methyl-pyridin-3-yloxy)-hexahydro-furo[3,2-b]furan-3-yl]-3-(2-trifluoromethoxy-benzyl)-urea, 1-(4,4-Difluoro-cyclohexyl)-3-[(3S,3aR,6S,6aS)-6-(4-fluoro-phenoxy)-hexahydro-furo[3,2-b]furan-3-yl]-urea, 1-Cyclohexyl-3-[(3S,3aR,6S,6aS)-6-(2-methyl-pyridin-3-yloxy)-hexahydro-furo[3,2-b]furan-3-yl]-urea, 1-Cyclohexyl-3-[(3S,3aR,6S,6aS)-6-(pyridin-3-yloxy)-hexahydro-furo[3,2-b]furan-3-yl]-urea; compound with trifluoro-acetic acid, 1-[(3S,3aR,6S,6aS)-6-(4-Fluoro-phenoxy)-hexahydro-furo[3,2-b]furan-3-yl]-3-[1-(2,2,2-trifluoro-acetyl)-piperidin-4-yl]-urea, 1-[(3S,3aR,6S,6aS)-6-(4-Fluoro-phenoxy)-hexahydro-furo[3,2-b]furan-3-yl]-3-(tetrahydro-pyran-4-yl)-urea, 1-Cyclohexyl-3-[(3S,3aR,6S,6aS)-6-(5-fluoro-pyridin-3-yloxy)-hexahydro-furo[3,2-b]furan-3-yl]-urea, 1-Cyclohexyl-3-[(3S,3aR,6S,6aS)-6-(5-methyl-pyridin-3-yloxy)-hexahydro-furo[3,2-b]furan-3-yl]-urea, 1-(1S,2S,4R)-Bicyclo[2.2.1]hept-2-yl-3-[(3S,3aR,6S,6aS)-6-(2-methyl-pyridin-3-yloxy)-hexahydro-furo[3,2-b]furan-3-yl]-urea, 1-Cyclohexyl-3-{(3S,3aR,6S,6aS)-6-[5-(1-hydroxy-1-methyl-ethyl)-pyridin-3-yloxy]-hexahydro-furo[3,2-b]furan-3-yl}-urea; hydrochloride, 1-Cyclohexyl-3-[(3S,3aR,6S,6aS)-6-(3-hydroxy-1,1-dimethyl-propylsulfanyl)-hexahydro-furo[3,2-b]furan-3-yl]-urea, 1-Cyclohexyl-3-[(3S,3aR,6S,6aS)-6-(3-cyclopropylaminomethyl-phenoxy)-hexahydro-furo[3,2-b]furan-3-yl]-urea; compound with trifluoro-acetic acid, 3-[(3S,3aS,6S,6aR)-6-(3-Cyclohexyl-ureido)-hexahydro-furo[3,2-b]furan-3-yloxy]-benzamide, 1-Cyclohexyl-3-[(3S,3aR,6S,6aS)-6-(6-methyl-5,6-dihydro-thieno[3,2-b]thiophen-3-yloxy)-hexahydro-furo[3,2-b]furan-3-yl]-urea, 1-[(3S,3aR,6S,6aS)-6-(2-Cyano-pyridin-3-yloxy)-hexahydro-furo[3,2-b]furan-3-yl]-3-cyclohexyl-urea, 1-Cyclohexyl-3-[(3S,3aR,6S,6aS)-6-(6-trifluoromethyl-pyridin-3-yloxy)-hexahydro-furo[3,2-b]furan-3-yl]-urea, 1-Chroman-4-yl-3-[(3S,3aR,6S,6aS)-6-(2-methyl-pyridin-3-yloxy)-hexahydro-furo[3,2-b]furan-3-yl]-urea, 1-Cyclohexyl-3-[(3S,3aR,6S,6aS)-6-(2,6-dimethyl-pyrimidin-4-ylsulfanyl)-hexahydro-furo[3,2-b]furan-3-yl]-urea, 1-Cyclohexyl-3-[(3S,3aR,6S,6aS)-6-(pyrazin-2-ylsulfanyl)-hexahydro-furo[3,2-b]furan-3-yl]-urea, 1-(2-Difluoromethoxy-benzyl)-3-[(3S,3aR,6S,6aS)-6-(2-methyl-pyridin-3-yloxy)-hexahydro-furo[3,2-b]furan-3-yl]-urea, 1-(4,4-Dimethyl-cyclohexyl)-3-[(3S,3aR,6S,6aS)-6-(2-methyl-pyridin-3-yloxy)-hexahydro-furo[3,2-b]furan-3-yl]-urea, 1((1R,2R)-2-Benzyloxy-cyclopentyl)-3-[(3S,3aR,6S,6aS)-6-(4-fluoro-phenoxy)-hexahydro-furo[3,2-b]furan-3-yl]-urea, 1-[(3S,3aR,6S,6aS)-6-(2-Methyl-pyridin-3-yloxy)-hexahydro-furo[3,2-b]furan-3-yl]-3-[2-(2-trifluoromethoxy-phenyl)-ethyl]-urea, 1-[(3S,3aR,6S,6aS)-6-(4-Fluoro-phenoxy)-hexahydro-furo[3,2-b]furan-3-yl]-3-[(R)-1-(4-fluoro-phenyl)-ethyl]-urea, 1-[(3S,3aR,6S,6aS)-6-(2-Methyl-pyridin-3-yloxy)-hexahydro-furo[3,2-b]furan-3-yl]-3-(tetrahydro-thiopyran-4-yl)-urea, and 1-Cyclohexyl-3-[(3S,3aR,6S,6aS)-6-(2,2,2-trifluoro-ethoxy)-hexahydro-furo[3,2-b]furan-3-yl]-urea.

As used herein, the term alkyl is to be understood in the broadest sense to mean hydrocarbon residues which can be linear, i. e. straight-chain or branched. All these statements also apply if an alkyl group occurs as a substituent on another residue, for example in an alkyloxy residue, an alkyloxycarbonyl residue or an arylalkyl residue. Examples of "—($C_1$-$C_4$)-alkyl" or "—($C_1$-$C_4$)-alkylene" are alkyl residues containing 1, 2, 3 or 4 carbon atoms are methyl, methylene, ethyl, ethylene, propyl, propylene, butyl, or butylene, the n-isomers of all these residues, isopropyl, isobutyl, sec-butyl, tert-butyl.

The term "—($C_3$-$C_8$)-cycloalkyl" is understood as meaning cyclic alkyl residues containing 3, 4, 5, 6, 7 or 8 ring carbon atoms like cyclopropyl, cyclobutyl, cyclopentyl, cyclohexyl, cycloheptyl or cyclooctyl, which can also be substituted and/or unsaturated. Unsaturated cyclic alkyl groups and unsaturated cycloalkyl groups like, for example, cyclopentenyl or cyclohexenyl can be bonded via any carbon atom.

The term "aryl" is understood as meaning aromatic hydrocarbon radicals containing from 6 to 14 carbon atoms depending on the number of carbon atoms in one, two or three rings. Examples of aryl radicals are phenyl, tetrahydronaphthalenyl, naphthyl, biphenylyl, anthryl, indanyl, and fluorenyl for example 2-biphenylyl, 3-biphenylyl and 4-biphenylyl, anthryl or fluorenyl. Biphenylyl radicals, naphthyl radicals and, in particular, phenyl radicals are preferred aryl radicals.

The term "-heterocyclyl" refers to a ring system containing 4 to 15 ring carbon atoms, wherein depending on the ring size one, two, three or four of the 4 to 15 ring carbon atoms are independently replaced by nitrogen, oxygen or sulfur atoms. Examples are acridinyl, azaindole (1H-pyrrolopyridinyl), azabenzimidazolyl, azaspirodecanyl, azepinyl, azetidinyl, benzimidazolyl, 2,3-dihydro-benzofuranyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydro-benzo[1,4]-dioxinyl, 4,5-dihydrooxazolinyl, dioxazolyl, dioxazinyl, 1,3-dioxanyl, 1,4-dioxanyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydro-furanyl, furanyl, furazanyl, imidazolidinyl, imidazolinyl, imidazolyl, imidazo[1,2a]-pyridyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 7-oxa-bicyclo[2.2.1]heptanelyl, oxadiazolyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2′]bi-pyridinyl, tetrahydro-isoquinolinyl, tetrahydroquinolinyl, tetrahydrofuranyl, tetrahydropyranyl, tetrahydropyridinyl, tetrahydrothiophenyl, tetrahydrothiophenyl-1,1-dioxide, tetrahydrothiopyranyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, The term "=O" refers to residues such as carbonyl (—C(O)—), sulfinyl (—S(O)—) or nitroso (—N=O).

The term "($C_3$-$C_{12}$)-cycloalkyl" means a ring system containing 3 to 12 carbon atoms in mono-, bi- or tricycles or bridged rings, such as the monocycles cyclopropane, cyclobutane, cyclopentane, cyclohexane, cycloheptane or cyclooctane, or bicycles such as bicyclo[4.2.0]octane, bicyclo[2.2.1]heptane, bicyclo[3.1.1]heptane, octahydroindene, decahydronaphthalene, decahydroazulene, decahydrobenzocycloheptene or dodecahydroheptalene, or tricycles such as adamantane or octahydro-4,7-methano-indene, or bridged rings such as spiro[2.5]octane, spiro[3.4]octane, spiro[3.5]nonane, bicyclo[3.1.1]heptane, bicyclo[2.2.1]heptane, bicyclo[2.2.2]octane, 1,4-dioxa-spiro[4.5]decane, or octahydro-4,7-methanindene.

The term "R1 and R12 together with the nitrogen atom to which they are bonded form a four- to eight-membered monocyclic heterocyclic ring which, as well as the nitrogen atom, may additionally, according to the ring size, also contain one or two identical or different heteroatoms from the group of oxygen, nitrogen and sulfur" is understood to mean radicals such as azepane, azepine, azetidine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, morpholine, [1,4]oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole.

The term "—($C_1$-$C_3$)-fluoroalkyl" is a partial or totally fluorinated alkyl-residue, which can be derived from residues such as —$CF_3$, —$CHF_2$, —$CH_2F$, —CHF—$CF_3$, —CHF—$CHF_2$, —CHF—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—CHF—$CF_3$, —$CH_2$—CHF—$CHF_2$, —$CH_2$—CHF—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —CHF—CHF—$CF_3$, —CHF—CHF—$CHF_2$, —CHF—CHF—$CH_2F$, —CHF—$CH_2$—$CF_3$, —CHF—$CH_2$—$CHF_2$, —CHF—$CH_2$—$CH_2F$, —CHF—$CF_2$—$CF_3$, —CHF—$CF_2$—$CHF_2$, —CHF—$CF_2$—$CH_2F$, —$CF_2$—CHF—$CF_3$, —$CF_2$—CHF—$CHF_2$, —$CF_2$—CHF—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$. Halogen is fluorine, chlorine, bromine or iodine, preferably fluorine, chlorine or bromine, particularly preferably chlorine or fluorine.

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formulae I.

Examples for stereoisomeric forms of the compound of formula I are e.g.:

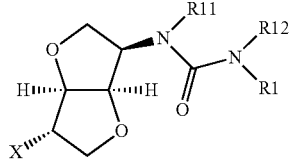
(a)

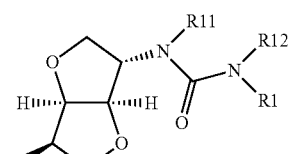
(b)

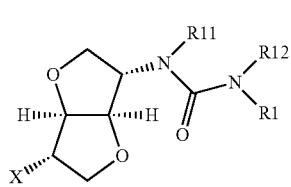
(c)

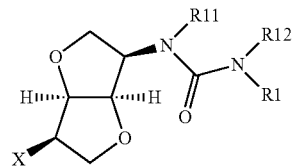
(d)

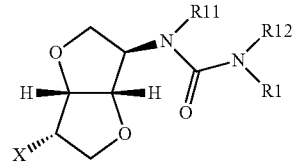
(e)

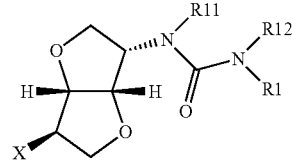
(f)

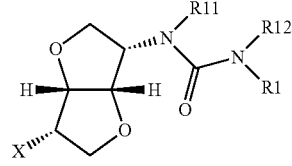
(g)

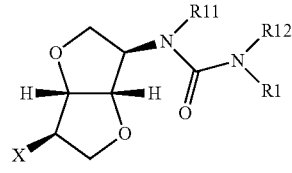
(h)

Preferred stereoisomeric form of the compound of formula I is the following compound of formula Ia:

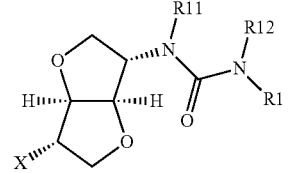
(Ia)

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

If the compounds of the formulae I or Ia comprise one or more acidic or basic groups, for example basic heterocyclic groups, the corresponding physiologically or toxicologically acceptable salts are also included in the invention, especially the pharmaceutically acceptable salts. The compounds of the formulae I or Ia may thus be deprotonated on an acidic group and be used for example as alkali metal salts or as ammonium salts. Compounds of the formulae I or Ia comprising at least one basic group may also be prepared and used in the form of their acid addition salts, for example in the form of pharmaceutically acceptable salts with inorganic acids and organic acids. Salts can in general be prepared from acidic and basic compounds of the formulae I or Ia by reaction with a base or an acid in a solvent or diluent according to customary procedures. If the compounds of the formulae I or Ia simultaneously contain an acidic and a basic group in the molecule, the invention also includes internal salts (betaines, zwitterions) in addition to the salt forms mentioned. The present invention also comprises all salts of the compounds of the formulae I or Ia which, because of low physiological tolerability, are not directly suitable for use as a pharmaceutical, but are suitable as intermediates for chemical reactions or for the preparation of physiologically acceptable salts, for example by means of anion exchange or cation exchange.

Salts of compounds of the formulae I or Ia can be obtained by customary methods known to those skilled in the art, for example by combining a compound of the formulae I or Ia with an inorganic or organic acid or base in a solvent or dispersant, or from other salts by cation exchange or anion exchange. The present invention furthermore includes all solvates of compounds of the formula I for example hydrates or adducts with alcohols.

The compounds of the formulae I or Ia can be prepared by utilising procedures and techniques, which per se are well known and appreciated by one of ordinary skill in the art. Starting materials or building blocks for use in the general synthetic procedures that can be applied in the preparation of the compounds of formulae I or Ia are readily available to one of ordinary skill in the art. In many cases they are commercially available or have been described in the literature. Otherwise they can be prepared from readily available precursor compounds analogously to procedures described in the literature, or by procedures or analogously to procedures described in this application.

The present invention also relates to processes for the preparation of the compounds of the formulae I and Ia which are outlined below and by which the compounds of the formulae I and Ia as well as intermediates occurring in the course of their synthesis are obtainable. The preparation of compounds of formula I is outlined below as an example, but can easily adopted also for the compounds of formula Ia. The following schemes are provided to more fully illustrate the present invention. Representative compounds of formula I have been prepared by the reaction schemes below. It is understood that other synthetic approaches to these structural classes are conceivable to one skilled in the art. It is within the abilities of a person skilled in the art to replace the exemplary compounds shown in the schemes and exemplary reagents given in the text by appropriate alternative compounds or reagents or to omit or add synthetic steps when appropriate.

The various organic group transformations and utilization of protecting groups described herein can be performed by a number of procedures other than those illustrated below. References can be found in, for example, P. G. M. Wuts, T. W. Greene, Protective Groups in Organic Synthesis, 2nd Edition, John Wiley and Sons (1999), 17-248, 369-453 and 494-653, and the references quoted therein.

In general, compounds of the formulae I and Ia can be prepared, for example in the course of a convergent synthesis, by linking two or more fragments which can be derived retrosynthetically from the formulae I and Ia.

The invention also relates to a process for preparing a compound of the formulae I and/or Ia and/or a stereoisomeric or tautomeric form of the compound of the formulae I and/or Ia and/or a physiologically tolerated salt of the compound of the formulae I and/or Ia which allows the preparation of the compounds of the formulae I and/or Ia, their stereoisomeric or tautomeric forms or their physiologically acceptable salts and which comprises a) linking the compound of formula II with a compound of formula III using a suitable 'CO'-equivalent

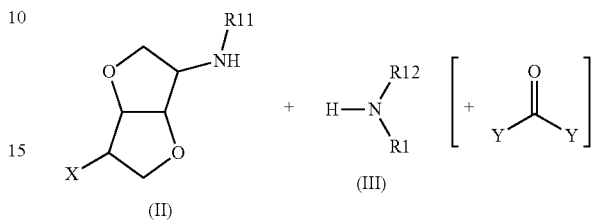

wherein X, R1, R11 and R12 are as defined for formulae I or Ia, and Y is chlorine or imidazol,
to form a compound of formulae I or Ia or
b) linking the compound of formula IV with a compound of formula V

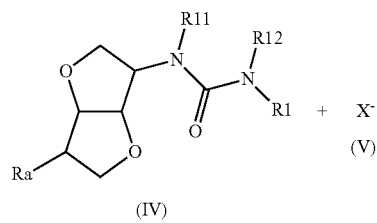

wherein X, R1, R11 and R12 are as defined for formulae I or Ia, and Ra is —OH or a —O-LG group, wherein LG is a leaving group such as triflate, mesylate, tosylate, or halides,
to form a compound of formulae I or Ia, or
c) fractionating the compound of the formulae I or Ia, which has been prepared by processes a) or b), which, owing to its chemical structure, occurs in enantiomeric or diastereomeric forms, by salt formation with enantiomerically pure acids or bases, chromatography on chiral stationary phases or derivatization by means of chiral enantiomerically pure compounds such as amino acids, separation of the diastereomers obtained in this way, and elimination of the chiral auxiliary groups, into the pure enantiomers or diastereomers; or
d) either isolating the compound of the formulae I or Ia prepared by processes a) to c) in free form or liberating it from non-physiologically acceptable salts or, in the case where acidic or basic groups are present, converting it into a physiologically acceptable salt.

For example, compounds of the formulae I and Ia can be prepared retro-synthetically by coupling of building blocks as shown in the following scheme:

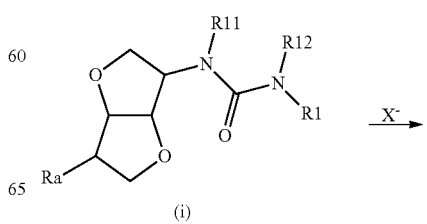

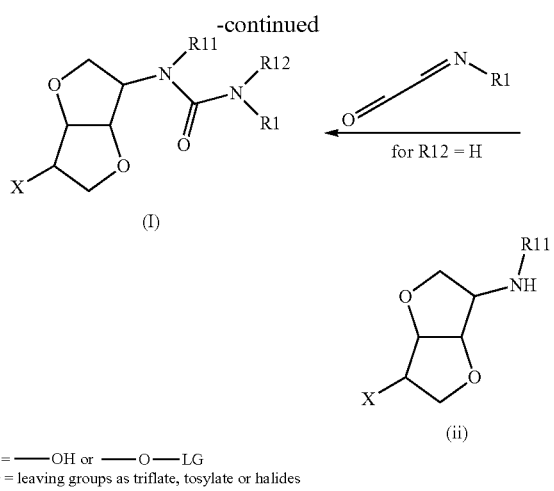

Ra = ——OH or ——O——LG
LG = leaving groups as triflate, tosylate or halides

Compounds of the general formula I can be assembled from a suitably substituted hexahydro-furo[3,2-b]furan-3,6-diol moiety (iii), which is commercially available in its specific stereoform or can be made from commercially available starting materials, and which can be transformed into a suitably derivatized building block like (v) or (vii) by a wide variety of methods.

Advanced Organic Chemistry, 6th Edition, Wiley-Interscience (2007), 425-656. Leaving groups can be preferably sulfonate esters as triflate, mesylate, or tosylate, or halides.

As shown in Scheme 1, in this process the compound of the formula (iii) can be first selectively mono-protected to give the compound of the formula (iv), for example by adding imidazole and tert-butyldimethylchlorosilane to a solution of the diol in an aprotic solvent such as for example N,N-dimethylformamide, for example at temperatures from about 0° C. to about 50° C. The obtained compound of the formula (iv) is treated with an excess of an appropriate sulfonyl chloride or sulfonyl anhydride such as trifluoromethanesulfonic anhydride in the presence of base such as pyridine or sodium hydroxide, with or without a suitable solvent such as for example tert.-butyl methyl ether or dichloromethane, at temperatures from about 0° C. to 80° C., to give building blocks of the formula (v) which can be converted to the appropriate compounds of the formula I.

Alternatively, the compounds of the formula (iii) can be selectively reacted to give compounds of the formula (vii) possessing two leaving groups with different reactivity which can be addressed consecutively by appropriate nucleophiles.

To access these building blocks, the hexahydro-furo[3,2-b]furan-3,6-diols (iii) are treated first with a small excess of a suitable sulfonyl chloride or sulfonyl anhydride such as p-toluenesulfonyl chloride in the presence of base such as Scheme 1

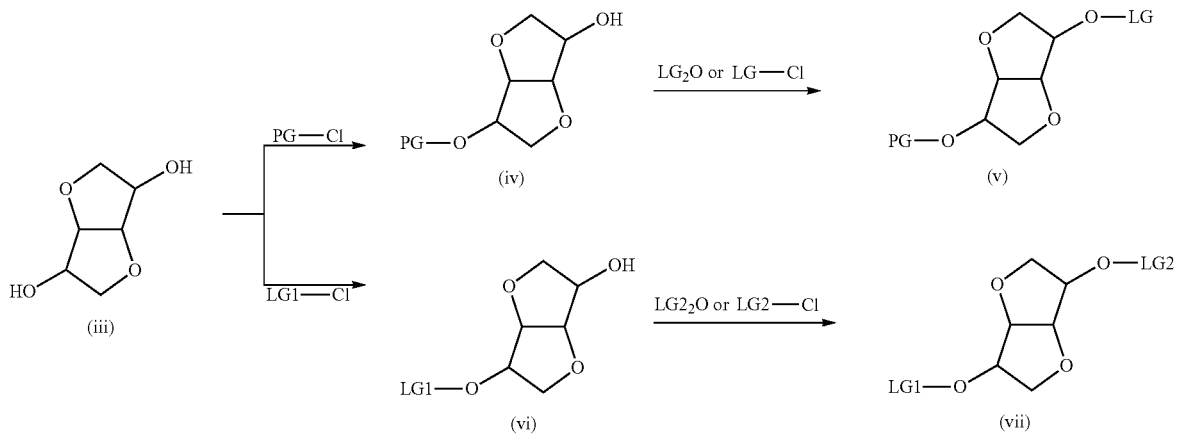

PG = silyl groups as TBS or TMS, alkyl groups as Bn or allyl
LG = leaving groups as triflate, tosylate or halides For example, one such process involves the selective derivatization of hydroxyl functionalities of hexahydro-furo[3,2-b]furan-3,6-diols of the formula (iii) to generate mono-derivatized alcohols by following similar synthetic methods as described, for example, in M. Vogler et al., Synthesis 2004, 8, 1211-1228; or V. Kumar et al., Org. Lett. 2007, 9, 3905-3908; and references within.

For the protection of alcohols many groups can be chosen, following processes known to a person skilled in the art described for example in P. G. M. Wuts and T. W. Greene, Greene's Protective Groups in Organic Synthesis, 2nd edition (1999), John Wiley & Sons, 17-245. Protecting groups (PG) for the alcohol functionality can be for example silyl groups as tert-butyl dimethyl silyl or alkyl and aryl groups such as benzyl or allyl.

For the conversion of alcohols into leaving groups (LG) many processes can be applied known to a person skilled in the art described for example in M. B. Smith, J. March, pyridine or sodium hydroxide, with or without a suitable solvent such as for example tert.-butyl methyl ether or dichloromethane, in a mono-phasic or bi-phasic system, at temperatures from about 0° C. to ambient temperature, to give the monoderivatized diol of the formula (vi), which can be isolated as a solid and purified via simple re-crystallization (similar transformations are described in WO2009/087379). The second free alcohol is then converted into another leaving group by employing a suitable reagent such as trifluoromethanesulfonic anhydride in a suitable solvent as for example dichloromethane, at temperatures from about 0° C. to about ambient temperature to give compounds of the formula (vii).

Alternatively, the intermediates (iv) and (vi) can be used directly as starting materials for the reaction with nucleophiles to introduce substituents like X or protected or unsubstituted amines following the routes described exemplary in schemes 2 and 4. The hydroxyl groups of the hexahydro-furo[3,2-b]furan scaffold of formulas (iii), (iv), (vi), or (vii) can be converted into substituted or un-substituted amino groups using processes and synthetic routes known to a person skilled in the art. The following general scheme (scheme 2) illustrates some of the possible ways to access these amines, but does not limit the present invention.

N,N-dimethylformamide, dimethylacetamide or dichloromethane, for example, at temperatures between RT and 120° C. With known procedures as catalytic hydrogenation, for example using palladium on charcoal or platinum oxide as catalyst, in a suitable solvent like methanol or ethyl acetate, or, in case of azides, treatment with triphenylphos-

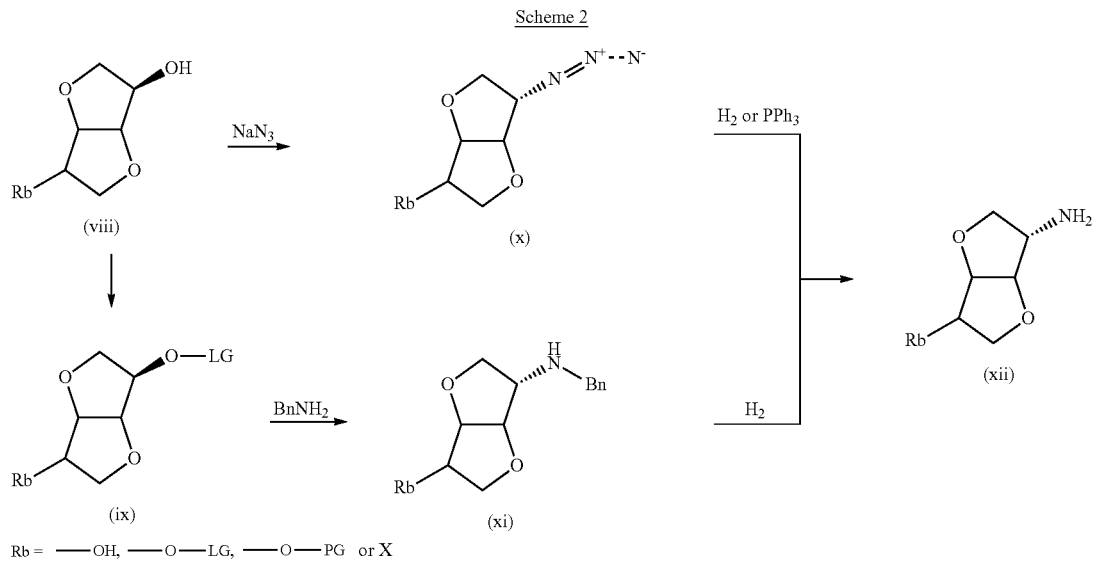

Compounds of the formula (x) can be synthesized from compounds of the formula (vii) with a free hydroxyl functionality using the Mitsunobu protocol. Alternatively, the leaving groups of compounds of the formula (ix) can be reacted with suitable amines, e.g. benzylamine, to give compounds of the formula (xi). These reactions can be carried out with or without a suitable aprotic solvent as phane following the Staudinger protocol, the free amines of the formula (xii) can be liberated.

The 6-amino-hexahydro-furo[3,2-b]furan-3-ols of the formula (xi) and (xii) can be converted to ureas using common procedures described for example in M. B. Smith, J. March, Advanced Organic Chemistry, 6th Edition, Wiley-Interscience (2007), 850-853 (scheme 3).

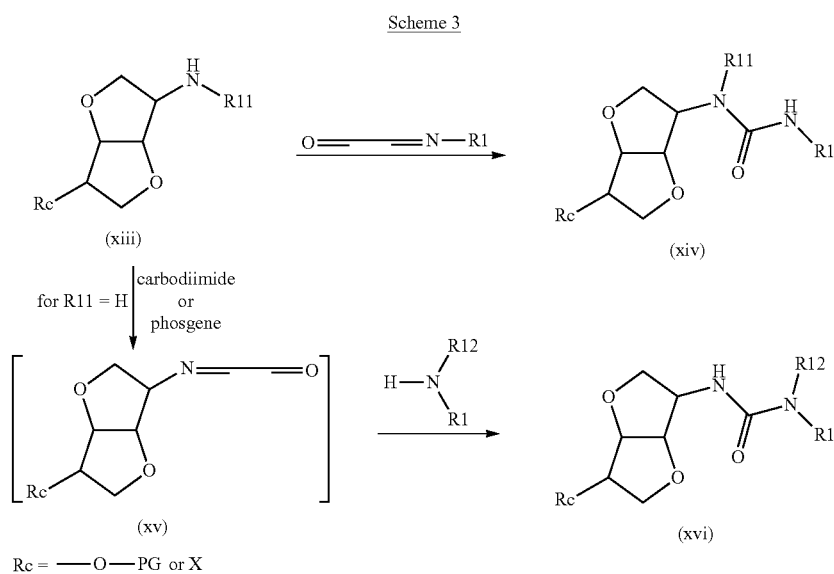

Amines of the formula (xiii) are reacted with isocyanates to produce ureas of the formula (xiv). This reaction works best in aprotic solvents as dichloromethane with addition of a base as triethylamine or Hünig's base, but other protocols known to a person skilled in the art can also be used.

Isocyanates of the formula (xv) can be generated from amines of the formula (xiii) by reaction with phosgene or phosgene equivalents to give ureas of the formula (xvi) after treatment with suitable amines.

Substituents X of compounds of the formula I can be introduced before or after the assembly of the urea moiety using synthetic routes and applying synthetic methods known to a person skilled in the art. The following general scheme (scheme 4) illustrates some of the possible ways, but does not limit the present invention. It is understood, that the hydroxyl group on the hexahydro-furo[3,2-b]furan scaffold can be liberated at a suitable stage of the synthesis. The hydroxy functionality can be liberated by methods known to the person skilled in art, in case of a tert-butyl dimethyl silyl protecting group, for example, by treatment with a suitable acid, e.g. hydrochloric acid or trifluoroacetic acid, without or in an appropriate solvent like dioxane or dichloromethane.

N,N-dimethylformamide, THF, acetonitrile or dimethylsulfoxide, at ambient temperature or with heating for example in a microwave oven up to 160° C., to give compounds of the formula (xix). The addition of carbonates, e.g. cesium carbonate, can lead to the formation or the respective carbamates.

A compound of the formula (xiv), (xvi) or (xix) can either represent compounds of the formula I or can be transformed into compounds of the formula I by deprotection steps and/or functional group transformations known to the person skilled in the art. In case of Rd being a protected or unprotected hydroxyl group or amine group, suitable transformation sequences have been described exemplary in schemes 2 and 3.

In general, protective groups that may still be present in the products obtained in the coupling reactions are then removed by standard procedures. For example, tert-butyl protecting groups, in particular a tert-butoxycarbonyl group, which is a protection form of an amino group, can be deprotected, i. e. converted into the amino group, by treatment with trifluoroacetic acid. As already explained, after

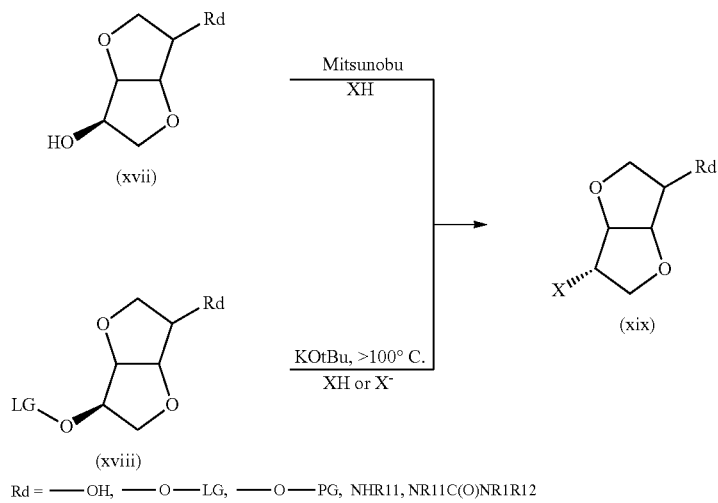

Scheme 4

Rd = ——OH, ——O——LG, ——O——PG, NHR11, NR11C(O)NR1R12

Starting from alcohols of the formula (xvii), nucleophiles can be introduced via the Mitsunobu reaction, using for example phenols, or thiophenols to give compounds of the formula (xix). The hydroxyl functionality of compounds of the formula (xvii) can also be transformed into a suitable leaving group, e.g. triflate or tosylate, by well-known procedures for example using pyridine and trifluoromethanesulfonic anhydride or tosyl chloride in dichloromethane at low temperatures (−10° C. to 15° C.) to give compounds of the formula (xviii). In case of building blocks of the formula (xviii) with suitable leaving groups, all common nucleophiles can be used for substitution of the hydroxyl functionality, for example described in R. C. Larock, Comprehensive Organic Transformations, A Guide to Functional Group Preparations, 2nd Edition, VCH Publishers, Inc. (1999), e.g. 77-128, 881-974, 1451-1460, and 1625-1676. The building block (xviii) is reacted with the nucleophile, e.g. a phenolate, thiophenolate, acetylene or cyanide, without or in the presence of a suitable base as potassium tert-butoxide, n-butyllithium or sodium hydroxide, in an aprotic solvent as the coupling reaction other functional groups can be generated from suitable precursor groups.

Both substituents of the hexahydro-furo[3,2-b]furan scaffold can be manipulated by procedures known to a person skilled in the art at all stages of the assembling sequence and functional groups can be substituted, deprotected, reduced, oxidized or transformed in another way into a different functional group.

These transformations can be, but are not limited to, oxidations of thioethers to sulfoxides and sulfones; derivatization of primary or secondary amines to give amides, ureas, or tertiary amines; reduction of nitriles to give aldehydes, alcohols or amines; reductive amination of aldehydes to give amines; ester formations or ester saponification; treatment of carbonyl functionalities with appropriate nucleophiles, e.g. Grignard reagents or hydrides, to give, for example, secondary or tertiary alcohols; coupling reactions using catalysts like palladium derivatives and aromatic or heteroaromatic halogen ides, e.g. chlorides or bromides, and amines as starting materials, for example using the Buchwald protocol.

In the preparation of the compounds of the formula I it can generally be advantageous or necessary in all reactions which are carried out in the course of the synthesis, to temporarily protect functional groups, which could lead to undesired reactions or side reactions in a synthesis step, or have them initially present in the form of precursor groups, and later deprotect them or convert them into the desired groups. Appropriate synthesis strategies and protective groups and precursor groups which are suitable for the respective case, are known to the person skilled in the art and can be found in P. G. M. Wuts and T. W. Greene, Greene's Protective Groups in Organic Synthesis, 2nd (1999), John Wiley & Sons, for example 17-248, 369-453 and 494-653. Protecting groups (or blocking groups) that may be present on functional groups include allyl, tert.-butyl, benzyl, allyloxycarbonyl (Alloc), tert-butoxycarbonyl (Boc), benzyloxycarbonyl (Z) and 9-fluorenylmethoxycarbonyl (Fmoc) as protecting groups for amino and amidino groups. Ester, alkyl, aryl and silyl protecting groups may be used to block hydroxyl groups. Carboxylic acids may be protected as esters for example methyl, ethyl and benzyl.

Protecting groups that may still be present in the products are then removed by standard procedures. In more detail, examples of protective groups which may be mentioned, are benzyl protective groups, for example benzyl ethers of hydroxy compounds, benzyl amines of amine compounds and benzyl esters of carboxylic acids, from which the benzyl group can be removed by catalytic hydrogenation in the presence of a palladium catalyst, tert-butyl protective groups, for example tert-butyl esters of carboxylic acids, from which the tert-butyl group can be removed by treatment with strong acids (e.g. hydrochloric acid, trifluoroacetic acid), acyl protective groups, for example ester and amides of hydroxy compounds and amino compounds, which can be cleaved by treatment with strong bases (e.g. LiOH, NaOH, KOH) or strong acids (e.g. HCl) in the presence of water, alkoxycarbonyl protective groups, for example tert-butoxycarbonyl derivatives of amino compounds, which can be cleaved by treatment with strong acids (e.g. hydrochloric acid, trifluoroacetic acid), or benzyloxycarbonyl derivatives of amino compounds, which can be cleaved by catalytic hydrogenation in the presence of a palladium catalyst. Other examples of precursors which may be mentioned, are halogen atoms which can be replaced by many other groups as outlined above, or nitro groups which can be converted into amino groups, for example by catalytic hydrogenation.

As is usual and applies to all reactions performed in the course of the synthesis of a compound of the formula I, appropriate details of the conditions applied in a specific preparation process, including the solvent, a base or acid, the temperature, the order of addition, the molar ratios and other parameters, are routinely chosen by the skilled person in view of the characteristics of the starting compounds and the target compound and the other particularities of the specific case. As is also known by the skilled person, not all processes described herein will in the same way be suitable for the preparation of all compounds of the formula I and their intermediates, and adaptations have to be made.

In all processes for the preparation of the compounds of the formula I, workup of the reaction mixture and the purification of the product is performed according to customary methods known to the skilled person which include, for example, quenching of a reaction mixture with water, adjustment to a certain pH, precipitation, extraction, drying, concentration, distillation, crystallization and chromatography including high performance liquid chromatography (HPLC) and reversed phase-high performance liquid chromatography (RP-HPLC) or other methods of separation based, for example, on the size, charge or hydrophobicity of the compound. Also for the characterization of the products, customary methods are used such as NMR, IR and mass spectroscopy (MS).

The compounds of the formula I can be isolated either in free form or, in the case of the presence of acidic or basic groups, converted into physiologically tolerable salts. Salts obtained by the processes described above can be converted into the corresponding free base by either subjecting them to ion exchange chromatography or for example by alkaline aqueous treatment and subsequent extraction with suitable organic solvents like for example methyl tert. butyl ether, chloroform, ethyl acetate or isopropanol/dichloromethane mixtures and subsequent evaporation to dryness.

The preparation of physiologically tolerable salts of compounds of the formula I capable of salt formation, including their stereoisomeric forms, is carried out in a manner known per se. If the compounds of the formula I contain basic groups, stable acid addition salts can be prepared using strong acids e.g. both inorganic and organic acids such as hydrochloric, p-toluenesulfonic, or trifluoroacetic acid.

The compounds of the present invention are soluble epoxide hydrolase inhibitors. They are specific hydrolase inhibitors inasmuch as they do not substantially inhibit the activity of other hydrolases whose inhibition is not desired. The activity of the compounds of the formula I can be determined, for example, in the assays described below or in other assays known to those skilled in the art. With respect to soluble epoxide hydrolase inhibition, a preferred embodiment of the invention comprises compounds which have a $K_i$<1 mM for soluble epoxide hydrolase inhibition as determined in the assays described below and which preferably do not substantially inhibit the activity of other hydrolases.

As inhibitors of soluble epoxide hydrolase the compounds of the formulae I and Ia and their physiologically tolerable salts are generally suitable for the therapy and prophylaxis of conditions in which the activity of soluble epoxide hydrolase plays a role or has an undesired extent, or which can favourably be influenced by inhibiting soluble epoxide hydrolase or decreasing their activity, or for the prevention, alleviation or cure of which an inhibition of soluble epoxide hydrolase or a decrease in their activity is desired by the physician.

The soluble epoxide hydrolase inhibitors according to the invention are generally suitable for treating hypertension, AngII-induced hypertension, salt-sensitive hypertension, for reducing blood pressure, for providing renal protection and for decreasing plasma levels of pro-inflammatory cytokines. Furthermore, the soluble epoxide hydrolase inhibitors according to the invention are also suitable for attenuating AngII- and TAC-induced hypertrophy or cardiac fibrosis. In addition, soluble epoxide hydrolase inhibitors according to the invention are suitable for improving glucose tolerance in diabetes mellitus or type 2 diabetes mellitus. Furthermore, soluble epoxide hydrolase inhibitors according to the invention are suitable for protecting kidney damage, especially in patients having diabetes mellitus or type 2 diabetes mellitus patients.

Important new fields emerging may include a role of CYP-derived epoxyeicosanoids in insulin secretion, in the mediation of inflammatory or anti-inflammatory processes and in pain.

The invention also relates to the treatment of disease states such as pain, inflammatory disease, atherosclerosis, coronary artery disease, aortic aneurysm, diabetes mellitus, diabetic complications like diabetic nephropathy, retinopathy, neuropathy, insulin resistance, renal failure/renal disease, peripheral vascular disease, vascular disease, cardiovascular disease including hypertension, cardiac failure, myocardial infarction, ischemic heart disease, angina, obesity, lipid metabolism disorder, peripheral vascular disease, stroke, chronic obstructive pulmonary disease, and wound healing.

The compounds of the formulae I or Ia and/or physiologically compatible salts thereof can also be used for the treatment and prevention of disorders where sEH requires only partial inhibition, for example by using a lower dosage.

The compounds of the formulae I or Ia and/or their pharmaceutically acceptable salts can be employed to produce medicaments with a sEH inhibitory effect for the therapy and prophylaxis of hypertension and organ failure or damage including maladaptive cardiac hypertrophy, heart failure, and liver failure, cardiac and renal fibrosis. The compounds of the formulae I or Ia and/or their pharmaceutically acceptable salts are further suitable for producing a medicament for the therapy or prophylaxis of ischemic limb disease, endothelial dysfunction, erectile dysfunction, diabetic nephropathy, diabetic vasculopathy and diabetic retinopathy.

The compounds of the formulae I or Ia and/or their pharmaceutically acceptable salts are further suitable for producing a medicament for the therapy or prevention of atherothrombotic disorders including coronary artery disease, coronary vasospasm, myocardial ischemia, and hyperlipidemia/lipid metabolism disorder.

sEH is indirectly involved in the regulation of platelet function through its EETs. Thus, compounds of the invention are further suitable for the inhibition of platelet aggregation which is believed to decrease the risk of atherthrombotic events.

The compounds of the formulae I or Ia and/or their pharmaceutically acceptable salts are further suitable for producing a medicament for the therapy or prophylaxis of metabolic disorders including insulin resistance and diabetes-associated disorders (e.g. diabetic retinopathy, diabetic nephropathy, diabetic neuropathy and diabetic wound healing).

The compounds of the formula I and/or their pharmaceutically acceptable salts are further suitable for producing a medicament for the therapy or prevention of inflammatory disorders including arthritis, inflammatory pain, overactive bladder, asthma, and chronic obstructive pulmonary disease.

The compounds of the formulae I and Ia and their physiologically tolerable salts can be administered to animals, preferably to mammals, and in particular to humans as pharmaceuticals for therapy or prophylaxis. They can be administered on their own, or in mixtures with one another or in the form of pharmaceutical preparations, which permit enteral or parenteral administration.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carriers being used in addition to the compound(s) of the formula Ia and/or its (their) physiologically tolerable salts. For the production of pills, tablets, coated tablets and hard gelatin capsules it is possible to use, for example, lactose, cornstarch or derivatives thereof, talc, stearic acid or its salts, etc. Carriers for soft gelatin capsules and suppositories are, for example, fats, waxes, semisolid and liquid polyols, natural or hardened oils, etc. Suitable carriers for the production of solutions, for example injection solutions, or of emulsions or syrups are, for example, water, saline, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5% to 90% by weight of the compounds of the formulae I or Ia and/or their physiologically tolerable salts and/or their prodrugs. The amount of the active ingredient of the formulae I or Ia and/or its physiologically tolerable salts and/or its prodrugs in the pharmaceutical preparations normally is from about 0.5 mg to about 1000 mg, preferably from about 1 mg to about 500 mg.

In addition to the active ingredients of the formulae I and Ia and/or their physiologically acceptable salts and to carrier substances, the pharmaceutical preparations can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formulae I and Ia and/or their physiologically tolerable salts. In case a pharmaceutical preparation contains two or more compounds of the formulae I and Ia, the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formulae I and Ia allow a great deal of control over the biological and physico-chemical properties of the compounds and thus allows the selection of such desired compounds. Furthermore, in addition to at least one compound of the formulae I and Ia and/or a physiologically tolerable salt, the pharmaceutical preparations can also contain one or more other therapeutically or prophylactically active ingredients.

When using the compounds of the formulae I and Ia the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg, preferably from 0.1 mg/kg to 50 mg/kg, in particular from 1 mg/kg to 10 mg/kg, (in each case in mg per kg of body weight). The daily dose can be divided, in particular in the case of the administration of relatively large amounts, into several, for example 2, 3 or 4, part administrations. As usual, depending on individual behaviour it may be necessary to deviate upwards or downwards from the daily dose indicated.

Further, the compounds of the formulae I and Ia can be used as synthesis intermediates for the preparation of other compounds, in particular of other pharmaceutical active ingredients, which are obtainable from the compounds of the formulae I and Ia, for example by introduction of substituents or modification of functional groups.

The general synthetic sequences for preparing the compounds useful in the present invention are outlined in the examples given below. Both an explanation of, and the actual procedure for, the various aspects of the present invention are described where appropriate. Those with skill in the art will readily understand that known variations of the conditions and processes described in the examples can be used to synthesize the compounds of the present invention. When in the final step of the synthesis of a compound an acid such as trifluoroacetic acid or hydrochloric acid was used, for example when trifluoroacetic acid was employed to remove a tert-butyl group, or when example compounds containing a basic group were purified by preparative HPLC on reversed phase (RP) column material and, as customary, the eluent was a gradient mixture of water and acetonitrile containing trifluoroacetic acid, they were, depending on the details of the work-up procedure such as evaporation or lyophilization conditions, obtained partially or completely in the form of a salt of the acid used, for example in the form of the trifluoroacetic acid salt or hydrochloric acid salt.

It is understood that modifications that do not substantially affect the activity of the various embodiments of this invention are included within the invention disclosed herein. Accordingly, the following examples are intended to illustrate but not limit the present invention.

EXAMPLES

The prepared compounds were in general characterized by spectroscopic data and chromatographic data, in particular mass spectra and HPLC retention times ($R_t$; in min) which were obtained by combined analytical HPLC/MS characterization (LC/MS), and/or nuclear magnetic resonance (NMR) spectra. Unless specified otherwise, $^1$H-NMR spectra were recorded at 500 MHz in $D_6$-dimethyl sulfoxide as solvent at RT or at 300 MHz in deuterochloroform (CDCl$_3$) as solvent at RT. In the NMR characterization, the chemical shift δ (in ppm), the number of hydrogen atoms (H) and the multiplicity (s: singlet, d: doublet, t: triplet, m: multiplet) of the peaks are given. In the MS characterization, in general the detected mass number (m/z) of the peak of the molecular ion (M), or of a related ion such as the ion (M+1), for example (M+1$^+$), i.e. the protonated molecular ion [M+H]$^+$ (MH$^+$), or the ion (M−1), for example (M−1)$^-$, i.e. the deprotonated molecular ion [M−H]$^-$, which was formed depending on the ionization method used, is given. The particulars of the LC/MS methods used were as follows. Unless specified otherwise, the MS ionization method was electrospray ionization ES+.

LC/MS spectra were recorded according to the following methods:

| Method 1: | column: | Atlantis C18, 2.1 × 50 mm; 3 µm |
| | solvent: | ACN + 0.1% TFA:H$_2$O + 0.1% TFA (flow 0.8 mL/min) |
| | gradient: | 5:95 (0 min) to 99:1 (6 min) |
| Method 2: | column: | Waters UPLC BEH C18, 2.1 × 50 mm; 1.7 µm |
| | solvent: | H$_2$O + 0.1% FA:ACN + 0.08% FA (flow 0.9 ml/min) |
| | gradient: | 95:5 (0 min) to 5:95 (1.1 min) to 5:95 (1.7 min) to 95:5 (1.8 min) to 95:5 (2 min) |
| Method 3: | column: | Waters UPLC BEH C18, 2.1 × 50 mm; 1.7 µm |
| | solvent: | H$_2$O + 0.05% FA:ACN + 0.035% FA (flow 0.9 ml/min) |
| | gradient: | 95:5 (0 min) to 5:95 (1.1 min) to 5:95 (1.7 min) to 95:5 (1.8 min) to 95:5 (2 min) |
| Method 4: | column: | Waters XBridge C18, 4.6 × 50 mm; 2.5 µm |
| | solvent: | H$_2$O + 0.1% FA:ACN + 0.1% FA (flow 1.3 ml/min) |
| | gradient: | 97:3 (0 min) to 40:60 (3.5 min) to 2:98 (4 min) to 2:98 (5 min) to 97:3 (5.2 min) to 97:3 (6.5 min) |
| Method 5: | column: | YMC J'sphere ODS H80, 20 × 2.1 mm; 4 µm |
| | solvent: | H$_2$O + 0.05% TFA:ACN (flow 1 ml/min) |
| | gradient: | 96:4 (0 min) to 5:95 (2.0 min) to 5:95 (2.4 min) to 96:4 (2.45 min) |
| Method 6: | column: | Waters UPLC BEH C18, 2.1 × 50 mm; 1.7 µm |
| | solvent: | H$_2$O + 0.05% FA:ACN + 0.035% FA (flow 0.9 ml/min) |
| | gradient: | 98:2 (0 min) to 5:95 (2 min) to 5:95 (2.6 min) to 95:5 (2.7 min) to 95:5 (3 min) |
| Method 7: | column: | MUX Atlantis T3, 3 × 50 mm; 3 µm |
| | solvent: | H$_2$O + 0.05% TFA:ACN + 0.05% TFA (flow 0.6 ml/min) |
| | gradient: | 95:5 (0 min) to 2:98 (4 min) to 2:98 (6.5 min) to 95:5 (9 min) |
| Method 8: | column: | LunaC18, 10 × 2.0 mm; 3 µm |
| | solvent: | H$_2$O + 0.05% TFA:ACN (flow 1.1 ml/min) |
| | gradient: | 93:7 (0 min) to 5:95 (1.0 min) to 5:95 (1.45 min) to 93:7 (1.5 min) |

List of Abbreviations
ACN acetonitrile
Alloc allyloxycarbonyl
Bn benzyl
Boc tert-butyloxycarbonyl
FA formic acid
Fmoc 9-fluorenylmethoxycarbonyl
HMPA hexamethylphosphoramide
HPLC high performance liquid chromatography
Hünig's base N,N-diisopropylethylamine
IR infrared spectroscopy
LG leaving group
MS mass spectra
NMR nuclear magnetic resonance
PG protecting group
RP-HPLC reversed phase high performance liquid chromatography
RT room temperature (20° C. to 25° C.)
SFC supercritical fluid chromatography
TBS tert-butyldimethylsilyl
TBAF tetrabutylammoniumflouride
tert. tertiary
TMS trimethylsilyl
THF tetrahydrofuran
Tf triflate, trifluoromethanesulfonate
TFA trifluoroacetic acid
Tos tosylate, p-toluenesulfonate
Z benzyloxy-carbonyl Synthesis Intermediates (3R,3aR,6R,6aS)-6-(tert-Butyl-dimethyl-silanyloxy)-hexahydro-furo[3,2-b]furan-3-ol (P1)

A solution of (3R,3aR,6R,6aR)-hexahydro-furo[3,2-b]furan-3,6-diol (5.00 g, 34.2 mmol) in N,N-dimethylformamide (50 mL) was treated with imidazole (2.33 g, 34.2 mmol) and tert-butyldimethylchlorosilane (5.67 g, 37.6 mmol) and was stirred at RT overnight. The reaction was quenched with saturated aqueous ammonium chloride solution and extracted twice with tert.-butyl methyl ether. The organic layers were combined and evaporated. The crude product was purified by flash chromatography (silica gel, elution with heptane/ethyl acetate) to give 3.17 g (36%) of (3R,3aR,6R,6aS)-6-(tert-butyl-dimethyl-silanyloxy)-hexahydro-furo[3,2-b]furan-3-ol. LC/MS (Method 5): $R_t$=1.31 min; detected mass: m/z=261.10 ([M+H]$^+$).

Trifluoromethanesulfonic acid (3R,3aS,6R,6aS)-6-(tert-butyl-dimethyl-silanyloxy)-hexahydro-furo[3,2-b]furan-3-yl ester (P2)

A mixture of (3R,3aR,6R,6aS)-6-(tert-butyl-dimethyl-silanyloxy)-hexahydro-furo[3,2-b]furan-3-ol (P1) (2.67 g, 10.3 mmol) and pyridine (0.97 g, 12.3 mmol) in dichloromethane (40 mL) was cooled in an ice bath and trifluoromethanesulfonic anhydride (3.47 g, 2.02 mL, 12.3 mmol) was added. The mixture was stirred at 0° C. for 1 h, diluted with dichloromethane (100 mL) and washed successively with 1M aqueous hydrochloric acid (100 mL), water (100 mL), saturated aqueous sodium bicarbonate solution (100 mL) and brine (100 mL). The organic layer was dried over magnesium sulfate, filtered and concentrated under reduced pressure. The purity of the resulting trifluoromethanesulfonic acid (3R,3aS,6R,6aS)-6-(tert-butyl-dimethyl-silanyloxy)-hexahydro-furo[3,2-b]furan-3-yl ester (3.50 g, 87%) was sufficient to be used in the next step without further purification. LC/MS (Method 8): $R_t$=1.30 min; detected mass: m/z=393.10 ([M+H]$^+$).

Toluene-4-sulfonic acid (3R,3aS,6R,6aR)-6-hydroxy-hexahydro-furo[3,2-b]furan-3-yl ester (P3)

A mixture of (3R,3aR,6R,6aR)-hexahydro-furo[3,2-b]furan-3,6-diol (200 g, 1.37 mol) and p-toluenesulfonyl chloride (287 g, 1.51 mol) in tert-butyl methyl ether (300 mL) was stirred vigorously, cooled in an ice bath and treated successively with ice-cold water (1.2 L) and ice-cold 10N aqueous potassium hydroxide solution (150 mL). The mixture was stirred for 3 h before water (500 mL) was added and the pH was adjusted to pH 11 by addition of 10N aqueous potassium hydroxide solution. The resulting white suspension was filtered; the isolated solid was washed with water and diisopropylether before being taken up in toluene (1.5 L). The suspension was heated to 90° C. for 15 min, the hot mixture was filtered and the filtrate was cooled to RT. The resulting solid was filtered off, washed with toluene and diisopropylether and dried under reduced pressure at 30° C. to give 250 g (61%) of toluene-4-sulfonic acid (3R,3aS,6R,6aR)-6-hydroxy-hexahydro-furo[3,2-b]furan-3-yl ester as a white solid.

$^1$H-NMR (500 MHz, (CD$_3$)$_2$CO): δ=7.81 (d, 2H), 7.50 (d, 2H), 4.97-4.87 (m, 2H), 4.48 (t, 1H), 4.21 (t, 1H), 4.14-4.03 (m, 1H), 3.83-3.72 (m, 2H), 3.60-3.53 (m, 1H), 3.35-3.30 (m, 1H), 2.43 (s, 3H) ppm.

Toluene-4-sulfonic acid (3R,3aS,6R,6aS)-6-trifluoromethanesulfonyloxy-hexahydro-furo[3,2-b]furan-3-yl ester (P4)

A mixture of toluene-4-sulfonic acid (3R,3aS,6R,6aR)-6-hydroxy-hexahydro-furo[3,2-b]furan-3-yl ester (P3) (352 g, 1.17 mol) and pyridine (237 mL, 232 g, 2.93 mol) in dichloromethane (1.5 L) was cooled to 0° C. and trifluoromethanesulfonic anhydride (364 g, 1.29 mol) was added slowly over a period of 20 min whilst stirring vigorously and keeping the temperature below 3° C. The reaction mixture was stirred for 1 h at 0° C., diluted with dichloromethane (2.0 L) and poured onto ice-cold water (2.0 L). The pH was adjusted to pH 1.5 to 2 with aqueous hydrochloric acid and the phases were separated. The organic layer was washed four times with water (1.0 L) and evaporated. The resulting solid was taken up in dichloromethane (100 mL), treated with methyl-tert-butylether (200 mL) and concentrated under reduced pressure to a volume of 100 mL. This procedure was repeated twice and the resulting suspension was stirred in an ice-bath for 1 h before being filtered. The solid was washed twice with methyl-tert-butylether (50 mL) and dried under reduced pressure at 30° C. to give 507 g (94%) of toluene-4-sulfonic acid (3R,3aS,6R,6aS)-6-trifluoromethanesulfonyloxy-hexahydro-furo[3,2-b]furan-3-yl ester as a white solid.

$^1$H-NMR (500 MHz, (CD$_3$)$_2$CO): δ=7.82 (d, 2H), 7.52 (d, 2H), 5.50 (d, 1H), 5.00-4.92 (m, 1H), 4.75 (t, 1H), 4.40 (t, 1H), 4.10-4.03 (m, 1H), 3.98-3.89 (m, 2H), 3.56 (t, 1H), 2.44 (s, 3H) ppm.

Toluene-4-sulfonic acid (3R,3aS,6S,6aR)-6-benzylamino-hexahydro-furo[3,2-b]furan-3-yl ester (P5)

A mixture of toluene-4-sulfonic acid (3R,3aS,6R,6aS)-6-trifluoromethanesulfonyloxy-hexahydro-furo[3,2-b]furan-3-yl ester (P4) (10.0 g, 23.1 mmol) in benzylamine (8.0 mL, 7.85 g, 73.2 mmol) was stirred for 3 days at RT until LCMS indicated the completion of the reaction. The mixture was treated with toluene and subsequently evaporated three times and the residue was taken up in ethyl acetate, washed successively twice with 0.1M aqueous hydrochloric acid, once with saturated aqueous sodium bicarbonate solution and once with brine. The organic layer was dried over magnesium sulfate, filtered and concentrated under reduced pressure to give 9.00 g (100%) of toluene-4-sulfonic acid (3R,3aS,6S,6aR)-6-benzylamino-hexahydro-furo[3,2-b]furan-3-yl ester which was used in the next step without further purification. LC/MS (Method 3): $R_t$=1.00 min; detected mass: m/z=390.05 ([M+H]$^+$).

Toluene-4-sulfonic acid (3R,3aS,6S,6aR)-6-amino-hexahydro-furo[3,2-b]furan-3-yl ester (P6)

Toluene-4-sulfonic acid (3R,3aS,6S,6aR)-6-benzylamino-hexahydro-furo[3,2-b]furan-3-yl ester (P5) (1.79 g, 4.59 mmol) was dissolved in ethyl acetate (100 mL), 10% palladium on charcoal (100 mg) was added and the resulting reaction mixture was stirred at RT under a hydrogen atmosphere (1 bar) overnight until LCMS indicated completion of the reaction. The catalyst was removed by filtration and the filtrate was evaporated to give 660 mg (48%) of toluene-4-sulfonic acid (3R,3aS,6S,6aR)-6-amino-hexahydro-furo[3,2-b]furan-3-yl ester which was used in the next step without further purification. LC/MS (Method 6): $R_t$=1.24 min; detected mass: m/z=300.15 ([M+H]$^+$).

((3R,3aS,6S,6aR)-6-Azido-hexahydrofuro[3,2-b]furan-3-yloxy)-tert-butyl-dimethyl-silane (P7)

A solution of trifluoromethanesulfonic acid (3R,3aS,6R,6aS)-6-(tert-butyl-dimethyl-silanyloxy)-hexahydro-furo[3,2-b]furan-3-yl ester (P2) (5.00 g, 12.4 mmol) in N,N-dimethylformamide (131 mL) was treated with sodium azide (1.24 g, 19.1 mmol) and stirred at 120° C. for 2 h. The mixture was cooled to RT, concentrated under reduced pressure and the residue was taken up in dichloromethane (100 mL). The salts were filtered off, the filtrate was washed with water (50 mL) and brine (50 mL), dried over magnesium sulfate, filtered and evaporated to give 3.00 g (83%) of ((3R,3aS,6S,6aR)-6-azido-hexahydrofuro[3,2-b]furan-3-yloxy)-tert-butyl-dimethylsilane which was used without further purification. LC/MS (Method 5): $R_t$=1.83 min; detected mass: m/z=286.15 ([M+H]$^+$).

Benzyl-[(3S,3aR,6R,6aS)-6-(tert-butyl-dimethyl-silanyloxy)-hexahydro-furo[3,2-b]furan-3-yl]-amine (P8)

Benzylamine (1.22 mL, 1.20 g, 11.2 mmol) was cooled in an ice bath and trifluoro-methanesulfonic acid (3R,3aS,6R,6aS)-6-(tert-butyl-dimethyl-silanyloxy)-hexahydro-furo[3,2-b]furan-3-yl ester (P2) (2.00 g, 5.10 mmol) was added. The reaction mixture was stirred for 3 days at RT until LCMS indicated the completion of the reaction. The mixture was concentrated under reduced pressure and stripped from toluene three times. The residue was taken up in ethyl acetate (20 mL) and washed successively with 0.1M aqueous hydrochloric acid, saturated aqueous sodium bicarbonate solution and brine. The organic layer was separated and concentrated under reduced pressure to give 1.74 g (98%) of benzyl-[(3S,3aR,6R,6aS)-6-(tert-butyl-dimethyl-silanyloxy)-hexahydro-furo[3,2-b]furan-3-yl]-amine which was used in the next step without further purification. LC/MS (Method 4): $R_t$=3.55 min; detected mass: m/z=350.27 ([M+H]$^+$).

(3S,3aR,6R,6aS)-6-(tert-Butyl-dimethyl-silanyloxy)-hexahydro-furo[3,2-b]furan-3-ylamine (P9)

Synthesis A: from benzyl-[(3S,3aR,6R,6aS)-6-(tert-butyl-dimethyl-silanyloxy)-hexahydro-furo[3,2-b]furan-3-yl]-amine (P8)

Benzyl-[(3S,3aR,6R,6aS)-6-(tert-butyl-dimethyl-silanyloxy)-hexahydro-furo[3,2-b]furan-3-yl]-amine (P8) (2.60 g, 7.44 mmol) was dissolved in methanol (5.0 mL), 5% palladium on charcoal (80 mg) was added and the resulting reaction mixture was stirred at RT under a hydrogen atmosphere (1 bar) overnight. The catalyst was filtered off, a new portion of 5% palladium on charcoal (80 mg) was added and the mixture was stirred under a hydrogen atmosphere (1 bar) until LCMS indicated completion of the reaction (72 h). The catalyst was removed by filtration and the filtrate was evaporated to give 1.92 g (87%) of (3S,3aR,6R,6aS)-6-(tert-butyl-dimethyl-silanyloxy)-hexahydro-furo[3,2-b]furan-3-ylamine which was used in the next step without further purification. LC/MS (Method 2): $R_t$=1.02 min; detected mass: m/z=260.18 ([M+H]$^+$).

Synthesis B: from ((3R,3aS,6S,6aR)-6-azido-hexahydrofuro[3,2-b]furan-3-yloxy)-tert-butyl-dimethyl-silane (P7)

(3S,3aR,6R,6aS)-6-(tert-Butyl-dimethyl-silanyloxy)-hexahydro-furo[3,2-b]furan-3-ylamine (P9) could be alternatively accessed from ((3R,3aS,6S,6aR)-6-azido-hexahydrofuro[3,2-b]furan-3-yloxy)-tert-butyl-dimethylsilane (P7) following the procedure described for the synthesis of (3S,3aR,6S,6aR)-6-benzo[1,3]dioxol-5-ylethynyl-hexahydro-furo[3,2-b]furan-3-ylamine (P25) using triphenylphosphane in methanol.

1-[(3S,3aR,6R,6aS)-6-(tert-Butyl-dimethyl-silanyloxy)-hexahydro-furo[3,2-b]furan-3-yl]-3-cyclohexyl-urea (P10)

A solution of (3S,3aR,6R,6aS)-6-(tert-butyl-dimethyl-silanyloxy)-hexahydro-furo[3,2-b]furan-3-ylamine (P9) (1.25 g, 4.82 mmol) in absolute dichloromethane (24 mL) was cooled in an ice bath and treated consecutively with triethylamine (730 mg, 1.01 mL, 7.23 mmol) and cyclohexylisocyanate (241 mg, 250 µL, 1.93 mmol). After stirring for 1 h at 0° C., another portion of cyclohexylisocyanate (120 mg, 125 µL, 0.96 mmol) was added and the reaction was quenched by addition of methanol (15 mL). After stirring overnight at RT, saturated aqueous sodium bicarbonate solution was added. The layers were separated; the aqueous layer was extracted three times with dichloromethane. The organic layers were combined, washed with brine (50 mL), dried over magnesium sulfate, filtered and evaporated. The crude product was purified by flash chromatography (silica gel, elution with dichloromethane/methanol) to give 1.45 g (78%) of pure 1-[(3S,3aR,6R,6aS)-6-(tert-butyl-dimethyl-silanyloxy)-hexahydro-furo[3,2-b]furan-3-yl]-3-cyclohexyl-urea. LC/MS (Method 3): $R_t$=1.22 min; detected mass: m/z=385.27 ([M+H]$^+$).

Trifluoromethanesulfonic acid (3R,3aS,6S,6aR)-6-(3-cyclohexyl-ureido)-hexahydro-furo[3,2-b]furan-3-yl ester (P11)

A solution of 1-cyclohexyl-3-((3S,3aR,6R,6aR)-6-hydroxy-hexahydro-furo[3,2-b]furan-3-yl)-urea (1) (360 mg, 1.34 mmol) and pyridine (127 mg, 130 µL, 1.60 mmol) in dichloromethane (11 mL) was cooled in an ice bath and trifluoromethanesulfonic anhydride (450 mg, 270 µL, 1.60 mmol) was added. The mixture was stirred at RT for 2 h before being evaporated. The crude product was purified by flash chromatography (silica gel, elution with heptane/ethyl acetate) to give 190 mg (35%) of trifluoro-methanesulfonic acid (3R,3aS,6S,6aR)-6-(3-cyclohexyl-ureido)-hexahydro-furo[3,2-b]furan-3-yl ester. LC/MS (Method 5): $R_t$=1.37 min; detected mass: m/z=403.15 ([M+H]$^+$).

1-Benzyl-1-[(3S,3aR,6R,6aS)-6-(tert-butyl-dimethyl-silanyloxy)-hexahydro-furo[3,2-b]furan-3-yl]-3-cyclohexyl-urea (P12)

A mixture of benzyl-[(3S,3aR,6R,6aS)-6-(tert-butyl-dimethyl-silanyloxy)-hexahydro-furo[3,2-b]furan-3-yl]-amine (P8) (16.0 g, 45.8 mmol) and triethylamine (6.95 g, 9.54 mL, 68.7 mmol) in absolute dichloromethane (130 mL) was cooled in an ice bath and treated dropwise with cyclohexylisocyanate (6.30 g, 6.43 mL, 50.4 mmol) over a period of 10 min. After stirring for 70 h at RT, methanol (50 mL) was added and the reaction mixture stirred for another 1.5 h before saturated aqueous sodium bicarbonate solution (150 mL) was added. The layers were separated; the aqueous layer was extracted three times with dichloromethane (300 mL). The organic layers were combined, washed with brine (50 mL), dried over magnesium sulfate, filtered and evaporated to give 26.3 g of crude 1-benzyl-1-[(3S,3aR,6R,6aS)-6-(tert-butyl-dimethyl-silanyloxy)-hexahydro-furo[3,2-b]furan-3-yl]-3-cyclohexyl-urea which was used in the next step without further purification. LC/MS (Method 3): $R_t$=1.48 min; detected mass: m/z=475.22 ([M+H]$^+$).

1-Benzyl-3-cyclohexyl-1-((3S,3aR,6R,6aR)-6-hydroxy-hexahydro-furo[3,2-b]furan-3-yl)-urea (P13)

1-Benzyl-1-[(3S,3aR,6R,6aS)-6-(tert-butyl-dimethyl-silanyloxy)-hexahydro-furo[3,2-b]furan-3-yl]-3-cyclohexyl-urea (P12) (26.3 g, crude from synthesis of P12) was dissolved in a 1:1 mixture of dioxane and water (70 mL) and cooled in an ice bath. 4M Hydrochloric acid in dioxane (47 mL, 188 mmol) was added dropwise whilst keeping the reaction temperature at 0° C. After 3 h stirring at 0° C., water was added (45 mL) and the pH was adjusted to pH 6 by addition of 1N aqueous sodium hydroxide solution (210 mL). The mixture was extracted three times with dichloromethane; the organic layers were combined, washed with brine, dried over sodium sulfate, filtered and concentrated under reduced pressure. 23.2 g of crude 1-benzyl-3-cyclohexyl-1-((3S,3aR,6R,6aR)-6-hydroxy-hexahydro-furo[3,2-b]furan-3-yl)-urea could be isolated and were used in the next step without further purification. LC/MS (Method 3): $R_t$=1.17 min; detected mass: m/z=361.16 ([M+H]$^+$).

Trifluoromethanesulfonic acid (3R,3aS,6S,6aR)-6-(1-benzyl-3-cyclohexyl-ureido)-hexahydro-furo[3,2-b]furan-3-yl ester (P14)

A mixture of 1-benzyl-3-cyclohexyl-1-((3S,3aR,6R,6aR)-6-hydroxy-hexahydro-furo[3,2-b]furan-3-yl)-urea (P13) (23.2 g, crude from synthesis of P13) and pyridine (12.7 g, 13.0 mL, 161 mmol) in dichloromethane (750 mL) was cooled in an ice bath and trifluoromethanesulfonic anhydride (20.0 g, 11.9 mL, 70.8 mmol) was added slowly. The mixture was stirred at RT for 1 h before being concentrated under reduced pressure. The crude product was dissolved in dichloromethane (100 mL) and washed with a 0.1N aqueous solution of hydrochloric acid (100 mL), saturated aqueous sodium bicarbonate solution (100 mL) and brine. The organic layer was dried over magnesium sulfate, filtered and evaporated. The residue was purified by reversed phase HPLC (acetonitrile/water) to give 12.8 g (40%) of trifluoromethanesulfonic acid (3R,3aS,6S,6aR)-6-(1-benzyl-3-cyclohexyl-ureido)-hexahydro-furo[3,2-b]furan-3-yl ester. LC/MS (Method 3): $R_t$=1.37 min; detected mass: m/z=493.06 ([M+H]$^+$).

1-Benzyl-1-((3S,3aR,6S,6aR)-6-cyano-hexahydro-furo[3,2-b]furan-3-yl)-3-cyclohexyl-urea (P15)

A solution of trifluoromethanesulfonic acid (3R,3aS,6S,6aR)-6-(1-benzyl-3-cyclohexyl-ureido)-hexahydro-furo[3,2-b]furan-3-yl ester (P14) (5.00 g, 10.2 mmol) in acetonitrile (25 mL) was treated with a solution of tetraethylammonium cyanide (1.75 g, 11.2 mmol) in acetonitrile (17.5 mL) whilst keeping the reaction temperature below 25° C. with a water bath. The reaction mixture was stirred at RT for 3.5 h, and then saturated aqueous ammonium chloride solution was added. The mixture was extracted with ethyl acetate, the organic layer was washed with water twice, dried over magnesium sulfate, filtered and evaporated to give 4.08 g (99%) of 1-benzyl-1-((3S,3aR,6S,6aR)-6-cyano-hexahydro-furo[3,2-b]furan-3-yl)-3-cyclohexyl-urea which was used without further purification. LC/MS (Method 4): $R_t$=4.47 min; detected mass: m/z=370.20 ([M+H]$^+$).

1-Benzyl-3-cyclohexyl-1-((3S,3aR,6S,6aR)-6-formyl-hexahydro-furo[3,2-b]furan-3-yl)-urea (P16)

To a solution of 1-benzyl-1-((3S,3aR,6S,6aR)-6-cyano-hexahydro-furo[3,2-b]furan-3-yl)-3-cyclohexyl-urea (P15) (200 mg, 0.54 mmol) in dichloromethane (6 mL) at −70° C. was added dropwise a solution of 1M diisobutylaluminium hydride in dichloromethane (540 μL, 0.54 mmol). The reaction mixture was kept at −70° C. for 10 min before being allowed to warm to −35° C. over a period of 1.5 h. The mixture was left standing over night at RT, was then cooled to 0° C., and methanol (1 mL) and water (3 mL) were added. Stirring was continued at 0° C. for 30 min and 2 h at RT, before the reaction mixture was diluted with water and dichloromethane. The phases were separated; the aqueous phase was extracted with dichloromethane twice and diethylether. The organic layers were combined, dried over magnesium sulfate, filtered and evaporated. The crude aldehyde (206 mg) was taken up in ethanol (3.5 mL) and used directly for the synthesis of Example 6.

Benzyl-[(3S,3aR,6S,6aS)-6-(4-fluoro-phenoxy)-hexahydro-furo[3,2-b]furan-3-yl]-amine (P17)

A solution of 4-fluorophenol (1.29 g, 11.6 mmol) in absolute N,N-dimethylformamide (30 mL) was treated with potassium tert-butoxide (1.73 g, 15.4 mmol) and stirred for 45 min at RT. Then, a solution of toluene-4-sulfonic acid (3R,3aS,6S,6aR)-6-benzylamino-hexahydro-furo[3,2-b]furan-3-yl ester (P5) (3.00 g, 7.70 mmol) in N,N-dimethylformamide (20 mL) was added and the reaction mixture was stirred at 80° C. for 5 h. The crude reaction mixture was concentrated under reduced pressure and partitioned between water (50 mL) and dichloromethane (50 mL). The phases were separated and the water phase extracted three times with dichloromethane. The combined organic layers were dried over magnesium sulfate, filtered and evaporated to give 2.60 g of crude benzyl-[(3S,3aR,6S,6aS)-6-(4-fluoro-phenoxy)-hexahydro-furo[3,2-b]furan-3-yl]-amine, which was used in the next step without further purification. LC/MS (Method 4): $R_t$=3.03 min; detected mass: m/z=330.14 ([M+H]$^+$).

(3S,3aR,6S,6aS)-6-(4-Fluoro-phenoxy)-hexahydro-furo[3,2-b]furan-3-ylamine; trifluoroacetate (P18)

Benzyl-[(3S,3aR,6S,6aS)-6-(4-fluoro-phenoxy)-hexahydro-furo[3,2-b]furan-3-yl]-amine (P17) (2.60 g, crude from P17) was dissolved in absolute methanol (50 mL) and 5% palladium on charcoal (30 mg) was added. Then, hydrogen was bubbled through the reaction mixture for 10 min and the suspension was stirred over night at RT under an atmosphere of hydrogen (1 bar). The catalyst was removed by filtration, washed with methanol and the combined filtrates were evaporated and subjected to purification by reversed phase HPLC (acetonitrile/water with 0.1% trifluoroacetic acid) to yield 1.85 g (66%) of (3S,3aR,6S,6aS)-6-(4-fluoro-phenoxy)-hexahydro-furo[3,2-b]furan-3-ylamine as its trifluoroacetic acid salt. LC/MS (Method 3): $R_t$=0.70 min; detected mass: m/z=240.09 ([M+H]$^+$).

Benzyl-[(3S,3aR,6S,6aS)-6-(2-methyl-pyridin-3-yloxy)-hexahydro-furo[3,2-b]furan-3-yl]-amine (P19)

A solution of 3-hydroxy-2-methylpiperidine (3.72 g, 34.1 mmol) in absolute N,N-dimethylformamide (200 mL) was treated with potassium tert-butoxide (5.10 g, 45.4 mmol) and stirred for 45 min at RT. Then, a solution of toluene-4-sulfonic acid (3R,3aS,6S,6aR)-6-benzylamino-hexahydro-furo[3,2-b]furan-3-yl ester (P5) (8.85 g, 22.7 mmol) in N,N-dimethylformamide (100 mL) was added and the reaction mixture was stirred at 80° C. for 8 h. The crude reaction mixture was concentrated under reduced pressure and partitioned between water (200 mL) and dichloromethane (200 mL). The phases were separated and the water phase extracted three times with dichloromethane. The combined organic layers were dried over magnesium sulfate, filtered and evaporated to give 8.20 g of crude benzyl-[(3S,3aR,6S,6aS)-6-(2-methyl-pyridin-3-yloxy)-hexahydro-furo[3,2-b]furan-3-yl]-amine, which was used in the next step without further purification. LC/MS (Method 6): $R_t$=0.86 min; detected mass: m/z=327.25 ([M+H]$^+$).

(3S,3aR,6S,6aS)-6-(2-Methyl-pyridin-3-yloxy)-hexahydro-furo[3,2-b]furan-3-ylamine (P20)

Benzyl-[(3S,3aR,6S,6aS)-6-(2-methyl-pyridin-3-yloxy)-hexahydro-furo[3,2-b]furan-3-yl]-amine (P19) (8.20 g, crude from P19) was dissolved in absolute methanol (100 mL) and 5% palladium on charcoal (30 mg) was added. Then, hydrogen was bubbled through the reaction mixture for 30 min and the suspension was stirred over night at RT under an atmosphere of hydrogen (1 bar). The catalyst was filtered off, a new portion of 5% palladium on charcoal (30 mg) was added. The reaction mixture was flooded with hydrogen again and stirred under an atmosphere of hydrogen (1 bar).

This process was repeated three times and stirring was continued until LCMS indicated completion of the reaction. The catalyst was removed by filtration and the filtrate was evaporated and the crude material was subjected to purification via flash chromatography (silica gel, elution with dichloromethane/methanol 100:0 to 98:2) to give 4.20 g (71%) of (3S,3aR,6S,6aS)-6-(2-methyl-pyridin-3-yloxy)-hexahydro-furo[3,2-b]furan-3-ylamine. LC/MS (Method 6): $R_t$=0.19 min; detected mass: m/z=237.22 ([M+H]$^+$).

((3R,3aS,6S,6aR)-6-Benzo[1,3]dioxol-5-ylethynyl-hexahydro-furo[3,2-b]furan-3-yloxy)-tert-butyl-dimethyl-silane (P21)

n-Butyllithium (1.20 mL, 3.0 mmol, 2.5M in hexanes) was added to a solution of 5-ethynyl-benzo[1,3]dioxole (560 mg, 3.84 mmol) in a mixture of THF (10 mL) and HMPA (1 mL) at 0° C. After stirring at 0° C. for 30 min, a solution of trifluoromethanesulfonic acid (3R,3aS,6R,6aS)-6-(tert-butyl-dimethyl-silanyloxy)-hexahydro-furo[3,2-b]furan-3-yl ester (P2) (600 mg, 1.53 mmol) in THF (2 mL) was added to the mixture drop wise. The reaction mixture was stirred at 0° C. for 2 h and quenched by addition of saturated aqueous ammonium chloride solution. The phases were separated and the aqueous phase was thoroughly extracted with diethylether. The combined organic extracts were washed with brine, dried over anhydrous sodium sulfate, filtered, and concentrated under under reduced pressure. The residue was purified by silica gel chromatography (elution with ethylacetate/hexanes 20:80 to 50:50) to give 300 mg (51%) of ((3R,3aS,6S,6aR)-6-benzo[1,3]dioxol-5-ylethynyl-hexahydro-furo[3,2-b]furan-3-yloxy)-tert-butyl-dimethyl-silane. $^1$H-NMR (300 MHz, CDCl$_3$): δ=6.79 (d, 1H), 6.70 (s, 1H), 6.59 (d, 1H), 5.83 (s, 2H), 4.58-4.52 (m, 1H), 4.40-4.35 (m, 1H), 4.19-4.10 (m, 1H), 4.06-3.96 (m, 1H), 3.89-3.80 (m, 1H), 3.71-3.64 (m, 1H), 3.53-3.47 (m, 1H), 3.10-3.06 (m, 1H), 0.80 (s, 9H), 0.02 (s, 6H) ppm.

(3R,3aR,6S,6aR)-6-Benzo[1,3]dioxol-5-ylethynyl-hexahydro-furo[3,2-b]furan-3-ol (P22)

A 1M solution of TBAF in THF (1.6 mL) was added to a solution of ((3R,3aS,6S,6aR)-6-benzo[1,3]dioxol-5-ylethynyl-hexahydro-furo[3,2-b]furan-3-yloxy)-tert-butyl-dimethyl-silane (P21) (300 mg, 0.77 mmol) in THF (5 mL) at 0° C. The mixture was stirred at 0° C. for 1 h and was quenched by addition of saturated aqueous ammonium chloride solution. The phases were separated and the aqueous phase was thoroughly extracted with ethyl acetate. The combined organic extracts were washed with brine, dried over anhydrous sodium sulfate, filtered, and concentrated under reduced pressure. The residue was purified by silica gel chromatography (elution with ethylacetate/hexanes 50:50) to give 191 mg (90%) (3R,3aR,6S,6aR)-6-benzo[1,3]dioxol-5-ylethynyl-hexahydro-furo[3,2-b]furan-3-ol. $^1$H-NMR (300 MHz, CDCl$_3$): δ=6.79 (d, 1H), 6.71 (s, 1H), 6.62 (d, 1H), 5.84 (s, 2H), 4.59-4.50 (m, 2H), 4.21-4.12 (m, 1H), 4.00-3.95 (m, 2H), 3.83-3.75 (m, 1H), 3.58-3.50 (m, 1H), 3.22-3.18 (m, 1H), 2.66-2.52 (m, 1H) ppm.

Trifluoromethanesulfonic acid (3R,3aS,6S,6aR)-6-benzo[1,3]dioxol-5-ylethynyl-hexahydro-furo[3,2-b]furan-3-yl ester (P23)

A mixture of (3R,3aR,6S,6aR)-6-benzo[1,3]dioxol-5-ylethynyl-hexahydro-furo[3,2-b]furan-3-ol (P22) (350 mg, 1.28 mmol) and pyridine (0.21 mL, 2.6 mmol) in dichloromethane (5 mL) was cooled in an ice bath and trifluoromethanesulfonic anhydride (0.26 mL, 1.55 mmol) was added slowly. The mixture was stirred at 0° C. for 30 min before being quenched with 1N aqueous hydrochloric acid. The phases were separated and the aqueous phase was thoroughly extracted with dichloromethane. The combined organic extracts were washed with brine, dried over anhydrous sodium sulfate, filtered, and concentrated under reduced pressure. The residue was used for the next step without further purification.

5-((3S,3aR,6S,6aR)-6-Azido-hexahydro-furo[3,2-b]furan-3-ylethynyl)-benzo[1,3]dioxole (P24)

To a solution of crude trifluoromethanesulfonic acid (3R,3aS,6S,6aR)-6-benzo[1,3]dioxol-5-ylethynyl-hexahydro-furo[3,2-b]furan-3-yl ester (P23) in DMF (5 mL) was added sodium azide (170 mg, 2.6 mmol) and the mixture was stirred at RT for 1 h before being quenched with saturated aqueous ammonium chloride solution. The phases were separated and the aqueous phase was thoroughly extracted with diethylether. The combined organic extracts were washed with brine, dried over anhydrous sodium sulfate, filtered, and concentrated under reduced pressure. The residue was used for the next step without further purification.

(3S,3aR,6S,6aR)-6-Benzo[1,3]dioxol-5-ylethynyl-hexahydro-furo[3,2-b]furan-3-ylamine (P25)

Triphenylphosphane (620 mg, 2.37 mmol) was added to a solution of the crude 5-((3S,3aR,6S,6aR)-6-azido-hexahydro-furo[3,2-b]furan-3-ylethynyl)-benzo[1,3]dioxole (P24) in methanol (5 mL). The mixture was stirred at RT for 12 h, filtered through a celite pad and concentrated under reduced pressure. The residue was purified by silica gel chromatography (elution with dichloromethane/methanol 100:0 to 90:10) to give 235 mg (67% for 3 steps) of (3S,3aR,6S,6aR)-6-benzo[1,3]dioxol-5-ylethynyl-hexahydro-furo[3,2-b]furan-3-ylamine which was directly used in the next step.

The following compounds have been prepared from trifluoromethanesulfonic acid (3R,3aS,6R,6aS)-6-(tert-butyl-dimethyl-silanyloxy)-hexahydro-furo[3,2-b]furan-3-yl ester (P2) and the respective alkynes following the synthesis sequence and procedures described for the synthesis of (3S,3aR,6S,6aR)-6-benzo[1,3]dioxol-5-ylethynyl-hexahydro-furo[3,2-b]furan-3-ylamine (P25).

| Intermediate No. | Starting compound | Chemical name | Mass (from LC/MS) | R$_t$ (from LC/MS) (min) | LC/MS Method |
|---|---|---|---|---|---|
| P26 | Ethynyl-benzene | (3S,3aR,6S,6aR)-6-Phenylethynyl-hexahydro-furo[3,2-b]furan-3-ylamine | 230.11 | 2.26 | 1 |
| P27 | 3-Ethynyl-thiophene | (3S,3aR,6S,6aR)-6-Thiophen-3-ylethynyl-hexahydro-furo[3,2-b]furan-3-ylamine | 236.07 | 2.16 | 1 |
| P28 | 2-Ethynyl-pyridine | (3S,3aR,6S,6aR)-6-Pyridin-2-ylethynyl-hexahydro-furo[3,2-b]furan-3-ylamine | used crude in the next step | | |

(3R,3aS,6S,6aR)-3-(tert-Butyl-dimethyl-silanyloxy)-6-trimethylsilanylethynyl-hexahydro-furo[3,2-b]furan (P29)

9.36 g (36%) of (3R,3aS,6S,6aR)-3-(tert-butyl-dimethyl-silanyloxy)-6-trimethylsilanylethynyl-hexahydro-furo[3,2-b]furan was prepared from trifluoro-methanesulfonic acid (3R,3aS,6R,6aS)-6-(tert-butyl-dimethyl-silanyloxy)-hexahydro-furo[3,2-b]furan-3-yl ester (P2) (30 g, 76.6 mmol) and trimethylsilylacetylene (27 mL, 191 mmol) following the procedure used for the synthesis of P21.
$^1$H-NMR (300 MHz, CDCl$_3$): δ=4.52-4.49 (m, 1H), 4.36-4.30 (m, 1H), 4.17-4.08 (m, 1H), 4.02-3.94 (m, 1H), 3.80-3.71 (m, 1H), 3.71-3.60 (m, 1H), 3.52-3.41 (m, 1H), 2.99-2.90 (m, 1H), 0.80 (s, 9H), 0.05 (s, 6H), 0.00 (s, 9H) ppm.

tert-Butyl-((3R,3aS,6S,6aR)-6-ethynyl-hexahydro-furo[3,2-b]furan-3-yloxy)-dimethyl-silane (P30)

A solution of (3R,3aS,6S,6aR)-3-(tert-butyl-dimethyl-silanyloxy)-6-trimethylsilanylethynyl-hexahydro-furo[3,2-b]furan (P29) (13.1 g, 38.5 mmol) in methanol (200 mL) was treated with potassium carbonate (10.6 g, 77.0 mmol) and the resulting mixture was stirred at RT for 2 h. The reaction mixture was quenched with water and thoroughly extracted with ethyl acetate. The combined organic extracts were washed with brine, dried over anhydrous sodium sulfate, filtered, and concentrated under reduced pressure. The residue was purified by silica gel chromatography (elution with ethyl acetate/hexanes 10:90) to give 8.6 g (83%) of tert-butyl-((3R,3aS,6S,6aR)-6-ethynyl-hexahydro-furo[3,2-b]furan-3-yloxy)-dimethyl-silane.
$^1$H-NMR (300 MHz, CDCl$_3$): δ=4.66-4.62 (m, 1H), 4.51-4.48 (m, 1H), 4.35-4.26 (m, 1H), 4.13-4.08 (m, 1H), 3.96-3.91 (m, 1H), 3.83-3.78 (m, 1H), 3.66-3.60 (m, 1H), 3.09-3.00 (m, 1H), 2.19 (s, 1H), 0.92 (s, 9H), 0.18 (s, 6H) ppm.

3-((3S,3aR,6R,6aR)-6-Hydroxy-hexahydro-furo[3,2-b]furan-3-yl)-propionic acid ethyl ester (P31)

n-Butyllithium (0.1 mL, 0.25 mmol, 2.5M in hexanes) was added to a solution of tert-butyl-((3R,3aS,6S,6aR)-6-ethynyl-hexahydro-furo[3,2-b]furan-3-yloxy)-dimethyl-silane (P30) (47 mg, 0.175 mmol) in THF (7 mL) at −78° C. After stirring at −78° C. for 30 min, ethyl chloroformate (50 µL, 0.52 mmol) was added to the mixture drop wise. The reaction mixture was slowly warmed to RT and stirred for 1 h before being quenched by addition of saturated aqueous ammonium chloride solution. The phases were separated and the aqueous phase was thoroughly extracted with diethylether. The combined organic extracts were washed with brine, dried over anhydrous sodium sulfate, filtered, and concentrated under reduced pressure.

The residue was dissolved in methanol (7 mL) and 10% palladium on charcoal (5 mg) was added. The mixture was stirred under hydrogen atmosphere (1 bar) for 12 h. The mixture was filtered through a celite pad and the filtrate was concentrated under reduced pressure. The residue was dissolved in THF (5 mL), cooled to 0° C. and a 1M solution of TBAF in THF (0.2 mL) was added. The mixture was stirred at 0° C. for 1 h and was quenched by addition of saturated aqueous ammonium chloride solution. The phases were separated and the aqueous phase was thoroughly extracted with ethyl acetate. The combined organic extracts were washed with brine, dried over anhydrous sodium sulfate, filtered, and concentrated under reduced pressure. The residue was purified by silica gel chromatography (elution with ethylacetate/hexanes 50:50) to give 20 mg (50% for 3 steps) of 3-((3S,3aR,6R,6aR)-6-hydroxy-hexahydro-furo[3,2-b]furan-3-yl)-propionic acid ethyl ester, which was used directly in the next step.

3-((3S,3aR,6S,6aR)-6-Amino-hexahydro-furo[3,2-b]furan-3-yl)-propionic acid ethyl ester (P32)

10 mg (0.04 mmol) of 3-((3S,3aR,6S,6aR)-6-amino-hexahydro-furo[3,2-b]furan-3-yl)-propionic acid ethyl ester was synthesized from 3-((3S,3aR,6R,6aR)-6-hydroxy-hexahydro-furo[3,2-b]furan-3-yl)-propionic acid ethyl ester (P31) (20 mg, 0.087 mmol) following procedures similar to those described for the synthesis of (3S,3aR,6S,6aR)-6-benzo[1,3]dioxol-5-ylethynyl-hexahydro-furo[3,2-b]furan-3-ylamine (P25) from (3R,3aR,6S,6aR)-6-benzo[1,3]dioxol-5-ylethynyl-hexahydro-furo[3,2-b]furan-3-ol (P22) using 30 µL (0.18 mmol) of trifluoromethanesulfonic anhydride, 30 µL (0.43 mmol) of pyridine and 12 mg (0.18 mmol) of sodium azide. The compound was used in the next step without further purification.

(3S,3aR,6R,6aS)-6-(tert-Butyl-dimethyl-silanyloxy)-hexahydro-furo[3,2-b]furan-3-carbonitrile (P33)

A solution of trifluoromethanesulfonic acid (3R,3aS,6R,6aS)-6-(tert-butyl-dimethyl-silanyloxy)-hexahydro-furo[3, 2-b]furan-3-yl ester (P2) (5.00 g, 12.7 mmol) in acetonitrile (32 mL) was treated with a solution of tetraethylammonium cyanide (2.19 g, 14.0 mmol) in acetonitrile (22 mL) whilst keeping the reaction temperature below 25° C. with a water bath. The reaction mixture was stirred at RT for 2 h, and then saturated aqueous ammonium chloride solution was added. The mixture was extracted with ethyl acetate, the organic layer was washed with water twice, dried over magnesium sulfate, filtered and evaporated to give 3.45 g (100%) of (3S,3aR,6R,6aS)-6-(tert-butyl-dimethyl-silanyloxy)-hexahydro-furo[3,2-b]furan-3-carbonitrile in a purity sufficient enough to be used in the next step without further purification. LC/MS (Method 8): $R_t$=1.16 min; detected mass: m/z=270.2 ([M+H]$^+$).

(3S,3aR,6S,6aR)-6-Amino-hexahydro-furo[3,2-b]furan-3-carbonitrile (P34)

333 mg (21% for 4 steps) of (3S,3aR,6S,6aR)-6-amino-hexahydro-furo[3,2-b]furan-3-carbonitrile were prepared from (3S,3aR,6R,6aS)-6-(tert-butyl-dimethyl-silanyloxy)-hexahydro-furo[3,2-b]furan-3-carbonitrile (P33) (3.45 g, 12.8 mmol) following the protocols described for the synthesis sequence to (3S,3aR,6S,6aR)-6-benzo[1,3]dioxol-5-ylethynyl-hexahydro-furo[3,2-b]furan-3-ylamine (P25) using 2.1 mL (12.5 mmol) of trifluoromethanesulfonic anhydride, 2.1 mL (26.0 mmol) of pyridine and 800 mg (12.3 mmol) of sodium azide. $^1$H-NMR (300 MHz, CDCl$_3$): δ=4.89-4.86 (m, 1H), 4.34-4.30 (m, 1H), 4.13-4.00 (m, 2H), 3.92-3.85 (m, 1H), 3.77-3.70 (m, 1H), 3.60-3.54 (m, 1H), 3.19-3.12 (m, 1H), 1.38 (s, 2H) ppm.

5-[(3S,3aS,6S,6aR)-6-(3-Cyclohexyl-ureido)-hexahydro-furo[3,2-b]furan-3-yloxy]-nicotinic acid ethyl ester (P35)

A solution of 5-hydroxy-nicotinic acid ethyl ester (350 mg, 2.12 mmol) in absolute N,N-dimethylformamide (10 mL) was treated with potassium tert-butoxide (320 mg, 2.83 mmol) and stirred for 45 min at RT. Then, a solution of toluene-4-sulfonic acid (3R,3aS,6S,6aR)-6-(3-cyclohexyl-ureido)-hexahydro-furo[3,2-b]furan-3-yl ester (2) (600 mg, 1.41 mmol) in N,N-dimethylformamide (10 mL) was added and the reaction mixture was stirred at 100° C. for 5 h, then cooled to RT, evaporated and partitioned between water (20 mL) and dichloromethane (20 mL). The phases were separated and the water phase extracted three times with dichloromethane. The combined organic layers were dried over magnesium sulfate, filtered, evaporated and purified by flash chromatography (silica gel, elution with dichloromethane/methanol 100:0 to 98:2) to give 460 mg (78%) of 5-[(3S,3aS,6S,6aR)-6-(3-cyclohexyl-ureido)-hexahydro-furo[3,2-b]furan-3-yloxy]-nicotinic acid ethyl ester, which was used in the next step without further purification. LC/MS (Method 6): $R_t$=1.76 min; detected mass: m/z=420.30 ([M+H]$^+$).

The following examples illustrate the invention.

Example 1

1-cyclohexyl-3-((3S,3aR,6R,6aR)-6-hydroxy-hexahydro-furo[3,2-b]furan-3-yl)-urea

1-[(3S,3aR,6R,6aS)-6-(tert-Butyl-dimethyl-silanyloxy)-hexahydro-furo[3,2-b]furan-3-yl]-3-cyclohexyl-urea (P10) (3.00 g, 7.80 mmol) was dissolved in 4M hydrochloric acid in dioxane (6.65 mL, 26.6 mmol) and stirred for 6 h at RT when LCMS indicated complete deprotection. The reaction mixture was concentrated under reduced pressure, concentrated twice under reduced pressure after the addition of toluene, taken up in water and the pH was adjusted to pH 7 with aqueous sodium hydroxide solution. The solution was freeze dried and the crude 1-cyclohexyl-3-((3S,3aR,6R,6aR)-6-hydroxy-hexahydro-furo[3,2-b]furan-3-yl)-urea was used in the next step without further purification. LC/MS (Method 4): $R_t$=2.53 min; detected mass: m/z=271.24 ([M+H]$^+$).

Example 2 toluene-4-sulfonic acid (3R,3aS,6S,6aR)-6-(3-cyclohexyl-ureido)-hexahydro-furo[3,2-b]furan-3-yl ester Synthesis A: from toluene-4-sulfonic acid (3R,3aS,6S,6aR)-6-amino-hexahydro-furo[3,2-b]furan-3-yl ester (P6)

A solution of toluene-4-sulfonic acid (3R,3aS,6S,6aR)-6-amino-hexahydro-furo[3,2-b]furan-3-yl ester (P6) (590 mg, 1.97 mmol) in absolute dichloromethane (10 mL) was treated consecutively with triethylamine (299 mg, 0.41 mL, 2.96 mmol) and cyclohexylisocyanate (197 mg, 0.20 mL, 1.58 mmol). After stirring for 5 h at RT, another portion of cyclohexylisocyanate (39.4 mg, 0.04 mL, 0.32 mmol) was added and stirring was continued for 30 min. The reaction was quenched by addition of methanol and stirred overnight before saturated aqueous sodium bicarbonate solution was added. The layers were separated; the aqueous layer was extracted twice with dichloromethane. The organic layers were combined, dried over magnesium sulfate, filtered and evaporated. The resulting crude product was purified by reversed phase HPLC (acetonitrile/water with 0.1% trifluoroacetic acid) to give 550 mg (66%) of pure toluene-4-sulfonic acid (3R,3aS,6S,6aR)-6-(3-cyclohexyl-ureido)-hexahydro-furo[3,2-b]furan-3-yl ester. LC/MS (Method 3): $R_t$=1.20 min; detected mass: m/z=425.05 ([M+H]$^+$).

Synthesis B: from 1-cyclohexyl-3-((3S,3aR,6R,6aR)-6-hydroxy-hexahydro-furo[3,2-b]furan-3-yl)-urea (1)

1-Cyclohexyl-3-((3S,3aR,6R,6aR)-6-hydroxy-hexahydro-furo[3,2-b]furan-3-yl)-urea (1) (500 mg, 1.48 mmol) and p-toluenesulfonyl chloride (560 mg, 2.96 mmol) were dissolved in pyridine (3.62 mL) and stirred at RT for 72 h. The reaction mixture was concentrated under reduced pressure; the residue was taken up in ethyl acetate (20 mL), washed three times with 0.1N aqueous hydrochloric acid (20 mL), dried over magnesium sulfate, filtered and evaporated. The crude material was purified by flash chromatography (silica gel, elution with dichloromethane/methanol 100:0 to 98:2) to give 400 mg (64%) of toluene-4-sulfonic acid (3R,3aS,6S,6aR)-6-(3-cyclohexyl-ureido)-hexahydro-furo[3,2-b]furan-3-yl ester.

Example 3

1-cyclohexyl-3-[(3S,3aR,6S,6aS)-6-(pyridin-2-yloxy)-hexahydro-furo[3,2-b]furan-3-yl]-urea A solution of 1H-pyridin-2-one (50.4 mg, 0.53 mmol) in absolute N,N-dimethylformamide (1.0 mL) was treated with potassium tert-butoxide (79.2 mg, 0.71 mmol) and stirred for 45 min at RT. Then, a solution of toluene-4-sulfonic acid (3R,3aS,6S,6aR)-6-(3-cyclohexyl-ureido)-hexahydro-furo[3,2-b]furan-3-yl ester (2) (150 mg, 0.35 mmol) in N,N-dimethylformamide (1.0 mL) was added and the reaction mixture was heated in the microwave oven for 30 min at 120° C. The crude reaction mixture was directly purified by reversed phase HPLC (acetonitrile/water with 0.1 trifluoroacetic acid) to give 41 mg (33%) of 1-cyclohexyl-3-[(3S,3aR,6S,6aS)-6-(pyridin-2-yloxy)-hexahydro-furo[3,2-b]furan-3-yl]-urea along with 19 mg (15%) of the regioisomeric 1-cyclohexyl-3-[(3S,3aR,6S,6aR)-6-(2-oxo-2H-pyridin-1-yl)-hexahydro-furo[3,2-b]furan-3-yl]-urea. LC/MS (Method 6): $R_f$=1.71 min; detected mass: m/z=348.26 ([M+H]$^+$).

Example 4 morpholine-4-carboxylic acid (3S,3aS,6S,6aR)-6-(3-cyclohexyl-ureido)-hexahydro-furo[3,2-b]furan-3-yl ester A solution of toluene-4-sulfonic acid (3R,3aS,6S,6aR)-6-(3-cyclohexyl-ureido)-hexahydro-furo[3,2-b]furan-3-yl ester (2) (50 mg, 0.12 mmol) in absolute dimethylsulfoxide (500 µL) was treated with cesium carbonate (115 mg, 0.35 mmol) and morpholine (12.3 mg, 10 µL, 0.14 mmol). The reaction mixture was stirred 3.5 h at RT before being heated in the microwave oven for 15 min to 80° C. and another 30 min to 120° C. The mixture was diluted with water and extracted twice with dichloromethane. The organic layers were combined and concentrated under reduced pressure. The crude product was purified by reversed phase HPLC (acetonitrile/water with 0.1% trifluoroacetic acid) to give 8.9 mg (20%) of morpholine-4-carboxylic acid (3S,3aS,6S,6aR)-6-(3-cyclohexyl-ureido)-hexahydro-furo[3,2-b]furan-3-yl ester. LC/MS (Method 6): $R_f$=1.39 min; detected mass: m/z=384.30 ([M+H]$^+$).

Example 5

1-cyclohexyl-3-[(3S,3aR,6S,6aS)-6-(1H-indol-3-yloxy)-hexahydro-furo[3,2-b]furan-3-yl]-urea A solution of indoxyl acetate (68.1 mg, 0.38 mmol) in absolute N,N-dimethylformamide (1.0 mL) was treated with potassium tert-butoxide (57.1 mg, 0.51 mmol) and stirred for 45 min at RT. Then, a solution of toluene-4-sulfonic acid (3R,3aS,6S,6aR)-6-(3-cyclohexyl-ureido)-hexahydro-furo[3,2-b]furan-3-yl ester (2) (80 mg, 0.19 mmol) in dry N,N-dimethylformamide (0.5 mL) was added and the reaction mixture was heated in the microwave oven for 30 min at 120° C. The crude reaction mixture was diluted with water and purified by reversed phase HPLC (acetonitrile/water with 0.1% trifluoroacetic acid) to give 48 mg (66%) of 1-cyclohexyl-3-[(3S,3aR,6S,6aS)-6-(1H-indol-3-yloxy)-hexahydro-furo[3,2-b]furan-3-yl]-urea. LC/MS (Method 6): $R_f$=1.66 min; detected mass: m/z=384.14 ([M+H]$^+$).

Example 6

1-benzyl-3-cyclohexyl-1-((3S,3aR,6S,6aR)-6-hydroxymethyl-hexahydro-furo[3,2-b]furan-3-yl)-urea A solution of 1-benzyl-3-cyclohexyl-1-((3S,3aR,6S,6aR)-6-formyl-hexahydro-furo[3,2-b]furan-3-yl)-urea (P16) (206 mg) in ethanol (3.5 mL, solution from synthesis of P16) was cooled to −10° C. and sodium borohydride (10.4 mg, 0.28 mmol) was added portionwise. The reaction mixture was stirred at −10° C. for 1.5 h, quenched by careful addition of 2N aqueous hydrogen chloride solution (to pH 5) and extracted with ethyl acetate. The organic layer was washed with saturated aqueous sodium bicarbonate solution, dried over magnesium sulfate, filtered and concentrated under reduced pressure. The crude product was purified by reversed phase HPLC (acetonitrile/water with 0.1% trifluoroacetic acid) to give 2.0 mg (1%) of 1-benzyl-3-cyclohexyl-1-((3S,3aR,6S,6aR)-6-hydroxymethyl-hexahydro-furo[3,2-b]furan-3-yl)-urea. LC/MS (Method 6): $R_f$=1.63 min; detected mass: m/z=375.38 ([M+H]$^+$).

Examples 7 and 8

1-((3S,3aR,6S,6aR)-6-aminomethyl-hexahydro-furo[3,2-b]furan-3-yl)-1-benzyl-3-cyclohexyl-urea; trifluoroacetate and 1-((3S,3aR,6S,6aR)-6-aminomethyl-hexahydro-furo[3,2-b]furan-3-yl)-3-cyclohexyl-urea; trifluoroacetate 1-Benzyl-1-((3S,3aR,6S,6aR)-6-cyano-hexahydro-furo[3,2-b]furan-3-yl)-3-cyclohexyl-urea (P15) (260 mg, 0.70 mmol) was dissolved in ethanol (120 mL) and 2N aqueous hydrogen chloride solution (172 µL, 0.34 mmol) was added. After the addition of 10% palladium on charcoal (23.2 mg, 0.02 mmol), the reaction mixture was flooded with hydrogen and stirred under an atmosphere of hydrogen (1 bar) for 2 h. Then, hydrogen was bubbled through the reaction mixture for 30 min and the mixture was stirred over night under an atmosphere of hydrogen (1 bar). The catalyst was filtered off, the solution was evaporated and the crude product was purified by reversed phase HPLC (acetonitrile/water with 0.1% trifluoroacetic acid) to give 16.7 mg (5%) of 1-((3S,3aR,6S,6aR)-6-aminomethyl-hexahydro-furo[3,2-b]furan-3-yl)-1-benzyl-3-cyclohexyl-urea (7) along with 125 mg (45%) of 1-((3S,3aR,6S,6aR)-6-aminomethyl-hexahydro-furo[3,2-b]furan-3-yl)-3-cyclohexyl-urea (8), both as their trifluoroacetic acid salts.

Example 7

LC/MS (Method 6): $R_f$=1.38 min; detected mass: m/z=374.36 ([M+H]$^+$).

Example 8

LC/MS (Method 8): $R_f$=0.53 min; detected mass: m/z=284.20 ([M+H]$^+$).

Example 9

1-cyclohexyl-3-((3S,3aR,6S,6aR)-6-dimethylaminomethyl-hexahydro-furo[3,2-b]furan-3-yl)-urea; trifluoroacetate A solution of 1-((3S,3aR,6S,6aR)-6-aminomethyl-hexahydro-furo[3,2-b]furan-3-yl)-3-cyclohexyl-urea (8) (120 mg, 0.30 mmol) in absolute methanol (1.5 mL) was cooled to 0° C. and was treated consecutively with powdered molecular sieves (3 Å, one spatula tip), triethylamine (126 µL, 0.24 mmol), acetic acid (173 µL, 3.02 mmol) and formaldehyde solution in water (37 wt %, 18 µL, 0.24 mmol). After stirring at 0° C. for 1 h, a solution of sodium cyanoborohydride (59.9 mg, 0.91 mmol) in methanol (500 µL) was added dropwise and the mixture was stirred at 0° C. for 1 h. The reaction mixture was filtered and the filtrate was evaporated to dryness. The residue was dissolved in dichloromethane and washed with saturated aqueous sodium bicarbonate solution. The aqueous phase was reextracted three times with dichloromethane; the combined organic layers were dried over magnesium sulfate, filtered, and evaporated. The crude material was purified by reversed phase HPLC (acetonitrile/water with 0.1% trifluoroacetic acid) to yield 87 mg (68%) of the desired product as trifluoroacetic acid salt. LC/MS (Method 6): $R_t$=1.14 min; detected mass: m/z=312.3 ([M+H]$^+$).

Example 10

4-[(3S,3aS,6S,6aR)-6-(3-cyclohexyl-ureido)-hexahydro-furo[3,2-b]furan-3-yloxy]-benzoic acid methyl ester A solution of 1-cyclohexyl-3-((3S,3aR,6R,6aR)-6-hydroxy-hexahydro-furo[3,2-b]furan-3-yl)-urea (1) (100 mg, 0.30 mmol) in tetrahydrofuran (1 mL) was treated sequentially with methyl 4-hydroxybenzoate (67.6 mg, 0.44 mmol), triphenylphosphane (157 mg, 0.59 mmol) and a 1M solution of diisopropyl azodicarboxylate in tetrahydrofuran (0.59 mL, 0.59 mmol). The reaction mixture was stirred over night at RT before another portion of triphenylphosphane (39.2 mg, 0.15 mmol) was added. The reaction mixture was heated to 50° C. for 1 h, then concentrated under reduced pressure and purified by reversed phase HPLC (acetonitrile/water with 0.1 trifluoroacetic acid) to give 84 mg (69%) of 4-[(3S,3aS,6S,6aR)-6-(3-cyclohexyl-ureido)-hexahydro-furo[3,2-b]furan-3-yloxy]-benzoic acid methyl ester. LC/MS (Method 3): $R_t$=1.22 min; detected mass: m/z=405.12 ([M+H]$^+$).

Example 11

4-[(3S,3aS,6S,6aR)-6-(3-cyclohexyl-ureido)-hexahydro-furo[3,2-b]furan-3-yloxy]-benzoic acid 4-[(3S,3aS,6S,6aR)-6-(3-Cyclohexyl-ureido)-hexahydro-furo[3,2-b]furan-3-yloxy]-benzoic acid methyl ester (10) (9.0 mg, 0.02 mmol) was dissolved in a 1:1 mixture of methanol and water (6 mL) and potassium hydroxide (12.5 mg, 0.22 mmol) was added. The mixture was stirred over night at RT, then the solution was acidified by addition of 1N aqueous hydrochloric acid solution and repeatedly extracted with ethyl acetate. The combined organic phases were washed with brine, dried over magnesium sulfate, filtered and evaporated. Purification by reversed phase HPLC (acetonitrile/water with 0.1% trifluoroacetic acid) yielded 3.5 mg (40%) of 4-[(3S,3aS,6S,6aR)-6-(3-cyclohexyl-ureido)-hexahydro-furo[3,2-b]furan-3-yloxy]-benzoic acid. LC/MS (Method 3): $R_t$=1.13 min; detected mass: m/z=391.10 ([M+H]$^+$).

Example 12

1-cyclohexyl-3-((3S,3aR,6S,6aS)-6-cyclohexylsulfanyl-hexahydro-furo[3,2-b]furan-3-yl)-urea A solution of cyclohexyl mercaptane (41.1 mg, 0.35 mmol) in absolute N,N-dimethylformamide (2 mL) was treated with potassium tert-butoxide (52.9 mg, 0.47 mmol) and stirred for 45 min at RT. Then, a solution of toluene-4-sulfonic acid (3R,3aS,6S,6aR)-6-(3-cyclohexyl-ureido)-hexahydro-furo[3,2-b]furan-3-yl ester (2) (100 mg, 0.24 mmol) in N,N-dimethylformamide (2 mL) was added and the reaction mixture was stirred at 50° C. for 5 h, then at RT over night and at 80° C. for an additional period of 6 h. Another portion of potassium cyclohexane thiolate [made from cyclohexyl mercaptane (41.1 mg, 0.35 mmol) and potassium tert-butoxide (52.9 mg, 0.47 mmol) in absolute N,N-dimethylformamide (2 mL) following the procedure above] was added and the reaction mixture was heated to 80° C. for 2 h. The crude reaction mixture was evaporated and partitioned between water (20 mL) and dichloromethane (20 mL). The phases were separated and the water phase extracted three times with dichloromethane. The combined organic layers were dried over magnesium sulfate, filtered, evaporated and purified by reversed phase HPLC (acetonitrile/water with 0.1% trifluoroacetic acid) to give 48 mg (55%) of 1-cyclohexyl-3-((3S,3aR,6S,6aS)-6-cyclohexylsulfanyl-hexahydro-furo[3,2-b]furan-3-yl)-urea. LC/MS (Method 3): $R_t$=1.29 min; detected mass: m/z=369.16 ([M+H]$^+$).

According to the previous example the following compounds were prepared in close analogy.

In case of trifluoroacetic acid salts formed by the procedure described above, the free base could be isolated via following procedure: The respective trifluoroacetic acid salt was partitioned between an organic solvent (dichloromethane, tert.-butyl methyl ether or ethyl acetate) and saturated aqueous sodium carbonate solution and stirred for 30 min. The organic layer was separated, washed with water, dried over magnesium sulfate, filtered and evaporated to give free base. Alternatively, the hydrochloride salts were made by addition of a 0.1N aqueous solution of hydrochloric acid to the trifluoroacetic acid salt and subsequent lyophilization.

| No | Starting compound | Chemical name | Mass (from LC/MS) | $R_t$ (from LC/MS) (min) | LC/MS Method |
|---|---|---|---|---|---|
| 13 | Thiazol-2-ylamine | 1-Cyclohexyl-3-[(3S,3aR,6S,6aR)-6-(thiazol-2-ylamino)-hexahydro-furo[3,2-b]furan-3-yl]-urea | 353.14 | 1.17 | 6 |
| 14 | 2-Mercapto-ethanol | 1-Cyclohexyl-3-[(3S,3aR,6S,6aS)-6-(2-hydroxy-ethylsulfanyl)-hexahydro-furo[3,2-b]furan-3-yl]-urea | 331.22 | 0.89 | 3 |
| 15 | 4-Fluorothio-phenol | 1-Cyclohexyl-3-[(3S,3aR,6S,6aS)-6-(4-fluoro-phenylsulfanyl)-hexahydro-furo[3,2-b]furan-3-yl]-urea | 381.19 | 1.12 | 3 |
| 16 | N-(2-Mercapto-ethyl)-acetamide | N-{2-[(3S,3aS,6S,6aR)-6-(3-Cyclohexyl-ureido)-hexahydro-furo[3,2-b]furan-3-ylsulfanyl]-ethyl}-acetamide | 372.11 | 1.04 | 3 |
| 17 | Propane-2-thiol | 1-Cyclohexyl-3-((3S,3aR,6S,6aS)-6-isopropylsulfanyl-hexahydro-furo[3,2-b]furan-3-yl)-urea | 329.14 | 1.22 | 3 |
| 18 | 4-Methoxy-phenol | 1-Cyclohexyl-3-[(3S,3aR,6S,6aS)-6-(4-methoxy-phenoxy)-hexahydro-furo[3,2-b]furan-3-yl]-urea | 377.12 | 1.22 | 3 |

-continued

| No | Starting compound | Chemical name | Mass (from LC/MS) | R_t (from LC/MS) (min) | LC/MS Method |
|----|---|---|---|---|---|
| 19 | 2,2,2-Trifluoro-ethanol | 1-Cyclohexyl-3-[(3S,3aR,6S,6aS)-6-(2,2,2-trifluoro-ethoxy)-hexahydro-furo[3,2-b]furan-3-yl]-urea | 352.95 | 1.08 | 3 |
| 20 | 2-(2-Methyl-thiazol-4-yl)-phenol | 1-Cyclohexyl-3-{(3S,3aR,6S,6aS)-6-[2-(2-methyl-thiazol-4-yl)-phenoxy]-hexahydro-furo[3,2-b]furan-3-yl}-urea | 444.11 | 1.25 | 3 |
| 21 | 2-Methyl-propane-2-thiol | 1-((3S,3aR,6S,6aS)-6-tert-Butylsulfanyl-hexahydro-furo[3,2-b]furan-3-yl)-3-cyclohexyl-urea | 343.15 | 1.23 | 3 |
| 22 | 3-Mercapto-3-methyl-butan-1-ol | 1-Cyclohexyl-3-[(3S,3aR,6S,6aS)-6-(3-hydroxy-1,1-dimethyl-propylsulfanyl)-hexahydro-furo[3,2-b]furan-3-yl]-urea | 373.22 | 0.99 | 3 |
| 23 | Biphenyl-2-ol | 1-[(3S,3aR,6S,6aS)-6-(Biphenyl-2-yloxy)-hexahydro-furo[3,2-b]furan-3-yl]-3-cyclohexyl-urea | 423.13 | 1.31 | 3 |
| 24 | 4-Fluoro-phenol | 1-Cyclohexyl-3-[(3S,3aR,6S,6aS)-6-(4-fluoro-phenoxy)-hexahydro-furo[3,2-b]furan-3-yl]-urea | 365.10 | 1.22 | 3 |
| 25 | Tetrahydro-thiophene-3-thiol-1,1-dioxide | 1-Cyclohexyl-3-[(3S,3aR,6S,6aS)-6-(1,1-dioxo-tetrahydro-1λ6-thiophen-3-ylsulfanyl)-hexahydro-furo[3,2-b]furan-3-yl]-urea | 405.06 | 1.06 | 3 |
| 26 | 5-(2-Hydroxy-phenyl)-1H-tetrazole | 1-Cyclohexyl-3-{(3S,3aR,6S,6aS)-6-[2-(1H-tetrazol-5-yl)-phenoxy]-hexahydro-furo[3,2-b]furan-3-yl}-urea | 415.11 | 1.11 | 3 |
| 27 | 3-Phenoxy-phenol | 1-Cyclohexyl-3-[(3S,3aR,6S,6aS)-6-(3-phenoxy-phenoxy)-hexahydro-furo[3,2-b]furan-3-yl]-urea | 439.15 | 1.32 | 3 |
| 28 | 6-Methyl-pyridin-3-ol | 1-Cyclohexyl-3-[(3S,3aR,6S,6aS)-6-(6-methyl-pyridin-3-yloxy)-hexahydro-furo[3,2-b]furan-3-yl]-urea | 362.36 | 1.14 | 6 |
| 29 | 3-Chloro-4-fluoro-phenol | 1-[(3S,3aR,6S,6aS)-6-(3-Chloro-4-fluoro-phenoxy)-hexahydro-furo[3,2-b]furan-3-yl]-3-cyclohexyl-urea | 399.08 | 1.27 | 3 |
| 30 | 3-[1,2,4]Triazol-4-yl-phenol | 1-Cyclohexyl-3-[(3S,3aR,6S,6aS)-6-(3-[1,2,4]triazol-4-yl-phenoxy)-hexahydro-furo[3,2-b]furan-3-yl]-urea | 414.10 | 1.06 | 3 |
| 31 | 3,5-Dichloro-phenol | 1-Cyclohexyl-3-[(3S,3aR,6S,6aS)-6-(3,5-dichloro-phenoxy)-hexahydro-furo[3,2-b]furan-3-yl]-urea | 415.01 | 1.33 | 3 |
| 32 | 4-(1-Methyl-1H-imidazol-2-yl)-phenol | 1-Cyclohexyl-3-{(3S,3aR,6S,6aS)-6-[4-(1-methyl-1H-imidazol-2-yl)-phenoxy]-hexahydro-furo[3,2-b]furan-3-yl}-urea | 427.43 | 1.18 | 6 |
| 33 | 5-Chloro-3-pyridinol | 1-[(3S,3aR,6S,6aS)-6-(5-Chloro-pyridin-3-yloxy)-hexahydro-furo[3,2-b]furan-3-yl]-3-cyclohexyl-urea | 382.30 | 1.61 | 6 |
| 34 | 2,6-Dimethyl-pyridin-3-ol | 1-Cyclohexyl-3-[(3S,3aR,6S,6aS)-6-(2,6-dimethyl-pyridin-3-yloxy)-hexahydro-furo[3,2-b]furan-3-yl]-urea | 376.41 | 1.09 | 6 |
| 35 | 5-Fluoro-pyridin-3-ol | 1-Cyclohexyl-3-[(3S,3aR,6S,6aS)-6-(5-fluoro-pyridin-3-yloxy)-hexahydro-furo[3,2-b]furan-3-yl]-urea | 366.31 | 1.52 | 6 |
| 36 | 5-Methyl-pyridin-3-ol | 1-Cyclohexyl-3-[(3S,3aR,6S,6aS)-6-(5-methyl-pyridin-3-yloxy)-hexahydro-furo[3,2-b]furan-3-yl]-urea | 362.31 | 1.42 | 6 |
| 37 | 2,4-Dimethyl-pyridin-3-ol | 1-Cyclohexyl-3-[(3S,3aR,6S,6aS)-6-(2,4-dimethyl-pyridin-3-yloxy)-hexahydro-furo[3,2-b]furan-3-yl]-urea | 376.33 | 1.35 | 6 |
| 38 | 2-Ethyl-6-methyl-pyridin-3-ol | 1-Cyclohexyl-3-[(3S,3aR,6S,6aS)-6-(2-ethyl-6-methyl-pyridin-3-yloxy)-hexahydro-furo[3,2-b]furan-3-yl]-urea | 390.36 | 1.37 | 6 |
| 39 | 4,6-Dimethyl-pyridin-3-ol | 1-Cyclohexyl-3-[(3S,3aR,6S,6aS)-6-(4,6-dimethyl-pyridin-3-yloxy)-hexahydro-furo[3,2-b]furan-3-yl]-urea | 376.25 | 1.18 | 6 |
| 40 | 3-Hydroxy-pyridine-2-carbonitrile | 1-[(3S,3aR,6S,6aS)-6-(2-Cyano-pyridin-3-yloxy)-hexahydro-furo[3,2-b]furan-3-yl]-3-cyclohexyl-urea | 373.27 | 1.67 | 6 |

| No | Starting compound | Chemical name | Mass (from LC/MS) | R_t (from LC/MS) (min) | LC/MS Method |
|---|---|---|---|---|---|
| 41 | 2-Methyl-pyrimidin-5-ol | 1-Cyclohexyl-3-[(3S,3aR,6S,6aS)-6-(2-methyl-pyrimidin-5-yloxy)-hexahydro-furo[3,2-b]furan-3-yl]-urea | 363.22 | 1.38 | 6 |
| 42 | 6-Trifluoromethyl-pyridin-3-ol | 1-Cyclohexyl-3-[(3S,3aR,6S,6aS)-6-(6-trifluoromethyl-pyridin-3-yloxy)-hexahydro-furo[3,2-b]furan-3-yl]-urea | 416.29 | 1.84 | 6 |
| 43 | 5-Methyl-[1,3,4]oxadiazole-2-thiol | 1-Cyclohexyl-3-[(3S,3aR,6S,6aS)-6-(5-methyl-[1,3,4]oxadiazol-2-ylsulfanyl)-hexahydro-furo[3,2-b]furan-3-yl]-urea | 369.24 | 1.61 | 6 |
| 44 | Pyrimidin-5-ol | 1-Cyclohexyl-3-[(3S,3aR,6S,6aS)-6-(pyrimidin-5-yloxy)-hexahydro-furo[3,2-b]furan-3-yl]-urea | 349.19 | 3.00 | 4 |
| 45 | 2,2,2-Trifluoro-ethanethiol | 1-Cyclohexyl-3-[(3S,3aR,6S,6aS)-6-(2,2,2-trifluoro-ethylsulfanyl)-hexahydro-furo[3,2-b]furan-3-yl]-urea | 369.43 | 1.63 | 6 |
| 46 | Pyrimidine-2-thiol | 1-Cyclohexyl-3-[(3S,3aR,6S,6aS)-6-(pyrimidin-2-ylsulfanyl)-hexahydro-furo[3,2-b]furan-3-yl]-urea | 365.22 | 1.64 | 6 |
| 47 | 4,6-Dimethyl-pyrimidine-2-thiol | 1-Cyclohexyl-3-[(3S,3aR,6S,6aS)-6-(4,6-dimethyl-pyrimidin-2-ylsulfanyl)-hexahydro-furo[3,2-b]furan-3-yl]-urea | 393.26 | 3.83 | 4 |
| 48 | 2-Mercapto-imidazole | 1-Cyclohexyl-3-[(3S,3aR,6S,6aS)-6-(1H-imidazol-2-ylsulfanyl)-hexahydro-furo[3,2-b]furan-3-yl]-urea | 353.28 | 1.24 | 6 |
| 49 | Pyrimidine-4-thiol | 1-Cyclohexyl-3-[(3S,3aR,6S,6aS)-6-(pyrimidin-4-ylsulfanyl)-hexahydro-furo[3,2-b]furan-3-yl]-urea; hydrochloride | 365.27 | 1.60 | 6 |
| 50 | 5-Methyl-pyrimidine-2-thiol | 1-Cyclohexyl-3-[(3S,3aR,6S,6aS)-6-(5-methyl-pyrimidin-2-ylsulfanyl)-hexahydro-furo[3,2-b]furan-3-yl]-urea; hydrochloride | 379.27 | 1.71 | 6 |
| 51 | 6-Chloro-pyridin-3-ol | 1-[(3S,3aR,6S,6aS)-6-(6-Chloro-pyridin-3-yloxy)-hexahydro-furo[3,2-b]furan-3-yl]-3-cyclohexyl-urea | 382.27 | 3.84 | 4 |
| 52 | 5-Chloro-pyrimidine-2-thiol | 1-[(3S,3aR,6S,6aS)-6-(5-Chloro-pyrimidin-2-ylsulfanyl)-hexahydro-furo[3,2-b]furan-3-yl]-3-cyclohexyl-urea | 399.15 | 1.80 | 6 |
| 53 | 4,6-Dimethyl-pyridine-3-thiol | 1-Cyclohexyl-3-[(3S,3aR,6S,6aS)-6-(4,6-dimethyl-pyridin-3-ylsulfanyl)-hexahydro-furo[3,2-b]furan-3-yl]-urea | 436.15 | 1.31 | 6 |
| 54 | Pyridine-2-thiol | 1-Cyclohexyl-3-[(3S,3aR,6S,6aS)-6-(pyridin-2-ylsulfanyl)-hexahydro-furo[3,2-b]furan-3-yl]-urea | 364.22 | 1.75 | 6 |
| 55 | Pyrazine-2-thiol | 1-Cyclohexyl-3-[(3S,3aR,6S,6aS)-6-(pyrazin-2-ylsulfanyl)-hexahydro-furo[3,2-b]furan-3-yl]-urea | 365.19 | 1.66 | 6 |
| 56 | Thiazole-2-thiol | 1-Cyclohexyl-3-[(3S,3aR,6S,6aS)-6-(thiazol-2-ylsulfanyl)-hexahydro-furo[3,2-b]furan-3-yl]-urea | 370.18 | 1.72 | 6 |
| 57 | 6-Methyl-pyridazine-3-thiol | 1-Cyclohexyl-3-[(3S,3aR,6S,6aS)-6-(6-methyl-pyridazin-3-ylsulfanyl)-hexahydro-furo[3,2-b]furan-3-yl]-urea | 379.24 | 1.61 | 6 |
| 58 | 4-Methyl-thiazole-2-thiol | 1-Cyclohexyl-3-[(3S,3aR,6S,6aS)-6-(4-methyl-thiazol-2-ylsulfanyl)-hexahydro-furo[3,2-b]furan-3-yl]-urea | 384.18 | 1.64 | 6 |
| 59 | 5-Methyl-pyridine-2-thiol | 1-Cyclohexyl-3-[(3S,3aR,6S,6aS)-6-(5-methyl-pyridin-2-ylsulfanyl)-hexahydro-furo[3,2-b]furan-3-yl]-urea | 378.25 | 1.67 | 6 |
| 60 | 6-Mercapto-nicotinonitrile | 1-[(3S,3aR,6S,6aS)-6-(5-Cyano-pyridin-2-ylsulfanyl)-hexahydro-furo[3,2-b]furan-3-yl]-3-cyclohexyl-urea | 389.18 | 1.76 | 6 |
| 61 | 2,6-Dimethyl-pyrimidine-4-thiol | 1-Cyclohexyl-3-[(3S,3aR,6S,6aS)-6-(2,6-dimethyl-pyrimidin-4-ylsulfanyl)-hexahydro-furo[3,2-b]furan-3-yl]-urea | 393.20 | 3.18 | 4 |

| No | Starting compound | Chemical name | Mass (from LC/MS) | R$_t$ (from LC/MS) (min) | LC/MS Method |
|---|---|---|---|---|---|
| 62 | 4,5-Dimethyl-thiazole-2-thiol | 1-Cyclohexyl-3-[(3S,3aR,6S,6aS)-6-(4,5-dimethyl-thiazol-2-ylsulfanyl)-hexahydro-furo[3,2-b]furan-3-yl]-urea | 398.21 | 4.17 | 4 |
| 63 | 5-Chloro-pyridine-2-thiol | 1-[(3S,3aR,6S,6aS)-6-(5-Chloro-pyridin-2-ylsulfanyl)-hexahydro-furo[3,2-b]furan-3-yl]-3-cyclohexyl-urea | 398.16 | 1.88 | 6 |
| 64 | 6-Chloro-5-fluoro-pyridin-3-ol | 1-[(3S,3aR,6S,6aS)-6-(6-Chloro-5-fluoro-pyridin-3-yloxy)-hexahydro-furo[3,2-b]furan-3-yl]-3-cyclohexyl-urea | 400.16 | 1.82 | 6 |
| 65 | 6-Chloro-5-methyl-pyridin-3-ol | 1-[(3S,3aR,6S,6aS)-6-(6-Chloro-5-methyl-pyridin-3-yloxy)-hexahydro-furo[3,2-b]furan-3-yl]-3-cyclohexyl-urea | 396.20 | 1.82 | 6 |
| 66 | 6-Chloro-4-methyl-pyridin-3-ol | 1-[(3S,3aR,6S,6aS)-6-(6-Chloro-4-methyl-pyridin-3-yloxy)-hexahydro-furo[3,2-b]furan-3-yl]-3-cyclohexyl-urea | 396.20 | 1.82 | 6 |
| 67 | 2,6-Dimethyl-pyridin-4-ol | 1-Cyclohexyl-3-[(3S,3aR,6S,6aS)-6-(2,6-dimethyl-pyridin-4-yloxy)-hexahydro-furo[3,2-b]furan-3-yl]-urea | 376.24 | 2.48 | 4 |

Example 68

1-cyclohexyl-3-{(3S,3aR,6S,6aS)-6-[5-(1-hydroxy-1-methyl-ethyl)-pyridin-3-yloxy]-hexahydro-furo[3,2-b]furan-3-yl}-urea; hydrochloride A solution of 5-[(3S,3aS,6S,6aR)-6-(3-cyclohexyl-ureido)-hexahydro-furo[3,2-b]furan-3-yloxy]-nicotinic acid ethyl ester (P35) (200 mg, 0.48 mmol) in absolute tetrahydrofuran (2 mL) was cooled to 0° C. and treated with a 1.4M solution of methyl magnesium bromide in tetrahydrofuran/toluene (1.02 mL, 1.43 mmol). The reaction mixture was warmed to RT and stirred for 2 h. Another portion of methyl magnesium bromide in tetrahydrofuran/toluene (0.5 mL, 0.72 mmol) was added and the reaction stirred at RT over night. Then, the reaction was stopped by addition of 2-propanol, the reaction mixture was evaporated and purified by reversed phase HPLC (acetonitrile/water with 0.1% trifluoroacetic acid). The hydrochloride was made by addition of 0.1N aqueous solution of hydrochloric acid to the trifluoroacetic acid salt and subsequent lyophilization to give 20 mg (9%) of 1-cyclohexyl-3-{(3S,3aR,6S,6aS)-6-[5-(1-hydroxy-1-methyl-ethyl)-pyridin-3-yloxy]-hexahydro-furo[3,2-b]furan-3-yl}-urea. LC/MS (Method 6): R$_t$=1.42 min; detected mass: m/z=406.34 ([M+H]$^+$).

Example 69

1-cyclohexyl-3-{(3S,3aR,6S,6aS)-6-[5-(1-ethyl-1-hydroxy-propyl)-pyridin-3-yloxy]-hexahydro-furo[3,2-b]furan-3-yl}-urea Starting from 5-[(3S,3aS,6S,6aR)-6-(3-cyclohexyl-ureido)-hexahydro-furo[3,2-b]furan-3-yloxy]-nicotinic acid ethyl ester (P35) (200 mg, 0.48 mmol) and a 1M solution of ethyl magnesium bromide in tetrahydrofuran (2.15 mL, 2.15 mmol), 20 mg (10%) of 1-cyclohexyl-3-{(3S,3aR,6S,6aS)-6-[5-(1-ethyl-1-hydroxy-propyl)-pyridin-3-yloxy]-hexahydro-furo[3,2-b]furan-3-yl}-urea were prepared in analogy to the procedure described for the synthesis of Example 68. LC/MS (Method 6): R$_t$=1.55 min; detected mass: m/z=434.32 ([M+H]$^+$).

Example 70

1-cyclohexyl-3-[(3S,3aR,6S,6aS)-6-(6-pyrrolidin-1-yl-pyridin-3-yloxy)-hexahydro-furo[3,2-b]furan-3-yl]-urea 1-[(3S,3aR,6S,6aS)-6-(6-Chloro-pyridin-3-yloxy)-hexahydro-furo[3,2-b]furan-3-yl]-3-cyclohexyl-urea (51) (100 mg, 0.26 mmol) was dissolved in toluene (2 mL) and pyrrolidine (37.3 mg, 0.52 mmol), tris(dibenzylideneacetone)dipalladium(0) (10.1 mg, 0.01 mmol), sodium tert-butoxide (50.4 mg, 0.52 mmol) and (R)-(+)-2,2'-bis(diphenylphosphino)-1,1'-binaphthyl (10.8 mg, 0.02 mmol) were added. The reaction mixture was heated to 95° C. for 5 h, diluted with toluene and tert.-butyl methyl ether, and washed with water. The organic layer was separated, concentrated under reduced pressure and purified by reversed phase HPLC (acetonitrile/water with 0.1% trifluoroacetic acid) to give 34 mg (31%) of 1-cyclohexyl-3-[(3S,3aR,6S,6aS)-6-(6-pyrrolidin-1-yl-pyridin-3-yloxy)-hexahydro-furo[3,2-b]furan-3-yl]-urea. LC/MS (Method 6): R$_t$=1.21 min; detected mass: m/z=417.35 ([M+H]$^+$).

According to the previous example the following compounds were prepared from 1-[(3S,3aR,6S,6aS)-6-(6-chloro-pyridin-3-yloxy)-hexahydro-furo[3,2-b]furan-3-yl]-3-cyclohexyl-urea (51) and the respective amines in close analogy.

In case of basic centers, the free base could be isolated via following procedure: The respective trifluoroacetic acid salt was partitioned between an organic solvent (dichloromethane, tert.-butyl methyl ether or ethyl acetate) and saturated aqueous sodium carbonate solution and stirred for 30 min. The organic layer was separated, washed with water, dried over magnesium sulfate, filtered and evaporated to give free base.

| No | Starting compound | Chemical name | Mass (from LC/MS) | R$_t$ (from LC/MS) (min) | LC/MS Method |
|---|---|---|---|---|---|
| 71 | 4,4-Difluoro-piperidine hydrochloride | 1-Cyclohexyl-3-[(3S,3aR,6S,6aS)-6-(4,4-difluoro-3,4,5,6-tetrahydro-2H-[1,2']bipyridinyl-5'-yloxy)-hexahydro-furo[3,2-b]furan-3-yl]-urea | 467.42 | 3.68 | 4 |
| 72 | Diethylamine | 1-Cyclohexyl-3-[(3S,3aR,6S,6aS)-6-(6-diethylamino-pyridin-3-yloxy)-hexa-hydro-furo[3,2-b]furan-3-yl]-urea | 419.37 | 2.75 | 4 |
| 73 | Morpholine | 1-Cyclohexyl-3-[(3S,3aR,6S,6aS)-6-(6-morpholin-4-yl-pyridin-3-yloxy)-hexahydro-furo[3,2-b]furan-3-yl]-urea | 433.33 | 1.38 | 6 |

Example 74

1-((3S,3aR,6S,6aS)-6-cyclohexanesulfonyl-hexahydro-furo[3,2-b]furan-3-yl)-3-cyclohexyl-urea A solution of 1-cyclohexyl-3-((3S,3aR,6S,6aS)-6-cyclohexylsulfanyl-hexahydro-furo[3,2-b]furan-3-yl)-urea (12) (40 mg, 0.11 mmol) in absolute dichloromethane (3 mL) was treated with 3-chloroperoxybenzoic acid (34.5 mg, 0.22 mmol) and stirred at RT over night. The reaction mixture was evaporated and purified by reversed phase HPLC (acetonitrile/water with 0.1% trifluoroacetic acid) to give 17 mg (39%) of 1-((3S,3aR,6S,6aS)-6-cyclohexanesulfonyl-hexahydro-furo[3,2-b]furan-3-yl)-3-cyclohexyl-urea. LC/MS (Method 3): R$_t$=1.16 min; detected mass: m/z=401.14 ([M+H]+)

Example 75

1-cyclohexyl-3-[(3S,3aR,6S,6aS)-6-(3-piperidin-1-yl-phenoxy)-hexahydro-furo[3,2-b]furan-3-yl]-urea A solution of 3-piperidinophenol (43.9 mg, 0.25 mmol) in absolute N,N-dimethylformamide (2 mL) was treated with potassium tert-butoxide (37.0 mg, 0.33 mmol) and stirred for 45 min at RT. Then, a solution of toluene-4-sulfonic acid (3R,3aS,6S,6aR)-6-(3-cyclohexyl-ureido)-hexahydro-furo[3,2-b]furan-3-yl ester (2) (70.0 mg, 0.17 mmol) in N,N-dimethylformamide (2 mL) was added and the reaction mixture was stirred first at RT, then at 90° C. for 5 h. The reaction mixture was concentrated under reduced pressure and partitioned between water (20 mL) and dichloromethane (20 mL). The phases were separated and the water phase extracted three times with dichloromethane. The combined organic layers were dried over magnesium sulfate, filtered, evaporated and purified by reversed phase HPLC (acetonitrile/water with 0.1% trifluoroacetic acid) to give the corresponding trifluoroacetic acid salt, which was partitioned between dichloromethane and saturated aqueous sodium carbonate solution and stirred for 30 min. The organic layer was separated, washed with water, dried over magnesium sulfate, filtered and evaporated to give 50.0 mg (71%) of 1-cyclohexyl-3-[(3S,3aR,6S,6aS)-6-(3-piperidin-1-yl-phenoxy)-hexahydro-furo[3,2-b]furan-3-yl]-urea. LC/MS (Method 3): R$_t$=1.11 min; detected mass: m/z=430.23 ([M+H]$^+$).

Example 76

1-cyclohexyl-3-[(3S,3aR,6S,6aS)-6-(2-methyl-pyridin-3-yloxy)-hexahydro-furo[3,2-b]furan-3-yl]-urea Synthesis A: from (3R,3aS,6S,6aR)-6-(3-cyclohexyl-ureido)-hexahydro-furo[3,2-b]furan-3-yl ester (2)

A solution of 3-hydroxy-2-methylpyridine (964 mg, 8.83 mmol) in absolute N,N-dimethylformamide (20 mL) was treated with potassium tert-butoxide (1.32 g, 11.8 mmol) and stirred for 45 min at RT. Then, a solution of toluene-4-sulfonic acid (3R,3aS,6S,6aR)-6-(3-cyclohexyl-ureido)-hexahydro-furo[3,2-b]furan-3-yl ester (2) (2.50 g, 5.89 mmol) in N,N-dimethylformamide (20 mL) was added and the reaction mixture was stirred at 80° C. for 5 h, then another portion of toluene-4-sulfonic acid (3R,3aS,6S,6aR)-6-(3-cyclohexyl-ureido)-hexahydro-furo[3,2-b]furan-3-yl ester (2) (100 mg, 0.24 mmol) was added and the reaction mixture was stirred at 100° C. for an additional period of 10 h. The reaction mixture was concentrated under reduced pressure and partitioned between water (20 mL) and dichloromethane (20 mL). The phases were separated and the water phase extracted three times with dichloromethane. The combined organic layers were dried over magnesium sulfate, filtered, evaporated and purified by flash chromatography (silica gel, elution with heptane/ethyl acetate) to give 2.10 g (98%) of 1-cyclohexyl-3-[(3S,3aR,6S,6aS)-6-(2-methyl-pyridin-3-yloxy)-hexahydro-furo[3,2-b]furan-3-yl]-urea as a white powder. LC/MS (Method 6): R$_t$=1.11 min; detected mass: m/z=362.23 ([M+H]$^+$).

Synthesis B: from (3S,3aR,6S,6aS)-6-(2-methyl-pyridin-3-yloxy)-hexahydro-furo[3,2-b]furan-3-ylamine (P20)

A solution of (3S,3aR,6S,6aS)-6-(2-methyl-pyridin-3-yloxy)-hexahydro-furo[3,2-b]furan-3-ylamine (P20) (150 mg, 0.64 mmol) in absolute N,N-dimethylformamide (1 mL) was cooled in an ice bath and a solution of carbonyl diimidazole (103 mg, 0.64 mmol) in N,N-dimethylformamide (1 mL) was added. The reaction mixture was stirred for 15 min at 0° C. and for 1 h at RT before a solution of cyclohexylamine (63.0 mg, 0.64 mmol) in N,N-dimethylformamide (1 mL) was added. The reaction mixture was heated to 80° C. for 1 h, cooled to RT, and evaporated. The crude product was purified by reversed phase HPLC (acetonitrile/water with 0.1% trifluoroacetic acid) to give the corresponding trifluoroacetic acid salt, which was parti-

Example 77

1-(4,4-difluoro-cyclohexyl)-3-[(3S,3aR,6S,6aS)-6-(4-fluoro-phenoxy)-hexahydro-furo[3,2-b]furan-3-yl]-urea A solution of (3S,3aR,6S,6aS)-6-(4-fluoro-phenoxy)-hexahydro-furo[3,2-b]furan-3-ylamine (P18) (350 mg, 1.46 mmol) in absolute N,N-dimethylformamide (2 mL) was cooled in an ice bath and a solution of 1,1'-carbonyl diimidazole (237 mg, 1.46 mmol) in N,N-dimethylformamide (2 mL) was added. The reaction mixture was stirred for 15 min at 0° C. and for 1 h at RT before N,N-diisopropylethylamine (284 mg, 2.20 mmol) and a solution of 4,4-difluorocyclohexylamine hydrochloride (251 mg, 1.46 mmol) in N,N-dimethylformamide (2 mL) were added. The reaction mixture was heated to 80° C. for 1 h, cooled to RT over night, and evaporated. The crude product was purified by reversed phase HPLC (acetonitrile/water with 0.1% trifluoroacetic acid) to give 429 mg (73%) of 1-(4,4-difluoro-cyclohexyl)-3-[(3S,3aR,6S,6aS)-6-(4-fluoro-phenoxy)-hexahydro-furo[3,2-b]furan-3-yl]-urea. LC/MS (Method 6): $R_t$=1.67 min; detected mass: m/z=401.22 ([M+H]$^+$).

Example 78

1-(3-methoxy-tetrahydro-pyran-4-yl)-3-[(3S,3aR,6S,6aS)-6-(2-methyl-pyridin-3-yloxy)-hexahydro-furo[3,2-b]furan-3-yl]-urea; hydrochloride Starting from (3S,3aR,6S,6aS)-6-(2-methyl-pyridin-3-yloxy)-hexahydro-furo[3,2-b]furan-3-ylamine (P20) (150 mg, 0.64 mmol), 1,1'-carbonyl diimidazole (103 mg, 0.64 mmol) and 3-methoxy-tetrahydro-pyran-4-ylamine (83.3 mg, 0.64 mmol), 232 mg (85%) of the title compound were prepared as its hydrochloride in analogy to the procedure described for the synthesis of Example 77. The hydrochloride was made by addition of 0.1N aqueous solution of hydrochloric acid to the trifluoroacetic acid salt and subsequent lyophilization. LC/MS (Method 6): $R_t$=0.95 min; detected mass: m/z=394.32 ([M+H]$^+$).

Example 79

1-(3-ethoxy-tetrahydro-pyran-4-yl)-3-[(3S,3aR,6S,6aS)-6-(2-methyl-pyridin-3-yloxy)-hexahydro-furo[3,2-b]furan-3-yl]-urea; hydrochloride Starting from (3S,3aR,6S,6aS)-6-(2-methyl-pyridin-3-yloxy)-hexahydro-furo[3,2-b]furan-3-ylamine (P20) (200 mg, 0.85 mmol), 1,1'-carbonyl diimidazole (137 mg, 0.85 mmol) and 3-ethoxy-tetrahydro-pyran-4-ylamine (123 mg, 0.85 mmol), 286 mg (76%) of the title compound 79 were prepared as its hydrochloride in analogy to the procedure described for the synthesis of Example 77. The hydrochloride was made by addition of 0.1N aqueous solution of hydrochloric acid to the trifluoroacetic acid salt and subsequent lyophilization. LC/MS (Method 4): $R_t$=1.83 min; detected mass: m/z=408.46 ([M+H]$^+$).

tioned between tert.-butyl methyl ether and saturated aqueous sodium carbonate solution. The organic layer was dried over magnesium sulfate, filtered and evaporated to give 140 mg (61%) of 1-cyclohexyl-3-[(3S,3aR,6S,6aS)-6-(2-methyl-pyridin-3-yloxy)-hexahydro-furo[3,2-b]furan-3-yl]-urea.

Example 80

1-(2,2-dimethyl-[1,3]dioxan-5-yl)-3-[(3S,3aR,6S,6aS)-6-(2-methyl-pyridin-3-yloxy)-hexahydro-furo[3,2-b]furan-3-yl]-urea Starting from (3S,3aR,6S,6aS)-6-(2-methyl-pyridin-3-yloxy)-hexahydro-furo[3,2-b]furan-3-ylamine (P20) (200 mg, 0.85 mmol), 1,1'-carbonyl diimidazole (137 mg, 0.85 mmol) and 2,2-dimethyl-[1,3]dioxan-5-ylamine (165 mg, 1.26 mmol), 60.0 mg (18%) of the title compound 80 were prepared in analogy to the procedure described for the synthesis of Example 77. LC/MS (Method 4): $R_t$=1.84 min; detected mass: m/z=394.29 ([M+H]$^+$).

Example 81

3-{3-[(3S,3aR,6S,6aS)-6-(2-methyl-pyridin-3-yloxy)-hexahydro-furo[3,2-b]furan-3-yl]-ureido}-piperidine-1-carboxylic acid tert-butyl ester Starting from (3S,3aR,6S,6aS)-6-(2-methyl-pyridin-3-yloxy)-hexahydro-furo[3,2-b]furan-3-ylamine (P20) (1.18 g, 4.99 mmol), 1,1'-carbonyl diimidazole (810 mg, 4.99 mmol) and 3-amino-piperidine-1-carboxylic acid tert-butyl ester (1.00 g, 4.99 mmol), 1.60 g (69%) of the title compound 81 were prepared in analogy to the procedure described for the synthesis of Example 77. LC/MS (Method 6): $R_t$=1.22 min; detected mass: m/z=463.48 ([M+H]$^+$).

Example 82

1-[(3S,3aR,6S,6aS)-6-(2-methyl-pyridin-3-yloxy)-hexahydro-furo[3,2-b]furan-3-yl]-3-piperidin-3-yl-urea; hydrochloride A solution of 3-{3-[(3S,3aR,6S,6aS)-6-(2-methyl-pyridin-3-yloxy)-hexahydro-furo[3,2-b]furan-3-yl]-ureido}-piperidine-1-carboxylic acid tert-butyl ester (81) (1.60 g, 3.46 mmol) in dichloromethane (10 mL) was treated with a 5M solution of hydrochloric acid in 2-propanol (4.0 mL, 20 mmol) and stirred for 3 h at RT. The mixture was concentrated under reduced pressure to give 1.35 g (98%) of 1-[(3S,3aR,6S,6aS)-6-(2-methyl-pyridin-3-yloxy)-hexahydro-furo[3,2-b]furan-3-yl]-3-piperidin-3-yl-urea as its hydrochloride. LC/MS (Method 6): $R_t$=0.21 min; detected mass: m/z=363.22 ([M+H]$^+$).

Example 83

1-[1-(4-fluoro-benzoyl)-piperidin-3-yl]-3-[(3S,3aR,6S,6aS)-6-(2-methyl-pyridin-3-yloxy)-hexahydro-furo[3,2-b]furan-3-yl]-urea To a solution of 1-[(3S,3aR,6S,6aS)-6-(2-methyl-pyridin-3-yloxy)-hexahydro-furo[3,2-b]furan-3-yl]-3-piperidin-3-yl-urea hydrochloride (82) (150 mg, 0.38 mmol) in dichloromethane (5 mL) was added N,N-diisopropylethylamine (97.2 mg, 0.75 mmol) and 4-fluorobenzoyl chloride (59.6 mg, 0.38 mmol) and the reaction mixture was stirred overnight at RT before being evaporated and purified by reversed phase HPLC (acetonitrile/water with 0.1% trifluoroacetic acid). The pure fractions were collected, and the acetonitrile distilled off. The resulting aqueous solution was made basic by addition of sodium carbonate and extracted with dichloromethane. The organic layer was dried over magnesium sulfate, filtered and evaporated to give 98 mg (54%) of 1-[1-(4-fluoro-benzoyl)-piperidin-3-yl]-3-[(3S,3aR,6S,6aS)-6-(2-methyl-pyridin-3-yloxy)-hexahydro-furo[3,2-b]furan-3-yl]-urea. LC/MS (Method 6): $R_t$=1.13 min; detected mass: m/z=485.29 ([M+H]$^+$).

According to the previous example the following compounds were prepared from 1-[(3S,3aR,6S,6aS)-6-(2-methyl-pyridin-3-yloxy)-hexahydro-furo[3,2-b]furan-3-yl]-3-piperidin-3-yl-urea hydrochloride (82) in close analogy to the procedure described above.

| No | Starting compound | Chemical name | Mass (from LC/MS) | $R_t$ (from LC/MS) (min) | LC/MS Method |
|---|---|---|---|---|---|
| 84 | Isobutyryl-chloride | 1-(1-Isobutyryl-piperidin-3-yl)-3-[(3S,3aR,6S,6aS)-6-(2-methyl-pyridin-3-yloxy)-hexahydro-furo[3,2-b]furan-3-yl]-urea | 433.32 | 0.99 | 6 |
| 85 | Cyclopropane-carbonyl-chloride | 1-(1-Cyclopropanecarbonyl-piperidin-3-yl)-3-[(3S,3aR,6S,6aS)-6-(2-methyl-pyridin-3-yloxy)-hexahydro-furo[3,2-b]furan-3-yl]-urea | 431.33 | 0.92 | 6 |
| 86 | Methane-sulfonyl-chloride | 1-(1-Methanesulfonyl-piperidin-3-yl)-3-[(3S,3aR,6S,6aS)-6-(2-methyl-pyridin-3-yloxy)-hexahydro-furo[3,2-b]furan-3-yl]-urea | 441.24 | 0.79 | 6 |
| 87 | Trifluoro-acetic anhydride | 1-[(3S,3aR,6S,6aS)-6-(2-Methyl-pyridin-3-yloxy)-hexahydro-furo[3,2-b]furan-3-yl]-3-[1-(2,2,2-trifluoro-acetyl)-piperidin-3-yl]-urea | 459.26 | 1.05 | 6 |
| 88 | Pivaloyl-chloride | 1-[1-(2,2-Dimethyl-propionyl)-piperidin-3-yl]-3-[(3S,3aR,6S,6aS)-6-(2-methyl-pyridin-3-yloxy)-hexahydro-furo[3,2-b]furan-3-yl]-urea | 447.34 | 1.12 | 6 |

Example 89

1-(4,4-difluoro-cyclohexyl)-3-[(3S,3aR,6S,6aS)-6-(2-methyl-pyridin-3-yloxy)-hexahydro-furo[3,2-b]furan-3-yl]-urea Starting from (3S,3aR,6S,6aS)-6-(2-methyl-pyridin-3-yloxy)-hexahydro-furo[3,2-b]furan-3-ylamine (P20) (150 mg, 0.64 mmol), 1,1'-carbonyl diimidazole (103 mg, 0.64 mmol) and 4,4-difluorocyclohexylamine hydrochloride (109 mg, 0.64 mmol), 185 mg (73%) of the title compound 89 were prepared in analogy to the procedure described for the synthesis of Example 77. LC/MS (Method 6): $R_t$=1.05 min; detected mass: m/z=398.26 ([M+H]$^+$).

Example 90

1-[(3S,3aR,6S,6aS)-6-(2-methyl-pyridin-3-yloxy)-hexahydro-furo[3,2-b]furan-3-yl]-3-(3-trifluoromethyl-cyclohexyl)-urea Starting from (3S,3aR,6S,6aS)-6-(2-methyl-pyridin-3-yloxy)-hexahydro-furo[3,2-b]furan-3-ylamine (P20) (100 mg, 0.42 mmol), 1,1'-carbonyl diimidazole (70.8 mg, 0.42 mmol) and 3-(trifluoromethyl)cyclohexylamine (530 mg, 0.63 mmol), 32 mg (18%) of the title compound 90 were prepared in analogy to the procedure described for the synthesis of Example 77. LC/MS (Method 6): $R_t$=1.47 min; detected mass: m/z=430.26 ([M+H]$^+$).

Example 91

1-[(3S,3aR,6S,6aS)-6-(2-methyl-pyridin-3-yloxy)-hexahydro-furo[3,2-b]furan-3-yl]-3-(2-methyl-tetrahydro-pyran-4-yl)-urea Starting from (3S,3aR,6S,6aS)-6-(2-methyl-pyridin-3-yloxy)-hexahydro-furo[3,2-b]furan-3-ylamine (P20) (200 mg, 0.85 mmol), 1,1'-carbonyl diimidazole (142 mg, 0.85 mmol) and 2-methyl-tetrahydro-pyran-4-ylamine (144 mg, 1.27 mmol), 175 mg (55%) of the title compound 91 were prepared in analogy to the procedure described for the synthesis of Example 77. LC/MS (Method 6): $R_t$=0.76 min; detected mass: m/z=378.25 ([M+H]$^+$).

Example 92

1-[(3S,3aR,6S,6aS)-6-(2-methyl-pyridin-3-yloxy)-hexahydro-furo[3,2-b]furan-3-yl]-3-(3-methyl-tetrahydro-pyran-4-yl)-urea Starting from (3S,3aR,6S,6aS)-6-(2-methyl-pyridin-3-yloxy)-hexahydro-furo[3,2-b]furan-3-ylamine (P20) (200 mg, 0.85 mmol), 1,1'-carbonyl diimidazole (142 mg, 0.85 mmol) and 2-methyl-tetrahydro-pyran-4-ylamine (144 mg, 1.27 mmol), 200 mg (62%) of the title compound 92 were prepared in analogy to the procedure described for the synthesis of Example 77. LC/MS (Method 6): $R_t$=0.74 min; detected mass: m/z=378.27 ([M+H]$^+$).

Example 93

(R)-1-((R)-3-methoxy-tetrahydro-pyran-4-yl)-3-[(3S,3aR,6S,6aS)-6-(2-methyl-pyridin-3-yloxy)-hexahydro-furo[3,2-b]furan-3-yl]-urea Starting from (3S,3aR,6S,6aS)-6-(2-methyl-pyridin-3-yloxy)-hexahydro-furo[3,2-b]furan-3-ylamine (P20) (200 mg, 0.85 mmol), 1,1'-carbonyl diimidazole (142 mg, 0.85 mmol) and cis-4-amino-3-(methoxy)tetrahydropyrane (164 mg, 1.27 mmol), 13.9 mg (4%) of the title compound were prepared in analogy to the procedure described for the synthesis of Example 77. LC/MS (Method 6): $R_t$=0.92 min; detected mass: m/z=394.24 ([M+H]$^+$).

Example 94

4,4-difluoro-piperidine-1-carboxylic acid [(3S,3aR, 6S,6aS)-6-(4-fluoro-phenoxy)-hexahydro-furo[3,2-b] furan-3-yl]-amide A solution of trichloromethylchloroformate (620 mg, 380 µL, 3.14 mmol) in dry 1,2-dichloroethane (6 mL) was cooled to −20° C. and treated dropwise with a solution of (3S,3aR, 6S,6aS)-6-(4-fluoro-phenoxy)-hexahydro-furo[3,2-b]furan-3-ylamine (P18) (300 mg, 1.25 mmol) in dichloroethane (1 mL). After the addition was complete, the reaction mixture was allowed to warm to RT slowly, was heated to 50° C. for 3 h and cooled to RT overnight. Then, the reaction mixture was concentrated under reduced pressure to give 330 mg of crude (3S,3aS,6S,6aR)-3-(4-fluoro-phenoxy)-6-isocyanato-hexahydro-furo[3,2-b]furan which was used directly in the next step. Part of the crude product (50 mg, 0.19 mmol) was taken up in acetonitrile (2 mL) and added dropwise to a solution of 4,4-difluoropiperidine in acetonitrile (3 mL). The reaction mixture was stirred overnight at RT, heated to 50° C., and then to reflux. The mixture was cooled to RT, evaporated and and purified by reversed phase HPLC (acetonitrile/water with 0.1% trifluoroacetic acid) to give 25 mg (34%) of 4,4-difluoro-piperidine-1-carboxylic acid [(3S, 3aR,6S,6aS)-6-(4-fluoro-phenoxy)-hexahydro-furo[3,2-b] furan-3-yl]-amide. LC/MS (Method 6): $R_t$=1.79 min; detected mass: m/z=387.20 ([M+H]$^+$).

The following examples have been prepared using the general protocol described subsequently:

The phenol (0.215 mmol) was weighed into a reaction tube and dissolved in dry N,N-dimethylformamide (0.5 ml). The tube was purged with argon. Potassium tert.-butoxide (1M in tetrahydrofuran, 0.215 mmol) was added, followed by toluene-4-sulfonic acid (3R,3aS,6S,6aR)-6-(3-cyclohexyl-ureido)-hexahydro-furo[3,2-b]furan-3-yl ester (2) (0.15 mmol) in absolute N,N-dimethylformamide (1 mL). The tube was closed with a screw cap and shaken for 4 h at 80° C. The cooled mixture was neutralized with trifluoroacetic acid (0.05 ml), the volume was adjusted to 2 ml with N,N-dimethylformamide. The solution was filtered and purified by reversed phase HPLC (acetonitrile/water with 0.1% trifluoroacetic acid) to give the corresponding example either as trifluroacetic acid salt or in its free form.

| No | Starting compound | Chemical name | Mass (from LC/MS) | $R_t$ (from LC/MS) (min) | LC/MS Method |
|---|---|---|---|---|---|
| 95 | 2-Fluoro-phenol | 1-Cyclohexyl-3-[(3S,3aR,6S,6aS)-6-(2-fluoro-phenoxy)-hexahydro-furo[3,2-b]furan-3-yl]-urea | 365.10 | 1.20 | 3 |
| 96 | 3-Hydroxy-pyridine | 1-Cyclohexyl-3-[(3S,3aR,6S,6aS)-6-(pyridin-3-yloxy)-hexahydro-furo[3,2-b]furan-3-yl]-urea; trifluoroacetate | 348.13 | 0.94 | 3 |
| 97 | 2,3-Dichloro-phenol | 1-Cyclohexyl-3-[(3S,3aR,6S,6aS)-6-(2,3-dichloro-phenoxy)-hexahydro-furo[3,2-b]furan-3-yl]-urea | 415.00 | 1.29 | 3 |
| 98 | 2-Chloro-phenol | 1-[(3S,3aR,6S,6aS)-6-(2-Chloro-phenoxy)-hexahydro-furo[3,2-b]furan-3-yl]-3-cyclohexyl-urea | 381.06 | 1.25 | 3 |
| 99 | 6-Bromo-naphthalen-2-ol | 1-[(3S,3aR,6S,6aS)-6-(6-Bromo-naphthalen-2-yloxy)-hexahydro-furo-[3,2-b]furan-3-yl]-3-cyclohexyl-urea | 475.01 | 1.35 | 3 |
| 100 | 3-Morpholino-phenol | 1-Cyclohexyl-3-[(3S,3aR,6S,6aS)-6-(3-morpholin-4-yl-phenoxy)-hexahydro-furo[3,2-b]furan-3-yl]-urea | 432.17 | 1.18 | 3 |
| 101 | 4-Trifluoro-methyl-phenol | 1-Cyclohexyl-3-[(3S,3aR,6S,6aS)-6-(4-trifluoromethyl-phenoxy)-hexahydro-furo[3,2-b]furan-3-yl]-urea | 415.08 | 1.28 | 3 |
| 102 | N-(3-Hydroxy-phenyl)-acetamide | N-{3-[(3S,3aS,6S,6aR)-6-(3-Cyclohexyl-ureido)-hexahydro-furo[3,2-b]furan-3-yloxy]-phenyl}-acetamide | 404.12 | 1.10 | 3 |
| 103 | 4-tert-Butyl-phenol | 1-[(3S,3aR,6S,6aS)-6-(4-tert-Butyl-phenoxy)-hexahydro-furo[3,2-b]furan-3-yl]-3-cyclohexyl-urea | 403.31 | 4.83 | 4 |
| 104 | 3-Phenyl-phenol | 1-[(3S,3aR,6S,6aS)-6-(Biphenyl-3-yloxy)-hexahydro-furo[3,2-b]furan-3-yl]-3-cyclohexyl-urea | 423.11 | 1.32 | 3 |
| 105 | 4-Phenyl-phenol | 1-[(3S,3aR,6S,6aS)-6-(Biphenyl-4-yloxy)-hexahydro-furo[3,2-b]furan-3-yl]-3-cyclohexyl-urea | 423.12 | 1.32 | 3 |
| 106 | 1-(3-Hydroxy-phenyl)-ethanone | 1-[(3S,3aR,6S,6aS)-6-(3-Acetyl-phenoxy)-hexahydro-furo[3,2-b]furan-3-yl]-3-cyclohexyl-urea | 389.32 | 3.92 | 4 |
| 107 | 1-(3-Hydroxy-phenyl)-pyrrolidin-2-one | 1-Cyclohexyl-3-{(3S,3aR,6S,6aS)-6-[3-(2-oxo-pyrrolidin-1-yl)-phenoxy]-hexahydro-furo[3,2-b]furan-3-yl}-urea | 430.13 | 1.15 | 3 |
| 108 | 4-(3-Hydroxy-phenyl)-piperidine | 1-Cyclohexyl-3-[(3S,3aR,6S,6aS)-6-(3-piperidin-4-yl-phenoxy)-hexahydro-furo[3,2-b]furan-3-yl]-urea; trifluoroacetate | 430.32 | 2.90 | 4 |
| 109 | 4-(Pyridin-2-yloxy)-phenol | 1-Cyclohexyl-3-{(3S,3aR,6S,6aS)-6-[4-(pyridin-2-yloxy)-phenoxy]-hexahydro-furo[3,2-b]furan-3-yl}-urea | 440.26 | 4.25 | 4 |

-continued

| No | Starting compound | Chemical name | Mass (from LC/MS) | R$_t$ (from LC/MS) (min) | LC/MS Method |
|---|---|---|---|---|---|
| 110 | 1-(2-Hydroxy-phenyl)-pyrrolidin-2-one | 1-Cyclohexyl-3-{(3S,3aR,6S,6aS)-6-[2-(pyrrolidine-1-carbonyl)-phenoxy]-hexahydro-furo[3,2-b]furan-3-yl}-urea | 444.14 | 1.14 | 3 |
| 111 | 5-Hydroxy-nicotinic acid methyl ester | 5-[(3S,3aS,6S,6aR)-6-(3-Cyclohexyl-ureido)-hexahydro-furo[3,2-b]furan-3-yloxy]-nicotinic acid methyl ester | 406.13 | 1.11 | 3 |
| 112 | 4-[(1,2,4)Tri-azol-1-yl]-phenol | 1-Cyclohexyl-3-[(3S,3aR,6S,6aS)-6-(4-[1,2,4]triazol-1-yl-phenoxy)-hexahydro-furo[3,2-b]furan-3-yl]-urea; trifluoroacetate | 414.30 | 3.48 | 4 |
| 113 | N-(4-Hydroxy-phenyl)-acetamide | N-{4-[(3S,3aS,6S,6aR)-6-(3-Cyclohexyl-ureido)-hexahydro-furo[3,2-b]furan-3-yloxy]-phenyl}-acetamide | 404.10 | 1.08 | 3 |
| 114 | 2,2-Dimethyl-6-hydroxy-4-chromanone | 1-Cyclohexyl-3-[(3S,3aR,6S,6aS)-6-(2,2-dimethyl-4-oxo-chroman-6-yloxy)-hexahydro-furo[3,2-b]furan-3-yl]-urea | 445.12 | 1.24 | 3 |
| 115 | Phenol | 1-Cyclohexyl-3-((3S,3aR,6S,6aS)-6-phenoxy-hexahydro-furo[3,2-b]furan-3-yl)-urea | 347.12 | 1.21 | 3 |
| 116 | 4-tert-Butoxy-phenol | 1-[(3S,3aR,6S,6aS)-6-(4-tert-Butoxy-phenoxy)-hexahydro-furo[3,2-b]furan-3-yl]-3-cyclohexyl-urea | 419.16 | 1.29 | 3 |
| 117 | (3-Hydroxy-phenyl)-acetonitrile | 1-[(3S,3aR,6S,6aS)-6-(3-Cyano-methyl-phenoxy)-hexahydro-furo-[3,2-b]furan-3-yl]-3-cyclohexyl-urea | 386.31 | 3.94 | 4 |
| 118 | 6-Hydroxy-1-indanone | 1-Cyclohexyl-3-[(3S,3aR,6S,6aS)-6-(3-oxo-indan-5-yloxy)-hexahydro-furo[3,2-b]furan-3-yl]-urea | 401.10 | 1.17 | 3 |
| 119 | (4-Hydroxy-phenyl)-(4-methyl-piperazin-1-yl)-methanone | 1-Cyclohexyl-3-{(3S,3aR,6S,6aS)-6-[4-(4-methyl-piperazine-1-carbonyl)-phenoxy]-hexahydro-furo[3,2-b]furan-3-yl}-urea; trifluoroacetate | 473.36 | 2.60 | 4 |
| 120 | (4-Hydroxy-phenyl)-morpholin-4-yl-methanone | 1-Cyclohexyl-3-{(3S,3aR,6S,6aS)-6-[4-(morpholine-4-carbonyl)-phenoxy]-hexahydro-furo[3,2-b]furan-3-yl}-urea | 460.13 | 1.09 | 3 |
| 121 | 4-(5-Methyl-[1,2,4]oxa-diazol-3-yl)-phenol | 1-Cyclohexyl-3-{(3S,3aR,6S,6aS)-6-[4-(5-methyl-[1,2,4]oxadiazol-3-yl)-phenoxy]-hexahydro-furo[3,2-b]furan-3-yl}-urea | 429.10 | 1.20 | 3 |
| 122 | 3-(1-Methoxy-1-thiazol-2-yl-propyl)-phenol | 1-Cyclohexyl-3-{(3S,3aR,6S,6aS)-6-[3-(1-methoxy-1-thiazol-2-yl-propyl)-phenoxy]-hexahydro-furo[3,2-b]furan-3-yl}-urea | 502.14 | 1.30 | 3 |
| 123 | 2-Morpholin-4-ylmethyl-phenol | 1-Cyclohexyl-3-[(3S,3aR,6S,6aS)-6-(2-morpholin-4-ylmethyl-phenoxy)-hexahydro-furo[3,2-b]furan-3-yl]-urea; trifluoroacetate | 446.18 | 0.94 | 3 |
| 124 | 4-(1-Methyl-cyclohexyl)-phenol | 1-Cyclohexyl-3-{(3S,3aR,6S,6aS)-6-[4-(1-methyl-cyclohexyl)-phenoxy]-hexahydro-furo[3,2-b]furan-3-yl}-urea | 443.19 | 1.43 | 3 |
| 125 | 3-Trifluoro-methyl-phenol | 1-Cyclohexyl-3-[(3S,3aR,6S,6aS)-6-(3-trifluoromethyl-phenoxy)-hexa-hydro-furo[3,2-b]furan-3-yl]-urea | 415.09 | 1.28 | 3 |
| 126 | (4-Hydroxy-phenyl)-piperazin-1-yl-methanone | 1-Cyclohexyl-3-{(3S,3aR,6S,6aS)-6-[4-(piperazine-1-carbonyl)-phenoxy]-hexahydro-furo[3,2-b]furan-3-yl}-urea; trifluoroacetate | 459.16 | 0.92 | 3 |
| 127 | 3-(Pyridin-2-yloxy)-phenol | 1-Cyclohexyl-3-{(3S,3aR,6S,6aS)-6-[3-(pyridin-2-yloxy)-phenoxy]-hexa-hydro-furo[3,2-b]furan-3-yl}-urea | 440.11 | 1.23 | 3 |
| 128 | 3-Cyclopropyl-aminomethyl-phenol | 1-Cyclohexyl-3-[(3S,3aR,6S,6aS)-6-(3-cyclopropylaminomethyl-phenoxy)-hexahydro-furo[3,2-b]furan-3-yl]-urea; trifluoroacetate | 416.17 | 0.97 | 3 |
| 129 | 3-(5-Methyl-[1,2,4]oxa-diazol-3-yl)-phenol | 1-Cyclohexyl-3-{(3S,3aR,6S,6aS)-6-[3-(5-methyl-[1,2,4]oxadiazol-3-yl)-phenoxy]-hexahydro-furo[3,2-b]furan-3-yl}-urea | 429.09 | 1.21 | 3 |

| No | Starting compound | Chemical name | Mass (from LC/MS) | R$_t$ (from LC/MS) (min) | LC/MS Method |
|---|---|---|---|---|---|
| 130 | Imidazo[1,2-a]pyridin-8-ol | 1-Cyclohexyl-3-[(3S,3aR,6S,6aS)-6-(imidazo[1,2-a]pyridin-8-yloxy)-hexahydro-furo[3,2-b]furan-3-yl]-urea | 387.29 | 2.45 | 4 |
| 131 | 2-Chloro-5-fluoro-phenol | 1-[(3S,3aR,6S,6aS)-6-(2-Chloro-5-fluoro-phenoxy)-hexahydro-furo[3,2-b]furan-3-yl]-3-cyclohexyl-urea | 399.04 | 1.26 | 3 |
| 132 | 3-Chloro-phenol | 1-[(3S,3aR,6S,6aS)-6-(3-Chloro-phenoxy)-hexahydro-furo[3,2-b]furan-3-yl]-3-cyclohexyl-urea | 381.06 | 1.26 | 3 |
| 133 | 3,5-Difluoro-phenol | 1-Cyclohexyl-3-[(3S,3aR,6S,6aS)-6-(3,5-difluoro-phenoxy)-hexahydro-furo[3,2-b]furan-3-yl]-urea | 383.23 | 4.44 | 4 |
| 134 | (2-Hydroxy-phenyl)-morpholin-4-yl-methanone | 1-Cyclohexyl-3-{(3S,3aR,6S,6aS)-6-[2-(morpholine-4-carbonyl)-phenoxy]-hexahydro-furo[3,2-b]furan-3-yl}-urea | 460.15 | 1.10 | 3 |
| 135 | 2-Piperidin-1-ylmethyl-phenol | 1-Cyclohexyl-3-[(3S,3aR,6S,6aS)-6-(2-piperidin-1-ylmethyl-phenoxy)-hexahydro-furo[3,2-b]furan-3-yl]-urea; trifluoroacetate | 444.20 | 0.99 | 3 |
| 136 | 2-{[(Tetrahydro-furan-2-ylmethyl)-amino]-methyl}-phenol | 1-Cyclohexyl-3-[(3S,3aR,6S,6aS)-6-(2-{[(tetrahydro-furan-2-ylmethyl)-ao]-methyl}-phenoxy)-hexahydro-furo[3,2-b]furan-3-yl]-urea; trifluoroacetate | 460.19 | 0.99 | 3 |
| 137 | 2-Pyrrolidin-1-yl-quinolin-8-ol | 1-Cyclohexyl-3-[(3S,3aR,6S,6aS)-6-(2-pyrrolidin-1-yl-quinolin-8-yloxy)-hexahydro-furo[3,2-b]furan-3-yl]-urea; trifluoroacetate | 467.20 | 1.01 | 3 |
| 138 | 4-Bromo-phenol | 1-[(3S,3aR,6S,6aS)-6-(4-Bromo-phenoxy)-hexahydro-furo[3,2-b]furan-3-yl]-3-cyclohexyl-urea | 425.00 | 1.27 | 3 |
| 139 | 3-Bromo-phenol | 1-[(3S,3aR,6S,6aS)-6-(3-Bromo-phenoxy)-hexahydro-furo[3,2-b]furan-3-yl]-3-cyclohexyl-urea | 425.00 | 1.27 | 3 |
| 140 | 3-Nitro-phenol | 1-Cyclohexyl-3-[(3S,3aR,6S,6aS)-6-(3-nitro-phenoxy)-hexahydro-furo[3,2-b]furan-3-yl]-urea | 392.09 | 1.21 | 3 |
| 141 | 3-Hydroxy-benzoic acid ethyl ester | 3-[(3S,3aS,6S,6aR)-6-(3-Cyclohexyl-ureido)-hexahydro-furo[3,2-b]furan-3-yloxy]-benzoic acid ethyl ester | 419.12 | 1.25 | 3 |
| 142 | 3-Piperazin-1-yl-phenol | 1-Cyclohexyl-3-[(3S,3aR,6S,6aS)-6-(3-piperazin-1-yl-phenoxy)-hexahydro-furo[3,2-b]furan-3-yl]-urea; trifluoroacetate | 431.17 | 0.96 | 3 |
| 143 | 3-Hydroxy-benzamide | 3-[(3S,3aS,6S,6aR)-6-(3-Cyclohexyl-ureido)-hexahydro-furo[3,2-b]furan-3-yloxy]-benzamide | 390.11 | 1.05 | 3 |
| 144 | 4-Hydroxy-indan-1-one | 1-Cyclohexyl-3-[(3S,3aR,6S,6aS)-6-(1-oxo-indan-4-yloxy)-hexahydro-furo[3,2-b]furan-3-yl]-urea | 401.10 | 1.15 | 3 |
| 145 | 6-Methyl-5,6-dihydro-thieno[3,2-b]thiophen-3-ol | 1-Cyclohexyl-3-[(3S,3aR,6S,6aS)-6-(6-methyl-5,6-dihydro-thieno[3,2-b]thiophen-3-yloxy)-hexahydro-furo[3,2-b]furan-3-yl]-urea | 425.08 | 1.20 | 3 |
| 146 | 3-Bromo-4-fluoro-phenol | 1-[(3S,3aR,6S,6aS)-6-(3-Bromo-4-fluoro-phenoxy)-hexahydro-furo[3,2-b]furan-3-yl]-3-cyclohexyl-urea | 443.00 | 1.28 | 3 |
| 147 | 5-Bromo-2-chloro-phenol | 1-[(3S,3aR,6S,6aS)-6-(5-Bromo-2-chloro-phenoxy)-hexahydro-furo[3,2-b]furan-3-yl]-3-cyclohexyl-urea | 458.96 | 1.30 | 3 |
| 148 | 6-Hydroxy-naphthalene-2-carboxylic acid methyl ester | 6-[(3S,3aS,6S,6aR)-6-(3-Cyclohexyl-ureido)-hexahydro-furo[3,2-b]furan-3-yloxy]-naphthalene-2-carboxylic acid methyl ester | 455.11 | 1.27 | 3 |

The following examples have been prepared using the general protocol described subsequently:

The respective isocyanate (0.25 mmol) was weighed into a reaction tube filled with argon. A solution of (3S,3aR,6S,6aS)-6-(4-fluoro-phenoxy)-hexahydro-furo[3,2-b]furan-3-ylamine (P18) as its trifluoroacetic acid salt (0.2 mmol) and diisopropyl ethyl amine (0.3 mmol) in absolute tetrahydrofuran (3 mL) was added, the tube was closed with a screw cap and shaken at RT over night. Water (0.1 ml) was added and the solvents were evaporated. The residue was dissolved in a mixture of N,N-dimethylformamide and TFA (19:1, 2 mL), filtered, and purified by reversed phase HPLC (acetonitrile/water with 0.1% trifluoroacetic acid) to give the corresponding urea.

| No | Starting compound | Chemical name | Mass (from LC/MS) | R_t (from LC/MS) (min) | LC/MS Method |
|---|---|---|---|---|---|
| 149 | tert-Butyl-isocyanate | 1-tert-Butyl-3-[(3S,3aR,6S,6aS)-6-(4-fluoro-phenoxy)-hexahydro-furo[3,2-b]furan-3-yl]-urea | 339.22 | 1.19 | 3 |
| 150 | (S)-1-Indanyl isocyanate | 1-[(3S,3aR,6S,6aS)-6-(4-Fluoro-phenoxy)-hexahydro-furo[3,2-b]furan-3-yl]-3-(S)-indan-1-yl-urea | 399.20 | 1.23 | 3 |
| 151 | trans-4-Methyl-cyclo-hexyl isocyanate | 1-[(3S,3aR,6S,6aS)-6-(4-Fluoro-phenoxy)-hexahydro-furo[3,2-b]furan-3-yl]-3-(4-methyl-cyclohexyl)-urea | 379.23 | 1.26 | 3 |
| 152 | ((1R,2R)-2-Benzyloxy-cyclopentyl isocyanate | 1-((1R,2R)-2-Benzyloxy-cyclopentyl)-3-[(3S,3aR,6S,6aS)-6-(4-fluoro-phenoxy)-hexahydro-furo[3,2-b]furan-3-yl]-urea | 457.25 | 1.28 | 3 |
| 153 | ((1S,2S)-2-Benzyloxy-cyclopentyl isocyanate | 1-((1S,2S)-2-Benzyloxy-cyclopentyl)-3-[(3S,3aR,6S,6aS)-6-(4-fluoro-phenoxy)-hexahydro-furo[3,2-b]furan-3-yl]-urea | 457.24 | 1.28 | 3 |
| 154 | (R)-1-Phenyl-propyl-isocyanate | 1-[(3S,3aR,6S,6aS)-6-(4-Fluoro-phenoxy)-hexahydro-furo[3,2-b]furan-3-yl]-3-((R)-1-phenyl-propyl)-urea | 401.21 | 1.25 | 3 |
| 155 | (R)-1-(3-Methoxy-phenyl)ethyl isocyanate | 1-[(3S,3aR,6S,6aS)-6-(4-Fluoro-phenoxy)-hexahydro-furo[3,2-b]furan-3-yl]-3-[(R)-1-(3-methoxy-phenyl)-ethyl]-urea | 417.22 | 1.21 | 3 |
| 156 | (S)-1-Cyclohexyl-ethyl isocyanate | 1-((S)-1-Cyclohexyl-ethyl)-3-[(3S,3aR,6S,6aS)-6-(4-fluoro-phenoxy)-hexahydro-furo[3,2-b]furan-3-yl]-urea | 393.24 | 1.28 | 3 |
| 157 | 4-Isocyanato-1-(trifluoro-acetyl)piperidine | 1-[(3S,3aR,6S,6aS)-6-(4-Fluoro-phenoxy)-hexahydro-furo[3,2-b]furan-3-yl]-3-[1-(2,2,2-trifluoro-acetyl)-piperidin-4-yl]-urea | 462.20 | 1.18 | 3 |
| 158 | 1,2,3,4-Tetrahydro-naphthalen-1-yl isocyanate | 1-[(3S,3aR,6S,6aS)-6-(4-Fluoro-phenoxy)-hexahydro-furo[3,2-b]furan-3-yl]-3-(1,2,3,4-tetrahydro-naphthalen-1-yl)-urea | 413.22 | 1.26 | 3 |
| 159 | (R)-1-(4-Fluoro-phenyl)-ethyl isocyanate | 1-[(3S,3aR,6S,6aS)-6-(4-Fluoro-phenoxy)-hexahydro-furo[3,2-b]furan-3-yl]-3-[(R)-1-(4-fluoro-phenyl)-ethyl]-urea | 405.20 | 1.22 | 3 |
| 160 | (S)-1-(4-Fluoro-phenyl)-ethyl isocyanate | 1-[(3S,3aR,6S,6aS)-6-(4-Fluoro-phenoxy)-hexahydro-furo[3,2-b]furan-3-yl]-3-[(S)-1-(4-fluoro-phenyl)-ethyl]-urea | 405.20 | 1.22 | 3 |
| 161 | (S)-1-Phenyl-ethyl isocyanate | 1-[(3S,3aR,6S,6aS)-6-(4-Fluoro-phenoxy)-hexahydro-furo[3,2-b]furan-3-yl]-3-((S)-1-phenyl-ethyl)-urea | 387.20 | 1.21 | 3 |
| 162 | (R)-1-Phenyl-ethyl isocyanate | 1-[(3S,3aR,6S,6aS)-6-(4-Fluoro-phenoxy)-hexahydro-furo[3,2-b]furan-3-yl]-3-((R)-1-phenyl-ethyl)-urea | 387.21 | 1.22 | 3 |
| 163 | (1S,2S)-2-Benzyloxy-cyclohexyl isocyanate | 1-((1S,2S)-2-Benzyloxy-cyclohexyl)-3-[(3S,3aR,6S,6aS)-6-(4-fluoro-phenoxy)-hexahydro-furo[3,2-b]furan-3-yl]-urea | 471.28 | 1.29 | 3 |
| 164 | (1R,2R)-2-Benzyloxy-cyclohexyl isocyanate | 1-((1R,2R)-2-Benzyloxy-cyclohexyl)-3-[(3S,3aR,6S,6aS)-6-(4-fluoro-phenoxy)-hexahydro-furo[3,2-b]furan-3-yl]-urea | 471.29 | 1.29 | 3 |
| 165 | (R)-1-Cyclohexyl-ethyl isocyanate | 1-((R)-1-Cyclohexyl-ethyl)-3-[(3S,3aR,6S,6aS)-6-(4-fluoro-phenoxy)-hexahydro-furo[3,2-b]furan-3-yl]-urea | 393.24 | 1.29 | 3 |
| 166 | (R)-1-(4-Chloro-phenyl)-ethyl isocyanate | 1-[(R)-1-(4-Chloro-phenyl)-ethyl]-3-[(3S,3aR,6S,6aS)-6-(4-fluoro-phenoxy)-hexahydro-furo[3,2-b]furan-3-yl]-urea | 421.17 | 1.26 | 3 |
| 167 | (S)-1-(4-Methoxy-phenyl)-ethyl isocyanate | 1-[(3S,3aR,6S,6aS)-6-(4-Fluoro-phenoxy)-hexahydro-furo[3,2-b]furan-3-yl]-3-[(S)-1-(4-methoxy-phenyl)-ethyl]-urea | 417.21 | 1.21 | 3 |
| 168 | (R)-1-(4-Methoxy-phenyl)-ethyl isocyanate | 1-[(3S,3aR,6S,6aS)-6-(4-Fluoro-phenoxy)-hexahydro-furo[3,2-b]furan-3-yl]-3-[(R)-1-(4-methoxy-phenyl)-ethyl]-urea | 417.22 | 1.21 | 3 |

| No | Starting compound | Chemical name | Mass (from LC/MS) | R$_t$ (from LC/MS) (min) | LC/MS Method |
|---|---|---|---|---|---|
| 169 | 4-Thiophen-2-yl-tetrahydro-pyran-4-yl isocyanate | 1-[(3S,3aR,6S,6aS)-6-(4-Fluoro-phenoxy)-hexahydro-furo[3,2-b]furan-3-yl]-3-(4-thiophen-2-yl-tetrahydro-pyran-4-yl)-urea | 449.20 | 1.19 | 3 |
| 170 | Tetrahydro-pyran-4-yl isocyanate | 1-[(3S,3aR,6S,6aS)-6-(4-Fluoro-phenoxy)-hexahydro-furo[3,2-b]furan-3-yl]-3-(tetrahydro-pyran-4-yl)-urea | 367.18 | 1.07 | 3 |

The following examples have been prepared using the general protocol described subsequently:

Preparation of stock solution: (3S,3aR,6S,6aS)-6-(2-Methyl-pyridin-3-yloxy)-hexahydro-furo[3,2-b]furan-3-ylamine (P20) (28.2 mmol) was weighed into a round-bottom flask and dissolved in dry N,N-dimethylformamide (150 mL). The flask was flushed with argon, fitted with a thermometer and an argon bubbler, and cooled in an ice bath. Carbonyl diimidazole (28.2 mmol, 1 eq.) was added in portions with stirring, keeping the internal temperature below 5° C. After completion of the addition, the cooling bath was removed and the mixture was stirred for 1 h at RT. The volume was adjusted with dry N,N-dimethylformamide to 188 mL.

The corresponding amine (0.45 mmol) was weighed into a reaction tube. Then, the stock solution (2 mL, 0.3 mmol of the intermediate in theory) was added. For amine hydrochlorides, diisopropyl ethyl amine (0.5 mmol per HCl) was added; the tube was flushed with argon, closed with a screw cap, and shaken at 80° C. over night.

For the reactions using amine hydrochlorides, polymer-bound hydrogen carbonate (1 mmol) was added and the mixture was shaken for 2 h at RT, and then filtered. The solution was submitted to SFC purification or reversed phase HPLC (acetonitrile/water with 0.1% trifluoroacetic acid) to give the corresponding urea.

| No | Starting compound | Chemical name | Mass (from LC/MS) | R$_t$ (from LC/MS) (min) | LC/MS Method |
|---|---|---|---|---|---|
| 171 | (3-Methyl-isoxazol-5-yl)methyl-amine | 1-(3-Methyl-isoxazol-5-ylmethyl)-3-[(3S,3aR,6S,6aS)-6-(2-methyl-pyridin-3-yloxy)-hexahydro-furo[3,2-b]furan-3-yl]-urea | 375.23 | 0.94 | 6 |
| 172 | Pyridin-2-yl-methyl-amine | 1-[(3S,3aR,6S,6aS)-6-(2-Methyl-pyridin-3-yloxy)-hexahydro-furo[3,2-b]furan-3-yl]-3-pyridin-2-ylmethyl-urea | 371.23 | 0.48 | 4 |
| 173 | (1R,2S,4R)-1,7,7-Tri-methyl-bicyclo[2.2.1]hept-2-yl-amine | 1-[(2R,3aS,5S,6S)-6-(2-Methyl-pyridin-3-yloxy)-hexahydro-furo[3,2-b]furan-3-yl]-3-((1R,2S,4R)-1,7,7-trimethyl-bicyclo[2.2.1]hept-2-yl)-urea | 416.33 | 1.58 | 6 |
| 174 | (1R,2S,5R)-2-Isopropyl-5-methyl-cyclo-hexyl-amine | 1-((1R,2S,5R)-2-Isopropyl-5-methyl-cyclohexyl)-3-[(3S,3aR,6S,6aS)-6-(2-methyl-pyridin-3-yloxy)-hexahydro-furo[3,2-b]furan-3-yl]-urea | 418.35 | 1.65 | 6 |
| 175 | 3-Methoxy-propyl-amine | 1-(3-Methoxy-propyl)-3-[(3S,3aR,6S,6aS)-6-(2-methyl-pyridin-3-yloxy)-hexahydro-furo[3,2-b]furan-3-yl]-urea | 352.23 | 0.96 | 6 |
| 176 | Tetrahydro-furan-2-ylmethyl-amine | 1-[(3S,3aR,6S,6aS)-6-(2-Methyl-pyridin-3-yloxy)-hexahydro-furo[3,2-b]furan-3-yl]-3-(tetrahydro-furan-2-ylmethyl)-urea | 364.24 | 1.00 | 6 |
| 177 | Pyridin-3-ylmethyl-amine | 1-[(3S,3aR,6S,6aS)-6-(2-Methyl-pyridin-3-yloxy)-hexahydro-furo[3,2-b]furan-3-yl]-3-pyridin-3-ylmethyl-urea | 371.23 | 0.32 | 6 |
| 178 | (1S,2S,3S,5R)-2,6,6-Trimethyl-bicyclo[3.1.1]hept-3-yl-methyl-amine | 1-[(3S,3aR,6S,6aS)-6-(2-Methyl-pyridin-3-yloxy)-hexahydro-furo[3,2-b]furan-3-yl]-3-((1S,2S,3S,5R)-2,6,6-trimethyl-bicyclo[3.1.1]hept-3-ylmethyl)-urea | 430.33 | 1.68 | 6 |
| 179 | 2-Trifluoro-methoxy-benzylamine | 1-[(3S,3aR,6S,6aS)-6-(2-Methyl-pyridin-3-yloxy)-hexahydro-furo[3,2-b]furan-3-yl]-3-(2-trifluoromethoxy-benzyl)-urea | 454.24 | 1.48 | 6 |
| 180 | 4-Fluoro-benzylamine | 1-(4-Fluoro-benzyl)-3-[(3S,3aR,6S,6aS)-6-(2-methyl-pyridin-3-yloxy)-hexahydro-furo[3,2-b]furan-3-yl]-urea | 388.23 | 1.27 | 6 |

-continued

| No | Starting compound | Chemical name | Mass (from LC/MS) | R_t (from LC/MS) (min) | LC/MS Method |
|---|---|---|---|---|---|
| 181 | (1S,2S,4R)-Bicyclo[2.2.1]hept-2-yl-amine | 1-(1S,2S,4R)-Bicyclo[2.2.1]hept-2-yl-3-[(3S,3aR,6S,6aS)-6-(2-methyl-pyridin-3-yloxy)-hexahydro-furo[3,2-b]furan-3-yl]-urea | 374.28 | 1.34 | 6 |
| 182 | 1-Hydroxy-cyclohexyl-methyl-amine | 1-(1-Hydroxy-cyclohexylmethyl)-3-[(3S,3aR,6S,6aS)-6-(2-methyl-pyridin-3-yloxy)-hexahydro-furo[3,2-b]furan-3-yl]-urea | 392.29 | 1.18 | 6 |
| 183 | 2-Methoxy-1-methyl-ethyl-amine | 1-(2-Methoxy-1-methyl-ethyl)-3-[(3S,3aR,6S,6aS)-6-(2-methyl-pyridin-3-yloxy)-hexahydro-furo[3,2-b]furan-3-yl]-urea | 352.23 | 0.98 | 6 |
| 184 | 1-Phenyl-cyclopentyl-methyl-amine | 1-[(3S,3aR,6S,6aS)-6-(2-Methyl-pyridin-3-yloxy)-hexahydro-furo[3,2-b]furan-3-yl]-3-(1-phenyl-cyclopentylmethyl)-urea | 438.32 | 1.58 | 6 |
| 185 | 2-(4-Fluoro-phenyl)-1,1-dimethyl-ethyl-amine | 1-[2-(4-Fluoro-phenyl)-1,1-dimethyl-ethyl]-3-[(3S,3aR,6S,6aS)-6-(2-methyl-pyridin-3-yloxy)-hexahydro-furo[3,2-b]furan-3-yl]-urea | 430.29 | 1.54 | 6 |
| 186 | (1S,2S,3S,5R)-2,6,6-Trimethyl-bicyclo[3.1.1]hept-3-yl)-amine | 1-[(3S,3aR,6S,6aS)-6-(2-Methyl-pyridin-3-yloxy)-hexahydro-furo[3,2-b]furan-3-yl]-3-((1S,2S,3S,5R)-2,6,6-trimethyl-bicyclo[3.1.1]hept-3-yl)-urea | 416.42 | 1.44 | 6 |
| 187 | 1-(4-Methane-sulfonyl-phenyl)-ethyl-amine | 1-[1-(4-Methanesulfonyl-phenyl)-ethyl]-3-[(3S,3aR,6S,6aS)-6-(2-methyl-pyridin-3-yloxy)-hexahydro-furo[3,2-b]furan-3-yl]-urea | 462.23 | 1.14 | 6 |
| 188 | 2-Difluoro-methoxy-benzylamine | 1-(2-Difluoromethoxy-benzyl)-3-[(3S,3aR,6S,6aS)-6-(2-methyl-pyridin-3-yloxy)-hexahydro-furo[3,2-b]furan-3-yl]-urea | 436.25 | 1.37 | 6 |
| 189 | 4-Difluoro-methoxy-benzylamine | 1-(4-Difluoromethoxy-benzyl)-3-[(3S,3aR,6S,6aS)-6-(2-methyl-pyridin-3-yloxy)-hexahydro-furo[3,2-b]furan-3-yl]-urea | 436.25 | 1.37 | 6 |
| 190 | 5-Methyl-pyrazin-2-ylmethyl-amine | 1-(5-Methyl-pyrazin-2-ylmethyl)-3-[(3S,3aR,6S,6aS)-6-(2-methyl-pyridin-3-yloxy)-hexahydro-furo[3,2-b]furan-3-yl]-urea | 386.25 | 0.96 | 6 |
| 191 | 2,2-(Di-methyl-[1,3]-dioxolan-4-yl)methyl-amine | 1-(2,2-Dimethyl-[1,3]dioxolan-4-ylmethyl)-3-[(3S,3aR,6S,6aS)-6-(2-methyl-pyridin-3-yloxy)-hexahydro-furo[3,2-b]furan-3-yl]-urea | 394.26 | 1.06 | 6 |
| 192 | 1-Methyl-1H-pyrazol-4-ylmethyl-amine | 1-(1-Methyl-1H-pyrazol-4-ylmethyl)-3-[(3S,3aR,6S,6aS)-6-(2-methyl-pyridin-3-yloxy)-hexahydro-furo[3,2-b]furan-3-yl]-urea | 374.24 | 0.91 | 6 |
| 193 | (1R,3S,5R,7S)-3-Hydroxy-adamantan-1-yl-amine | 1-((1R,3S,5R,7S)-3-Hydroxy-adamantan-1-yl)-3-[(3S,3aR,6S,6aS)-6-(2-methyl-pyridin-3-yloxy)-hexahydro-furo[3,2-b]furan-3-yl]-urea | 430.31 | 1.20 | 6 |
| 194 | [1,4]Dioxan-2-ylmethyl-amine | 1-[1,4]Dioxan-2-ylmethyl-3-[(3S,3aR,6S,6aS)-6-(2-methyl-pyridin-3-yloxy)-hexahydro-furo[3,2-b]furan-3-yl]-urea | 380.25 | 0.91 | 6 |
| 195 | (1S,4R)-1,3,3-Trimethyl-bicyclo[2.2.1]hept-2-yl)-amine | 1-[(2R,3aS,5S,6S)-6-(2-Methyl-pyridin-3-yloxy)-hexahydro-furo[3,2-b]furan-3-yl]-3-((1S,4R)-1,3,3-tri-methyl-bicyclo[2.2.1]hept-2-yl)-urea | 416.34 | 1.59 | 6 |
| 196 | 2,3-Dihydro-benzo[1,4]dioxin-2-yl-methyl-amine | 1-(2,3-Dihydro-benzo[1,4]dioxin-2-ylmethyl)-3-[(3S,3aR,6S,6aS)-6-(2-methyl-pyridin-3-yloxy)-hexahydro-furo[3,2-b]furan-3-yl]-urea | 428.26 | 1.35 | 6 |
| 197 | 1,1-Di-methyl-2-morpholin-4-yl-ethyl-amine | 1-(1,1-Dimethyl-2-morpholin-4-yl-ethyl)-3-[(3S,3aR,6S,6aS)-6-(2-methyl-pyridin-3-yloxy)-hexahydro-furo[3,2-b]furan-3-yl]-urea | 421.32 | 0.81 | 6 |

| No | Starting compound | Chemical name | Mass (from LC/MS) | R$_t$ (from LC/MS) (min) | LC/MS Method |
|---|---|---|---|---|---|
| 198 | 1-Methyl-1H-imidazol-4-ylmethyl-amine | 1-(1-Methyl-1H-imidazol-4-ylmethyl)-3-[(3S,3aR,6S,6aS)-6-(2-methyl-pyridin-3-yloxy)-hexahydro-furo[3,2-b]furan-3-yl]-urea | 373.98 | 0.22 | 6 |
| 199 | 4-Methyl-thiazol-2-ylmethyl-amine | 1-[(3S,3aR,6S,6aS)-6-(2-Methyl-pyridin-3-yloxy)-hexahydro-furo[3,2-b]furan-3-yl]-3-(4-methyl-thiazol-2-ylmethyl)-urea | 391.20 | 1.08 | 6 |
| 200 | 2,3-Dihydro-benzo[1,4]dioxin-5-yl-methyl-amine | 1-(2,3-Dihydro-benzo[1,4]dioxin-5-ylmethyl)-3-[(3S,3aR,6S,6aS)-6-(2-methyl-pyridin-3-yloxy)-hexahydro-furo[3,2-b]furan-3-yl]-urea | 428.25 | 1.28 | 6 |
| 201 | 5-Amino-methyl-pyrrolidin-2-one | 1-[(3S,3aR,6S,6aS)-6-(2-Methyl-pyridin-3-yloxy)-hexahydro-furo[3,2-b]furan-3-yl]-3-(5-oxo-pyrrolidin-2-ylmethyl)-urea | 377.32 | 0.37 | 6 |
| 202 | 6-Methoxy-pyridin-2-yl-methyl-amine | 1-(6-Methoxy-pyridin-2-ylmethyl)-3-[(3S,3aR,6S,6aS)-6-(2-methyl-pyridin-3-yloxy)-hexahydro-furo[3,2-b]furan-3-yl]-urea | 401.23 | 1.17 | 6 |
| 203 | 2-Methoxy-pyridin-4-yl-methyl-amine | 1-(2-Methoxy-pyridin-4-ylmethyl)-3-[(3S,3aR,6S,6aS)-6-(2-methyl-pyridin-3-yloxy)-hexahydro-furo[3,2-b]furan-3-yl]-urea | 401.24 | 1.01 | 6 |
| 204 | 1-(4-Fluoro-phenyl)-1-methyl-ethyl-amine | 1-[1-(4-Fluoro-phenyl)-1-methyl-ethyl]-3-[(3S,3aR,6S,6aS)-6-(2-methyl-pyridin-3-yloxy)-hexahydro-furo[3,2-b]furan-3-yl]-urea | 416.29 | 1.42 | 6 |
| 205 | 2-(3-Methyl-pyridin-2-yl)-ethyl-amine | 1-[2-(3-Methyl-pyridin-2-yl)-ethyl]-3-[(3S,3aR,6S,6aS)-6-(2-methyl-pyridin-3-yloxy)-hexahydro-furo[3,2-b]furan-3-yl]-urea | 399.27 | 0.35 | 6 |
| 206 | 2-(2-Trifluoro-methoxy-phenyl)-ethyl-amine | 1-[(3S,3aR,6S,6aS)-6-(2-Methyl-pyridin-3-yloxy)-hexahydro-furo[3,2-b]furan-3-yl]-3-[2-(2-trifluoro-methoxy-phenyl)-ethyl]-urea | 468.27 | 1.53 | 6 |
| 207 | 1-Chroman-4-ylamine | 1-Chroman-4-yl-3-[(3S,3aR,6S,6aS)-6-(2-methyl-pyridin-3-yloxy)-hexahydro-furo[3,2-b]furan-3-yl]-urea | 412.26 | 1.31 | 6 |
| 208 | 5-Chloro-thiophen-2-ylmethyl-amine | 1-(5-Chloro-thiophen-2-ylmethyl)-3-[(3S,3aR,6S,6aS)-6-(2-methyl-pyridin-3-yloxy)-hexahydro-furo[3,2-b]furan-3-yl]-urea | 410.16 | 1.37 | 6 |
| 209 | 2-Methyl-tetra-hydro-furan-2-ylmethyl-amine | 1-[(3S,3aR,6S,6aS)-6-(2-Methyl-pyridin-3-yloxy)-hexahydro-furo[3,2-b]furan-3-yl]-3-(2-methyl-tetrahydro-furan-2-ylmethyl)-urea | 378.27 | 1.10 | 6 |
| 210 | 1-Methoxy-methyl-cyclopentyl-amine | 1-(1-Methoxymethyl-cyclopentyl)-3-[(3S,3aR,6S,6aS)-6-(2-methyl-pyridin-3-yloxy)-hexahydro-furo[3,2-b]furan-3-yl]-urea | 392.30 | 1.28 | 6 |
| 211 | 2-Methoxy-1-(2-methyl-2H-pyrazol-3-yl)-ethyl-amine | 1-[2-Methoxy-1-(2-methyl-2H-pyrazol-3-yl)-ethyl]-3-[(3S,3aR,6S,6aS)-6-(2-methyl-pyridin-3-yloxy)-hexahydro-furo[3,2-b]furan-3-yl]-urea | 418.27 | 1.03 | 6 |
| 212 | 1-Isobutyryl-piperidin-4-yl-amine | 1-(1-Isobutyryl-piperidin-4-yl)-3-[(3S,3aR,6S,6aS)-6-(2-methyl-pyridin-3-yloxy)-hexahydro-furo[3,2-b]furan-3-yl]-urea | 433.32 | 1.16 | 6 |
| 213 | (1R,2R,3R,5S)-2,6,6-Tri-methyl-bicyclo[3.1.1]hept-3-ylmethyl-amine | 1-[(3S,3aR,6S,6aS)-6-(2-Methyl-pyridin-3-yloxy)-hexahydro-furo[3,2-b]furan-3-yl]-3-((1R,2R,3R,5S)-2,6,6-trimethyl-bicyclo[3.1.1]hept-3-ylmethyl)-urea | 430.35 | 1.68 | 6 |
| 214 | 1-(4-Fluoro-phenyl)-ethyl-amine | 1-[1-(4-Fluoro-phenyl)-ethyl]-3-[(3S,3aR,6S,6aS)-6-(2-methyl-pyridin-3-yloxy)-hexahydro-furo[3,2-b]furan-3-yl]-urea | 402.26 | 1.35 | 6 |
| 215 | 5-tert-Butyl-1H-pyrazol-3-yl-amine | 1-(5-tert-Butyl-1H-pyrazol-3-yl)-3-[(3S,3aR,6S,6aS)-6-(2-methyl-pyridin-3-yloxy)-hexahydro-furo[3,2-b]furan-3-yl]-urea | 402.26 | 1.52 | 6 |

| No | Starting compound | Chemical name | Mass (from LC/MS) | R$_t$ (from LC/MS) (min) | LC/MS Method |
|---|---|---|---|---|---|
| 216 | Tetrahydro-pyran-4-yl-amine | 1-[(3S,3aR,6S,6aS)-6-(2-Methyl-pyridin-3-yloxy)-hexahydro-furo[3,2-b]furan-3-yl]-3-(tetrahydro-pyran-4-yl)-urea | 364.31 | 0.56 | 6 |
| 217 | 2-tert-Butoxy-ethyl-amine | 1-(2-tert-Butoxy-ethyl)-3-[(3S,3aR,6S,6aS)-6-(2-methyl-pyridin-3-yloxy)-hexahydro-furo[3,2-b]furan-3-yl]-urea | 380.29 | 1.23 | 6 |
| 218 | 2-(2-Methyl-thiazol-4-yl)-ethyl-amine | 1-[(3S,3aR,6S,6aS)-6-(2-Methyl-pyridin-3-yloxy)-hexahydro-furo[3,2-b]furan-3-yl]-3-[2-(2-methyl-thiazol-4-yl)-ethyl]-urea | 405.22 | 1.08 | 6 |
| 219 | 4-Methyl-morpholin-2-ylmethyl | 1-(4-Methyl-morpholin-2-ylmethyl)-3-[(3S,3aR,6S,6aS)-6-(2-methyl-pyridin-3-yloxy)-hexahydro-furo[3,2-b]furan-3-yl]-urea | 393.28 | 0.31 | 6 |
| 220 | 1-Cyano-cyclohexyl-amine | 1-(1-Cyano-cyclohexyl)-3-[(3S,3aR,6S,6aS)-6-(2-methyl-pyridin-3-yloxy)-hexahydro-furo[3,2-b]furan-3-yl]-urea | 387.29 | 1.27 | 6 |
| 221 | Tetrahydro-pyran-3-yl-amine | 1-[(3S,3aR,6S,6aS)-6-(2-Methyl-pyridin-3-yloxy)-hexahydro-furo[3,2-b]furan-3-yl]-3-(tetrahydro-pyran-3-yl)-urea | 364.25 | 0.99 | 6 |
| 222 | 3,5-Dimethyl-1H-pyrazol-4-ylmethyl-amine | 1-(3,5-Dimethyl-1H-pyrazol-4-ylmethyl)-3-[(3S,3aR,6S,6aS)-6-(2-methyl-pyridin-3-yloxy)-hexahydro-furo[3,2-b]furan-3-yl]-urea | 388.27 | 0.85 | 6 |
| 223 | 2-(4-Methane-sulfonyl-phenyl)-ethyl-amine hydrochloride | 1-[2-(4-Methanesulfonyl-phenyl)-ethyl]-3-[(3S,3aR,6S,6aS)-6-(2-methyl-pyridin-3-yloxy)-hexahydro-furo[3,2-b]furan-3-yl]-urea | 462.26 | 1.14 | 6 |
| 224 | 2,2-Dimethyl-2,3-dihydro-benzofuran-7-ylmethyl-amine | 1-(2,2-Dimethyl-2,3-dihydro-benzofuran-7-ylmethyl)-3-[(3S,3aR,6S,6aS)-6-(2-methyl-pyridin-3-yloxy)-hexahydro-furo[3,2-b]furan-3-yl]-urea | 440.31 | 1.47 | 6 |
| 225 | 1-Isopropyl-3-methyl-1H-pyrazol-4-yl-amine | 1-(1-Isopropyl-3-methyl-1H-pyrazol-4-yl)-3-[(3S,3aR,6S,6aS)-6-(2-methyl-pyridin-3-yloxy)-hexahydro-furo[3,2-b]furan-3-yl]-urea | 402.27 | 1.14 | 6 |
| 226 | 2-tert-Butoxy-1,1-dimethyl-ethyl-amine | 1-(2-tert-Butoxy-1,1-dimethyl-ethyl)-3-[(3S,3aR,6S,6aS)-6-(2-methyl-pyridin-3-yloxy)-hexahydro-furo[3,2-b]furan-3-yl]-urea | 408.33 | 1.49 | 6 |
| 227 | 2-Methyl-thiazol-4-ylmethyl-amine | 1-[(3S,3aR,6S,6aS)-6-(2-Methyl-pyridin-3-yloxy)-hexahydro-furo[3,2-b]furan-3-yl]-3-(2-methyl-thiazol-4-ylmethyl)-urea | 391.20 | 1.06 | 6 |
| 228 | Tetrahydro-thiopyran-4-yl-amine | 1-[(3S,3aR,6S,6aS)-6-(2-Methyl-pyridin-3-yloxy)-hexahydro-furo[3,2-b]furan-3-yl]-3-(tetrahydro-thiopyran-4-yl)-urea | 380.22 | 1.14 | 6 |
| 229 | 1-(3-Fluoro-phenyl)-cyclopentyl-amine | 1-[1-(3-Fluoro-phenyl)-cyclopentyl]-3-[(3S,3aR,6S,6aS)-6-(2-methyl-pyridin-3-yloxy)-hexahydro-furo[3,2-b]furan-3-yl]-urea | 442.30 | 1.53 | 6 |
| 230 | (1R,3S,5R,7S)-3-Hydroxy-5,7-dimethyl-adamantan-1-yl-amine | 1-((1R,3S,5R,7S)-3-Hydroxy-5,7-dimethyl-adamantan-1-yl)-3-[(3S,3aR,6S,6aS)-6-(2-methyl-pyridin-3-yloxy)-hexahydro-furo[3,2-b]furan-3-yl]-urea | 458.36 | 1.40 | 6 |
| 231 | (1R,4R)-1,7,7-Trimethyl-bicyclo[2.2.1]hept-2-yl-amine | 1-[(2R,3aS,5S,6S)-6-(2-Methyl-pyridin-3-yloxy)-hexahydro-furo[3,2-b]furan-3-yl]-3-((1R,4R)-1,7,7-trimethyl-bicyclo[2.2.1]hept-2-yl)-urea | 416.35 | 1.58 | 6 |
| 232 | 2,2,2-Trifluoro-1,1-dimethyl-ethyl-amine | 1-[(3S,3aR,6S,6aS)-6-(2-Methyl-pyridin-3-yloxy)-hexahydro-furo[3,2-b]furan-3-yl]-3-(2,2,2-trifluoro-1,1-dimethyl-ethyl)-urea | 390.25 | 1.28 | 6 |
| 233 | 1-Methyl-1-pyridin-3-yl-ethyl-amine | 1-(1-Methyl-1-pyridin-3-yl-ethyl)-3-[(3S,3aR,6S,6aS)-6-(2-methyl-pyridin-3-yloxy)-hexahydro-furo[3,2-b]furan-3-yl]-urea | 399.26 | 0.38 | 6 |

| No | Starting compound | Chemical name | Mass (from LC/MS) | R_t (from LC/MS) (min) | LC/MS Method |
|---|---|---|---|---|---|
| 234 | 1-(1,3,5-Trimethyl-1H-pyrazol-4-yl)-ethyl-amine | 1-[(3S,3aR,6S,6aS)-6-(2-Methyl-pyridin-3-yloxy)-hexahydro-furo[3,2-b]furan-3-yl]-3-[1-(1,3,5-trimethyl-1H-pyrazol-4-yl)-ethyl]-urea | 416.30 | 1.07 | 6 |
| 235 | 2-(Tetrahydro-pyran-2-yl)-ethyl-amine | 1-[(3S,3aR,6S,6aS)-6-(2-Methyl-pyridin-3-yloxy)-hexahydro-furo[3,2-b]furan-3-yl]-3-[2-(tetrahydro-pyran-2-yl)-ethyl]-urea | 392.29 | 1.22 | 6 |
| 236 | 2-(2-Oxo-pyrrolidin-1-yl)-ethyl-amine | 1-[(3S,3aR,6S,6aS)-6-(2-Methyl-pyridin-3-yloxy)-hexahydro-furo[3,2-b]furan-3-yl]-3-[2-(2-oxo-pyrrolidin-1-yl)-ethyl]-urea | 391.26 | 0.91 | 6 |
| 237 | (S)-2-Methoxy-1-phenyl-ethyl-amine | 1-((S)-2-Methoxy-1-phenyl-ethyl)-3-[(3S,3aR,6S,6aS)-6-(2-methyl-pyridin-3-yloxy)-hexahydro-furo[3,2-b]furan-3-yl]-urea | 414.29 | 1.29 | 6 |
| 238 | 1-Pyridin-3-yl-cyclopropyl-amine | 1-[(3S,3aR,6S,6aS)-6-(2-Methyl-pyridin-3-yloxy)-hexahydro-furo[3,2-b]furan-3-yl]-3-(1-pyridin-3-yl-cyclopropyl)-urea | 397.25 | 0.42 | 6 |
| 239 | (7-Oxa-bicyclo[2.2.1]hept-2-yl)-methyl-amine | 1-[(3S,3aR,6S,6aS)-6-(2-Methyl-pyridin-3-yloxy)-hexahydro-furo[3,2-b]furan-3-yl]-3-[(1R,4S)-1-(7-oxa-bicyclo[2.2.1]hept-2-yl)methyl]-urea | 390.29 | 0.90 | 6 |
| 240 | 3-Methyl-oxetan-3-yl-amine | 1-(3-Methyl-oxetan-3-yl)-3-[(3S,3aR,6S,6aS)-6-(2-methyl-pyridin-3-yloxy)-hexahydro-furo[3,2-b]furan-3-yl]-urea | 350.25 | 0.87 | 6 |
| 241 | 1-Cyclohexyl-1-methyl-ethyl-amine | 1-(1-Cyclohexyl-1-methyl-ethyl)-3-[(3S,3aR,6S,6aS)-6-(2-methyl-pyridin-3-yloxy)-hexahydro-furo[3,2-b]furan-3-yl]-urea | 404.35 | 1.60 | 6 |
| 242 | (1R,2R)-2-Hydroxy-2-methyl-cyclohexyl-methyl-amine | 1-((1R,2R)-2-Hydroxy-2-methyl-cyclohexylmethyl)-3-[(3S,3aR,6S,6aS)-6-(2-methyl-pyridin-3-yloxy)-hexahydro-furo[3,2-b]furan-3-yl]-urea | 406.30 | 1.22 | 6 |
| 243 | 3-(5-Methyl-3-trifluoro-methyl-pyrazol-1-yl)-propyl-amine | 1-[(3S,3aR,6S,6aS)-6-(2-Methyl-pyridin-3-yloxy)-hexahydro-furo[3,2-b]furan-3-yl]-3-[3-(5-methyl-3-trifluoromethyl-pyrazol-1-yl)-propyl]-urea | 470.31 | 1.42 | 6 |
| 244 | 1-Methyl-2-(2-oxo-pyrrolidin-1-yl)-ethyl-amine | 1-[1-Methyl-2-(2-oxo-pyrrolidin-1-yl)-ethyl]-3-[(3S,3aR,6S,6aS)-6-(2-methyl-pyridin-3-yloxy)-hexahydro-furo[3,2-b]furan-3-yl]-urea | 405.28 | 1.00 | 6 |
| 245 | 1-Methyl-6-oxo-piperidin-3-yl-amine | 1-(1-Methyl-6-oxo-piperidin-3-yl)-3-[(3S,3aR,6S,6aS)-6-(2-methyl-pyridin-3-yloxy)-hexahydro-furo[3,2-b]furan-3-yl]-urea | 391.27 | 0.87 | 6 |
| 246 | 1-Isopropyl-5-oxo-pyrrolidin-3-yl-amine | 1-(1-Isopropyl-5-oxo-pyrrolidin-3-yl)-3-[(3S,3aR,6S,6aS)-6-(2-methyl-pyridin-3-yloxy)-hexahydro-furo[3,2-b]furan-3-yl]-urea | 405.34 | 1.78 | 4 |
| 247 | 5-Oxo-1-phenyl-pyrrolidin-3-yl-amine | 1-[(3S,3aR,6S,6aS)-6-(2-Methyl-pyridin-3-yloxy)-hexahydro-furo[3,2-b]furan-3-yl]-3-(5-oxo-1-phenyl-pyrrolidin-3-yl)-urea | 439.27 | 1.25 | 6 |
| 248 | 4-Cyano-tetrahydro-pyran-4-yl-amine | 1-(4-Cyano-tetrahydro-pyran-4-yl)-3-[(3S,3aR,6S,6aS)-6-(2-methyl-pyridin-3-yloxy)-hexahydro-furo[3,2-b]furan-3-yl]-urea | 389.26 | 0.98 | 6 |
| 249 | 1-Methyl-cyclohexyl-amine | 1-(1-Methyl-cyclohexyl)-3-[(3S,3aR,6S,6aS)-6-(2-methyl-pyridin-3-yloxy)-hexahydro-furo[3,2-b]furan-3-yl]-urea | 376.31 | 1.42 | 6 |
| 250 | 1-Methyl-1-pyridin-4-yl-ethyl-amine | 1-(1-Methyl-1-pyridin-4-yl-ethyl)-3-[(3S,3aR,6S,6aS)-6-(2-methyl-pyridin-3-yloxy)-hexahydro-furo[3,2-b]furan-3-yl]-urea | 399.34 | 0.49 | 4 |
| 251 | 2-(2-Oxo-piperidin-1-yl)-ethyl-amine | 1-[(3S,3aR,6S,6aS)-6-(2-Methyl-pyridin-3-yloxy)-hexahydro-furo[3,2-b]furan-3-yl]-3-[2-(2-oxo-piperidin-1-yl)-ethyl]-urea | 405.28 | 1.02 | 6 |

| No | Starting compound | Chemical name | Mass (from LC/MS) | R$_t$ (from LC/MS) (min) | LC/MS Method |
|---|---|---|---|---|---|
| 252 | 1-Methyl-2-oxo-pyrrolidin-3-yl-amine | 1-(1-Methyl-2-oxo-pyrrolidin-3-yl)-3-[(3S,3aR,6S,6aS)-6-(2-methyl-pyridin-3-yloxy)-hexahydro-furo[3,2-b]furan-3-yl]-urea | 377.24 | 0.82 | 6 |
| 253 | 1-Isopropyl-5-oxo-pyrrolidin-3-ylmethyl-amine | 1-(1-Isopropyl-5-oxo-pyrrolidin-3-ylmethyl)-3-[(3S,3aR,6S,6aS)-6-(2-methyl-pyridin-3-yloxy)-hexahydro-furo[3,2-b]furan-3-yl]-urea | 419.30 | 1.08 | 6 |
| 254 | 1-Ethyl-5-oxo-pyrrolidin-3-ylmethyl-amine | 1-(1-Ethyl-5-oxo-pyrrolidin-3-ylmethyl)-3-[(3S,3aR,6S,6aS)-6-(2-methyl-pyridin-3-yloxy)-hexahydro-furo[3,2-b]furan-3-yl]-urea | 405.29 | 0.98 | 6 |
| 255 | 1-Methyl-5-oxo-pyrrolidin-2-ylmethyl-amine | 1-(1-Methyl-5-oxo-pyrrolidin-2-ylmethyl)-3-[(3S,3aR,6S,6aS)-6-(2-methyl-pyridin-3-yloxy)-hexahydro-furo[3,2-b]furan-3-yl]-urea | 391.29 | 1.54 | 4 |
| 256 | 3,3,5-Trimethyl-cyclohexyl-amine | 1-[(3S,3aR,6S,6aS)-6-(2-Methyl-pyridin-3-yloxy)-hexahydro-furo[3,2-b]furan-3-yl]-3-(3,3,5-trimethyl-cyclohexyl)-urea | 404.34 | 1.60 | 6 |
| 257 | 4-Methyl-cyclohexyl-amine | 1-(4-Methyl-cyclohexyl)-3-[(3S,3aR,6S,6aS)-6-(2-methyl-pyridin-3-yloxy)-hexahydro-furo[3,2-b]furan-3-yl]-urea | 376.32 | 1.23 | 6 |
| 258 | 3-Methyl-cyclohexyl-amine | 1-(3-Methyl-cyclohexyl)-3-[(3S,3aR,6S,6aS)-6-(2-methyl-pyridin-3-yloxy)-hexahydro-furo[3,2-b]furan-3-yl]-urea | 376.22 | 1.27 | 6 |
| 259 | 2-Methyl-cyclohexyl-amine | 1-(2-Methyl-cyclohexyl)-3-[(3S,3aR,6S,6aS)-6-(2-methyl-pyridin-3-yloxy)-hexahydro-furo[3,2-b]furan-3-yl]-urea | 420.35 | 1.16 | 6 |
| 260 | 4-tert-Butyl-cyclohexyl-amine | 1-(4-tert-Butyl-cyclohexyl)-3-[(3S,3aR,6S,6aS)-6-(2-methyl-pyridin-3-yloxy)-hexahydro-furo[3,2-b]furan-3-yl]-urea | 418.36 | 1.66 | 6 |
| 261 | 2,3-Dimethyl-cyclohexyl-amine | 1-(2,3-Dimethyl-cyclohexyl)-3-[(3S,3aR,6S,6aS)-6-(2-methyl-pyridin-3-yloxy)-hexahydro-furo[3,2-b]furan-3-yl]-urea | 390.30 | 1.48 | 6 |
| 262 | Octahydro-4,7-methano-inden-5-yl-amine | 1-[(3S,3aR,6S,6aS)-6-(2-Methyl-pyridin-3-yloxy)-hexahydro-furo[3,2-b]furan-3-yl]-3-(octahydro-4,7-methano-inden-5-yl)-urea | 414.32 | 1.54 | 6 |
| 263 | 2-Isopropyl-5-methyl-cyclohexyl-amine | 1-(2-Isopropyl-5-methyl-cyclohexyl)-3-[(3S,3aR,6S,6aS)-6-(2-methyl-pyridin-3-yloxy)-hexahydro-furo[3,2-b]furan-3-yl]-urea | 418.36 | 1.66 | 6 |
| 264 | 4-Phenyl-cyclohexyl-amine | 1-[(3S,3aR,6S,6aS)-6-(2-Methyl-pyridin-3-yloxy)-hexahydro-furo[3,2-b]furan-3-yl]-3-(4-phenyl-cyclohexyl)-urea | 438.31 | 1.58 | 6 |
| 265 | (1R,2S)-2-tert-Butyl-cyclohexyl-amine | 1-((1R,2S)-2-tert-Butyl-cyclohexyl)-3-[(3S,3aR,6S,6aS)-6-(2-methyl-pyridin-3-yloxy)-hexahydro-furo[3,2-b]furan-3-yl]-urea | 418.39 | 3.32 | 4 |
| 266 | 1,4-Dioxa-spiro[4.5]dec-8-yl-amine | 1-(1,4-Dioxa-spiro[4.5]dec-8-yl)-3-[(3S,3aR,6S,6aS)-6-(2-methyl-pyridin-3-yloxy)-hexahydro-furo[3,2-b]furan-3-yl]-urea | 420.29 | 1.12 | 6 |
| 267 | trans-4-Methyl-cyclohexyl-amine | 1-(trans-4-Methyl-cyclohexyl)-3-[(3S,3aR,6S,6aS)-6-(2-methyl-pyridin-3-yloxy)-hexahydro-furo[3,2-b]furan-3-yl]-urea | 376.29 | 1.43 | 6 |
| 268 | 4,4-Dimethyl-cyclohexyl-amine | 1-(4,4-Dimethyl-cyclohexyl)-3-[(3S,3aR,6S,6aS)-6-(2-methyl-pyridin-3-yloxy)-hexahydro-furo[3,2-b]furan-3-yl]-urea | 390.32 | 1.50 | 6 |
| 269 | 2,6-Dimethyl-cyclohexyl-amine | 1-(2,6-Dimethyl-cyclohexyl)-3-[(3S,3aR,6S,6aS)-6-(2-methyl-pyridin-3-yloxy)-hexahydro-furo[3,2-b]furan-3-yl]-urea | 390.30 | 1.49 | 6 |

| No | Starting compound | Chemical name | Mass (from LC/MS) | R_t (from LC/MS) (min) | LC/MS Method |
|---|---|---|---|---|---|
| 270 | 2,2-Dimethyl-cyclohexyl-amine | 1-(2,2-Dimethyl-cyclohexyl)-3-[(3S,3aR,6S,6aS)-6-(2-methyl-pyridin-3-yloxy)-hexahydro-furo[3,2-b]furan-3-yl]-urea | 390.30 | 1.47 | 6 |
| 271 | 2-tert-Butyl-cyclohexyl-amine | 1-(2-tert-Butyl-cyclohexyl)-3-[(3S,3aR,6S,6aS)-6-(2-methyl-pyridin-3-yloxy)-hexahydro-furo[3,2-b]furan-3-yl]-urea | 418.30 | 1.48 | 6 |
| 272 | cis-4-Methyl-cyclohexyl-amine | 1-(cis-4-Methyl-cyclohexyl)-3-[(3S,3aR,6S,6aS)-6-(2-methyl-pyridin-3-yloxy)-hexahydro-furo[3,2-b]furan-3-yl]-urea | 376.23 | 1.27 | 6 |
| 273 | 3,3,5,5-Tetramethyl-cyclohexyl-amine | 1-[(3S,3aR,6S,6aS)-6-(2-Methyl-pyridin-3-yloxy)-hexahydro-furo[3,2-b]furan-3-yl]-3-(3,3,5,5-tetramethyl-cyclohexyl)-urea | 418.31 | 1.52 | 6 |
| 274 | (1R,2R)-2-Fluoro-cyclohexyl-amine | 1-((1R,2R)-2-Fluoro-cyclohexyl)-3-[(3S,3aR,6S,6aS)-6-(2-methyl-pyridin-3-yloxy)-hexahydro-furo[3,2-b]furan-3-yl]-urea | 380.19 | 0.97 | 6 |
| 275 | 2-Trifluoro-methyl-cyclohexyl-amine | 1-[(3S,3aR,6S,6aS)-6-(2-Methyl-pyridin-3-yloxy)-hexahydro-furo[3,2-b]furan-3-yl]-3-(2-trifluoromethyl-cyclohexyl)-urea | 430.22 | 1.23 | 6 |
| 276 | 2,4-Dimethyl-cyclohexyl-amine | 1-(2,4-Dimethyl-cyclohexyl)-3-[(3S,3aR,6S,6aS)-6-(2-methyl-pyridin-3-yloxy)-hexahydro-furo[3,2-b]furan-3-yl]-urea | 390.26 | 1.37 | 6 |
| 277 | 2,2-Difluoro-cyclohexyl-amine | 1-(2,2-Difluoro-cyclohexyl)-3-[(3S,3aR,6S,6aS)-6-(2-methyl-pyridin-3-yloxy)-hexahydro-furo[3,2-b]furan-3-yl]-urea | 398.21 | 1.05 | 6 |
| 278 | 3,3-Difluoro-piperidine | 3,3-Difluoro-piperidine-1-carboxylic acid [(3S,3aR,6S,6aS)-6-(2-methyl-pyridin-3-yloxy)-hexahydro-furo[3,2-b]furan-3-yl]-amide | 384.16 | 0.93 | 6 |
| 279 | 5-Fluoro-2-trifluoro-methoxy-benzylamine | 1-(5-Fluoro-2-trifluoromethoxy-benzyl)-3-[(3S,3aR,6S,6aS)-6-(2-methyl-pyridin-3-yloxy)-hexahydro-furo[3,2-b]furan-3-yl]-urea | 472.20 | 1.36 | 6 |
| 280 | 4-(1-Hydroxy-1-methyl-ethyl)-amine | 1-[4-(1-Hydroxy-1-methyl-ethyl)-cyclohexyl]-3-[(3S,3aR,6S,6aS)-6-(2-methyl-pyridin-3-yloxy)-hexahydro-furo[3,2-b]furan-3-yl]-urea | 420.30 | 1.20 | 6 |

Example 281

1-((3S,3aR,6S,6aR)-6-benzo[1,3]dioxol-5-ylethynyl-hexahydro-furo[3,2-b]furan-3-yl)-3-cyclohexyl-urea Cyclohexyl isocyanate (96 µL, 0.76 mmol) was added to a solution of (3S,3aR,6S,6aR)-6-benzo[1,3]dioxol-5-ylethynyl-hexahydro-furo[3,2-b]furan-3-ylamine (P25) (94 mg, 0.34 mmol) in dichloromethane (4 mL) at RT. The mixture was stirred at RT for 12 h and was quenched with silica bound amine. The mixture was filtered through a celite pad and was concentrated under reduced pressure. The residue was purified by silica gel chromatography (elution with ethylacetate/hexanes 50:50) to yield 118 mg (86%) of 1-((3S,3aR,6S,6aR)-6-benzo[1,3]dioxol-5-ylethynyl-hexahydro-furo[3,2-b]furan-3-yl)-3-cyclohexyl-urea. LC/MS (Method 1): $R_t$=3.34 min; detected mass: m/z=399.18 ([M+H]$^+$).

According to the previous example the following compounds were prepared in close analogy from the respective ethynyl-hexahydro-furo[3,2-b]furan-3-ylamine using an appropriate isocyanate.

| No | Starting compounds | Chemical name | Mass (from LC/MS) | R_t (from LC/MS) (min) | LC/MS Method |
|---|---|---|---|---|---|
| 282 | P26 + Isocyanato-cyclohexane | 1-Cyclohexyl-3-((3S,3aR,6S,6aR)-6-phenylethynyl-hexahydro-furo[3,2-b]furan-3-yl)-urea | 355.19 | 3.41 | 1 |
| 283 | P26 + 1-Butoxy-4-isocyanato-benzene | 1-(4-Butoxy-phenyl)-3-[(3S,3aR,6R)-6-((S)-phenylethynyl)-hexahydro-furo[3,2-b]furan-3-yl]-urea | 421.20 | 3.68 | 1 |

-continued

| No | Starting compounds | Chemical name | Mass (from LC/MS) | R$_t$ (from LC/MS) (min) | LC/MS Method |
|---|---|---|---|---|---|
| 284 | P26 + 1-Isocyanato-3,5-dimethoxy-benzene | 1-(3,5-Dimethoxy-phenyl)-3-[(3S,3aR,6R)-6-((S)-phenylethynyl)-hexahydro-furo[3,2-b]furan-3-yl]-urea | 409.17 | 3.40 | 1 |
| 285 | P26 + 1-Isocyanato-3,5-dimethyl-benzene | 1-(3,5-Dimethyl-phenyl)-3-[(3S,3aR,6R)-6-((S)-phenylethynyl)-hexahydro-furo[3,2-b]furan-3-yl]-urea | 377.18 | 3.61 | 1 |
| 286 | P26 + Isocyanato-benzene | 1-Phenyl-3-[(3S,3aR,6R)-6-((S)-phenylethynyl)-hexa-hydro-furo[3,2-b]furan-3-yl]-urea | 349.15 | 3.34 | 1 |
| 287 | P26 + 1-Benzyloxy-4-isocyanato-benzene | 1-(4-Benzyloxy-phenyl)-3-[(3S,3aR,6R)-6-((S)-phenylethynyl)-hexahydro-furo[3,2-b]furan-3-yl]-urea | 455.19 | 3.69 | 1 |
| 288 | P26 + 1-Fluoro-4-isocyanato-methyl-benzene | 1-(4-Fluoro-benzyl)-3-[(3S,3aR,6R)-6-((S)-phenylethynyl)-hexahydro-furo[3,2-b]furan-3-yl]-urea | 381.15 | 3.27 | 1 |
| 289 | P26 + 1-Isocyanato-3-methyl-benzene | 1-[(3S,3aR,6R)-6-((S)-Phenylethynyl)-hexahydro-furo[3,2-b]furan-3-yl]-3-m-tolyl-urea | 363.16 | 3.45 | 1 |
| 290 | P26 + 1,2-Dichloro-4-isocyanato-benzene | 1-(3,4-Dichloro-phenyl)-3-[(3S,3aR,6R)-6-((S)-phenylethynyl)-hexahydro-furo[3,2-b]furan-3-yl]-urea | 418.07 | 3.71 | 1 |
| 291 | P26 + 1-Isocyanato-methyl-3-methyl-benzene | 1-(3-Methyl-benzyl)-3-[(3S,3aR,6R)-6-((S)-phenylethynyl)-hexahydro-furo[3,2-b]furan-3-yl]-urea | 377.18 | 3.37 | 1 |
| 292 | P26 + 1-Fluoro-4-isocyanato-benzene | 1-(4-Fluoro-phenyl)-3-[(3S,3aR,6R)-6-((S)-phenylethynyl)-hexahydro-furo[3,2-b]furan-3-yl]-urea | 367.14 | 3.40 | 1 |
| 293 | P26 + 5-Isocyanato-benzo[1,3]-dioxole | 1-Benzo[1,3]dioxol-5-yl-3-((3S,3aR,6S,6aR)-6-phenylethynyl-hexahydro-furo[3,2-b]furan-3-yl)-urea | 393.14 | 3.27 | 1 |
| 294 | P26 + 1-Fluoro-3-isocyanato-benzene | 1-(3-Fluoro-phenyl)-3-((3S,3aR,6S,6aR)-6-phenylethynyl-hexahydro-furo[3,2-b]furan-3-yl)-urea | 367.14 | 3.48 | 1 |
| 295 | P26 + 6-Isocyanato-2,3-dihydro-benzo[1,4]-dioxine | 1-(2,3-Dihydro-benzo[1,4]dioxin-6-yl)-3-((3S,3aR,6S,6aR)-6-phenylethynyl-hexahydro-furo[3,2-b]furan-3-yl)-urea | 407.15 | 3.23 | 1 |
| 296 | P26 + 2-(2-Isocyanato-ethyl)-thiophene | 1-((3S,3aR,6S,6aR)-6-Phenylethynyl-hexahydro-furo[3,2-b]furan-3-yl)-3-(2-thiophen-2-yl-ethyl)-urea | 383.14 | 3.30 | 1 |
| 297 | P26 + (2-Isocyanato-ethyl)-benzene | 1-Phenethyl-3-((3S,3aR,6S,6aR)-6-phenylethynyl-hexahydro-furo[3,2-b]furan-3-yl)-urea | 377.18 | 3.31 | 1 |
| 298 | P26 + 1-Isocyanato-4-trifluoro-methoxy-benzene | 1-((3S,3aR,6S,6aR)-6-Phenylethynyl-hexahydro-furo[3,2-b]furan-3-yl)-3-(4-trifluoromethoxy-phenyl)-urea | 433.13 | 3.64 | 1 |
| 299 | P26 + 1-Isocyanato-3-trifluoromethyl-benzene | 1-((3S,3aR,6S,6aR)-6-Phenylethynyl-hexahydro-furo[3,2-b]furan-3-yl)-3-(3-trifluoromethyl-phenyl)-urea | 417.13 | 3.64 | 1 |
| 300 | P28 + Isocyanato-cyclohexane | 1-Cyclohexyl-3-((3S,3aR,6S,6aR)-6-pyridin-2-ylethynyl-hexahydro-furo[3,2-b]furan-3-yl)-urea; trifluoroacetate | 356.19 | 2.35 | 1 |

-continued

| No | Starting compounds | Chemical name | Mass (from LC/MS) | R$_t$ (from LC/MS) (min) | LC/MS Method |
|---|---|---|---|---|---|
| 301 | P27 + 1-Isocyanato-3,5-dimethoxy-benzene | 1-(3,5-Dimethoxy-phenyl)-3-((3S,3aR,6S,6aR)-6-thiophen-3-ylethynyl-hexahydro-furo[3,2-b]furan-3-yl)-urea | 415.12 | 3.29 | 1 |
| 302 | P27 + 1-Isocyanato-3,5-dimethyl-benzene | 1-(3,5-Dimethyl-phenyl)-3-((3S,3aR,6S,6aR)-6-thiophen-3-ylethynyl-hexahydro-furo[3,2-b]furan-3-yl)-urea | 383.14 | 3.55 | 1 |
| 303 | P27 + Isocyanato-benzene | 1-Phenyl-3-((3S,3aR,6S,6aR)-6-thiophen-3-ylethynyl-hexahydro-furo[3,2-b]furan-3-yl)-urea | 355.10 | 3.24 | 1 |
| 304 | P27 + 1-Fluoro-4-isocyanato-methyl-benzene | 1-(4-Fluoro-benzyl)-3-((3S,3aR,6S,6aR)-6-thiophen-3-ylethynyl-hexahydro-furo[3,2-b]furan-3-yl)-urea | 387.11 | 3.22 | 1 |
| 305 | P27 + 1-Isocyanato-methyl-3-methyl-benzene | 1-(3-Methyl-benzyl)-3-((3S,3aR,6S,6aR)-6-thiophen-3-ylethynyl-hexahydro-furo[3,2-b]furan-3-yl)-urea | 383.14 | 3.33 | 1 |
| 306 | P27 + 1-Fluoro-4-isocyanato-benzene | 1-(4-Fluoro-phenyl)-3-((3S,3aR,6S,6aR)-6-thiophen-3-ylethynyl-hexahydro-furo[3,2-b]furan-3-yl)-urea | 373.09 | 3.30 | 1 |
| 307 | P27 + 2-Isocyanato-biphenyl | 1-Biphenyl-2-yl-3-((3S,3aR,6S,6aR)-6-thiophen-3-ylethynyl-hexahydro-furo[3,2-b]furan-3-yl)-urea | 431.14 | 3.18 | 1 |
| 308 | P27 + 1-Isocyanato-4-trifluoro-methyl-benzene | 1-((3S,3aR,6S,6aR)-6-Thiophen-3-ylethynyl-hexahydro-furo[3,2-b]furan-3-yl)-3-(4-trifluoromethyl-phenyl)-urea | 423.4 | 2.39 | 1 |
| 309 | P27 + 3-Isocyanato-benzoic acid methyl ester | 3-[3-((3S,3aR,6S,6aR)-6-Thiophen-3-ylethynyl-hexahydro-furo[3,2-b]furan-3-yl)-ureido]-benzoic acid methyl ester | 413.4 | 2.16 | 1 |
| 310 | P27 + 5-Isocyanato-indan | 1-Indan-5-yl-3-((3S,3aR,6S,6aR)-6-thiophen-3-ylethynyl-hexahydro-furo[3,2-b]furan-3-yl)-urea | 395.4 | 2.35 | 1 |
| 311 | P27 + 1-Fluoro-3-isocyanato-benzene | 1-(3-Fluoro-phenyl)-3-((3S,3aR,6S,6aR)-6-thiophen-3-ylethynyl-hexahydro-furo[3,2-b]furan-3-yl)-urea | 373.09 | 3.37 | 1 |
| 312 | P27 + 1-Isocyanato-3-methyl-sulfanyl-benzene | 1-(3-Methylsulfanyl-phenyl)-3-((3S,3aR,6S,6aR)-6-thiophen-3-ylethynyl-hexahydro-furo[3,2-b]furan-3-yl)-urea | 401.09 | 3.44 | 1 |
| 313 | P27 + 2-(2-Isocyanato-ethyl)-thiophene | 1-(2-Thiophen-2-yl-ethyl)-3-((3S,3aR,6S,6aR)-6-thiophen-3-ylethynyl-hexahydro-furo[3,2-b]furan-3-yl)-urea | 389.09 | 3.20 | 1 |
| 314 | P27 + (2-Isocyanato-ethyl)-benzene | 1-Phenethyl-3-((3S,3aR,6S,6aR)-6-thiophen-3-ylethynyl-hexahydro-furo[3,2-b]furan-3-yl)-urea | 383.14 | 3.26 | 1 |
| 315 | P27 + 1-Isocyanato-4-trifluoro-methoxy-benzene | 1-((3S,3aR,6S,6aR)-6-Thiophen-3-ylethynyl-hexahydro-furo[3,2-b]furan-3-yl)-3-(4-trifluoromethoxy-phenyl)-urea | 439.09 | 3.58 | 1 |
| 316 | P27 + 1-Isocyanato-3-trifluoro-methyl-benzene | 1-((3S,3aR,6S,6aR)-6-Thiophen-3-ylethynyl-hexahydro-furo[3,2-b]furan-3-yl)-3-(3-trifluoromethyl-phenyl)-urea | 423.09 | 3.61 | 1 |

Example 317

1-[(3S,3aR,6S,6aR)-6-((Z)-2-Benzo[1,3]dioxol-5-yl-vinyl)-hexahydro-furo[3,2-b]furan-3-yl]-3-cyclohexyl-urea Lindlar catalyst (2 mg) was added to a solution of 1-((3S,3aR,6S,6aR)-6-benzo[1,3]dioxol-5-ylethynyl-hexahydro-furo[3,2-b]furan-3-yl)-3-cyclohexyl-urea (281) (19 mg, 0.048 mmol) in a mixture of 1-hexene (1 mL), ethyl acetate (1 mL) and quinolone (0.5 mL). The mixture was stirred under hydrogen atmosphere (1 bar) until LCMS indicated completion of the reaction. The mixture was filtered through a celite pad and the filtrate was concentrated under reduced pressure. The residue was purified by reversed phase HPLC (acetonitrile/water with 0.1% trifluoroacetic acid) to give 16 mg (84%) of 1-[(3S,3aR,6S,6aR)-6-((Z)-2-benzo[1,3]dioxol-5-yl-vinyl)-hexahydro-furo[3,2-b]furan-3-yl]-3-cyclohexyl-urea. LC/MS (Method 1): $R_t$=3.37 min; detected mass: m/z=401.20 ([M+H]$^+$).

According to the previous example the following compounds were prepared in close analogy from the respective ethynyl-hexahydro-furo[3,2-b]furan-3-yl-ureas.

| No | Starting compound from example No | Chemical name | Mass (from LC/MS) | $R_t$ (from LC/MS) (min) | LC/MS Method |
|---|---|---|---|---|---|
| 318 | 295 | 1-(2,3-Dihydro-benzo[1,4]dioxin-6-yl)-3-[(3S,3aR,6S,6aR)-6-((Z)-styryl)-hexahydro-furo[3,2-b]furan-3-yl]-urea | 409.17 | 3.23 | 1 |
| 319 | 282 | 1-Cyclohexyl-3-[(3S,3aR,6S,6aR)-6-((Z)-styryl)-hexahydro-furo[3,2-b]furan-3-yl]-urea | 357.21 | 3.41 | 1 |
| 320 | 283 | 1-(4-Butoxy-phenyl)-3-[(3S,3aR,6R)-6-((S)-(Z)-styryl)-hexahydro-furo[3,2-b]furan-3-yl]-urea | 423.22 | 3.69 | 1 |
| 321 | 284 | 1-(3,5-Dimethoxy-phenyl)-3-[(3S,3aR,6R)-6-((S)-(Z)-styryl)-hexahydro-furo[3,2-b]furan-3-yl]-urea | 411.18 | 3.40 | 1 |
| 322 | 285 | 1-(3,5-Dimethyl-phenyl)-3-[(3S,3aR,6R)-6-((S)-(Z)-styryl)-hexa-hydro-furo[3,2-b]furan-3-yl]-urea | 379.19 | 3.60 | 1 |
| 323 | 286 | 1-Phenyl-3-[(3S,3aR,6R)-6-((S)-(Z)-styryl)-hexahydro-furo[3,2-b]furan-3-yl]-urea | 351.16 | 3.36 | 1 |
| 324 | 287 | 1-(4-Benzyloxy-phenyl)-3-[(3S,3aR,6R)-6-((S)-(Z)-styryl)-hexa-hydro-furo[3,2-b]furan-3-yl]-urea | 457.20 | 3.68 | 1 |
| 325 | 288 | 1-(4-Fluoro-benzyl)-3-[(3S,3aR,6R)-6-((S)-(Z)-styryl)-hexahydro-furo[3,2-b]furan-3-yl]-urea | 383.17 | 3.33 | 1 |
| 326 | 290 | 1-(3,4-Dichloro-phenyl)-3-[(3S,3aR,6R)-6-((S)-(Z)-styryl)-hexa-hydro-furo[3,2-b]furan-3-yl]-urea | 419.09 | 3.69 | 1 |
| 327 | 291 | 1-(3-Methyl-benzyl)-3-[(3S,3aR,6R)-6-((S)-(Z)-styryl)-hexahydro-furo[3,2-b]furan-3-yl]-urea | 379.19 | 3.43 | 1 |
| 328 | 292 | 1-(4-Fluoro-phenyl)-3-[(3S,3aR,6R)-6-((S)-(Z)-styryl)-hexahydro-furo[3,2-b]furan-3-yl]-urea | 369.15 | 3.39 | 1 |
| 329 | 294 | 1-(3-Fluoro-phenyl)-3-[(3S,3aR,6S,6aR)-6-((Z)-styryl)-hexahydro-furo[3,2-b]furan-3-yl]-urea | 369.15 | 3.48 | 1 |
| 330 | 296 | 1-[(3S,3aR,6S,6aR)-6-((Z)-Styryl)-hexahydro-furo[3,2-b]furan-3-yl]-3-(2-thiophen-2-yl-ethyl)-urea | 385.15 | 3.31 | 1 |
| 331 | 297 | 1-Phenethyl-3-[(3S,3aR,6S,6aR)-6-((Z)-styryl)-hexahydro-furo[3,2-b]furan-3-yl]-urea | 379.19 | 3.32 | 1 |
| 332 | 298 | 1-[(3S,3aR,6S,6aR)-6-((Z)-Styryl)-hexahydro-furo[3,2-b]furan-3-yl]-3-(4-trifluoromethoxy-phenyl)-urea | 435.15 | 3.67 | 1 |
| 333 | 299 | 1-[(3S,3aR,6S,6aR)-6-((Z)-Styryl)-hexahydro-furo[3,2-b]furan-3-yl]-3-(3-trifluoromethyl-phenyl)-urea | 419.15 | 3.63 | 1 |
| 334 | 300 | 1-Cyclohexyl-3-[(3S,3aR,6S,6aR)-6-((Z)-2-pyridin-2-yl-vinyl)-hexahydro-furo[3,2-b]furan-3-yl]-urea; trifluoroacetate | 358.21 | 2.18 | 1 |
| 335 | 301 | 1-(3,5-Dimethoxy-phenyl)-3-[(3S,3aR,6S,6aR)-6-((Z)-2-thiophen-3-yl-vinyl)-hexahydro-furo[3,2-b]furan-3-yl]-urea | 417.14 | 3.32 | 1 |
| 336 | 302 | 1-(3,5-Dimethyl-phenyl)-3-[(3S,3aR,6S,6aR)-6-((Z)-2-thiophen-3-yl-vinyl)-hexahydro-furo[3,2-b]furan-3-yl]-urea | 385.15 | 3.58 | 1 |

-continued

| No | Starting compound from example No | Chemical name | Mass (from LC/MS) | R<sub>t</sub> (from LC/MS) (min) | LC/MS Method |
|---|---|---|---|---|---|
| 337 | 303 | 1-Phenyl-3-[(3S,3aR,6S,6aR)-6-((Z)-2-thiophen-3-yl-vinyl)-hexahydro-furo[3,2-b]furan-3-yl]-urea | 357.12 | 3.26 | 1 |
| 338 | 304 | 1-(4-Fluoro-benzyl)-3-[(3S,3aR,6S,6aR)-6-((Z)-2-thiophen-3-yl-vinyl)-hexahydro-furo[3,2-b]furan-3-yl]-urea | 389.13 | 3.24 | 1 |
| 339 | 305 | 1-(3-Methyl-benzyl)-3-[(3S,3aR,6S,6aR)-6-((Z)-2-thiophen-3-yl-vinyl)-hexahydro-furo[3,2-b]furan-3-yl]-urea | 385.15 | 3.32 | 1 |
| 340 | 306 | 1-(4-Fluoro-phenyl)-3-[(3S,3aR,6S,6aR)-6-((Z)-2-thiophen-3-yl-vinyl)-hexahydro-furo[3,2-b]furan-3-yl]-urea | 375.11 | 3.27 | 1 |
| 341 | 310 | 1-Indan-5-yl-3-[(3S,3aR,6S,6aR)-6-((Z)-2-thiophen-3-yl-vinyl)-hexa-hydro-furo[3,2-b]furan-3-yl]-urea | 397.15 | 2.35 | 1 |
| 342 | 308 | 1-[(3S,3aR,6S,6aR)-6-((Z)-2-Thio-phen-3-yl-vinyl)-hexahydro-furo[3,2-b]furan-3-yl]-3-(4-trifluoromethyl-phenyl)-urea | 425.4 | 2.46 | 1 |
| 343 | 309 | 3-{3-[(3S,3aR,6S,6aR)-6-((Z)-2-Thiophen-3-yl-vinyl)-hexahydro-furo[3,2-b]furan-3-yl]-ureido}-benzoic acid methyl ester | 415.4 | 2.18 | 1 |
| 344 | 314 | 1-Phenethyl-3-[(3S,3aR,6S,6aR)-6-((Z)-2-thiophen-3-yl-vinyl)-hexa-hydro-furo[3,2-b]furan-3-yl]-urea | 385.15 | 3.29 | 1 |
| 345 | 315 | 1-[(3S,3aR,6S,6aR)-6-((Z)-2-Thiophen-3-yl-vinyl)-hexahydro-furo[3,2-b]furan-3-yl]-3-(4-trifluoromethoxy-phenyl)-urea | 441.10 | 3.63 | 1 |
| 346 | 316 | 1-[(3S,3aR,6S,6aR)-6-((Z)-2-Thiophen-3-yl-vinyl)-hexahydro-furo[3,2-b]furan-3-yl]-3-(3-trifluoromethyl-phenyl)-urea | 425.11 | 3.58 | 1 |

Example 347

1-[(3S,3aR,6S,6aR)-6-(2-benzo[1,3]dioxol-5-yl-ethyl)-hexahydro-furo[3,2-b]furan-3-yl]-3-cyclohexyl-urea 1-((3S,3aR,6S,6aR)-6-Benzo[1,3]dioxol-5-ylethynyl-hexahydro-furo[3,2-b]furan-3-yl)-3-cyclohexyl-urea (281) (20 mg, 0.05 mmol) was dissolved in absolute methanol (2 mL) and 10% palladium on charcoal (4 mg) was added. The suspension was stirred for 12 h at RT under an atmosphere of hydrogen (1 bar). The catalyst was removed by filtration through a celite pad, the filtrate was evaporated and the residue was subjected to purification via flash chromatography (silica gel, elution with ethyl acetate/hexanes 50:50) to give 18 mg (90%) of 1-((3S,3aR,6S,6aR)-6-benzo[1,3]dioxol-5-ylethynyl-hexahydro-furo[3,2-b]furan-3-yl)-3-cyclohexyl-urea. LC/MS (Method 1): R<sub>t</sub>=3.30 min; detected mass: m/z=403.22 ([M+H]<sup>+</sup>). According to the previous example the following compounds were prepared in close analogy from the respective ethynyl-hexahydro-furo[3,2-b]furan-3-yl-ureas.

| No | Starting compound from example No | Chemical name | Mass (from LC/MS) | R<sub>t</sub> (from LC/MS) (min) | LC/MS Method |
|---|---|---|---|---|---|
| 348 | 293 | 1-Benzo[1,3]dioxol-5-yl-3-((3S,3aR,6S,6aR)-6-phenethyl-hexahydro-furo[3,2-b]furan-3-yl)-urea | 397.17 | 3.25 | 1 |
| 349 | 282 | 1-Cyclohexyl-3-((3S,3aR,6S,6aR)-6-phenethyl-hexahydro-furo[3,2-b]furan-3-yl)-urea | 359.23 | 3.36 | 1 |
| 350 | 300 | 1-Cyclohexyl-3-[(3S,3aR,6S,6aR)-6-(2-pyridin-2-yl-ethyl)-hexahydro-furo[3,2-b]furan-3-yl]-urea; trifluoroacetate | 360.22 | 2.13 | 1 |
| 351 | 283 | 1-(4-Butoxy-phenyl)-3-[(3S,3aR,6R)-6-((S)-phenethyl)-hexahydro-furo[3,2-b]furan-3-yl]-urea | 425.24 | 3.67 | 1 |
| 352 | 284 | 1-(3,5-Dimethoxy-phenyl)-3-[(3S,3aR,6R)-6-((S)-phenethyl)-hexa-hydro-furo[3,2-b]furan-3-yl]-urea | 413.20 | 3.37 | 1 |
| 353 | 285 | 1-(3,5-Dimethyl-phenyl)-3-[(3S,3aR,6R)-6-((S)-phenethyl)-hexa-hydro-furo[3,2-b]furan-3-yl]-urea | 381.21 | 3.57 | 1 |

-continued

| No | Starting compound from example No | Chemical name | Mass (from LC/MS) | $R_t$ (from LC/MS) (min) | LC/MS Method |
|---|---|---|---|---|---|
| 354 | 286 | 1-[(3S,3aR,6R)-6-((S)-Phenethyl)-hexa-hydro-furo[3,2-b]furan-3-yl]-3-phenyl-urea | 353.18 | 3.27 | 1 |
| 355 | 287 | 1-(4-Benzyloxy-phenyl)-3-[(3S,3aR,6R)-6-((S)-phenethyl)-hexahydro-furo[3,2-b]furan-3-yl]-urea | 459.22 | 3.66 | 1 |
| 356 | 288 | 1-(4-Fluoro-benzyl)-3-[(3S,3aR,6R)-6-((S)-phenethyl)-hexahydro-furo[3,2-b]furan-3-yl]-urea | 385.18 | 3.25 | 1 |
| 357 | 289 | 1-[(3S,3aR,6R)-6-((S)-Phenethyl)-hexahydro-furo[3,2-b]furan-3-yl]-3-m-tolyl-urea | 367.19 | 3.46 | 1 |
| 358 | 290 | 1-(3,4-Dichloro-phenyl)-3-[(3S,3aR,6R)-6-((S)-phenethyl)-hexahydro-furo[3,2-b]furan-3-yl]-urea | 421.10 | 3.68 | 1 |
| 359 | 291 | 1-(3-Methyl-benzyl)-3-[(3S,3aR,6R)-6-((S)-phenethyl)-hexahydro-furo[3,2-b]furan-3-yl]-urea | 381.21 | 3.40 | 1 |
| 360 | 292 | 1-(4-Fluoro-phenyl)-3-[(3S,3aR,6R)-6-((S)-phenethyl)-hexahydro-furo[3,2-b]furan-3-yl]-urea | 371.17 | 3.37 | 1 |
| 361 | 301 | 1-(3,5-Dimethoxy-phenyl)-3-[(3S,3aR,6R)-6-((S)-2-thiophen-3-yl-ethyl)-hexahydro-furo[3,2-b]furan-3-yl]-urea | 419.16 | 3.30 | 1 |
| 362 | 302 | 1-(3,5-Dimethyl-phenyl)-3-[(3S,3aR,6R)-6-((S)-2-thiophen-3-yl-ethyl)-hexahydro-furo[3,2-b]furan-3-yl]-urea | 387.17 | 3.54 | 1 |
| 363 | 303 | 1-Phenyl-3-[(3S,3aR,6R)-6-((S)-2-thiophen-3-yl-ethyl)-hexahydro-furo[3,2-b]furan-3-yl]-urea | 359.14 | 3.19 | 1 |
| 364 | 304 | 1-(4-Fluoro-benzyl)-3-[(3S,3aR,6R)-6-((S)-2-thiophen-3-yl-ethyl)-hexa-hydro-furo[3,2-b]furan-3-yl]-urea | 391.14 | 3.22 | 1 |
| 365 | 305 | 1-(3-Methyl-benzyl)-3-[(3S,3aR,6R)-6-((S)-2-thiophen-3-yl-ethyl)-hexa-hydro-furo[3,2-b]furan-3-yl]-urea | 387.17 | 3.32 | 1 |
| 366 | 306 | 1-(4-Fluoro-phenyl)-3-[(3S,3aR,6R)-6-((S)-2-thiophen-3-yl-ethyl)-hexa-hydro-furo[3,2-b]furan-3-yl]-urea | 377.13 | 3.29 | 1 |
| 367 | 310 | 1-Indan-5-yl-3-[(3S,3aR,6S,6aR)-6-(2-thiophen-3-yl-ethyl)-hexahydro-furo[3,2-b]furan-3-yl]-urea | 399.4 | 2.33 | 1 |
| 368 | 299 | 1-((3S,3aR,6S,6aR)-6-Phenethyl-hexahydro-furo[3,2-b]furan-3-yl)-3-(3-trifluoromethyl-phenyl)-urea | 421.17 | 3.64 | 1 |
| 369 | 295 | 1-(2,3-Dihydro-benzo[1,4]dioxin-6-yl)-3-((3S,3aR,6S,6aR)-6-phenethyl-hexahydro-furo[3,2-b]furan-3-yl)-urea | 411.18 | 3.19 | 1 |
| 370 | 296 | 1-((3S,3aR,6S,6aR)-6-Phenethyl-hexahydro-furo[3,2-b]furan-3-yl)-3-(2-thiophen-2-yl-ethyl)-urea | 387.17 | 3.28 | 1 |
| 371 | 297 | 1-Phenethyl-3-((3S,3aR,6S,6aR)-6-phenethyl-hexahydro-furo[3,2-b]furan-3-yl)-urea | 381.21 | 3.34 | 1 |
| 372 | 298 | 1-((3S,3aR,6S,6aR)-6-Phenethyl-hexahydro-furo[3,2-b]furan-3-yl)-3-(4-trifluoromethoxy-phenyl)-urea | 437.16 | 3.65 | 1 |
| 373 | 314 | 1-Phenethyl-3-[(3S,3aR,6S,6aR)-6-(2-thiophen-3-yl-ethyl)-hexahydro-furo[3,2-b]furan-3-yl]-urea | 387.17 | 3.26 | 1 |
| 374 | 315 | 1-[(3S,3aR,6S,6aR)-6-(2-Thiophen-3-yl-ethyl)-hexahydro-furo[3,2-b]furan-3-yl]-3-(4-trifluoromethoxy-phenyl)-urea | 443.12 | 3.62 | 1 |
| 375 | 316 | 1-[(3S,3aR,6S,6aR)-6-(2-Thiophen-3-yl-ethyl)-hexahydro-furo[3,2-b]furan-3-yl]-3-(3-trifluoromethyl-phenyl)-urea | 427.12 | 3.60 | 1 |

Example 376

3-[(3S,3aR,6S,6aR)-6-(3-Cyclohexyl-ureido)-hexahydro-furo[3,2-b]furan-3-yl]-propionic acid ethyl ester Cyclohexyl isocyanate (20 μL, 0.16 mmol) was added to a solution of 3-((3S,3aR,6S,6aR)-6-amino-hexahydro-furo[3,2-b]furan-3-yl)-propionic acid ethyl ester (P32) (10 mg, 0.044 mmol) in dichloromethane (1 mL) at RT. The mixture was stirred at RT for 12 h and was quenched with silica bound amine. The mixture was filtered through a celite pad and was concentrated under reduced pressure. The residue was subjected to purification by reversed phase HPLC (acetonitrile/water with 0.1 trifluoroacetic acid) to yield 12 mg (70%) of 3-[(3S,3aR,6S,6aR)-6-(3-cyclohexyl-ureido)-hexahydro-furo[3,2-b]furan-3-yl]-propionic acid ethyl ester. LC/MS (Method 1): $R_t$=2.86 min; detected mass: m/z=355.22 ([M+H]$^+$).

Example 377

3-[(3S,3aR,6S,6aR)-6-(3-cyclohexyl-ureido)-hexahydro-furo[3,2-b]furan-3-yl]-propionic acid A saturated aqueous solution of potassium carbonate (0.5 mL) was added to a solution of 3-[(3S,3aR,6S,6aR)-6-(3-cyclohexyl-ureido)-hexahydro-furo[3,2-b]furan-3-yl]-propionic acid ethyl ester (376) (5 mg, 0.014 mmol) in methanol (1 mL) at RT. The mixture was stirred at RT for 6 h and was quenched by addition of a 1N aqueous solution of hydrochloric acid. The phases were separated and the aqueous phase was thoroughly extracted with ethyl acetate. The combined organic extracts were washed with brine, dried over anhydrous sodium sulfate, filtered, and concentrated under reduced pressure. The residue was subjected to purification by reversed phase HPLC (acetonitrile/water with 0.1% trifluoroacetic acid) to give 2 mg (44%) of 3-[(3S,3aR,6S,6aR)-6-(3-cyclohexyl-ureido)-hexahydro-furo[3,2-b]furan-3-yl]-propionic acid. LC/MS (Method 1): $R_t$=2.32 min; detected mass: m/z=327.18 ([M+H]$^+$).

Example 378

1-((3S,3aR,6S,6aR)-6-cyano-hexahydro-furo[3,2-b]furan-3-yl)-3-(4-trifluoromethoxy-phenyl)-urea 1-Isocyanato-4-(trifluoromethoxy)-benzene (40 mg, 0.2 mmol) was added to a solution of (3S,3aR,6S,6aR)-6-amino-hexahydro-furo[3,2-b]furan-3-carbonitrile (P34) (10 mg, 0.06 mmol) in dichloromethane (1 mL) at RT. The mixture was stirred at RT for 12 h and was quenched with silica bound amine. The mixture was filtered through a celite pad and was concentrated under reduced pressure. The residue was purified by reversed phase HPLC (acetonitrile/water with 0.1% trifluoroacetic acid) to give 8 mg (44%) of 1-((3S,3aR,6S,6aR)-6-cyano-hexahydro-furo[3,2-b]furan-3-yl)-3-(4-trifluoromethoxy-phenyl)-urea. LC/MS (Method 1): $R_t$=2.01 min; detected mass: m/z=358.09 ([M+H]+).

According to the previous example the following compounds were prepared in close analogy from (3S,3aR,6S,6aR)-6-amino-hexahydro-furo[3,2-b]furan-3-carbonitrile (P34) and the respective isocyanates.

| No | Starting compound | Chemical name | Mass (from LC/MS) | $R_t$ (from LC/MS) (min) | LC/MS Method |
|---|---|---|---|---|---|
| 379 | 6-Isocyanato-2,3-dihydro-benzo[1,4]dioxine | 1-((3S,3aR,6R,6aR)-6-Cyano-hexahydro-furo[3,2-b]furan-3-yl)-3-(2,3-dihydro-benzo[1,4]dioxin-6-yl)-urea | 332.12 | 2.24 | 1 |
| 380 | 1-Butoxy-4-isocyanato-benzene | (S)-1-(4-Butoxy-phenyl)-3-((6S,6aR)-(R)-6-cyano-hexahydro-furo[3,2-b]furan-3-yl)-urea | 346.17 | 3.11 | 1 |
| 381 | 1-Isocyanato-3,5-dimethyl-benzene | (S)-1-((6S,6aR)-(R)-6-Cyano-hexahydro-furo[3,2-b]furan-3-yl)-3-(3,5-dimethyl-phenyl)-urea | 302.14 | 2.83 | 1 |
| 382 | 1-Benzyloxy-4-isocyanato-benzene | (S)-1-(4-Benzyloxy-phenyl)-3-((6S,6aR)-(R)-6-cyano-hexahydro-furo[3,2-b]furan-3-yl)-urea | 380.15 | 3.10 | 1 |
| 383 | 1-Isocyanato-3-methyl-benzene | (S)-1-((6S,6aR)-(R)-6-Cyano-hexahydro-furo[3,2-b]furan-3-yl)-3-m-tolyl-urea | 288.13 | 2.59 | 1 |
| 384 | 1,2-Dichloro-4-isocyanato-benzene | (S)-1-((6S,6aR)-(R)-6-Cyano-hexahydro-furo[3,2-b]furan-3-yl)-3-(3,4-dichloro-phenyl)-urea | 343.03 | 3.07 | 1 |

Pharmacological Testing:

The ability of the compounds of the formula I to inhibit soluble epoxide hydrolase can be determined as follows:

Compounds were tested in a biochemical screening assay using recombinant sEH purified from Sf9 insect cells and an artificial substrate, (3-phenyl-oxiranyl)-acetic acid cyano-(6-methoxy-naphtalen-2-yl)-methyl ester, Phome. The biochemical assay was performed in analogy to a fluorometric method described in the literature (P. D. Jones et al., Anal. Biochem. 2005, 343, 66-75). The assay principle bases on the sEH-catalyzed hydrolysis of an artificial α-cyano-ester substrate. 0-deacetylation liberates a cyanohydrin intermediate that rapidly decomposes to the highly fluorescent 6-methoxy-2-naphtaldehyde. To discriminate sample auto-fluorescence, the assay was carried out as a kinetic measurement with two time points. The first measurement is performed immediately before addition of the substrate and the second measurement is done after completion of the assay. The assay format is either in 96- or in 384-well format. Details of the assay using a 96-well plate format are described below. 40 μL recombinant sEH enzyme and 5 μL test compound are pre-incubated for 15 minutes at 30° C. Following pre-incubation, the reaction is started by addition of 5 μL Phome. The assay mixture containing 2 nM final sEH concentration, test compound ranging in a concentration from 0.0001-10 μM and 5 μM Phome is incubated for 60 minutes at 30° C.

Fluorescence can be measured with any suitable detector for instance a TECAN Safire or Tecan Ultra at 340 nm emission and 465 nm extinction. % inhibition of recombinant sEH activity is used for calculation of corresponding IC50 values as illustrated and described in the examples.

The NCBI gene bank reference sequence with the accession number NM_001979 for EPHX2/sEH was applied for recombinant protein production:

The following commercially available materials have been used:
Incubation reagent: 25 mM Hepes (Sigma-Aldrich, Cat. No H-3375), 0.01% bovine albumin (Sigma-Aldrich Cat. No PA9205)
Substrate: 3-Phenyl-oxiranyl)-acetic acid cyano-(6-methoxy-naphtalen-2-yl)-methyl ester, Phome (Biozol Cat. No 10003134)
Microtiter plates: 96-well plates (Greiner Cat. No 655180; Costar Cat. No 3915)

The results for inhibition of soluble epoxide hydrolase are shown in Table 1.

TABLE 1

| Example | sEH IC$_{50}$ (μM) |
|---|---|
| 1 | 0.305 |
| 2 | 0.019 |
| 3 | 0.012 |
| 4 | 0.016 |
| 5 | 0.003 |
| 6 | 8.000 |
| 7 | 0.258 |
| 8 | 14.50 |
| 9 | 0.450 |
| 10 | 0.003 |
| 11 | 0.005 |
| 12 | 0.001 |
| 13 | 0.167 |
| 14 | 0.019 |
| 15 | <0.001 |
| 16 | 0.008 |
| 17 | 0.001 |

TABLE 1-continued

| Example | sEH IC$_{50}$ (μM) |
|---|---|
| 18 | 0.001 |
| 19 | 0.009 |
| 20 | 0.002 |
| 21 | 0.001 |
| 22 | 0.003 |
| 23 | 0.001 |
| 24 | 0.004 |
| 25 | 0.008 |
| 26 | 0.454 |
| 27 | 0.003 |
| 28 | 0.008 |
| 29 | 0.002 |
| 30 | 0.002 |
| 31 | 0.003 |
| 32 | 0.003 |
| 33 | 0.003 |
| 34 | 0.002 |
| 35 | 0.012 |
| 36 | 0.001 |
| 37 | 0.001 |
| 38 | 0.001 |
| 39 | 0.002 |
| 40 | 0.011 |
| 41 | 0.025 |
| 42 | 0.047 |
| 43 | 0.086 |
| 44 | 0.042 |
| 45 | 0.025 |
| 46 | 0.050 |
| 47 | 0.051 |
| 48 | 0.011 |
| 49 | 0.003 |
| 50 | 0.010 |
| 51 | 0.008 |
| 52 | 0.001 |
| 53 | <0.001 |
| 54 | 0.001 |
| 55 | <0.001 |
| 56 | 0.002 |
| 57 | 0.003 |
| 58 | 0.002 |
| 59 | 0.002 |
| 60 | 0.004 |
| 61 | <0.001 |
| 62 | 0.001 |
| 63 | 0.001 |
| 64 | 0.002 |
| 65 | 0.002 |
| 66 | 0.002 |
| 67 | 0.001 |
| 68 | 0.002 |
| 69 | 0.002 |
| 70 | 0.001 |
| 71 | 0.007 |
| 72 | <0.001 |
| 73 | 0.004 |
| 74 | 0.005 |
| 75 | 0.002 |
| 76 | 0.002 |
| 77 | 0.017 |
| 78 | 1.330 |
| 79 | 0.987 |
| 80 | 1.160 |
| 81 | 0.016 |
| 82 | 2.620 |
| 83 | 0.182 |
| 84 | 0.059 |
| 85 | 0.020 |
| 86 | 0.041 |
| 87 | 0.010 |
| 88 | 0.053 |
| 89 | 0.005 |
| 90 | 0.001 |
| 91 | 0.022 |
| 92 | 0.036 |
| 93 | 0.032 |
| 94 | 2.480 |

TABLE 1-continued

| Example | sEH IC$_{50}$ (µM) |
|---|---|
| 95 | 0.005 |
| 96 | 0.004 |
| 97 | 0.003 |
| 98 | 0.002 |
| 99 | 0.012 |
| 100 | 0.002 |
| 101 | 0.004 |
| 102 | 0.002 |
| 103 | 0.007 |
| 104 | 0.005 |
| 105 | 0.007 |
| 106 | 0.003 |
| 107 | 0.002 |
| 108 | 0.023 |
| 109 | 0.001 |
| 110 | 0.140 |
| 111 | 0.001 |
| 112 | 0.001 |
| 113 | 0.003 |
| 114 | 0.004 |
| 115 | 0.003 |
| 116 | 0.003 |
| 117 | 0.005 |
| 118 | 0.003 |
| 119 | 0.021 |
| 120 | 0.007 |
| 121 | 0.001 |
| 122 | 0.002 |
| 123 | 0.004 |
| 124 | 0.004 |
| 125 | 0.003 |
| 126 | 0.030 |
| 127 | 0.007 |
| 128 | 0.010 |
| 129 | 0.002 |
| 130 | 0.038 |
| 131 | 0.002 |
| 132 | 0.002 |
| 133 | <0.001 |
| 134 | 0.020 |
| 135 | 0.020 |
| 136 | 0.220 |
| 137 | 0.004 |
| 138 | 0.003 |
| 139 | 0.002 |
| 140 | 0.003 |
| 141 | 0.002 |
| 142 | 0.030 |
| 143 | 0.006 |
| 144 | 0.001 |
| 145 | 0.014 |
| 146 | 0.002 |
| 147 | 0.002 |
| 148 | 0.003 |
| 149 | 2.160 |
| 150 | 0.016 |
| 151 | 0.008 |
| 152 | 0.002 |
| 153 | 0.062 |
| 154 | 0.051 |
| 155 | 0.038 |
| 156 | 0.024 |
| 157 | 0.011 |
| 158 | 0.027 |
| 159 | 0.005 |
| 160 | 0.031 |
| 161 | 0.047 |
| 162 | 0.039 |
| 163 | 0.192 |
| 164 | 0.487 |
| 165 | 0.021 |
| 166 | 0.018 |
| 167 | 0.066 |
| 168 | 0.006 |
| 169 | 4.460 |
| 170 | 0.103 |
| 171 | 2.350 |
| 172 | 1.240 |
| 173 | 0.005 |
| 174 | 0.031 |
| 175 | 0.975 |
| 176 | 1.450 |
| 177 | 0.456 |
| 178 | 0.005 |
| 179 | <0.001 |
| 180 | 0.055 |
| 181 | 0.001 |
| 182 | 0.096 |
| 183 | 0.846 |
| 184 | 0.006 |
| 185 | 0.029 |
| 186 | 0.002 |
| 187 | 0.044 |
| 188 | 0.001 |
| 189 | 0.023 |
| 190 | 0.475 |
| 191 | 0.489 |
| 192 | 1.730 |
| 193 | 0.051 |
| 194 | 1.470 |
| 195 | 0.056 |
| 196 | 0.026 |
| 197 | 1.140 |
| 198 | 0.997 |
| 199 | 2.070 |
| 200 | 0.088 |
| 201 | 5.790 |
| 202 | 0.345 |
| 203 | 0.028 |
| 204 | 0.734 |
| 205 | 0.528 |
| 206 | 0.002 |
| 207 | 0.003 |
| 208 | 0.015 |
| 209 | 0.819 |
| 210 | 0.144 |
| 211 | 1.080 |
| 212 | 0.037 |
| 213 | 0.003 |
| 214 | 0.014 |
| 215 | 0.238 |
| 216 | 0.125 |
| 217 | 0.371 |
| 218 | 0.389 |
| 219 | 1.900 |
| 220 | 0.506 |
| 221 | 0.096 |
| 222 | 0.054 |
| 223 | 0.262 |
| 224 | 0.039 |
| 225 | 0.043 |
| 226 | 0.475 |
| 227 | 1.680 |
| 228 | 0.009 |
| 229 | 1.160 |
| 230 | 0.019 |
| 231 | 0.010 |
| 232 | 0.268 |
| 233 | 3.560 |
| 234 | 0.172 |
| 235 | 0.086 |
| 236 | 3.840 |
| 237 | 0.177 |
| 238 | 2.060 |
| 239 | 0.078 |
| 240 | 3.430 |
| 241 | 0.117 |
| 242 | 0.037 |
| 243 | 0.041 |
| 244 | 0.577 |
| 245 | 0.825 |
| 246 | 0.317 |
| 247 | 0.065 |
| 248 | 3.500 |

TABLE 1-continued

| Example | sEH IC$_{50}$ (μM) |
|---|---|
| 249 | 0.073 |
| 250 | 3.120 |
| 251 | 1.560 |
| 252 | 3.520 |
| 253 | 0.792 |
| 254 | 0.882 |
| 255 | 0.545 |
| 256 | 0.003 |
| 257 | 0.003 |
| 258 | 0.002 |
| 259 | 0.005 |
| 260 | 0.008 |
| 261 | 0.003 |
| 262 | 0.002 |
| 263 | 0.025 |
| 264 | 0.006 |
| 265 | 0.111 |
| 266 | 0.016 |
| 267 | 0.002 |
| 268 | 0.002 |
| 269 | 0.002 |
| 270 | 0.016 |
| 271 | 0.099 |
| 272 | 0.001 |
| 273 | 0.001 |
| 274 | 0.014 |
| 275 | 0.019 |
| 276 | 0.001 |
| 277 | 0.002 |
| 278 | 0.924 |
| 279 | 0.001 |
| 280 | 0.012 |
| 281 | 0.075 |
| 282 | 0.012 |
| 283 | 0.070 |
| 284 | 0.071 |
| 285 | 0.021 |
| 286 | 0.227 |
| 287 | 0.082 |
| 288 | 0.147 |
| 289 | 0.035 |
| 290 | 0.013 |
| 291 | 0.037 |
| 292 | 0.046 |
| 293 | 0.071 |
| 294 | 0.123 |
| 295 | 0.112 |
| 296 | 0.100 |
| 297 | 0.067 |
| 298 | 0.025 |
| 299 | 1.250 |
| 300 | 0.019 |
| 301 | 0.104 |
| 302 | 0.072 |
| 303 | 0.241 |
| 304 | 0.279 |
| 305 | 0.243 |
| 306 | 0.192 |
| 307 | 0.059 |
| 308 | 0.048 |
| 309 | 0.016 |
| 310 | 0.073 |
| 311 | 0.146 |
| 312 | 0.107 |
| 313 | 0.056 |
| 314 | 0.033 |
| 315 | 0.015 |
| 316 | 0.087 |
| 317 | 0.003 |
| 318 | 0.227 |
| 319 | 0.017 |
| 320 | 0.140 |
| 321 | 0.066 |
| 322 | 0.007 |
| 323 | 0.190 |
| 324 | 0.081 |
| 325 | 0.075 |
| 326 | 0.027 |
| 327 | 0.098 |
| 328 | 0.098 |
| 329 | 0.095 |
| 330 | 0.069 |
| 331 | 0.018 |
| 332 | 0.011 |
| 333 | 0.044 |
| 334 | 0.159 |
| 335 | 0.665 |
| 336 | 0.047 |
| 337 | 0.423 |
| 338 | 0.392 |
| 339 | 0.418 |
| 340 | 0.089 |
| 341 | 0.090 |
| 342 | 0.017 |
| 343 | 0.102 |
| 344 | 0.042 |
| 345 | 0.011 |
| 346 | 0.062 |
| 347 | 0.128 |
| 348 | 0.229 |
| 349 | 0.037 |
| 350 | 0.022 |
| 351 | 0.161 |
| 352 | 0.149 |
| 353 | 0.017 |
| 354 | 0.127 |
| 355 | 0.080 |
| 356 | 0.140 |
| 357 | 0.084 |
| 358 | 0.022 |
| 359 | 0.111 |
| 360 | 0.081 |
| 361 | 0.039 |
| 362 | 0.009 |
| 363 | 0.025 |
| 364 | 0.029 |
| 365 | 0.145 |
| 366 | 0.009 |
| 367 | 0.012 |
| 368 | 0.068 |
| 369 | 0.022 |
| 370 | 0.043 |
| 371 | 0.024 |
| 372 | 0.011 |
| 373 | 0.039 |
| 374 | 0.235 |
| 375 | 0.017 |
| 376 | 0.026 |
| 377 | 2.940 |
| 378 | 0.024 |
| 379 | 0.086 |
| 380 | 0.304 |
| 381 | 0.108 |
| 382 | 0.339 |
| 383 | 0.694 |
| 384 | 0.061 |

The invention claimed is:

1. A compound of formula (I), a stereoisomeric form thereof, or a physiologically tolerable salt of any of the foregoing,

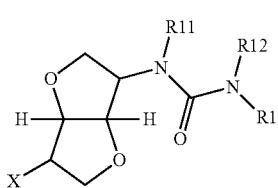

(I)

wherein
R1 is
- —($C_1$-$C_4$)-alkylene-($C_3$-$C_{12}$)-cycloalkyl, wherein said cycloalkyl is a ring system containing 3 to 12 carbon atoms in mono-, bi- or tricycles or bridged rings, and wherein said cycloalkyl is mono-, di-, tri- or tetrasubstituted independently of one another by R2,
- —($C_1$-$C_4$)-alkylene-aryl, wherein said aryl is an aromatic hydrocarbon radical containing from 6 to 14 carbon atoms depending on the number of carbon atoms in one, two or three rings, and wherein said alkylene or aryl is independently from each other mono-, di- or trisubstituted independently of one another by R3,
- —($C_1$-$C_4$)-alkylene-heterocyclyl, wherein said heterocyclyl is a ring system containing 4 to 15 ring carbon atoms, wherein depending on the ring size one, two, three or four of the 4 to 15 ring carbon atoms are independently replaced by nitrogen, oxygen or sulfur atoms, and wherein said alkylene or heterocyclyl is independently from each other unsubstituted or mono-, di- or trisubstituted independently of one another by R4,
- -cyclopropyl-heterocyclyl, wherein said heterocyclyl is a ring system containing 4 to 15 ring carbon atoms, wherein depending on the ring size one, two, three or four of the 4 to 15 ring carbon atoms are independently replaced by nitrogen, oxygen or sulfur atoms, and wherein said heterocyclyl is unsubstituted or mono-, di- or trisubstituted independently of one another by R4,
- -heterocyclyl, wherein said heterocyclyl is a ring system containing 4 to 15 ring carbon atoms, wherein depending on the ring size one, two, three or four of the 4 to 15 ring carbon atoms are independently replaced by nitrogen, oxygen or sulfur atoms, and wherein said heterocyclyl is unsubstituted or mono-, di- or trisubstituted independently of one another by R4,
- -aryl, wherein said aryl is an aromatic hydrocarbon radical containing from 6 to 14 carbon atoms depending on the number of carbon atoms in one, two or three rings, and wherein said aryl is mono-, di- or trisubstituted independently of one another by R3, or
- —($C_3$-$C_{12}$)-cycloalkyl, wherein said cycloalkyl is a ring system containing 3 to 12 carbon atoms in mono-, bi- or tricycles or bridged rings, and wherein said cycloalkyl is mono-, di-, tri- or tetrasubstituted independently of one another by R2;

X is
- —O-aryl, wherein said aryl is an aromatic hydrocarbon radical containing from 6 to 14 carbon atoms depending on the number of carbon atoms in one, two or three rings, and wherein said aryl is mono-, di- or trisubstituted independently of one another by R6,
- —O-heterocyclyl, wherein said heterocyclyl is a ring system containing 4 to 15 ring carbon atoms, wherein depending on the ring size one, two, three or four of the 4 to 15 ring carbon atoms are independently replaced by nitrogen, oxygen or sulfur atoms, and wherein said heterocyclyl is unsubstituted or mono-, di- or trisubstituted independently of one another by R7,
- —($C_1$-$C_4$)-alkyl-R17, wherein said alkyl is unsubstituted or mono-, di- or trisubstituted independently of one another by R17,
- —($C_1$-$C_4$)-alkyl-aryl, wherein said aryl is an aromatic hydrocarbon radical containing from 6 to 14 carbon atoms depending on the number of carbon atoms in one, two or three rings, and wherein said aryl is mono-, di- or trisubstituted independently of one another by R8,
- —($C_1$-$C_4$)-alkyl-heterocyclyl, wherein said heterocyclyl is a ring system containing 4 to 15 ring carbon atoms, wherein depending on the ring size one, two, three or four of the 4 to 15 ring carbon atoms are independently replaced by nitrogen, oxygen or sulfur atoms, and wherein said heterocyclyl is unsubstituted or mono-, di- or trisubstituted independently of one another by R7,
- —(CH=CH)-aryl, wherein said aryl is an aromatic hydrocarbon radical containing from 6 to 14 carbon atoms depending on the number of carbon atoms in one, two or three rings, and wherein said aryl is mono-, di- or trisubstituted independently of one another by R8,
- —(CH=CH)-heterocyclyl, wherein said heterocyclyl is a ring system containing 4 to 15 ring carbon atoms, wherein depending on the ring size one, two, three or four of the 4 to 15 ring carbon atoms are independently replaced by nitrogen, oxygen or sulfur atoms, and wherein said heterocyclyl is unsubstituted or mono-, di- or trisubstituted independently of one another by R7,
- —(C≡C)-aryl, wherein said aryl is an aromatic hydrocarbon radical containing from 6 to 14 carbon atoms depending on the number of carbon atoms in one, two or three rings, and wherein said aryl is mono-, di- or trisubstituted independently of one another by R8,
- —(C≡C)-heterocyclyl, wherein said heterocyclyl is a ring system containing 4 to 15 ring carbon atoms, wherein depending on the ring size one, two, three or four of the 4 to 15 ring carbon atoms are independently replaced by nitrogen, oxygen or sulfur atoms, and wherein said heterocyclyl is unsubstituted or mono-, di- or trisubstituted independently of one another by R7,
- —CN,
- —O—($C_1$-$C_3$)-fluoroalkyl,
- —O—C(O)-heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, and wherein said heterocyclyl is mono-, di- or trisubstituted independently of one another by R7,
- —N(R10)heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, and wherein said heterocyclyl is unsubstituted or mono-, di- or trisubstituted independently of one another by R7,
—S—($C_1$-$C_4$)-alkyl-R17, wherein said alkyl is unsubstituted or mono-, di- or trisubstituted independently of one another by R17,
—S—($C_3$-$C_8$)-cycloalkyl, wherein said cycloalkyl is unsubstituted or mono-, di- or trisubstituted independently of one another by R17,
—$SO_2$—($C_3$-$C_8$)-cycloalkyl, wherein said cycloalkyl is unsubstituted or mono-, di- or trisubstituted independently of one another by R17,
—O—$SO_2$-aryl, wherein said aryl is an aromatic hydrocarbon radical containing from 6 to 14 carbon atoms depending on the number of carbon atoms in one, two or three rings, and wherein said aryl is mono-, di- or trisubstituted independently of one another by R8,
—S-aryl, wherein said aryl is an aromatic hydrocarbon radical containing from 6 to 14 carbon atoms depending on the number of carbon atoms in one, two or three rings, and wherein said aryl is mono-, di- or trisubstituted independently of one another by R8,
—S-heterocyclyl, wherein said heterocyclyl is a ring system containing 4 to 15 ring carbon atoms, wherein depending on the ring size one, two, three or four of the 4 to 15 ring carbon atoms are independently replaced by nitrogen, oxygen or sulfur atoms, and wherein said heterocyclyl is unsubstituted or mono-, di- or trisubstituted independently of one another by R7, or
—S—($C_1$-$C_4$)-alkyl, wherein said alkyl is unsubstituted or mono-, di- or trisubstituted independently of one another by R18;

R2, R3, R14, R17 and R18 are independent of one another, are identical or different, and are selected from the group consisting of a hydrogen atom, —($C_1$-$C_4$)-alkyl, —OH, —($C_1$-$C_4$)-alkyl-OH, halogen, —($C_1$-$C_3$)-fluoroalkyl, —C(O)—OH, —C(O)—O—($C_1$-$C_4$)-alkyl, —O—($C_1$-$C_4$)-alkyl, —CN, —O—($C_1$-$C_3$)-fluoroalkyl, —N(R10)-R21, —NH—C(O)—($C_1$-$C_4$)-alkyl, —S—($C_1$-$C_4$)-alkyl, —S(O)$_2$—$C_1$-$C_3$-alkyl, —($C_1$-$C_3$)-alkyl —O—($C_1$-$C_3$)-alkyl, phenyl, and —O—($C_1$-$C_4$)-alkyl-phenyl;

R6 is
-aryl, wherein said aryl is an aromatic hydrocarbon radical containing from 6 to 14 carbon atoms depending on the number of carbon atoms in one, two or three rings, and wherein said aryl is mono-, di- or trisubstituted independently of one another by R10,
—O-aryl, wherein said aryl is an aromatic hydrocarbon radical containing from 6 to 14 carbon atoms depending on the number of carbon atoms in one, two or three rings, and wherein said aryl is mono-, di- or trisubstituted independently of one another by R10,
—($C_1$-$C_4$)-alkylene-aryl, wherein said aryl is an aromatic hydrocarbon radical containing from 6 to 14 carbon atoms depending on the number of carbon atoms in one, two or three rings, and wherein said aryl is mono-, di- or trisubstituted independently of one another by R10,
-heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, and wherein said heterocyclyl is unsubstituted or mono-, di- or trisubstituted independently of one another by R10,
—O-heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, and wherein said heterocyclyl is unsubstituted or mono-, di- or trisubstituted independently of one another by R10,
—C(O)-heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, and wherein said heterocyclyl is unsubstituted or mono-, di- or trisubstituted independently of one another by R10,
—($C_1$-$C_4$)-alkylene-heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, and wherein said heterocyclyl is unsubstituted or mono-, di- or trisubstituted independently of one another by R10,
—O—($C_1$-$C_4$)-alkylene-heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, and wherein said heterocyclyl is unsubstituted or mono-, di- or trisubstituted independently of one another by R10,
—($C_3$-$C_8$)-cycloalkyl, wherein said cycloalkyl is unsubstituted or mono-, di- or trisubstituted independently of one another by R10, or
is selected from the group consisting of a hydrogen atom, —($C_1$-$C_4$)-alkylene-N(R10)-R21, —C(O)—N(R10)-R20, —N(R10)-R21, —($C_1$-$C_4$)-alkyl, —($C_1$-$C_4$)-alkyl-CN, —($C_1$-$C_3$)-fluoroalkyl, —O—($C_1$-$C_4$)-alkyl, halogen, —C(O)—O—R10, —($C_1$-$C_3$)-alkylene-C(O)—O—R10, —NH—C(O)—($C_1$-$C_4$)-alkyl, —C(O)—($C_1$-$C_4$)-alkyl, and —$NO_2$;

R4 and R7 are independent of one another, are identical or different, and are selected from the group consisting of a hydrogen atom, —($C_1$-$C_4$)-alkyl, —O—($C_1$-$C_4$)-alkyl, —($C_1$-$C_5$)-alkyl-OH, halogen, —C(O)—O—R10, =O , phenyl, —($C_1$-$C_3$)-alkylene-C(O)—O—R10, —C(O)—N(R10)-R20, —N(R10)-R21, —CN, —($C_1$-$C_3$)-fluoroalkyl, —($C_1$-$C_3$)-alkyl-O—($C_1$-$C_3$)-alkyl, —C(O)—($C_1$-$C_4$)-alkyl, —C(O)—($C_1$-$C_3$)-fluoroalkyl, and —C(O)—($C_3$-$C_8$)-cycloalkyl,
—C(O)-aryl, wherein said aryl is an aromatic hydrocarbon radical containing from 6 to 14 carbon atoms depending on the number of carbon atoms in one, two or three rings, and wherein said aryl is mono-, di- or trisubstituted independently of one another by R6,
aryl, wherein said aryl is an aromatic hydrocarbon radical containing from 6 to 14 carbon atoms depending on the number of carbon atoms in one, two or three rings, and wherein said aryl is mono-, di- or trisubstituted independently of one another by R6, methanesulfonyl, or
heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl;

R8 and R9 are independent of one another, are identical or different, and are selected from the group consisting of a hydrogen atom, halogen, —OH, —N(R10)-C(O)—R20, and —($C_1$-$C_4$)-alkyl;

R10 is a hydrogen atom, —($C_1$-$C_4$)-alkyl or —O—($C_1$-$C_4$)-alkyl;

R11 is a hydrogen atom, —($C_1$-$C_4$)-alkyl or benzyl;

R12 is a hydrogen atom or

R1 and R12 together with the nitrogen atom to which they are bonded form a four- to eight-membered monocyclic heterocyclic ring which, as well as the nitrogen atom, may additionally, according to the ring size, also contain one or two identical or different heteroatoms selected from the group consisting of oxygen, nitrogen and sulfur, wherein the four- to eight-membered monocyclic heterocyclic ring is mono-, di- or trisubstituted independently of one another by —($C_1$-$C_4$)-alkyl or halogen;

R20 is a hydrogen atom or —($C_1$-$C_4$)-alkyl; and

R21 is selected from the group consisting of a hydrogen atom, —($C_1$-$C_4$)-alkyl, —C(O)—R20, —($C_1$-$C_4$)-alkyl-heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, and
—($C_3$-$C_8$)-cycloalkyl, wherein said cycloalkyl is unsubstituted or mono-, di- or trisubstituted independently of one another by R10.

2. The compound according to claim 1, a stereoisomeric form thereof, or a physiologically tolerable salt of any of the foregoing, wherein said compound of formula (I) is a compound of formula (Ia)

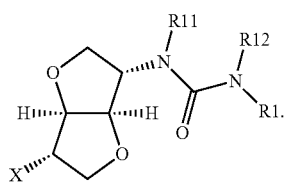

(Ia)

3. The compound of claim 1, a stereoisomeric form thereof, or a physiologically tolerable salt of any of the foregoing, wherein R1 is
—($C_1$-$C_3$)-alkylene-($C_3$-$C_8$)-cycloalkyl, wherein said cycloalkyl is monosubstituted by R2,
—($C_1$-$C_4$)-alkylene-aryl, wherein said aryl is selected from the group consisting of phenyl, tetrahydronaphthalenyl, naphthyl, biphenyl, and indanyl, and wherein said alkylene or aryl is independently from each other mono- or disubstituted independently of one another by R3, —($C_1$-$C_4$)-alkylene-heterocyclyl, wherein said heterocyclyl is selected from the group consisting of 2,3-dihydro-benzofuranyl, benzofuranyl, benzo[1,3]dioxolyl, chromanyl, 2,3-dihydro-benzo[1,4]-dioxinyl, 1,3-dioxanyl, 1,4-dioxanyl, 1,3-dioxolanyl, imidazolyl, imidazo[1,2a]-pyridyl, isoxazolyl, morpholinyl, oxetanyl, piperidinyl, pyrazolyl, pyridyl, pyrimidinyl, pyrrolidinyl, tetrahydro-2H[1,2']bi-pyridinyl, tetrahydrofuranyl, tetrahydropyranyl, tetrahydrothiopyranyl, thiazolyl, thienothiophenyl, and thienyl, and wherein said alkylene or heterocyclyl is independently from each other unsubstituted or mono-, di- or trisubstituted independently of one another by R4, -cyclopropyl-heterocyclyl, wherein said heterocyclyl is selected from the group consisting of 2,3-dihydro-benzofuranyl, benzofuranyl, benzo [1,3]dioxolyl, chromanyl, 2,3-dihydro-benzo [1,4]-dioxinyl, 1,3-dioxanyl, 1,4-dioxanyl, 1,3-dioxolanyl, imidazolyl, imidazo[1,2a]-pyridyl, isoxazolyl, morpholinyl, oxetanyl, piperidinyl, pyrazolyl, pyridyl, pyrimidinyl, pyrrolidinyl, tetrahydro-2H[1,2']bi-pyridinyl, tetrahydrofuranyl, tetrahydropyranyl, tetrahydrothiopyranyl, thiazolyl, thienothiophenyl, and thienyl, and wherein said heterocyclyl is unsubstituted or mono-, di- or trisubstituted independently of one another by R4, -heterocyclyl, wherein said heterocyclyl is selected from the group consisting of 2,3-dihydro-benzofuranyl, benzofuranyl, benzo[1,3]dioxolyl, chromanyl, 2,3-dihydro-benzo[1,4]-dioxinyl, 1,3-dioxanyl, 1,4-dioxanyl, 1,3-dioxolanyl, imidazolyl, imidazo[1,2a]-pyridyl, isoxazolyl, morpholinyl, oxetanyl, piperidinyl, pyrazolyl, pyridyl, pyrimidinyl, pyrrolidinyl, tetrahydro-2H[1,2']bi-pyridinyl, tetrahydrofuranyl, tetrahydropyranyl, tetrahydrothiopyranyl, thiazolyl, thienothiophenyl, and thienyl and wherein said heterocyclyl is unsubstituted or mono-, di- or trisubstituted independently of one another by R4, -aryl, wherein said aryl is selected from the group consisting of phenyl, tetrahydronaphthalenyl, naphthyl, biphenyl, and indanyl, and wherein said aryl is mono- or disubstituted independently of one another by R3, or —($C_3$-$C_8$)-cycloalkyl, wherein said cycloalkyl is mono- di-, tri- or tetrasubstituted independently of one another by R2;

X is
—O-aryl, wherein said aryl is selected from the group consisting of phenyl, indanyl, indanyl-1-one, and biphenyl, and wherein said aryl is mono- or disubstituted independently of one another by R6, —O-heterocyclyl, wherein said heterocyclyl is selected from the group consisting of benzo[1,3]dioxolyl, chromanyl, chromenyl, cinnolinyl, decahydrochinolinyl, 2,3-dihydro-benzofuranyl, 2,3-dihydro-benzo [1,4]-dioxinyl, 1,4-dioxanyl, imidazolyl, imidazo[1,2a]pyridyl, indolyl, 1,3,4-oxadiazolyl, piperidinyl, pyrazolyl, pyridazinyl, pyridinyl, pyridyl, pyrimidinyl, pyrrolidinyl, quinolinyl, tetrahydro-2H[1,2']bipyridinyl, tetrahydrofuranyl, tetrahydropyranyl, tetrahydrothiophenyl, tetrahydrothiophenyl-1,1-dioxide, tetrazolyl, thiazolyl, thienothiophenyl, thienyl, and 1,2,4-triazolyl, and wherein said heterocyclyl is unsubstituted or mono-, di- or trisubstituted independently of one another by R7, —($C_1$-$C_3$)-alkyl-R17, wherein said alkyl is unsubstituted or mono-, di- or trisubstituted independently of one another by R17,
—($C_1$-$C_4$)-alkyl-aryl, wherein said aryl is selected from the group consisting of phenyl, indanyl, indanyl-1-one, and biphenyl, and wherein aryl is mono- or disubstituted independently of one another by R8,
—($C_1$-$C_3$)-alkyl-heterocyclyl, wherein said heterocyclyl is selected from the group consisting of benzo[1,3]dioxolyl, chromanyl, chromenyl, cinnolinyl, decahydrochinolinyl, 2,3-dihydro-benzofuranyl, 2,3-dihydro-benzo[1,4]-dioxinyl, 1,4-dioxanyl, imidazolyl, imidazo[1,2a]pyridyl, indolyl, 1,3,4-oxadiazolyl, piperidinyl, pyrazolyl, pyridazinyl, pyridinyl, pyridyl, pyrimidinyl, pyrrolidinyl, quinolinyl, tetrahydro-2H[1,2']bi-pyridinyl, tetrahydrofuranyl, tetrahydropyranyl, tetrahydrothiophenyl, tetrahydrothiophenyl-1,1-dioxide, tetrazolyl, thiazolyl, thienothiophenyl, thienyl, and 1,2,4-triazolyl,
—(CH═CH)-aryl, wherein said aryl is selected from the group consisting of phenyl, indanyl, indanyl-1-one, and biphenyl, and wherein aryl is mono- or disubstituted independently of one another by R8,
—(CH═CH)-heterocyclyl, wherein said heterocyclyl is selected from the group consisting of benzo[1,3]dioxolyl, chromanyl, chromenyl, cinnolinyl, decahydrochinolinyl, 2,3-dihydro-benzofuranyl, 2,3-dihydro-benzo[1,4]-dioxinyl, 1,4-dioxanyl, imidazolyl, imidazo[1,2a]pyridyl, indolyl, 1,3,4-oxadiazolyl, piperidinyl, pyrazolyl, pyridazinyl, pyridinyl, pyridyl, pyrimidinyl, pyrrolidinyl, quinolinyl, tetrahydro-2H[1,2']bi-pyridinyl, tetrahydrofuranyl, tetrahydropyranyl, tetrahydrothiophenyl, tetrahydrothiophenyl-1,1-dioxide, tetrazolyl, thiazolyl, thienothiophenyl, thienyl, and 1,2,4-triazolyl, and wherein said heterocyclyl is unsubstituted or mono-, di- or trisubstituted independently of one another by R7,
—(C≡C)-aryl, wherein said aryl is selected from the group consisting of phenyl, indanyl, indanyl-1-one, and biphenyl, and wherein said aryl is mono- or disubstituted independently of one another by R8,
—(C≡C)-heterocyclyl, wherein said heterocyclyl is selected from the group consisting of benzo[1,3]dioxolyl, chromanyl, chromenyl, cinnolinyl, decahydrochinolinyl, 2,3-dihydro-benzofuranyl, 2,3-dihydro-benzo[1,4]-dioxinyl, 1,4-dioxanyl, imidazolyl, imidazo[1,2a]pyridyl, indolyl, 1,3,4-oxadiazolyl, piperidinyl, pyrazolyl, pyridazinyl, pyridinyl, pyridyl, pyrimidinyl, pyrrolidinyl, quinolinyl, tetrahydro-2H[1,2']bi-pyridinyl, tetrahydrofuranyl, tetrahydropyranyl, tetrahydrothiophenyl, tetrahydrothiophenyl-1,1-dioxide, tetrazolyl, thiazolyl, thienothiophenyl, thienyl, and 1,2,4-triazolyl, and wherein said heterocyclyl is unsubstituted or mono-, di- or trisubstituted independently of one another by R7,
—CN or —O—($C_1$-$C_3$)-fluoroalkyl,
—O—C(O)-heterocyclyl, wherein said heterocyclyl is selected from the group consisting of imidazolyl, morpholinyl, oxadiazolyl, piperazinyl, piperidinyl, pyridyl, pyrrolidinyl, tetrahydrofuranyl, tetrazolyl, thiazolyl, thiophenyl, and triazolyl, and wherein said heterocyclyl is mono- or disubstituted independently of one another by R7,
—N(R10)-heterocyclyl, wherein said heterocyclyl is selected from the group consisting of imidazolyl, morpholinyl, oxadiazolyl, piperazinyl, piperidinyl, pyridyl, pyrrolidinyl, tetrahydrofuranyl, tetrazolyl, thiazolyl, thiophenyl, and triazolyl, and wherein said heterocyclyl is mono- or disubstituted independently of one another by R7,
—S—($C_1$-$C_4$)-alkyl-R17, wherein said alkyl is unsubstituted or mono- or disubstituted independently of one another by R17,
—S—($C_3$-$C_8$)-cycloalkyl, wherein said cycloalkyl is unsubstituted or mono- or ditrisubstituted independently of one another by R17,
—$SO_2$—($C_3$-$C_8$)-cycloalkyl, wherein said cycloalkyl is unsubstituted or mono-, di- or trisubstituted independently of one another by R17,
—O—$SO_2$-phenyl, wherein said phenyl is mono- or disubstituted independently of one another by R8,
—S-phenyl, wherein said phenyl is mono- or disubstituted independently of one another by R8,
—S-heterocyclyl, wherein said heterocyclyl is selected from the group consisting of benzo[1,3]dioxolyl, chromanyl, chromenyl, cinnolinyl, decahydrochinolinyl, 2,3-dihydro-benzofuranyl, 2,3-dihydro-benzo[1,4]-dioxinyl, 1,4-dioxanyl, imidazolyl, imidazo[1,2a]pyridyl, indolyl, 1,3,4-oxadiazolyl, piperidinyl, pyrazolyl, pyridazinyl, pyridinyl, pyridyl, pyrimidinyl, pyrrolidinyl, quinolinyl, tetrahydro-2H[1,2']bi-pyridinyl, tetrahydrofuranyl, tetrahydropyranyl, tetrahydrothiophenyl, tetrahydrothiophenyl-1,1-dioxide, tetrazolyl, thiazolyl, thienothiophenyl, thienyl, and 1,2,4-triazolyl, and wherein said heterocyclyl is unsubstituted or is mono- or disubstituted independently of one another by R7, or
—S—($C_1$-$C_4$)-alkyl, wherein said alkyl is unsubstituted or is mono- or disubstituted independently of one another by R18;

R2, R3, R14, R17 and R18 are independent of one another, are identical or different, and are selected from the group consisting of a hydrogen atom, —($C_1$-$C_4$)-alkyl, —OH, —($C_1$-$C_4$)-alkyl-OH, halogen, —($C_1$-$C_3$)-fluoroalkyl, —C(O)—OH, —C(O)—O—($C_1$-$C_4$)-alkyl, —O—($C_1$-$C_4$)-alkyl, —CN, —O—($C_1$-$C_3$)-fluoroalkyl, —N(R10)-R21, —NH—C(O)—($C_1$-$C_4$)-alkyl, —S—($C_1$-$C_4$)-alkyl, —S(O)$_2$—($C_1$-$C_3$)-alkyl, —($C_1$-$C_3$)-alkyl-O—($C_1$-$C_3$)-alkyl, phenyl, and —O—($C_1$-$C_4$)-alkyl-phenyl;

R6 is
phenyl, wherein said phenyl is mono- or disubstituted independently of one another by R10,
—O-phenyl, wherein said phenyl is mono- or disubstituted independently of one another by R10,
—($C_1$-$C_4$)-alkylene-phenyl, wherein said phenyl is mono- or disubstituted independently of one another by R10,
-heterocyclyl, wherein said heterocyclyl is selected from the group consisting of imidazolyl, morpholinyl, oxadiazolyl, piperazinyl, piperidinyl, pyridyl, pyrrolidinyl, tetrahydrofuranyl, tetrazolyl, thiazolyl, thiophenyl, and triazolyl, and wherein said heterocyclyl is unsubstituted or mono- or disubstituted independently of one another by R10,
—O-heterocyclyl, wherein said heterocyclyl is selected from the group consisting of imidazolyl, morpholinyl, oxadiazolyl, piperazinyl, piperidinyl, pyridyl, pyrrolidinyl, tetrahydrofuranyl, tetrazolyl, thiazolyl, thiophenyl, and triazolyl, and wherein said heterocyclyl is unsubstituted or mono- or disubstituted independently of one another by R10,
—C(O)-heterocyclyl, wherein said heterocyclyl is selected from the group consisting of imidazolyl, morpholinyl, oxadiazolyl, piperazinyl, piperidinyl, pyridyl, pyrrolidinyl, tetrahydrofuranyl, tetrazolyl, thiazolyl, thiophenyl, and triazolyl, and wherein said heterocyclyl is unsubstituted or mono- or disubstituted independently of one another by R10,
—($C_1$-$C_4$)-alkylene-heterocyclyl, wherein said heterocyclyl is selected from the group consisting of imidazolyl, morpholinyl, oxadiazolyl, piperazinyl, piperidinyl, pyridyl, pyrrolidinyl, tetrahydrofuranyl, tetrazolyl, thiazolyl, thiophenyl, and triazolyl, and wherein said heterocyclyl is unsubstituted or mono- or disubstituted independently of one another by R10,
—O—($C_1$-$C_4$)-alkylene-heterocyclyl, wherein said heterocyclyl is selected from the group consisting of imidazolyl, morpholinyl, oxadiazolyl, piperazinyl, piperidinyl, pyridyl, pyrrolidinyl, tetrahydrofuranyl, tetrazolyl, thiazolyl, thiophenyl, and triazolyl, and wherein said heterocyclyl is unsubstituted or mono- or disubstituted independently of one another by R10,
—($C_3$-$C_6$)-cycloalkyl, wherein said cycloalkyl is unsubstituted or mono- or disubstituted independently of one another by R10, or
is selected from the group consisting of a hydrogen atom, —($C_1$-$C_4$)-alkylene-N(R10)-R21, —C(O)—N(R10)-R20, —N(R10)-R21, —($C_1$-$C_4$)-alkyl, —($C_1$-$C_4$)-alkyl-CN, —($C_1$-$C_3$)-fluoroalkyl, —O—($C_1$-$C_4$)-alkyl, halogen, —C(O)—O—R10, —($C_1$-$C_3$)-alkylene-C(O)—O—R10, —NH—C(O)—($C_1$-$C_4$)-alkyl, —C(O)—($C_1$-$C_4$)-alkyl, and —$NO_2$;

R4 and R7 are independent of one another, are identical or different, and are selected from the group consisting of a hydrogen atom, —($C_1$-$C_4$)-alkyl, —O—($C_1$-$C_4$)-alkyl, —($C_1$-$C_5$)-alkyl-OH, halogen, —C(O)—O—R10, =O, phenyl, —($C_1$-$C_3$)-alkylene-C(O)—O—R10, —C(O)—N(R10)-R20, —N(R10)-R21, —CN, —($C_1$-$C_3$)-fluoroalkyl, —($C_1$-$C_3$)-alkyl-O—($C_1$-$C_3$)-alkyl, —C(O)—($C_1$-$C_4$)-alkyl, —C(O)—($C_1$-$C_3$)-fluoroalkyl, and —C(O)—($C_3$-$C_8$)-cycloalkyl,
—C(O)-phenyl, wherein said phenyl is mono- or disubstituted independently of one another by R6,
phenyl, wherein said phenyl is mono- or disubstituted independently of one another by R6,
methanesulfonyl, or
heterocyclyl, wherein said heterocyclyl is selected from the group consisting of imidazolyl, morpholinyl, oxadiazolyl, piperazinyl, piperidinyl, pyridyl, pyrrolidinyl, tetrahydrofuranyl, tetrazolyl, thiazolyl, thiophenyl, and triazolyl;

R8 and R9 are independent of one another, are identical or different, and are selected from the group consisting of a hydrogen atom, halogen, —OH, —N(R10)-C(O)—R20, and —($C_1$-$C_4$)-alkyl;
R10 is a hydrogen atom, —($C_1$-$C_4$)-alkyl or —O—($C_1$-$C_4$)-alkyl;
R11 is a hydrogen atom, —($C_1$-$C_4$)-alkyl or benzyl;
R12 is a hydrogen atom, or
R1 and R12 together with the nitrogen atom to which they are bonded form a piperidine ring and wherein said piperidine ring is mono- or disubstituted independently of one another by —($C_1$-$C_4$)-alkyl or halogen;
R20 is a hydrogen atom or —($C_1$-$C_4$)-alkyl; and
R21 is selected from the group consisting of a hydrogen atom, —($C_1$-$C_4$)-alkyl, —C(O)—R20, —($C_1$-$C_4$)-alkyl-heterocyclyl, wherein said heterocyclyl is selected from the group consisting of imidazolyl, morpholinyl, oxadiazolyl, piperazinyl, piperidinyl, pyridyl, pyrrolidinyl, tetrahydrofuranyl, tetrazolyl, thiazolyl, thiophenyl, and triazolyl, heterocyclyl, wherein said heterocyclyl is selected from the group consisting of imidazolyl, morpholinyl, oxadiazolyl, piperazinyl, piperidinyl, pyridyl, pyrrolidinyl, tetrahydrofuranyl, tetrazolyl, thiazolyl, thiophenyl, and triazolyl, and
—($C_3$-$C_8$)-cycloalkyl, wherein said cycloalkyl is unsubstituted or mono-, di- or trisubstituted independently of one another by R10.

4. The compound of claim 1, a stereoisomeric form thereof, or a physiologically tolerable salt of any of the foregoing, wherein
R1 is
—($C_1$-$C_4$)-alkylene-($C_3$-$C_{12}$)-cycloalkyl, wherein said cycloalkyl is mono-, di- or trisubstituted independently of one another by R2,
—($C_1$-$C_4$)-alkylene-aryl, wherein said aryl is selected from the group consisting of phenyl, tetrahydronaphthalenyl, naphthyl, biphenyl, anthryl, indanyl, and fluorenyl, and wherein said alkylene or aryl is independently from each other mono-, di- or trisubstituted independently of one another by R3,
—($C_1$-$C_4$)-alkylene-heterocyclyl, wherein said heterocyclyl is selected from the group consisting of acridinyl, azaindole (1H-pyrrolopyridinyl), azabenzimidazolyl, azaspirodecanyl, azepinyl, azetidinyl, benzimidazolyl, 2,3-dihydro-benzofuranyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydro-benzo[1,4]-dioxinyl, 4,5-dihydrooxazolinyl, dioxazolyl, dioxazinyl, 1,3-dioxanyl, 1,4-dioxanyl, 1,3-dioxolanyl, 1,3-dioxolenyl, 3,3-dioxo[1,3,4]oxa-thiazinyl, 6H-1,5,2-dithiazinyl, dihydrofuro[2,3-b]-tetrahydro-furanyl, furanyl, furazanyl, imidazolidinyl, imidazolinyl, imidazolyl, imidazo[1,2a]-pyridyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 7-oxa-bicyclo[2.2.1]heptanelyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2']bi-pyridinyl, tetrahydro-isoquinolinyl, tetrahydroquinolinyl, tetrahydrofuranyl, tetrahydropyranyl, tetrahydropyridinyl, tetrahydrothiophenyl, tetrahydrothiophenyl-1,1-dioxide, tetrahydrothiopyranyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein said alkylene or heterocyclyl is independently from each other unsubstituted or mono-, di- or trisubstituted independently of one another by R4, -cyclopropyl-heterocyclyl, wherein said heterocyclyl is selected from the group consisting of acridinyl, azaindole (1H-pyrrolopyridinyl), azabenzimidazolyl, azaspirodecanyl, azepinyl, azetidinyl, benzimidazolyl, 2,3-dihydro-benzofuranyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydro-benzo[1,4]-dioxinyl, 4,5-dihydrooxazolinyl, dioxazolyl, dioxazinyl, 1,3-dioxanyl, 1,4-dioxanyl, 1,3-dioxolanyl, 1,3-dioxolenyl, 3,3-dioxo[1,3,4]oxa-thiazinyl, 6H-1,5,2-dithiazinyl, dihydrofuro[2,3-b]-tetrahydro-furanyl, furanyl, furazanyl, imidazolidinyl, imidazolinyl, imidazolyl, imidazo[1,2a]-pyridyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 7-oxa-bicyclo[2.2.1]heptanelyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2']bi-pyridinyl, tetrahydro-isoquinolinyl, tetrahydroquinolinyl, tetrahydrofuranyl, tetrahydropyranyl, tetrahydropyridinyl, tetrahydrothiophenyl, tetrahydrothiophenyl-1,1-dioxide, tetrahydrothiopyranyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R4, -heterocyclyl, wherein said heterocyclyl is selected from the group consisting of acridinyl, azaindole (1H-pyrrolopyridinyl), azabenzimidazolyl, azaspirodecanyl, azepinyl, azetidinyl, benzimidazolyl, 2,3-dihydro-benzofuranyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydro-benzo[1,4]-dioxinyl, 4,5-dihydrooxazolinyl, dioxazolyl, dioxazinyl, 1,3-dioxanyl, 1,4-dioxanyl, 1,3-dioxolanyl, 1,3-dioxolenyl, 3,3-dioxo[1,3,4]oxa-thiazinyl, 6H-1,5,2-dithiazinyl, dihydrofuro[2,3]-tetrahydro-furanyl, furanyl, furazanyl, imidazolidinyl, imidazolinyl, imidazolyl, imidazo[1,2a]-pyridyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 7-oxa-bicyclo[2.2.1]heptanelyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2']bi-pyridinyl, tetrahydro-isoquinolinyl, tetrahydroquinolinyl, tetrahydrofuranyl, tetrahydropyranyl, tetrahydropyridinyl, tetrahydrothiophenyl, tetrahydrothiophenyl-1,1-dioxide, tetrahydrothiopyranyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R4, -aryl, wherein said aryl is selected from the group consisting of phenyl, naphthyl, biphenyl, tetrahydronaphthalenyl, anthryl, indanyl, and fluorenyl, and wherein said aryl is mono-, di- or trisubstituted independently of one another by R3, or —($C_3$-$C_{12}$)-cycloalkyl, wherein said cycloalkyl is mono-, di-, tri- or tetrasubstituted independently of one another by R2;

X is

—O-aryl, wherein said aryl is selected from the group consisting of phenyl, naphthyl, indanyl, indanyl-1-one, biphenyl, anthryl and fluorenyl, and wherein said aryl is mono-, di- or trisubstituted independently of one another by R6, —O-heterocyclyl, wherein said heterocyclyl is selected from the group consisting of acridinyl, azaindole (1H-pyrrolopyridinyl), azabenzimidazolyl, azaspirodecanyl, azepinyl, azetidinyl, benzimidazolyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydro-benzofuranyl, 2,3-dihydro-benzo[1,4]-dioxinyl, 4,5-dihydrooxazolinyl, dioxazolyl, dioxazinyl, 1,3-dioxanyl, 1,4-dioxanyl, 1,3-dioxolanyl, 1,3-dioxolenyl, 3,3-dioxo[1,3,4]oxathia-zinyl, 6H-1,5,2-dithiazinyl, dihydrofuro[2,3-b]-tetrahydrofuranyl, furanyl, furazanyl, imidazolidinyl, imidazolinyl, imidazolyl, imidazo[1,2a]pyridyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 7-oxa-bicyclo[2.2.1]heptanelyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2']bi-pyridinyl, tetrahydrofuranyl, tetrahydro-isoquinolinyl, tetrahydroquinolinyl, tetrahydropyranyl, tetrahydropyridinyl, tetrahydrothiophenyl, tetrahydrothiophenyl-1,1-dioxide, tetrahydrothiopyranyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R7, —(C$_1$-C$_4$)-alkyl-R17, wherein said alkyl is unsubstituted or mono-, di- or trisubstituted independently of one another by R17, —(C$_1$-C$_4$)-alkyl-aryl, wherein said aryl is selected from the group consisting of phenyl, naphthyl, indanyl, indanyl-1-one, biphenyl, anthryl and fluorenyl, and wherein said aryl is mono-, di- or trisubstituted independently of one another by R8, —(C$_1$-C$_4$)-alkyl-heterocyclyl, wherein said heterocyclyl is selected from the group consisting of acridinyl, azaindole (1H-pyrrolopyridinyl), azabenzimidazolyl, azaspirodecanyl, azepinyl, azetidinyl, benzimidazolyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl,_chromenyl, cinnolinyl, decahydrochinolinyl, 2,3-dihydro-benzofuranyl, 2,3-dihydro-benzo[1,4]-dioxinyl, 4,5-dihydrooxazolinyl, dioxazolyl, dioxazinyl, 1,3-dioxanyl, 1,4-dioxanyl, 1,3-dioxolanyl, 1,3-dioxolenyl, 3,3-dioxo[1,3,4]oxathia-zinyl, 6H-1,5,2-dithiazinyl, dihydrofuro[2,3]-tetrahydrofuranyl, furanyl, furazanyl, imidazolidinyl, imidazolinyl, imidazolyl, imidazo[1,2a]pyridyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 7-oxa-bicyclo[2.2.1]heptanelyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2']bi-pyridinyl, tetrahydrofuranyl, tetrahydro-isoquinolinyl, tetrahydroquinolinyl, tetrahydropyranyl, tetrahydropyridinyl, tetrahydrothiophenyl, tetrahydrothiophenyl-1,1-dioxide, tetrahydrothiopyranyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R7, —(CH═CH)-aryl, wherein said aryl is selected from the group consisting of phenyl, naphthyl, indanyl, indanyl-1-one, biphenyl, anthryl and fluorenyl, and wherein said aryl is mono-, di- or trisubstituted independently of one another by R8, —(CH═CH)-heterocyclyl, wherein said heterocyclyl is selected from the group consisting of acridinyl, azaindole (1H-pyrrolopyridinyl), azabenzimidazolyl, azaspirodecanyl, azepinyl, azetidinyl, benzimidazolyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydro-benzofuranyl, 2,3-dihydro-benzo[1,4]-dioxinyl, 4,5-dihydrooxazolinyl, dioxazolyl, dioxazinyl, 1,3-dioxanyl, 1,4-dioxanyl, 1,3-dioxolanyl, 1,3-dioxolenyl, 3,3-dioxo

[1,3,4]oxathia-zinyl, 6H-1,5,2-dithiazinyl, dihydrofuro[2,3]-tetrahydrofuranyl, furanyl, furazanyl, imidazolidinyl, imidazolinyl, imidazolyl, imidazo[1,2a]pyridyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 7-oxa-bicyclo[2.2.1]heptanelyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2']bi-pyridinyl, tetrahydrofuranyl, tetrahydro-isoquinolinyl, tetrahydroquinolinyl, tetrahydropyranyl, tetrahydropyridinyl, tetrahydrothiophenyl, tetrahydrothiophenyl-1,1-dioxide, tetrahydrothiopyranyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R7, —(C≡C)-aryl, wherein said aryl is selected from the group consisting of phenyl, naphthyl, indanyl, indanyl-1-one, biphenyl, anthryl and fluorenyl, and wherein said aryl is mono-, di- or trisubstituted independently of one another by R8, —(C≡C)-heterocyclyl, wherein said heterocyclyl is selected from the group consisting of acridinyl, azaindole (1H-pyrrolopyridinyl), azabenzimidazolyl, azaspirodecanyl, azepinyl, azetidinyl, benzimidazolyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydro-benzofuranyl, 2,3-dihydro-benzo[1,4]-dioxinyl, 4,5-dihydrooxazolinyl, dioxolyl, dioxazinyl, 1,3-dioxanyl, 1,4-dioxanyl, 1,3-dioxolanyl, 1,3-dioxolenyl, 3,3-dioxo[1,3,4]oxathia-zinyl, 6H-1,5,2-dithiazinyl, dihydrofuro[2,3-b]-tetrahydrofuranyl, furanyl, furazanyl, imidazolidinyl, imidazolinyl, imidazolyl, imidazo[1,2a]pyridyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 7-oxa-bicyclo[2.2.1]heptanelyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2']bi-pyridinyl, tetrahydrofuranyl, tetrahydro-isoquinolinyl, tetrahydroquinolinyl, tetrahydropyranyl, tetrahydropyridinyl, tetrahydrothiophenyl, tetrahydrothiophenyl-1,1-dioxide, tetrahydrothiopyranyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R7, —CN or —O—($C_1$-$C_3$)-fluoroalkyl, —O—C(O)-heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, and wherein said heterocyclyl is mono-, di- or trisubstituted independently of one another by R7, —N(R10) heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, and wherein said heterocyclyl is unsubstituted or mono-, di- or trisubstituted independently of one another by R7, —S—($C_1$-$C_4$)-alkyl-R17, wherein said alkyl is unsubstituted or mono-, di- or trisubstituted independently of one another by R17, —S—($C_3$-$C_8$)-cycloalkyl, wherein said cycloalkyl is unsubstituted or mono-, di- or trisubstituted independently of one another by R17, —$SO_2$—($C_3$-$C_8$)-cycloalkyl, wherein said cycloalkyl is unsubstituted or mono-, di- or trisubstituted independently of one another by R17, —O—$SO_2$-aryl, wherein said aryl is selected from the group consisting of phenyl, naphthyl, indanyl, indanyl-1-one, biphenyl, anthryl and fluorenyl, and wherein said aryl is mono-, di- or trisubstituted independently of one another by R8, —S-aryl, wherein said aryl is selected from the group consisting of phenyl, naphthyl, indanyl, indanyl-1- one, biphenyl, anthryl and fluorenyl, and wherein said aryl is mono-, di- or trisubstituted independently of one another by R8, —S-heterocyclyl, wherein said heterocyclyl is selected from the group consisting of acridinyl, azaindole (1H-pyrrolopyridinyl), azabenzimidazolyl, azaspirodecanyl, azepinyl, azetidinyl, benzimidazolyl, benzofuranyl, benzo[1,3]dioxolyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydro-benzofuranyl, 2,3-dihydro-benzo[1,4]-dioxinyl, 4,5-dihydrooxazolinyl, dioxazolyl, dioxazinyl, 1,3-dioxanyl, 1,4-dioxanyl, 1,3-dioxolanyl, 1,3-dioxolenyl, 3,3-dioxo[1,3,4]oxathia-zinyl, 6H-1,5,2-dithiazinyl, dihydrofuro[2,3-b]-tetrahydrofuranyl, furanyl, furazanyl, imidazolidinyl, imidazolinyl, imidazolyl, imidazo[1,2a]pyridyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 7-oxa-bicyclo[2.2.1]heptanelyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-2H[1,2']bi-pyridinyl, tetra-hydrofuranyl, tetrahydro-isoquinolinyl, tetrahydro-quinolinyl, tetrahydropyranyl, tetrahydropyridinyl, tetrahydrothiophenyl, tetrahydrothiophenyl-1,1-dioxide, tetrahydrothiopyranyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienothiophenyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein said heterocyclyl is unsubstituted or mono-, di- or trisubstituted independently of one another by R7, or —S—$(C_1-C_4)$-alkyl, wherein said alkyl is unsubstituted or mono-, di- or trisubstituted independently of one another by R18;

R2, R3, R14, R17 and R18 are independent of one another, are identical or different, and are selected from the group consisting of a hydrogen atom, —$(C_1-C_4)$-alkyl, —OH, —$(C_1-C_4)$-alkyl-OH, halogen, —$(C_1-C_3)$-fluoroalkyl, —C(O)—OH, —C(O)—O—$(C_1-C_4)$-alkyl, —O—$(C_1-C_4)$-alkyl, —CN, —O—$(C_1-C_3)$-fluoroalkyl, —N(R10)-R21, —NH—C(O)—$(C_1-C_4)$-alkyl, —S—$(C_1-C_4)$-alkyl, —S(O)_2—$(C_1-C_3)$-alkyl, —$(C_1-C_3)$-alkyl-O—$(C_1-C_3)$-alkyl, phenyl, and —O—$(C_1-C_4)$-alkyl-phenyl;

R6 is aryl, wherein said aryl is selected from the group consisting of phenyl, naphthyl, indanyl, indanyl-1-one, biphenyl, anthryl and fluorenyl, and wherein said aryl is mono-, di- or trisubstituted independently of one another by R10, —O-aryl, wherein said aryl is selected from the group consisting of phenyl, naphthyl, indanyl, indanyl-1-one, biphenyl, anthryl and fluorenyl, and wherein said aryl is mono-, di- or trisubstituted independently of one another by R10, —$(C_1-C_4)$-alkylene-aryl, wherein said aryl is selected from the group consisting of phenyl, naphthyl, indanyl, indanyl-1-one, biphenyl, anthryl and fluorenyl, and wherein said aryl is mono-, di- or trisubstituted independently of one another by R10, heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, and wherein said heterocyclyl is unsubstituted or mono-, di- or trisubstituted independently of one another by R10, —O-heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, and wherein said heterocyclyl is unsubstituted or mono-, di- or trisubstituted independently of one another by R10, —C(O)-heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, and wherein said heterocyclyl is unsubstituted or mono-, di- or trisubstituted independently of one another by R10, —$(C_1-C_4)$-alkylene-heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, and wherein said heterocyclyl is unsubstituted or mono-, di- or trisubstituted independently of one another by R10, —O—$(C_1-C_4)$-alkylene-heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, and wherein said heterocyclyl is unsubstituted or mono-, di- or trisubstituted independently of one another by R10, —$(C_3-C_8)$-cycloalkyl, wherein said cycloalkyl is unsubstituted or mono-, di- or trisubstituted independently of one another by R10, or is selected from the group consisting of hydrogen atom, —$(C_1-C_4)$-alkylene-N(R10)-R21, —C(O)—N(R10)-R20, —N(R10)-R21, —$(C_1-C_4)$-alkyl, —$(C_1-C_4)$-alkyl-CN, —$(C_1-C_3)$-fluoroalkyl, —O—$(C_1-C_4)$-alkyl, halogen, —C(O)—O—R10, —$(C_1-C_3)$-alkylene-C(O)—O—R10, —NH—C(O)—$(C_1-C_4)$-alkyl, —C(O)—$(C_1-C_4)$-alkyl, and —NO_2;

R4 and R7 are independent of one another, are identical or different, and are selected from the group consisting of a hydrogen atom, —($C_1$-$C_4$)-alkyl, —O—($C_1$-$C_4$)-alkyl, —($C_1$-$C_5$)-alkyl-OH, halogen, —C(O)—O—R10, =O, phenyl, —($C_1$-$C_3$)-alkylene-C(O)—O—R10, —C(O)—N(R10)-R20, —N(R10)-R21, —CN, —($C_1$-$C_3$)-fluoroalkyl, —($C_1$-$C_3$)-alkyl-O—($C_1$-$C_3$)-alkyl, —C(O)—($C_1$-$C_4$)-alkyl, —C(O)—($C_1$-$C_3$)-fluoroalkyl, and —C(O)—($C_3$-$C_8$)-cycloalkyl,
- —C(O)-aryl, wherein said aryl is selected from the group consisting of phenyl, naphthyl, indanyl, indanyl-1-one, biphenyl, anthryl and fluorenyl, and wherein said aryl is mono-, di- or trisubstituted independently of one another by R6,
- aryl, wherein said aryl is selected from the group consisting of phenyl, naphthyl, indanyl, indanyl-1-one, biphenyl, anthryl and fluorenyl, and wherein said aryl is mono-, di- or trisubstituted independently of one another by R6,
- methanesulfonyl, or
- heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl;

R8 and R9 are independent of one another, are identical or different, and are selected from the group consisting of a hydrogen atom, halogen, —OH, —N(R10)-C(O)—R20, and —($C_1$-$C_4$)-alkyl;

R10 is a hydrogen atom, —($C_1$-$C_4$)-alkyl or —O—($C_1$-$C_4$)-alkyl;

R11 is a hydrogen atom, —($C_1$-$C_4$)-alkyl or benzyl;

R12 is hydrogen atom or

R1 and R12 together with the nitrogen atom to which they are bonded form a four- to eight-membered monocyclic heterocyclic ring which, as well as the nitrogen atom, may additionally, according to the ring size, also contain one or two identical or different heteroatoms selected from the group consisting of oxygen, nitrogen and sulfur, wherein the four- to eight-membered monocyclic heterocyclic ring is mono-, di- or trisubstituted independently of one another by —($C_1$-$C_4$)-alkyl or halogen;

R20 is a hydrogen atom or —($C_1$-$C_4$)-alkyl; and

R21 is selected from the group consisting of a hydrogen atom, —($C_1$-$C_4$)-alkyl, —C(O)—R20, —($C_1$-$C_4$)-alkyl heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, heterocyclyl, wherein said heterocyclyl is selected from the group consisting of imidazolyl, morpholinyl, oxadiazolyl, piperazinyl, piperidinyl, pyrazinyl, pyridyl, pyrrolidinyl, tetrahydrofuranyl, tetrazolyl, thiazolyl, thiophenyl, and triazolyl, and
- —($C_3$-$C_8$)-cycloalkyl, wherein said cycloalkyl is unsubstituted or mono-, di- or trisubstituted independently of one another by R10.

5. The compound of claim 1, a stereoisomeric form thereof, or a physiologically tolerable salt of any of the foregoing, wherein R1 is
- —($C_1$-$C_4$)-alkylene-aryl, wherein said aryl is selected from the group consisting of phenyl, tetrahydronaphthalenyl, naphthyl, biphenyl, anthryl, indanyl, and fluorenyl, and wherein said alkylene or aryl is independently from each other mono-, or disubstituted independently of one another by R3,
- heterocyclyl, wherein said heterocyclyl is selected from the group consisting of chromanyl, piperidinyl, pyridyl, pyrimidinyl, pyrrolidinyl, tetrahydropyranyl, tetrahydrothiopyranyl, thienothiophenyl, thiophenyl and thiopyranyl, and wherein said heterocyclyl is unsubstituted or mono-substituted by R4, or
- —($C_3$-$C_{12}$)-cycloalkyl, wherein said cycloalkyl is mono- or-, disubstituted independently of one another by R2, X is
- —O-aryl, wherein said aryl is selected from the group consisting of phenyl, naphthyl, indanyl, indanyl-1-one, biphenyl, anthryl and fluorenyl, and wherein said aryl is mono-, di- or trisubstituted independently of one another by R6,
- —O-heterocyclyl, wherein said heterocyclyl is selected from the group consisting of chromanyl, piperidinyl, pyridyl, pyrimidinyl, pyrrolidinyl, tetrahydropyranyl, tetrahydrothiopyranyl, thienothiophenyl, thiophenyl and thiopyranyl, and wherein said heterocyclyl is unsubstituted or mono-, di- or trisubstituted independently of one another by R7,
- —O—($C_1$-$C_3$)-fluoroalkyl,
- —S—($C_1$-$C_4$)-alkyl-R17, wherein said alkyl is unsubstituted or mono-, di- or trisubstituted independently of one another by R17, or
- —S-heterocyclyl, wherein said heterocyclyl is selected from the group consisting of chromanyl, piperidinyl, pyridyl, pyrimidinyl, pyrrolidinyl, tetrahydropyranyl, tetrahydrothiopyranyl, thienothiophenyl, thiophenyl and thiopyranyl, and wherein said heterocyclyl is unsubstituted or mono-, di- or trisubstituted independently of one another by R7;

R2, R3 and R17 are independent of one another, are identical or different, and are selected from the group consisting of a hydrogen atom, —(C-$C_4$)-alkyl, —($C_1$-$C_4$)-alkyl-OH, halogen, —($C_1$-$C_3$)-fluoroalkyl, —O—($C_1$-$C_3$)-fluoroalkyl and —O—($C_1$-$C_4$)-alkyl-phenyl;

R6 is a hydrogen atom, —($C_1$-$C_4$)-alkylene-N(R10)-R21, —C(O)—N(R10)-R20 or halogen;

R4 and R7 are independent of one another, are identical or different, and are selected from the group consisting of a hydrogen atom, —($C_1$-$C_4$)-alkyl, —($C_1$-$O_5$)-alkyl-OH, halogen, —CN, —($C_1$-$C_3$)-fluoroalkyl, and —C(O)—($C_1$-$C_3$)-fluoroalkyl;

R10, R11, R12 and R20 are each a hydrogen atom; and

R21 is a hydrogen atom or —($C_3$-$C_8$)-cycloalkyl.

6. The compound of claim 1, a stereoisomeric form thereof, or a physiologically tolerable salt of any of the foregoing, wherein R1 is
- —($C_1$-$C_4$)-alkylene-phenyl, wherein said alkylene or phenyl is independently from each other mono-, or disubstituted independently of one another by R3,
- heterocyclyl, wherein said heterocyclyl is selected from the group consisting of chromanyl, piperidinyl, tetrahydropyranyl, tetrahydrothiopyranyl, and thiopyranyl, and wherein said heterocyclyl is unsubstituted or mono-substituted by R4, or
- —($C_3$-$C_{12}$)-cycloalkyl, wherein said cycloalkyl is cyclopentanyl, cyclohexyl or bicyclo[2.2.1]heptanyl, and wherein said cycloalkyl is mono- or-, disubstituted independently of one another by R2;

X is
- —O-phenyl, wherein said phenyl is mono- or di-substituted independently of one another by R6,
- —O-heterocyclyl, wherein said heterocyclyl is selected from the group consisting of chromanyl, pyridyl, pyrimidinyl and thienothiophenyl, and wherein said heterocyclyl is unsubstituted or mono-, di- or trisubstituted independently of one another by R7,
- —O—($C_1$-$C_3$)-fluoroalkyl,
- —S—($C_1$-$C_4$)-alkyl-R17, wherein said alkyl is unsubstituted or mono-, di- or trisubstituted independently of one another by R17, or
- —S-pyrimidinyl or S-pyrazinyl, wherein said pyrimidinyl or pyrazinyl is each unsubstituted or mono-, di- or trisubstituted independently of one another by R7;

R2, R3 and R17 are independent of one another, are identical or different, and are selected from the group consisting of a hydrogen atom, —($C_1$-$C_4$)-alkyl, —($C_1$-$C_4$)-alkyl-OH, halogen, —($C_1$-$C_3$)-fluoroalkyl, —O—($C_1$-$C_3$)-fluoroalkyl and —O—($C_1$-$C_4$)-alkyl-phenyl;

R6 is a hydrogen atom, —($C_1$-$C_4$)-alkylene-N(R10)-R21, —C(O)—N(R10)-R20 or halogen;

R4 and R7 are independent of one another, are identical or different, and are selected from the group consisting of a hydrogen atom, —($C_1$-$C_4$)-alkyl, —($C_1$-$C_5$)-alkyl-OH, halogen, —CN, —($C_1$-$C_3$)-fluoroalkyl, and —C(O)—($C_1$-$C_3$)-fluoroalkyl;

R10, R11, R12 and R20 are each a hydrogen atom; and R21 is a hydrogen atom or —($C_3$-$C_8$)-cycloalkyl.

7. The compound of claim 1, a stereoisomeric form thereof, or a physiologically tolerable salt of any of the foregoing, wherein the compound is selected from the group consisting of:
- 1-Cyclohexyl-3-[(3S,3aR,6S,6aS)-6-(4-fluoro-phenoxy)-hexahydro-furo[3,2-b]furan-3-yl]-urea;
- 1-Cyclohexyl-3-[(3S,3aR,6S,6aS)-6-(6-methyl-pyridin-3-yloxy)-hexahydro-furo[3,2-b]furan-3-yl]-urea;
- 1-Cyclohexyl-3-[(3S,3aR,6S,6aS)-6-(2-methyl-pyrimidin-5-yloxy)-hexahydro-furo[3,2-b]furan-3-yl]-urea;
- 1-[(3S,3aR,6S,6aS)-6-(2-Methyl-pyridin-3-yloxy)-hexahydro-furo[3,2-b]furan-3-yl] -3-(2-trifluoromethoxy-benzyl)-urea;
- 1-(4,4-Difluoro-cyclohexyl)-3-[(3S,3aR,6S,6aS)-6-(4-fluoro-phenoxy)-hexahydro-furo[3,2-b]furan-3-yl]-urea;
- 1-Cyclohexyl-3-[(3S,3aR,6S,6aS)-6-(2-methyl-pyridin-3-yloxy)-hexahydro-furo[3,2-b]furan-3-yl]-urea;
- 1-Cyclohexyl-3-[(3S,3aR,6S,6a5)-6-(pyridin-3-yloxy)-hexahydro-furo[3 ,2-b]furan-3-yl]-urea;
- 1-[(3S,3aR,6S,6aS)-6-(4-Fluoro-phenoxy)-hexahydro-furo[3,2-b]furan-3-yl]-3-[1-(2,2,2-trifluoro-acetyl)-piperidin-4-yl]-urea;
- 1-[(3S,3aR,6S,6aS)-6-(4-Fluoro-phenoxy)-hexahydro-furo[3,2-b]furan-3-yl]-3-(tetrahydro-pyran-4-yl)-urea;
- 1-Cyclohexyl-3-[(3S,3aR,6S,6aS)-6-(5-fluoro-pyridin-3-yloxy)-hexahydro-furo[3,2-b]furan-3-yl]-urea;
- 1-Cyclohexyl-3-[(3S,3aR,6S,6aS)-6-(5-methyl-pyridin-3-yloxy)-hexahydro-furo[3,2-b]furan-3-yl]-urea;
- 1-(1S,2S,4R)-Bicyclo [2.2.1]hept-2-yl-3-[(3S,3aR,6S,6aS)-6-(2-methyl-pyridin-3-yloxy)-hexahydro-furo[3 ,2-b]furan-3-yl]-urea;
- 1-Cyclohexyl-3- {(3S,3aR,6S,6aS)-6-[5-(1-hydroxy-1-methyl-ethyl)-pyridin-3-yloxy]-hexahydro-furo[3,2-b]furan-3-yl}-urea;
- 1-Cyclohexyl-3-[(3S,3aR,6S,6aS)-6-(3-hydroxy-1,1-dimethyl-propylsulfanyl)-hexahydro-furo[3,2-b]furan-3-yl]-urea;
- 1-Cyclohexyl-3-[(3S,3aR,6S,6aS)-6-(3-cyclopropylaminomethyl-phenoxy)-hexahydro-furo[3,2-b]furan-3-yl]-urea;
- 3-[(3S,3aS,6S,6aR)-6-(3-Cyclohexyl-ureido)-hexahydro-furo[3,2-b]furan-3-yloxy]-benzamide;
- 1-Cyclohexyl-3-[(3S,3aR,6S,6aS)-6-(6-methyl-5,6-dihydro-thieno[3,2-b]thiophen-3-yloxy)-hexahydro-furo[3,2-b]furan-3-yl]-urea;
- 1-[(3S,3aR,6S,6aS)-6-(2-Cyano-pyridin-3-yloxy)-hexahydro-furo[3,2-b]furan-3-yl]-3-cyclohexyl-urea;
- 1-Cyclohexyl-3-[(3S,3aR,6S,6aS)-6-(6-trifluoromethyl-pyridin-3-yloxy)-hexahydro-furo[3,2-b]furan-3-yl]-urea;
- 1-Chroman-4-yl-3-[(3S,3aR,6S,6aS)-6-(2-methyl-pyridin-3-yloxy)-hexahydro-furo[3,2-b]furan-3-yl]-urea;
- 1-Cyclohexyl-3-[(3S,3aR,6S,6a5)-6-(2,6-dimethyl-pyrimidin-4-ylsulfanyl)-hexahydro-furo[3,2-b]furan-3-yl]-urea;
- 1-Cyclohexyl-3-[(3S,3aR,6S,6a5)-6-(pyrazin-2-ylsulfanyl)-hexahydro-furo[3,2-b]furan-3-yl]-urea;
- 1-(2-Difluoromethoxy-benzyl)-3-[(3S,3aR,6S,6aS)-6-(2-methyl-pyridin-3-yloxy)-hexahydro-furo[3,2-b]furan-3-yl]-urea;
- 1-(4,4-Dimethyl-cyclohexyl)-3-[(3S,3aR,6S,6aS)-6-(2-methyl-pyridin-3-yloxy)-hexahydro-furo[3,2-b]furan-3-yl]-urea;
- 1-((1R,2R)-2-Benzyloxy-cyclopentyl)-3-[(3S,3aR,6S,6aS)-6-(4-fluoro-phenoxy)-hexahydro-furo[3,2-b]furan-3-yl]-urea;
- 1-[(3S,3aR,6S,6aS)-6-(2-Methyl-pyridin-3-yloxy)-hexahydro-furo[3,2-b]furan-3-yl]-3-[2-(2-trifluoromethoxy-phenyl)-ethyl]-urea;
- 1-[(3S,3aR,6S,6aS)-6-(4-Fluoro-phenoxy)-hexahydro-furo[3,2-b]furan-3-yl]-3-[(R)-1-(4-fluoro-phenyl)-ethyl]-urea;
- 1-[(3S,3aR,6S,6aS)-6-(2-Methyl-pyridin-3-yloxy)-hexahydro-furo[3,2-b]furan-3-yl]-3-(tetrahydro-thiopyran-4-yl)-urea; and
- 1-Cyclohexyl-3-[(3S,3aR,6S,6aS)-6-(2,2,2-trifluoro-ethoxy)-hexahydro-furo[3,2-b]furan-3-yl]-urea.

8. A pharmaceutical composition comprising at least one compound of claim 1, a stereoisomeric form thereof or a mixture of stereoisomeric forms thereof in any ratio, or a physiologically tolerable salt of any of the foregoing, and a pharmaceutically acceptable carrier.

* * * * *